(12) United States Patent
Berdini et al.

(10) Patent No.: US 8,778,936 B2
(45) Date of Patent: Jul. 15, 2014

(54) PYRAZOLE COMPOUNDS THAT MODULATE THE ACTIVITY OF CDK, GSK AND AURORA KINASES

(75) Inventors: Valerio Berdini, Cambridge (GB); Maria Grazia Carr, Luton (GB); Adrian Liam Gill, Buxton (GB); Steven Howard, Cambridge (GB); Eva Figueroa Navarro, Cambridge (GB); Gary Trewartha, Stevenage (GB); David Charles Rees, Cambridge (GB); Mladen Vinkovic, Cambridge (GB); Paul Graham Wyatt, Perth (GB)

(73) Assignee: Astex Therapeutics Limited, Cambridge (GB)

( * ) Notice: Subject to any disclaimer, the term of this patent is extended or adjusted under 35 U.S.C. 154(b) by 45 days.

(21) Appl. No.: 13/329,952

(22) Filed: Dec. 19, 2011

(65) Prior Publication Data
US 2012/0190673 A1    Jul. 26, 2012

Related U.S. Application Data

(62) Division of application No. 11/813,031, filed as application No. PCT/GB2005/005097 on Dec. 30, 2005, now Pat. No. 8,110,573.

(60) Provisional application No. 60/640,597, filed on Dec. 30, 2004, provisional application No. 60/640,475, filed on Dec. 30, 2004.

(30) Foreign Application Priority Data

Dec. 30, 2004  (GB) .................................. 0428552.4
Dec. 30, 2004  (GB) .................................. 0428554.0

(51) Int. Cl.
*A61K 31/535*    (2006.01)

(52) U.S. Cl.
USPC ........................................................ 514/234.5

(58) Field of Classification Search
USPC ............................................. 514/234.5, 394
See application file for complete search history.

(56) References Cited

U.S. PATENT DOCUMENTS

| | | | |
|---|---|---|---|
| 5,952,368 | A | 9/1999 | Kertesz et al. |
| 6,350,746 | B1 | 2/2002 | Buckman et al. |
| 6,358,978 | B1 | 3/2002 | Ritzeler et al. |
| 6,696,437 | B1 | 2/2004 | Lubisch et al. |
| 7,087,616 | B2 | 8/2006 | Fischer et al. |
| 7,977,477 | B2 | 7/2011 | Berdini et al. |
| 8,110,573 | B2 | 2/2012 | Berdini et al. |
| 8,399,442 | B2 | 3/2013 | Berdini et al. |
| 8,435,970 | B2 | 5/2013 | Curry et al. |
| 2003/0207883 | A1 | 11/2003 | Renhowe et al. |
| 2004/0048868 | A1 | 3/2004 | Edwards et al. |
| 2004/0082798 | A1 | 4/2004 | Alonso-Alija et al. |
| 2004/0214814 | A1 | 10/2004 | Bebbington et al. |
| 2004/0242559 | A1 | 12/2004 | Ugolini et al. |

(Continued)

FOREIGN PATENT DOCUMENTS

| | | |
|---|---|---|
| EP | 0169051 A2 | 1/1986 |
| EP | 0711768 A1 | 5/1996 |

(Continued)

OTHER PUBLICATIONS

Cancer and Metastasis Reviews (1998), 17(1), 91-106.*

(Continued)

*Primary Examiner* — Rebecca Anderson
(74) *Attorney, Agent, or Firm* — Heslin Rothenberg Farley & Mesiti P.C.

(57) ABSTRACT

The invention provides a compound of the formula (I): or a salt, solvate, tautomer or N-oxide thereof, wherein M is selected from a group D1 and a group D2: and R', E, A and X are as defined in the claims. Also provided are pharmaceutical compositions containing the compounds, processes for making the compounds and the use of the compounds in the prophylaxis or treatment of a disease state mediated by a CDK kinase, GSK-3 kinase or Aurora kinase.

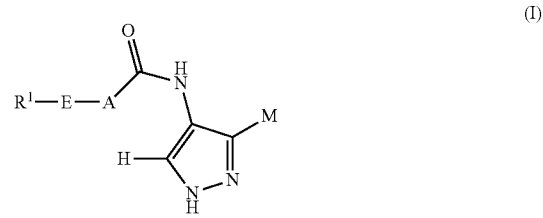

(I)

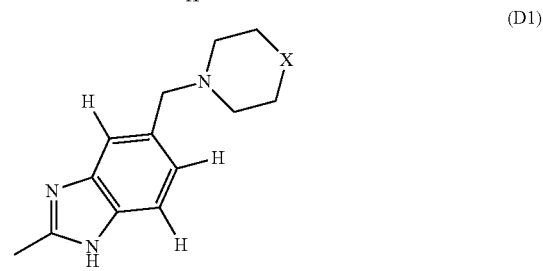

(D1)

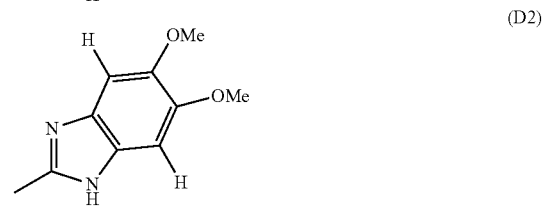

(D2)

20 Claims, 8 Drawing Sheets

(56) References Cited

U.S. PATENT DOCUMENTS

| | | |
|---|---|---|
| 2005/0009894 A1 | 1/2005 | Babin et al. |
| 2006/0293336 A1 | 12/2006 | Sutton et al. |
| 2007/0021472 A1 | 1/2007 | Zhu et al. |
| 2007/0105900 A1 | 5/2007 | Berdini et al. |
| 2007/0135477 A1 | 6/2007 | Berdini et al. |
| 2007/0208007 A1 | 9/2007 | Saitou et al. |
| 2008/0132495 A1 | 6/2008 | Berdini et al. |
| 2008/0312223 A1 | 12/2008 | Berdini et al. |
| 2010/0004232 A1 | 1/2010 | Berdini et al. |
| 2010/0055094 A1 | 3/2010 | Curry et al. |
| 2011/0105501 A1 | 5/2011 | Gallagher et al. |
| 2011/0159111 A1 | 6/2011 | Curry et al. |
| 2011/0224203 A1 | 9/2011 | Berdini et al. |

FOREIGN PATENT DOCUMENTS

| | | |
|---|---|---|
| EP | 1264820 A1 | 12/2002 |
| EP | 1460067 A1 | 9/2004 |
| JP | 2007/045752 A | 2/2007 |
| WO | 94/14435 A1 | 7/1994 |
| WO | 94/29300 A1 | 12/1994 |
| WO | 96/00218 A1 | 1/1996 |
| WO | 97/12615 A1 | 4/1997 |
| WO | 97/36585 A1 | 10/1997 |
| WO | 99/46244 A1 | 9/1999 |
| WO | 99/50247 A1 | 10/1999 |
| WO | 99/61426 A1 | 12/1999 |
| WO | 00/39108 A1 | 7/2000 |
| WO | 00/43384 A1 | 7/2000 |
| WO | 00/59902 A2 | 10/2000 |
| WO | 00/64888 A1 | 11/2000 |
| WO | 01/02385 A1 | 1/2001 |
| WO | 01/19788 A2 | 3/2001 |
| WO | 01/19798 A2 | 3/2001 |
| WO | 01/57022 A2 | 8/2001 |
| WO | 01/64642 A2 | 9/2001 |
| WO | 01/64643 A2 | 9/2001 |
| WO | 01/79198 A1 | 10/2001 |
| WO | 02/00647 A1 | 1/2002 |
| WO | 02/00651 A2 | 1/2002 |
| WO | 02/00655 A1 | 1/2002 |
| WO | 02/059111 A2 | 8/2002 |
| WO | 02/072549 A1 | 9/2002 |
| WO | 02/096426 A1 | 12/2002 |
| WO | 03/002566 A1 | 1/2003 |
| WO | 03/004488 A1 | 1/2003 |
| WO | 03/006465 A1 | 1/2003 |
| WO | 03/035065 A1 | 5/2003 |
| WO | 03/044014 A1 | 5/2003 |
| WO | 03/053941 A2 | 7/2003 |
| WO | 03/066629 A2 | 8/2003 |
| WO | 2004/041277 A1 | 5/2004 |
| WO | 2004/050636 A2 | 6/2004 |
| WO | 2004/052370 A1 | 6/2004 |
| WO | 2004/054515 A2 | 7/2004 |
| WO | 2004/056815 A1 | 7/2004 |
| WO | 2005/002552 A2 | 1/2005 |
| WO | 2005/002576 A2 | 1/2005 |
| WO | 2005/005414 A2 | 1/2005 |
| WO | 2005/028624 A2 | 3/2005 |
| WO | 2005/047266 A1 | 5/2005 |
| WO | 2006/071940 A2 | 7/2006 |
| WO | 2006/092430 A1 | 9/2006 |
| WO | 2006/094209 A2 | 9/2006 |
| WO | 2006/094235 A1 | 9/2006 |
| WO | 2006/124780 A2 | 11/2006 |
| WO | 2007/019416 A1 | 2/2007 |
| WO | 2007/063031 A2 | 6/2007 |
| WO | 2007/077435 A1 | 7/2007 |
| WO | 2008/001101 A2 | 1/2008 |
| WO | 2008/001115 A2 | 1/2008 |

OTHER PUBLICATIONS

Science (1999), vol. 286, 531-537.*

Essassi et al., Synthese et Hererocyclisation Des (Pyrazoly1-3-(5))-2 Benzimidazoles en Catalyse Par Transfert de Phase, Bull. Soc. Chim Belg. vol. 96, 1987, pp. 63-67.

Blankley et al., Antihypertensive Activity of 6-Arylpyrido[2,3-d] Pyrimidim-7-Amine Derivatives. 2. 7-Acyl Amide Analogues, Journal of Medicinal Chemistry, vol. 26, No. 3, Mar. 1, 1983, pp. 403-411.

Sarhan et al., Synthesis, Characterization and Reactions of 2-Deoxo-5-Deazaalloxazines, Bioorganic & Medicinal Chemistry, vol. 9, Jan. 1, 2001, pp. 2993-2998.

Mesguiche et al., 4-Alkoxy-2,6-Diaminopyrimidine Derivatives. Inhibitors of Cyclin Dependent Kinases 1 and 2, Bioorganic & Medicinal Chemistry Letters, vol. 13, Jan. 1, 2003, pp. 217-222.

Morissette et al., High-throughput crystallization: polymorphs, salts, co-crystals and solvates of pharmaceutical solids, Advanced Drug Delivery Reviews, 2004, 56, pp. 275-300.

Souillac et al., Characterization of Delivery Systems, Differential Scanning Calorimetry, Encyclopedia of Controlled Drug Delivery, Wiley, 1999, pp. 212-227.

Vippagunta et al., Crystalline solids, Advanced Drug Delivery Reviews, 2001, 48, pp. 3-26.

International Search Report for PCT/GB2004/002824 (Apr. 7, 2005).

GB Search Report for GB 0315657.7 (Oct. 28, 2003).

GB Search Report for GB 0324919.0 (Feb. 25, 2004).

European Supplementary Search Report for EP 04 743 172.1 (Jan. 27, 2009).

GB Search Report for GB 0428552.4 (Mar. 23, 2005).

GB Search Report for GB 0428554.0 (Mar. 23, 2005).

International Search Report for PCT/GB/2005/005097 (Apr. 4, 2006).

GB Search Report for GB 0526607.7 (May 19, 2006).

International Search Report for PCT/GB2006/004954 (Jun. 6, 2007).

Essassi et al., Synthese et Hererocyclisation Des (Pyrazolyl-3-(5))-2 Benzimidazoles en Catalyse Par Transfert de Phase, Bull. Soc. Chim Belg. vol. 96, 1987, pp. 63-67.

Mukherjee, S., The Emperor of All Maladies—A Biography of Cancer, 2010, p. 80.

Damia et al., Contemporary pre-clinical development of anticancer agents—What are the optimal preclinical models?, Eur. J. Cancer, 2009, 45, pp. 2768-2781.

Zhang et al., Targeting cancer with small molecule kinase inhibitors, Nature Rev. Cancer., 2009, 9, pp. 28-39.

Fojo, www.esmo.org (2011).

Boss et al., Clinical Experience with Aurora Kinase Inhibitors: A Review, The Oncologist, 2009, 14, pp. 780-793.

Evans et al., Prognostic Factors in Neuroblastoma, Cancer, 1987, 59, pp. 1853-1859.

* cited by examiner

PYRAZOLE COMPOUNDS THAT MODULATE THE ACTIVITY OF CDK, GSK AND AURORA KINASES

CROSS REFERENCE TO RELATED APPLICATIONS

This application is a divisional application of U.S. application Ser. No. 11/813,031 (which published on Jun. 5, 2008 as US 2008-0132495), which is a national stage filing under section 371 of International Application No. PCT/GB2005/005097, having an international filing date of Dec. 30, 2005, and published in English on Jul. 6, 2006 under Publication No. WO2006/070195, which claims priority from Application No. GB 0428554.0, filed Dec. 30, 2004; Application No. GB 0428552.4, filed Dec. 30, 2004; U.S. Provisional Application No. 60/640,475, filed Dec. 30, 2004; and U.S. Provisional Application No. 60/640,597, filed Dec. 30, 2004. The entire disclosures of each of the prior applications are hereby incorporated herein by reference.

This invention relates to pyrazole compounds that inhibit or modulate the activity of Cyclin-Dependent Kinases (CDK), Glycogen Synthase Kinases (GSK) and Aurora kinases to the use of the compounds in the treatment or prophylaxis of disease states or conditions mediated by the kinases, and to novel compounds having kinase inhibitory or modulating activity. Also provided are pharmaceutical compositions containing the compounds and novel chemical intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al, *Science*, 253:407-414 (1991); Hiles, et al, *Cell*, 70:419-429 (1992); Kunz, et al, *Cell*, 73:585-596 (1993); Garcia-Bustos, et al, *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the (H to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and pi 30 by the cdk(4/6)/cyclin-D complexes. Hyperphosphorylation of Rb and pi 30 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cycliii partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-I, synapsinl, DARPP32 and the Munc18/SyntaxinlA complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-I transcription via a Tat-mediated biochemical pathway. Cdk8 hinds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-I genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as weel, Mytl and Mikl Dephosphorylation is performed by phosphatases such as cdc25 (a & c), pp2a, or KAP.

Cdk/cyclin complex activity may be further regulated by two families of endogenous cellular proteinaceous inhibitors: the Kip/Cip family, or the INK family. The INK proteins specifically bind cdk4 and cdkó. p16$^{mk4}$ (also known as MTS1) is a potential tumour suppressor gene that is mutated, or deleted, in a large number of primary cancers. The Kip/Cip family contains proteins such as p21$^{Cip1'Waf1}$, p27$^{Kip1}$ and p57$^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Diffuse Large B-cell Lymphomas (DLBCL)

Cell cycle progression is regulated by the combined action of cyclins, cyclin-dependent kinases (CDKs), and CDK-inhibitors (CDKi), which are negative cell cycle regulators. p27KIP1 is a CDKi key in cell cycle regulation, whose degradation is required for G1/S transition. In spite of the absence of p27KIP1 expression in proliferating lymphocytes, some aggressive B-cell lymphomas have been reported to show an anomalous p27KIP1 staining. An abnormally high expression of p27KIP1 was found in lymphomas of this type. Analysis of the clinical relevance of these findings showed that a high level of p27KIP1 expression in this type of tumour is an adverse prognostic marker, in both univariate and multivariate analysis. These results show that there is abnormal p27KIP1 expression in Diffuse Large B-cell Lymphomas (DLBCL), with adverse clinical significance, suggesting that this anomalous p27KIP1 protein may be rendered non¬ functional through interaction with other cell cycle regulator proteins. (Br. J. Cancer. 1999 July; 80(9): 1427-34. p27KIP1 is abnormally expressed in Diffuse Large B-cell Lymphomas and is associated with an adverse clinical outcome. Saez A, Sanchez E, Sanchez-Beato M, Cruz M A, Chacon I, Munoz E, Camacho F I, Martinez-Montero J C, Mollejo M, Garcia J F, Piris M A. Department of Pathology, Virgen de Ia Salud Ilospital, Toledo, Spain.)

Chronic Lymphocytic Leukemia

B-Cell chronic lymphocytic leukaemia (CLL) is the most common leukaemia in the Western hemisphere, with approximately 10,000 new cases diagnosed each year (Parker S L, Tong T, Bolden S, Wingo P A: Cancer statistics, 1997. Ca. Cancer. J. Clin. 47:5, (1997)). Relative to other forms of leukaemia, the overall prognosis of CLL is good, with even the most advanced stage patients having a median survival of 3 years.

The addition of fludarabine as initial therapy for symptomatic CLL patients has led to a higher rate of complete responses (27% v 3%) and duration of progression-free survival (33 v 17 months) as compared with previously used alkylator-based therapies. Although attaining a complete clinical response after therapy is the initial step toward improving survival in CLL, the majority of patients either do not attain complete remission or fail to respond to fludarabine. Furthermore, all patients with CLL treated with fludarabine eventually relapse, making its role as a single agent purely palliative (Rai K R, Peterson B, Elias L, Shepherd L, Hines J, Nelson D, Cheson B, Kolitz J, Schiffer C A: A randomized comparison of fludarabine and chlorambucil for patients with previously untreated chronic lymphocytic leukemia. A CALGB SWOG, CTG/NCI-C and ECOG Inter-Group Study. Blood 88:141a, 1996 (abstr 552, suppl 1). Therefore, identifying new agents with novel mechanisms of action that complement fludarabine's cytotoxicity and abrogate the resistance induced by intrinsic CLL drug-resistance factors will be necessary if further advances in the therapy of this disease are to be realized.

The most extensively studied, uniformly predictive factor for poor response to therapy and inferior survival in CLL patients is aberrant p53 function, as characterized by point mutations or chromosome 17p13 deletions. Indeed, virtually no responses to either alkylator or purine analog therapy have been documented in multiple single institution case series for those CLL patients with abnormal p53 function. Introduction of a therapeutic agent that has the ability to overcome the drug resistance associated with p53 mutation in CLL would potentially be a major advance for the treatment of the disease.

Flavopiridol and CYC 202, inhibitors of cyclin-dependent kinases induce in vitro apoptosis of malignant cells from B-cell chronic lymphocytic leukemia (B-CLL).

Flavopiridol exposure results in the stimulation of caspase 3 activity and in caspase-dependent cleavage of p27 (kip1), a negative regulator of the cell cycle, which is overexpressed in B-CLL (Blood. 1998 Nov. 15; 92(10):3804-16 Flavopiridol induces apoptosis in chronic lymphocytic leukemia cells via activation of caspase-3 without evidence of bcl-2 modulation or dependence on functional p53. Byrd J C, Shinn C, Waselenko J K, Fuchs E J, Lehman T A, Nguyen P L, Flinn I W, Diehl L F, Sausville E, Greyer M R).

Aurora Kinases

Relatively recently, a new family of serine/threonine kinases known as the Aurora kinases has been discovered that are involved in the G2 and M phases of the cell cycle, and which are important regulators of mitosis.

The precise role of Aurora kinases has yet to be elucidated but that they play a part in mitotic checkpoint control, chromosome dynamics and cytokinesis (Adams et al., *Trends Cell Biol*, 11: 49-54 (2001). Aurora kinases are located at the centrosomes of interphase cells, at the poles of the bipolar spindle and in the mid-body of the mitotic apparatus.

Three members of the Aurora kinase family have been found in mammals so far (E. A. Nigg, *Nat. Rev. Mol. Cell. Biol.* 2:21-32, (2001)). These are:

Aurora A (also referred to in the literature as Aurora 2);
Aurora B (also referred to in the literature as Aurora 1); and
Aurora C (also referred to in the literature as Aurora 3).

The Aurora kinases have highly homologous catalytic domains but differ considerably in their N-temiinal portions (Katayama H, Brinkley W R, Sen S.; The Aurora kinases: role in cell transformation and tumorigenesis; Cancer Metastasis Rev. 2003 December; 22(4):451-64).

The substrates of the Aurora kinases A and B have been identified as including a kinesin-like motor protein, spindle apparatus proteins, histone H3 protein, kinetochore protein and the tumour suppressor protein p53.

Aurora A kinases are believed to be involved in spindle formation and become localised on the centrosome during the early G2 phase where they phosphorylate spindle-associated proteins (Prigent et al, *Cell*, 114: 531-535 (2003). Hirota et al, *Cell*, 114:585-598, (2003) found that cells depleted of Aurora A protein kinase were unable to enter mitosis. Furthermore, it has been found (Adams, 2001) that mutation or disruption of the Aurora A gene in various species leads to mitotic abnormalities, including centrosome separation and maturation defects, spindle aberrations and chromosome segregation defects.

The Aurora kinases are generally expressed at a low level in the majority of normal tissues, the exceptions being tissues with a high proportion of dividing cells such as the thymus and testis. However, elevated levels of Aurora kinases have been found in many human cancers (Giet et al, *J. Cell. Sci.* 112: 3591-361, (1999) and Katayama (2003). Furthermore, Aurora A kinase maps to the chromosome 20q1 3 region that has frequently been found to be amplified in many human cancers.

Thus, for example, significant Aurora A over-expression has been detected in human breast, ovarian and pancreatic cancers (see Zhou et al, *Nat. Genet.* 20: 189-193, (1998), Tanaka et al, *Cancer Res.,* 59: 2041-2044, (1999) and Han et al, *cancer Res.,* 62: 2890-2896, (2002).

Moreover, Isola, *American Journal of Pathology* 147,905-91 1 (1995) has reported that amplification of the Aurora A locus (20q13) correlates with poor prognosis for patients with node-negative breast cancer.

Amplification and/or over-expression of Aurora-A is observed in human bladder cancers and amplification of Aurora-A is associated with aneuploidy and aggressive clinical behaviour, see Sen et al., *J. Natl. Cancer Inst,* 94: 1320-1329 (2002).

Elevated expression of Aurora-A has been detected in over 50% of colorectal cancers, (see Bischoff et al, *EMBO J.,* 17: 3052-3065, (1998) and Takahashi et al., *Jpn. J. Cancer Res.,* 91: 1007-1014 (2000)) ovarian cancers (see Gritsko et al. *Clin. Cancer Res.,* 9: 1420-1426 (2003), and gastric tumours Sakakura et al, *British Journal of Cancer,* 84: 824-831 (2001).

Tanaka et al. *Cancer Research,* 59: 2041-2044 (1999) found evidence of over-expression of Aurora A in 94% of invasive duct adenocarcinomas of the breast.

High levels of Aurora A kinase have also been found in renal, cervical, neuroblastoma, melanoma, lymphoma, pancreatic and prostate tumour cell lines Bischoff et al. (1998), EMBO J., 17: 3052-3065 (1998); Kimura et al. J. Biol. Chem., 274: 7334-7340 (1999); Zhou et al., Nature Genetics, 20: 189-193 (1998); Li et al., Clin Cancer Res. 9 (3): 991-7 (2003)].

Aurora-B is highly expressed in multiple human tumour cell lines, including leukemic cells [Katayama et al., Gene 244: 1-7)]. Levels of this enzyme increase as a function of Duke's stage in primary colorectal cancers Katayama et al., J. Natl Cancer Inst, 91: 1160-1 162 (1999)].

High levels of Aurora-3 (Aurora-C) have been detected in several tumour cell lines, even though this kinase tends to be restricted to germ cells in normal tissues (sec Kimura et al *Journal of Biological Chemistry,* 21A: 7334-7340 (1999)). Over-expression of Aurora-3 in approximately 50% of colorectal cancers has also been reported in the article by Takahashi et al, *Jpn J. Cancer Res.* 9 1: 1007-1014 (2001)].

Other reports of the role of Aurora kinases in proliferative disorders may be found in Bischoff et al, *Trends in Cell Biology* 9: 454-459 (1999); Giet et al *Journal of Cell Science,* 112: 3591-3601 (1999) and Dutertre, et al *Oncogene,* 21: 6175-6183 (2002).

Royce et al report that the expression of the Aurora 2 gene (known as STK1 5 or BTAK) has been noted in approximately one-fourth of primary breast tumours. (Royce M E, Xia W, Sahin A A, Katayama H, Johnston D A, Hortobagyi G, Sen S, Hung M C; STK15/Aurora-A expression in primary breast tumours is con-elated with nuclear grade but not with prognosis; *Cancer.* 2004 Jan. 1; 100(1):12-9).

Endometrial carcinoma (EC) comprises at least two types of cancer: endometrioid carcinomas (EECs) are estrogen-related tumours, which are frequently euploid and have a good prognosis. Nonendometrioid carcinomas (NEECs; serous and clear cell forms) are not estrogen related, are frequently aneuploid, and are clinically aggressive. It has also been found that Aurora was amplified in 55.5% of NEECs but not in any EECs (P< or =0.001) (Moreno-Bueno G, Sanchez-Estevez C, Cassia R, Rodriguez-Perales S, Diaz-Uriarte R, Dominguez O, Hardisson D, Andujar M, Prat J, Matias-Guiu X, Cigudosa J C, Palacios *J. Cancer Res.* 2003 Sep. 15; 63(18):5697-702).

Reichardt et al {*Oncol Rep.* 2003 September-October; 10(5):1275-9) have reported that quantitative DNA analysis by PCR to search for Aurora amplification in gliomas revealed that five out of 16 tumours (31%) of different WHO grade (I× grade II, I× grade III, 3× grade IV) showed DNA amplification of the Aurora 2 gene. It was hypothesized that amplification of the Aurora 2 gene may be a non-random genetic alteration in human gliomas playing a role in the genetic pathways of tumourigenesis.

Results by Hamada et al (*Br. J. Haernatol.* 2003 May; 121(3):439-47) also suggest that Aurora 2 is an effective candidate to indicate not only disease activity but also tumourigenesis of non-Hodgkin's lymphoma. Retardation of tumour cell growth resulting from the restriction of this gene's functions could be a therapeutic approach for non-Hodgkin's lymphoma.

In a study by Gritsko et al (*Clin Cancer Res.* 2003 April; 9(4): 1420-6)), the kinase activity and protein levels of Aurora A were examined in 92 patients with primary ovarian tumours. In vitro kinase analyses revealed elevated Aurora A kinase activity in 44 cases (48%). Increased Aurora A protein levels were detected in 52 (57%) specimens. High protein levels of Aurora A correlated well with elevated kinase activity.

Results obtained by Li et al (*Clin. Cancer Res.* 2003 March; 9(3):991-7) showed that the Aurora A gene is overexpressed in pancreatic tumours and carcinoma cell lines and suggest that overexpression of Aurora A may play a role in pancreatic carcinogenesis.

Similarly, it has been shown that Aurora A gene amplification and associated increased expression of the mitotic kinase it encodes are associated with aneuploidy and aggressive clinical behaviour in human bladder cancer. (*J. Natl. Cancer Inst.* 2002 Sep. 4; 94(17): 1320-9).

Investigation by several groups (Dutertre S, Prigent C., Aurora-A overexpression leads to override of the microtubule-kinetochore attachment checkpoint; *Mol. Intern.* 2003 May; 3(3): 127-30 and Anand S, Penrhyn-Lowe S, Venkitaraman A R., Aurora-A amplification overrides the mitotic spindle assembly checkpoint, inducing resistance to Taxol, *Cancer Cell.* 2003 January; 3(1):51-62) suggests that overexpression of Aurora kinase activity is associated with resistance to some current cancer therapies. For example overexpression of Aurora A in mouse embryo fibroblasts can reduce the sensitivity of these cells to the cytotoxic effects of taxane derivatives. Therefore Aurora kinase inhibitors may find particular use in patients who have developed resistance to existing therapies.

On the basis of work carried out to date, it is envisaged that inhibition of Aurora kinases, particularly Aurora kinase A and Aurora kinase B, will prove an effective means of arresting tumour development.

Harrington et al (*Nat. Med.* 2004 March; 10(3):262-7) have demonstrated that an inhibitor of the Aurora kinases suppresses tumour growth and induces tumour regression in vivo. In the study, the Aurora kinase inhibitor blocked cancer cell proliferation, and also triggered cell death in a range of cancer cell lines including leukaemic, colorectal and breast cell lines. In addition, it has shown potential for the treatment of leukemia by inducing apoptosis in leukemia cells. VX-680 potently killed treatment-refractory primary Acute Myelogenous Leukemia (AML) cells from patients (Andrews, *Oncogene*, 2005, 24, 5005-5015).

Cancers which may be particularly amenable to Aurora inhibitors include breast, bladder, colorectal, pancreatic, ovarian, non-Hodgkin's lymphoma, gliomas and nonendometrioid endometrial carcinomas. Leukemias particularly amenable to Aurora inhibitors include Acute Myelogenous Leukemia (AML), chronic myelogenous leukaemia (CML), B-cell lymphoma (Mantle cell), and Acute Lymphoblastic Leukemia (ALL).

Glycogen Synthase Kinase

Glycogen Synthase Kinase-3 (GSK3) is a serine-threonine kinase that occurs as two ubiquitously expressed isoforms in humans (GSK3α & beta GSK3β. GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X-X-X-(pSer/pThr), where X is any amino acid (at positions (n+1), (n+2), (n+3)) and pSer and pTlir are phospho-serine and phospho-threonine respectively (n+4). GSK3 phosphorylates the first serine, or threonine, at position (n). Phospho-serine, or phospho-threonine, at the (n+4) position appear necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSKβ may be subtly regulated by phosphorylation of tyrosines 279 and 216 respectively. Mutation of these residues to a Phe caused a reduction in in vivo kinase activity. The X-ray crystallographic structure of GSK3β has helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type II, or non-insulin-dependent diabetes mellitus (NIDDM): a condition in which body tissues become resistant to insulin stimulation. The cellular insulin response in liver, adipose, or muscle tissues, is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dedependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycuï" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimuli.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimuli. This can lead to the dephosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-I) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

PRIOR ART

WO 02/34721 from Du Pont discloses a class of indeno[1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (cdks) and hence their use in the treatment of proliferative disorders such as cancer, leukaemia, psoriasis and the like.

WO 99/21845 from Agouron describes 4-aminothiazole derivatives for inhibiting cyclin-dependent kinases (cdks), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group.

WO 01/98290 (Pharmacia & Upjohn) discloses a class of 3-aminocarbonyl-2-carboxamido thiophene derivatives as protein kinase inhibitors. The compounds are stated to have multiple protein kinase activity.

WO 01/53268 and WO 01/02369 from Agouron disclose compounds that mediate or inhibit cell proliferation through the inhibition of protein kinases such as cyclin dependent kinase or tyrosine kinase.

WO 00/39108 and WO 02/00651 (both to Du Pont Pharmaceuticals) describe broad classes of heterocyclic compounds that are inhibitors of trypsin-like serine protease enzymes, especially factor Xa and thrombin. The compounds are stated to be useful as anticoagulants or for the prevention of thromboembolic disorders.

US 2002/0091 116 (Zhu et al), WO 01/1978 and WO 01/64642 each disclose diverse groups of heterocyclic compounds that have activity against Factor Xa.

WO 03/035065 (Aventis) discloses a broad class of benzimidazole derivatives as protein kinase inhibitors but does not disclose activity against CDK kinases or GSK kinases.

WO 97/36585 and U.S. Pat. No. 5,874,452 (both to Merck) disclose biheteroaryl compounds that are inhibitors of farnesyl transferase.

WO 03/066629 (Vertex) discloses benzimidazolylpyrazole amines as GSK-3 inhibitors.

WO 97/12615 (Warner Lambert) discloses benzimidazoles as 15-lipoxygenase inhibitors.

WO 2004/545 15 (SmithKline Beecham Corporation) discloses a class of benzimidazoles as thrombopoictin mimetics.

WO 2004/41277 (Merck) discloses a class of amino-benzimidazoles as androgen receptor modulators.

WO 2005/028624 (Plexxikon) discloses molecular scaffolds for compounds having activity against protein kinases.

Our earlier International patent application number PCT/GB2004/002824 (WO 2005/002552) discloses a class of substituted 1H-benzimidazol-2-yl)-1H-pyrazol-4-yl]-ureas as CDK, Aurora kinase and GSK kinase inhibitors. One of the compounds specifically named and exemplified in WO 2005/002552 is 1-(2,6-difluorophenyl)-N-[3-(5-morpholin-4-yl-methyl-1H-benzimidazol-2-yl)-1H-pyrazol-4-yl]-urea. In the experimental section of WO 2005/002552, there is described the preparation of 1-(2,6-difluorophenyl)-N-[3-(5-morpholin-4-ylmethyl-1H-benzimidazol-2-yl)-1H-pyrazol-4-yl]-urea in free base form.

SUMMARY OF THE INVENTION

The invention provides compounds that have cyclin dependent kinase inhibiting or modulating activity and glycogen synthase kinase-3 (GSK3) inhibiting or modulating activity, and/or Aurora kinase inhibiting or modulating activity, and which it is envisaged will be useful in preventing or treating disease states or conditions mediated by the kinases.

Thus, for example, it is envisaged that the compounds of the invention will be useful in alleviating or reducing the incidence of cancer.

In a first aspect, the invention provides a compound of the formula (I)

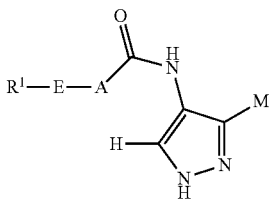

(I)

or a salt, solvate, tautomer or N-oxide thereof,
wherein M is selected from a group D1 and a group D2:

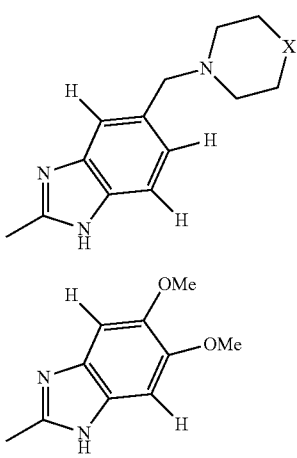

and wherein:
(A) when M is a group D1:
X is selected from O, NH and NCH$_3$;
A is selected from a bond and a group NR$^2$ where R$^2$ is hydrogen or methyl;
E is selected from a bond, CH$_2$, CH(CN) and C(CH$_3$)$_2$;
R$^1$ is selected from:
  (i) a cycloalkyl group of 3 to 5 ring members optionally substituted by hydroxy, fluorine, amino, methylamino, methyl or ethyl;
  (ii) a saturated heterocyclic group of 4 to 6 ring members containing 1 or 2 heteroatom ring members selected from O, N, S and SO$_2$, the heterocyclic group being optionally substituted by C$_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl;
  (iii) a 2,5-substituted phenyl group of the formula:

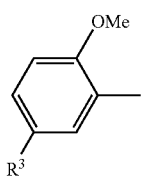

wherein (a) when X is NH or N—CH$_3$, R$^3$ is selected from chlorine and cyano; and (b) when X is O, R$^3$ is CN;
  (iv) a group CR$^6$R$^7$R$^8$ wherein R$^6$ and R$^7$ are each selected from hydrogen and methyl, and R$^8$ is selected from hydrogen, methyl, C$_{1-4}$ alkylsulphonylm ethyl, hydroxymethyl and cyano;

(v) a pyridazin-4-yl group optionally substituted by one or two substituents selected from methyl, ethyl, methoxy and ethoxy;
  (vi) a substituted imidazothiazole group wherein the substituents are selected from methyl, ethyl, amino, fluorine, chlorine, amino and methylamino; and
  (vii) an optionally substituted 1,3-dihydro-isoindol-2-yl or optionally substituted 2,3-dihydro-indol-1-yl group wherein the optional substituents in each case are selected from halogen, cyano, amino, C$_{1-4}$ mono- and dialkylamino, CONH$_2$ or CONH—C$_{1-4}$ alkyl C$_1$, alkyl and C$_{1-4}$ alkoxy wherein the C$_{1-4}$ alkyl and C$_{1-4}$ alkoxy groups are optionally substituted by hydroxy, methoxy, or amino;
  (viii) 3-pyridyl optionally substituted by one or two substituents selected from hydroxy, halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino; but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide;
  (ix) thiomorpholine or an S-oxide or S,S-dioxide thereof optionally substituted by one or two substitutents selected from halogen, cyano, amino, C$_{1-4}$ mono- and dialkylamino, CONH$_2$ or CONH—C$_{1-4}$ alkyl C$_{1-4}$ alkyl and C$_{1-4}$ alkoxy wherein the C$_{1-4}$ alkyl and C$_{1-4}$ alkoxy groups are optionally substituted by hydroxy, methoxy, or amino; and
when E-A is NR$^2$, R$^1$ is additionally selected from:
  (x) 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl;
  (xi) a group NR$^{10}$R$^{11}$ where R$^{10}$ and R$^{11}$ are each C$_{1-4}$ alkyl or R$^{10}$ and R$^{11}$ are linked so that NR$^{10}$R$^{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy;
  (xii) pyridone optionally substituted by one or two substituents selected from hydroxy, halogen, cyano, amino, C$_{1-4}$ mono- and dialkylamino, CONH$_2$, CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino;
when E-A is C(CH$_3$)$_2$NR$^2$ or CH$_2$—NR$^2$, R$^1$ is additionally selected from:
  (xiii) unsubstituted 2-furyl and 2,6-difluorophenyl; and
when E-A is C(CH$_3$)$_2$NR$^2$, R$^1$ is additionally selected from:
  (xiv) unsubstituted phenyl; and
when E is CH$_2$, R$^1$ is additionally selected from:
  (xv) unsubstituted tetrahydropyran-4-yl; and
(B) when M is a group D2:
A is selected from a bond and a group NR$^2$ where R$^2$ is hydrogen or methyl;
E is selected from a bond, CH$_2$, CH(CN) and C(CH$_3$)$_2$;

R¹ is selected from:

(xvi) a 2-substituted 3-furyl group of the formula:

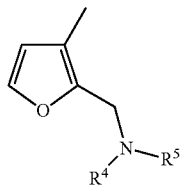

wherein R⁴ and R⁵ are the same or different and are selected from hydrogen and $C_{1-4}$ alkyl, or R⁴ and R⁵ are linked so that NR⁴R⁵ forms a 5- or 6-membered saturated heterocyclic group optionally containing a second heteroatom or group selected from O, NH, NMe, S or $SO_2$, the 5- or 6-membered saturated ring being optionally substituted by hydroxy, fluorine, amino, methylamino, methyl or ethyl;

(xvii) a 5-substituted 2-furyl group of the formula:

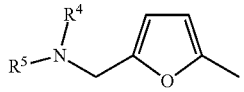

wherein R⁴ and R⁵ are the same or different and are selected from hydrogen and $C_{1-4}$ alkyl, or R⁴ and R⁵ are linked so that NR⁴R⁵ forms a 5- or 6-membered saturated heterocyclic group optionally containing a second heteroatom or group selected from O, NH, NMe, S or $SO_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide;

(xviii) a group of the formula:

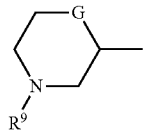

wherein R⁹ is hydrogen, methyl, ethyl or isopropyl; G is CH, O, S, SO, $SO_2$ or NH and the group is optionally substituted by one, two or three substituents selected from $C_{1-4}$ hydrocarbyl, hydroxy, $C_{1-4}$ hydrocarbyloxy, fluorine, amino, mono- and di-$C_{1-4}$ alkylamino and wherein the $C_{1-4}$ hydrocarbyl and $C_{1-4}$ hydrocarbyloxy groups are each optionally substituted by hydroxy, fluorine, amino, mono- or di-$C_{1-4}$ alkylamino; and (xix) a 3,5-disubstituted phenyl group of the formula:

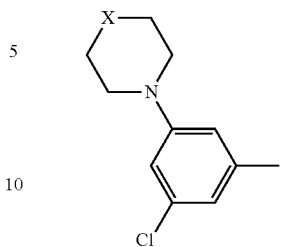

wherein X is selected from O, NH and $NCH_3$;

(C) when M is a group D1:

and X is O; A is a group NR² where R² is hydrogen; E is a bond; and R¹ is 2,6-difluorophenyl; then the compound of the formula (I) is an acid addition salt selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. l>-toluenesulphonic), valeric and xinafoic acids.

In one embodiment, the group M is a group D1 or D2 as defined in sub-groups (A) and (B) of formula (I) above.

In another embodiment, the group M is a group D1 and the compound of the formula (I) is an acid addition salt of 1-(2,6-difluorophenyl)-N-[3-(5-morpholin-4-ylmethyl-1H-benzimidazol-2-yl)-1H-pyrazol-4-yl]-urea as defined in sub-group (C) of formula (I) above.

In a particular embodiment, the invention provides a salt or free base of 1-cyclopropyl-3-[3-(5-morpholin-4-ylmethyl-1H-benzoimidazol-2-yl)-1H-pyrazol-4-yl]-urea, and in particular the lactate salt thereof.

The invention further provides new uses of 1-cyclopropyl-3-[3-(5-morpholin-4-ylmethyl-1H-benzoimidazol-2-yl)-1H-pyrazol-4-yl]-urea and its salts (e.g. acid addition salts), solvates, tautomers or N-oxides.

The invention also provides inter alia:

The use of a compound of the formula (I), (II), (III) or (XXX) or any sub-groups or examples thereof as defined herein for the manufacture of a medicament for the prophylaxis or treatment of a disease state or condition mediated by a cyclin dependent kinase or glycogen synthase kinase-3.

A method for the prophylaxis or treatment of a disease state or condition mediated by a cyclin dependent kinase or glycogen synthase kinase-3, which method comprises administering to a subject in need thereof a compound of the formula (I), (II), (III) or (XXX) or any sub-groups or examples thereof as defined herein.

A method for alleviating or reducing the incidence of a disease state or condition mediated by a cyclin dependent kinase or glycogen synthase kinase-3, which method comprises administering to a subject in need thereof a compound of the formula (I), (II), (III) or (XXX) or any sub-groups or examples thereof as defined herein.

A method for treating a disease or condition comprising or arising from abnormal cell growth in a mammal, which method comprises administering to the mammal a compound of the formula (I), (II), (III) or (XXX) or any sub-groups or examples thereof as defined herein in an amount effective in inhibiting abnormal cell growth.

A method for alleviating or reducing the incidence of a disease or condition comprising or arising from abnormal cell growth in a mammal, which method comprises administering to the mammal a compound of the formula (I), (II), (III) or (XXX) or any sub-groups or examples thereof as defined herein in an amount effective in inhibiting abnormal cell growth.

A method for treating a disease or condition comprising or arising from abnormal cell growth in a mammal, the method comprising administering to the mammal a compound of the formula (I), (II), (III) or (XXX) or any sub-groups or examples thereof as defined herein in an amount effective to inhibit a cdk kinase (such as cdk1 or cdk2) or glycogen synthase kinase-3 activity.

A method for alleviating or reducing the incidence of a disease or condition comprising or arising from abnormal cell growth in a mammal, the method comprising administering to the mammal a compound of the formula (I), (II), (III) or (XXX) or any sub-groups or examples thereof as defined herein in an amount effective to inhibit a cdk kinase (such as cdk1 or cdk2) or glycogen synthase kinase-3 activity.

A method of inhibiting a cyclin dependent kinase or glycogen synthase kinase-3, which method comprises contacting the kinase with a kinase-inhibiting compound of the formula (I), (II), (III) or (XXX) or any sub-groups or examples thereof as defined herein.

A method of modulating a cellular process (for example cell division) by inhibiting the activity of a cyclin dependent kinase or glycogen synthase kinase-3 using a compound of the formula (I), (II), (III) or (XXX) or any sub-groups or examples thereof as defined herein.

The use of a compound of the formula (I), (II), (III) or (XXX) or any sub-groups or examples thereof as defined herein for the manufacture of a medicament for prophylaxis or treatment of a disease or condition characterised by up-regulation of an Aurora kinase (e.g. Aurora A kinase and/or Aurora B kinase).

The use of a compound of the formula (I), (II), (III) or (XXX) or any sub-groups or examples thereof as defined herein for the manufacture of a medicament for the prophylaxis or treatment of a cancer, the cancer being one which is characterised by up-regulation of an Aurora kinase (e.g. Aurora A kinase and/or Aurora B kinase).

The use of a compound of the formula (I), (II), (III) or (XXX) or any sub-groups or examples thereof as defined herein for the manufacture of a medicament for the prophylaxis or treatment of cancer in a patient selected from a sub-population possessing the Ile31 variant of the Aurora A gene.

The use of a compound of the formula (I), (II), (III) or (XXX) or any sub-groups or examples thereof as defined herein for the manufacture of a medicament for the prophylaxis or treatment of cancer in a patient who has been diagnosed as forming part of a sub-population possessing the Ile31 variant of the Aurora A gene.

A method for the prophylaxis or treatment of a disease or condition characterised by up-regulation of an Aurora kinase (e.g. Aurora A kinase and/or Aurora B kinase), the method comprising administering a compound of the formula (I), (II), (III) or (XXX) or any sub-groups or examples thereof as defined herein.

A method for alleviating or reducing the incidence of a disease or condition characterised by up-regulation of an Aurora kinase (e.g. Aurora A kinase and/or Aurora B kinase), the method comprising administering a compound of the formula (I), (II), (III) or (XXX) or any sub-groups or examples thereof as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses the Ile31 variant of the Aurora A gene; and (ii) where the patient does possess the said variant, thereafter administering to the patient a compound of the formula (I), (II), (III) or (XXX) or any sub-groups or examples thereof as defined herein having Aurora kinase inhibiting activity.

A method for the prophylaxis or treatment of (or alleviating or reducing the incidence of) a disease state or condition characterised by up-regulation of an Aurora kinase (e.g. Aurora A kinase and/or Aurora B kinase); which method comprises (i) subjecting a patient to a diagnostic test to detect a marker characteristic of up-regulation of the Aurora kinase and (ii) where the diagnostic test is indicative of up-regulation of Aurora kinase, thereafter administering to the patient a compound of the formula (I), (II), (III) or (XXX) or any sub-groups or examples thereof as defined herein having Aurora kinase inhibiting activity.

A method for the prophylaxis or treatment of (or alleviating or reducing the incidence of) a disease state or condition characterised by (a) over-activation of CDK kinase; and/or (b) sensitisation of a pathway to normal CDK activity; and/or (c) up-regulation of cyclin E; which method comprises (i) subjecting a patient to a diagnostic test to detect a marker characteristic of (a) and/or (b) and/or (c); and (ii) where the diagnostic test is indicative of (a) and/or (b) and/or (c), thereafter administering to the patient a compound of the formula (I), (II), (III) or (XXX) or any sub-groups or examples thereof as defined herein having CDK kinase inhibiting activity.

A method of treatment, medical use or compound for use wherein a compound of the formula (I), (II), (III) or (XXX), or any sub-groups or examples thereof as defined herein, is administered (e.g. in a therapeutically effective amount) to a sub-population of patients identified through any one or more of the diagnostics tests described herein as having a disease or condition which should be susceptible to treatment with the said compound.

The use of a compound of the formula (I), (II), (III) or (XXX) or any sub-groups or examples thereof as defined herein for the manufacture of a medicament for the prophylaxis or treatment of a disease state as described herein.

A compound of the formula (I), (II), (III) or (XXX) or any sub-groups or examples thereof as defined herein for use in the prophylaxis or treatment of a disease state as described herein.

A method for the prophylaxis or treatment of (or alleviating or reducing the incidence of) a disease state or condition as described herein, the method comprising administering to the mammal a therapeutically effective amount of a compound of the formula (I), (II), (III) or (XXX) or any sub-groups or examples thereof as defined herein.

A pharmaceutical composition comprising a compound of the formula (I), (II), (III) or (XXX) or any sub-groups or examples thereof as defined herein and a pharmaceutically acceptable carrier.

A pharmaceutical composition for administration in an aqueous solution form, the pharmaceutical composition comprising a compound of the formula (I), (II), (III) or (XXX) or any sub-groups or examples thereof as defined herein in the four of a salt having a solubility in water of greater than 1 mg/ml, typically greater than 5 mg/ml, more typically greater than 15 mg/ml, more typically greater than 20 mg/ml and preferably greater than 25 mg/ml.

A compound of the formula (I), (II), (III) or (XXX) or any sub-groups or examples thereof as defined herein for use in medicine.

A compound as defined herein for any of the uses and methods set forth above, and as described elsewhere herein.

A compound of formula (I), (II), (III) or (XXX) or any sub-groups or examples thereof as defined herein or a salt (e.g. an acid addition salt), solvate, tautomer or N-oxide thereof for use in the treatment of B-cell lymphoma.

A compound of formula (I), (II), (III) or (XXX) or any sub-groups or examples thereof as defined herein or a salt (e.g. an acid addition salt), solvate, tautomer or N-oxide thereof for use in the treatment of chronic lymphocytic leukaemia.

A compound of formula (I), (II), (III) or (XXX) or any sub-groups or examples thereof as defined herein or a salt (e.g. an acid addition salt), solvate, tautomer or N-oxide thereof for use in the treatment of diffuse large B cell lymphoma.

A method of treatment of B-cell lymphoma, diffuse large B cell lymphoma or chronic lymphocytic leukaemia by administering to a patient in need of such treatment a compound of formula (I), (II), (III) or (XXX) or any sub¬ groups or examples thereof as defined herein or a salt (e.g. an acid addition salt), solvate, tautomer or N-oxide thereof.

A compound of formula (I), (II), (III) or (XXX) or any sub-groups or examples thereof as defined herein or a salt (e.g. an acid addition salt), solvate, tautomer or N-oxide thereof for use in the treatment of leukaemia in particular relapsed or refractory acute myelogenous leukemia, myelodysplastic syndrome, acute lymphocytic leukemia and chronic myelogenous leukemia.

An acid addition salt or free base of 1-cyclopropyl-3-[3-(5-morpholin-4-ylmethyl-1H-benzoimidazol-2-yl)-1H-pyrazol-4-yl]-urea and in particular the lactate for any of the uses and methods set forth above and as described elsewhere herein.

General Preferences and Definitions

The following general preferences and definitions shall apply to each of the moieties D1, D2, A, E, X, $X^a$ and $R^1$ to $R^9$, and their various sub-groups, sub-definitions, examples and embodiments unless the context indicates otherwise.

Any references to formula (I) herein shall also be taken to refer to formulae (II) to (VIII) and any other sub-group of compounds within formula (I) unless the context requires otherwise.

The term upregulation of Aurora kinase as used herein is defined as including elevated expression or over-expression of Aurora kinase, including gene amplification (i.e. multiple gene copies) and increased expression by a transcriptional effect, and hyperactivity and activation of Aurora kinase, including activation by mutations.

The term "saturated" as used herein refers to rings where there are no multiple bonds between ring atoms.

The term "hydrocarbyl" as used herein, whether on its own or as part of a composite term such as "hydrocarbyloxy" is a generic term encompassing aliphatic and alicyclic groups having an all-carbon backbone. Examples of hydrocarbyl groups include alkyl, cycloalkyl, cycloalkenyl, alkenyl, alkynyl, cycloalkylalkyl, cycloalkenylalkyl. Particular hydrocarbyl groups are saturated groups such as alkyl and cycloalkyl groups.

Examples of hydrocarbyloxy groups include alkoxy, cycloalkoxy, cycloalkenoxy, alkenyloxy, alkynyloxy, cycloalkylalkyloxy, cycloalkenylalkyoxy. Particular hydrocarbyloxy groups are saturated groups such as alkoxy.

The prefix "$C_{1-n}$" (where n is an integer) as used herein refers to the number of carbon atoms in a given group. Thus, a $C_{1-4}$ hydrocarbyl group contains from 1 to 4 carbon atoms, whilst a $C_{1-3}$ hydrocarbyloxy group contains from 1 to 3 carbon atoms, and so on.

Examples Of $C_{1-4}$ hydrocarbyl groups include $C_{1-3}$ hydrocarbyl groups or $C_{1-2}$ hydrocarbyl groups, specific examples being any individual value or combination of values selected from $C_1$, $C_2$, $C_3$ and $C_4$ hydrocarbyl groups.

The term "alkyl" covers both straight chain and branched chain alkyl groups. Examples of alkyl groups are methyl, ethyl, propyl, isopropyl, n-butyl, isobutyl, and tert-butyl.

Examples of cycloalkyl groups are those derived from cyclopropane, cyclobutane and cyclopentane.

Examples of alkenyl groups are ethenyl(vinyl), 1-propenyl, 2-propenyl(allyl), isopropenyl, butenyl and buta-1,4-dienyl.

Examples of cycloalkenyl groups are cyclopropenyl and cyclobutenyl.

Examples of alkynyl groups are ethynyl and 2-propynyl (propargyl) groups.

Examples of cycloalkylalkyl and cycloalkenylalkyl include cyclopropylmethyl.

Examples of alkoxy groups are methoxy, ethoxy, 7-z-propyloxy, z-propyloxy, n-butoxy, isobutoxy and tert-butoxy.

When an alkyl group forms part of a mono-alkylamino or dialkylamino group, the alkyl group may be any of the examples of alkyl groups set out above. Particular alkylamino and dialkylamino groups are methylamino, dimethylamino, ethylamino, diethylamino, n-propylamino, isopropylamino, butylamino, isobutylamino and i-butylamino. Particular alkyl- and dialkylamino groups are methylamino and dimethylamino.

The term "saturated heterocyclic group" as used herein refers to a heterocyclic group containing no multiple bonds between adjacent ring members. The saturated heterocyclic groups may contain 1 or 2 heteroatom ring members selected from O, S and N.

Depending on the context, the heterocylic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactonc), cyclic sulphones (e.g. as in sulpholane and sulpholene), cyclic sulphoxides, cyclic sulphonamides and combinations thereof (e.g. thiomorpholine).

The saturated heterocyclic groups are typically monocyclic and usually contain 4, 5 or 6 ring members unless otherwise stated.

A particular example of saturated heterocyclic groups containing 4 ring members is the azetidine group.

Examples of saturated heterocyclic groups containing 5 ring members include pyrrolidine (e.g. 1-pyrrolidinyl, 2-pyrrolidinyl and 3-pyrrolidinyl), pyrrolidone, tetrahydrofuran, and tetrahydrothiophene.

Examples of saturated heterocyclic groups containing 6 ring members include morpholine, thiomorpholine, thiomorpholine S-oxide, thiomorpholine S,S-dioxide, piperidine (e.g. 1-piperidinyl, 2-piperidinyl, 3-piperidinyl and 4-piperidinyl), piperidone, dioxane, tetrahydropyran (e.g. 4-tetrahydropyranyl), piperazone, piperazine, and N-alkyl piperazines such as N-methyl piperazine.

Specific Embodiments of and Preferences for D1, D2, A, E, $R^1$ to $R^9$ and X in Sub¬Groups (A) and (B) of Formula (I)

In one general embodiment, M is a group D1.

In another general embodiment, M is a group D2.

X is selected from O, NH and $NCH_3$. In one particular embodiment X is O.

A is selected from a bond and a group $NR^2$ where $R^2$ is hydrogen or methyl.

In one embodiment, A is a bond.

In another embodiment, A is a group $NR^2$ where $R^2$ is hydrogen or methyl.

E is selected from a bond, $CH_2$, CH(CN) and $C(CH_3)_2$.

In one sub-group of compounds E is a bond.

In another sub-group of compounds E is $CH_2$.

In a further sub-group of compounds E is CH(CN).

In another sub-group of compounds E is $C(CH_3)_2$.

When M is a group D1, $R^1$ can be selected from groups (i), (ii), (iii), (iv), (v), (vi), (vii), (viii), (ix), (x), (xi) and (xii).

When M is a group D1, and E-A is $C(CH_3)_2NR^2$ or $CH_2$—$NR^2$, $R^1$ can additionally be selected from:

(xiii) unsubstituted 2-furyl and 2,6-difluorophenyl.

When M is a group D1, and E-A is $C(CH_3)_2NR^2$, $R^1$ can additionally be selected from:

(xiv) unsubstituted phenyl.

When M is a group D1, and E is $CH_2$, $R^1$ can additionally be selected from:

(xv) unsubstituted tetrahydropyran-4-yl.

Each individual group in the list of groups (i) to (xv) represents a separate embodiment of the invention.

In embodiment (i) $R^1$ is a cycloalkyl group of 3 to 5 ring members optionally substituted by hydroxy, fluorine, amino, methylamino, methyl or ethyl.

Particular cycloalkyl groups are optionally substituted cyclopropyl and cyclobutyl groups, more typically optionally substituted cyclopropyl groups. In a preferred embodiment, $R^1$ is an unsubstituted cyclopropyl group.

In embodiment (ii), $R^1$ is a saturated heterocyclic group of 4 to 6 ring members containing 1 or 2 heteroatom ring members selected from O, N, S and $SO_2$, the heterocyclic group being optionally substituted by $C_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl.

Examples of saturated heterocyclic groups are as set out in the General Preferences and Definitions section above.

Particular examples of saturated heterocyclic groups include:

five membered rings containing a single heteroatom ring member selected from O, N and S (other than unsubstituted 2-pyrrolidinyl);

six membered rings containing two heteroatom ring members selected from O, N and S (other than unsubstituted 4-morpholinyl).

The saturated heterocyclic groups may be substituted or unsubstituted. In one embodiment, they are unsubstituted. In another embodiment, they are substituted by one or two $C_{1-4}$ alkyl groups, for example one or two methyl groups.

One particular saturated heterocyclic group is an optionally substituted tetrahydrofuran group (e.g. tetrahydrofuran-2yl and tetrahydrofuran-3-yl), more preferably an unsubstituted tetrahydrofuran group.

In embodiment (iii) $R^1$ is a 2,5-substituted phenyl group of the formula:

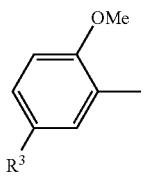

wherein (a) when X is NH or N—$CH_3$, $R^3$ is selected from chlorine and cyano; and (b) when X is O, $R^3$ is CN.

In one sub-group of compounds within embodiment (iii), X is N—$CH_3$ and $R^3$ is selected from chlorine and cyano.

In another sub-group of compounds within embodiment (iii), X is O and $R^3$ is CN.

In embodiment (iv) $R^1$ is a group $CR^6R^7R^8$ wherein $R^6$ and $R^7$ are each selected from hydrogen and methyl, and $R^8$ is selected from hydrogen, methyl, $C_{1-4}$ alkylsulphonylmethyl, hydroxymethyl and cyano.

Within embodiment (iv), particular examples of $R^1$ are methyl, cyanomethyl, $HOCH_2C(CH_3)_2$— and 2-methylsulphonylethyl.

Within embodiment (iv), further particular examples of $R^1$ are methyl and isopropyl.

In embodiment (v) $R^1$ is a pyridazin-4-yl group optionally substituted by one or two substituents selected from methyl, ethyl, methoxy and ethoxy. The pyridazinyl group may be a pyridazin-3-yl or pyridazin-4-yl group but typically is a pyridazin-4-yl. Particular substituents are methoxy groups and, for example, the pyridazinyl group may bear two methoxy substituents.

In embodiment (vi) $R^1$ is a substituted imidazothiazole group wherein the substituents are selected from methyl, ethyl, amino, fluorine, chlorine, amino and methylamino. A particular substituent is methyl.

In embodiment (vii) $R^1$ is an optionally substituted 1,3-dihydro-isoindol-2-yl or optionally substituted 2,3-dihydro-indol-1-yl group wherein the optional substituents in each case are selected from halogen, cyano, amino, $C_{1-4}$ mono- and dialkylamino, $CONH_2$ or CONH—$C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

Particular substituents are selected from methyl, ethyl, fluorine, chlorine (preferably only on the aryl ring of the dihydroindole or dihydroisoindole), $CONH_2$, amino, methylamino, dimethylamino and methoxy.

In one sub-group of compounds in embodiment (vii), the dihydroisoindole or dihydroindole are each unsubstituted.

In embodiment (viii) R¹ is 3-pyridyl optionally substituted by one or two substituents selected from hydroxy, halogen, cyano, amino, $C_{1-4}$ mono- and dialkylamino, $CONH_2$ or $CONH—C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino; with the proviso that it does not form the compound 2,6-diniethoxy-N-[3-(5-morpholin-4-ylmethyl-1H-benzoimidazol-2-yl)-1H-pyrazol-4-yl]-nicotinamide or the compound 2-oxo-1,2-dihydro-pyridine-3-carboxylic acid [3-(5-morpholin-4-ylmethyl-1H-benzoimidazol-2-yl)-1H-pyrazol-4-yl]-amide.

In one embodiment R¹ is 3-pyridyl optionally substituted by one or two substituents selected from hydroxy, halogen, cyano, amino, $C_{1-4}$ mono- and dialkylamino, $CONH_2$ or $CONH—C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino, but where R¹ is 3-pyridyl, X is O, A is a bond and E is a bond the pyridyl has one or two substituents selected from halogen, cyano, amino, $C_{1-4}$ mono- and dialkylamino, $CONH_2$ or $CONH—C_{1-4}$ alkyl, $C_{1-4}$ alkyl and $C_{2-4}$ alkoxy wherein the $C_{1-4}$ alkyl and $C_{1-4}$ alkoxy groups are optionally substituted by hydroxy, methoxy, or amino.

Particular substituents are selected from methyl, ethyl, fluorine, chlorine, $CONH_2$, amino, methylamino, dimethylamino and methoxy. Further particular substituents are selected from methyl, ethyl, fluorine, chlorine, $CONH_2$, amino, methylamino, and dimethylamino.

In one sub-group of compounds, the 3-pyridyl group is unsubstituted.

In embodiment (ix) R¹ is thiomorpholine or an S-oxide or S,S-dioxide thereof optionally substituted by one or two substituents selected from halogen, cyano, amino, $C_{1-4}$ mono- and dialkylamino, $CONH_2$ or $CONII—C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

In one sub-group of compounds, the thiomorpholine or S-oxide or S,S-dioxide thereof is unsubstituted.

In embodiment (x), E-A is $NR^2$ and R¹ is selected from: 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl.

In embodiment (xi) E-A is $NR^2$ and R¹ is a group $NR^{10}R^{11}$ where $R^{10}$ and $R^{11}$ are each $C_{1-4}$ alkyl or $R^{10}$ and $R^{11}$ are linked so that $NR^{10}R^{11}$ forms a saturated heterocyclic group of 4 to 6 ring members optionally containing a second heteroatom ring member selected from O, N, S and $SO_2$, the heterocyclic group being optionally substituted by $C_{1-4}$ alkyl, amino or hydroxy.

Within this embodiment, one sub-group of compounds is the group of compounds wherein $R^{10}$ and $R^{11}$ are each $C_{1-4}$ alkyl, particularly methyl.

Another sub-group of compounds is the group of compounds wherein $R^{10}$ and $R^{11}$ are linked so that $NR^{10}R^{11}$ forms a saturated heterocyclic group of 4 to 6 ring members optionally containing a second heteroatom ring member selected from O, N, S and $SO_2$, the heterocyclic group being optionally substituted by $C_{1-4}$ alkyl, amino or hydroxy. The saturated heterocyclic group can be any of the nitrogen containing saturated heterocyclic groups listed above in the General Preferences and Definitions section but particular saturated heterocyclic groups include pyrrolidinyl, morpholinyl, piperazinyl and $N—C_{1-4}$ alkyl-piperazinyl groups. Such groups are typically unsubstituted or substituted by one or two methyl groups and, in one particular embodiment, are unsubstituted.

In embodiment (xii), E-A is $NR^2$ and R¹ is a pyridone group optionally substituted by one or two sub stituents selected from hydroxy, halogen, cyano, amino, $C_{1-4}$ mono- and dialkylamino, $CONH_2$, $CONH—C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

The pyridone group may be N-substituted, for example with an alkyl group such as methyl, and may otherwise be unsubstituted.

In embodiment (xiii), E-A is $C(CH_3)_2NR^2$ or $CH_2—NR^2$ and R¹ is selected from unsubstituted 2-furyl and 2,6-difluorophenyl.

In embodiment (xiv), E-A is $C(C_{1-3})_2NR^2$ and R¹ is unsubstituted phenyl.

In embodiment (xv), E is $CH_2$ and R¹ is unsubstituted tetrahydropyran-4-yl.

When M is a group D2, R¹ can be selected from groups (xvi), (xvii), (xviii) and (xix).

Each individual group in the list of groups (xvi) to (xix) represents a separate embodiment of the invention.

In embodiment (xvi) R¹ is a 2-substituted 3-furyl group of the formula:

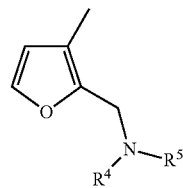

wherein $R^4$ and $R^5$ are the same or different and are selected from hydrogen and $C_{1-4}$ alkyl, or $R^4$ and $R^5$ are linked so that $NR^4R^5$ forms a 5- or 6-membered saturated heterocyclic group optionally containing a second heteroatom or group selected from O, NH, NMe, S or $SO_2$, the 5- or 6-membered saturated ring being optionally substituted by hydroxy, fluorine, amino, methylamino, methyl or ethyl. In one embodiment R¹ is a 2-substituted 3-furyl group of the formula:

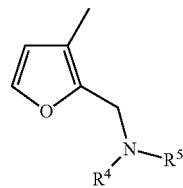

wherein $R^4$ and $R^5$ are the same or different and are selected from hydrogen and $C]_{1-4}$ alkyl, or $R^4$ and $R^5$ are linked so that $NR^4R^5$ forms a 5- or 6-membered saturated heterocyclic group optionally containing a second heteroatom or group selected from O, NH, NMe, S or $SO_2$, the 5- or 6-membered saturated ring being optionally substituted by hydroxy, fluorine, amino, methylamino, methyl or ethyl but where A is bond and E is a bond, $R^4$ and $R^5$ are not linked so that $NR^4R^5$ forms a unsubstituted piperidine Particular saturated heterocyclic groups are as set out above in the General Preferences and Definitions section but particular saturated heterocyclic groups include pyrrolidinyl, morpholinyl, piperazinyl and N—$C_{1-4}$ alkyl-piperazinyl groups. Such groups are typically unsubstituted or substituted by one or two methyl groups and, in one particular embodiment, are unsubstituted.

Particular examples of compounds wherein $R^4$ and $R^5$ are selected from hydrogen and $C_{1-4}$ alkyl are methylamino and dimethylamino groups, more typically a dimethylamino group.

In embodiment (xvii), $R^1$ is a 5-substituted 2-furyl group of the formula:

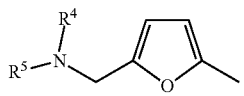

wherein $R^4$ and $R^5$ are the same or different and are selected from hydrogen and $C_{1-4}$ alkyl, or $R^4$ and $R^5$ are linked so that $NR^4R^5$ forms a 5- or 6-membered saturated heterocyclic group optionally containing a second heteroatom or group selected from O, $NH_5NMe$, S or $SO_2$, the 5- or 6-membered saturated heterocyclic group being optionally substituted by hydroxy, fluorine, amino, methylamino, methyl or ethyl; with the proviso that the compound does not form 5-piperidin-1-ylmethyl-furan-2-carboxylic acid [3-(5,6-dimemoxy-1H-benzoimidazol-2-yl)-1H-pyrazol-4-yl]-amide.

Particular saturated heterocyclic groups are as set out above in the General Preferences and Definitions section but particular saturated heterocyclic groups include pyrrolidinyl, morpholinyl, piperazinyl and N—$C_{1-4}$ alkyl-piperazinyl groups. Such groups are typically unsubstituted or substituted by one or two methyl groups and, in one particular embodiment, are unsubstituted.

In embodiment (xviii), $R^1$ is a group of the formula:

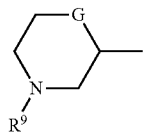

wherein $R^9$ is hydrogen, methyl, ethyl or isopropyl; G is CH, O, S, SO, $SO_2$ or NH and the group is optionally substituted by one, two or three substituents selected from $C_{1-4}$ hydrocarbyl, hydroxy, $C_{1-4}$ hydrocarbyloxy, fluorine, amino, mono- and di-$C_{1-4}$ alkylamino and wherein the $C_{1-4}$ hydrocarbyl and $C_{1-4}$ hydrocarbyloxy groups are each optionally substituted by hydroxy, fluorine, amino, mono- or di-$C_{1-4}$ alkylamino.

In one sub-group of compounds within embodiment (xix), G is selected from O and CH.

In embodiment (xviii), the group $R^1$ is typically unsubstituted or substituted by one or two methyl groups, and more typically is unsubstituted.

In embodiment (xix) $R^1$ is a 3,5-disubstituted phenyl group of the formula:

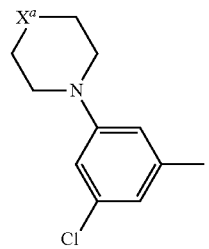

wherein Xa is as X is selected from O, NH and $NCH_3$.
Preferably Xa is N—$CH_3$.

Particular examples of the moiety $R^1$-A- are shown in Table 1, the asterisk indicating the point of attachment to the carbonyl group C=O in the group $R^\wedge$-E-A-C($^\wedge$O)—NH—.

TABLE 1

Examples of the Moiety $R^1$—E—A—

| | |
|---|---|
| ![A1 structure: 4-methoxy-3-cyano phenyl] | A1 |
| ![A2 structure: imidazo[2,1-b]thiazole with methyl] | A2 |
| ![A3 structure: cyanomethyl] | A3 |
| ![A4 structure: cyclopropyl with CN] | A4 |
| ![A5 structure: tetrahydropyran-4-ylmethyl] | A5 |
| ![A6 structure: cyclopropyl] | A6 |
| ![A7 structure: methyl] | A7 |
| ![A8 structure: 2-hydroxy-2-methylpropyl] | A8 |
| ![A9 structure: tetrahydrofuran-3-yl] | A9 |

TABLE 1-continued
Examples of the Moiety R¹—E—A—
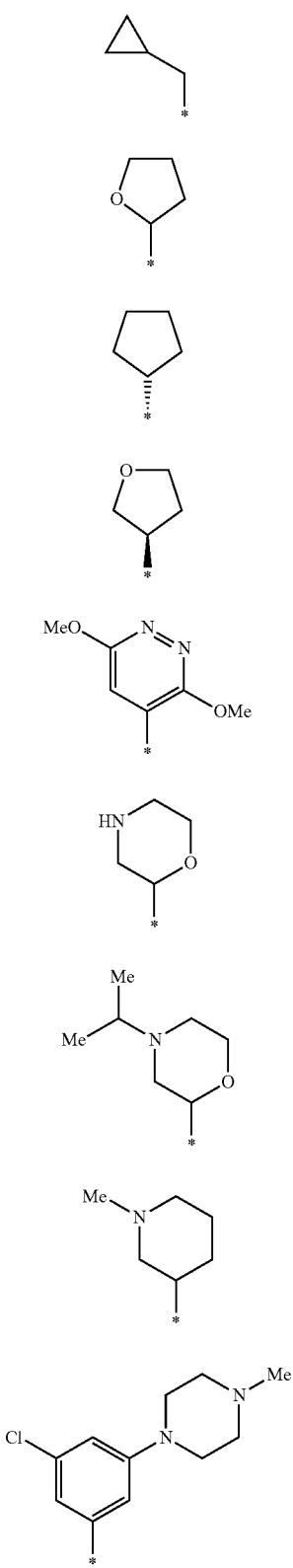
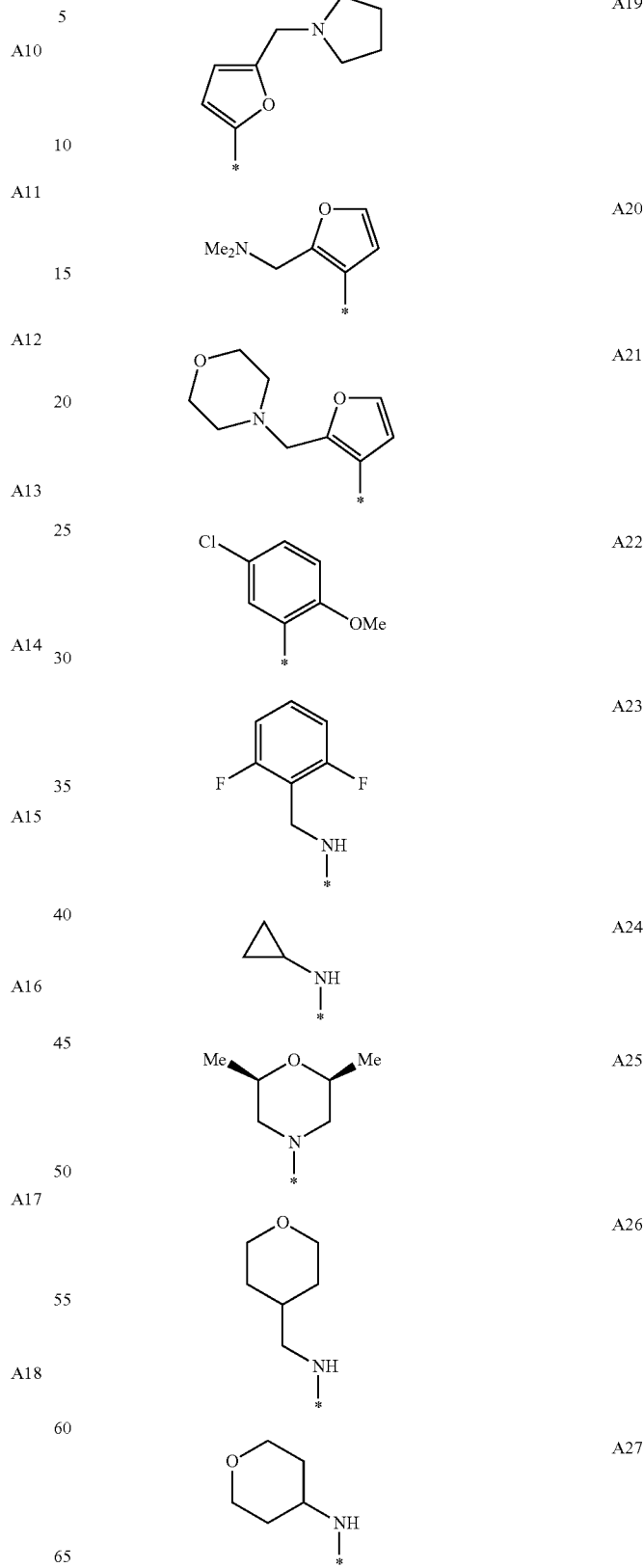

TABLE 1-continued
Examples of the Moiety R¹—E—A—
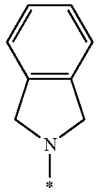 [SMILES: *N1Cc2ccccc2C1] A28
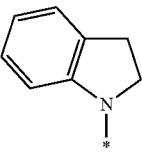 A29
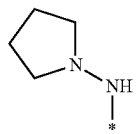 [SMILES: *NN1CCCC1] A30
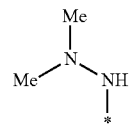 A31
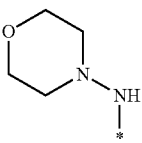 [SMILES: *NN1CCOCC1] A32
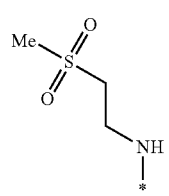 A33
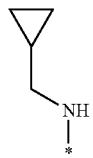 34
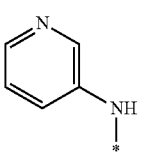 A35
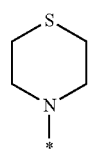 A36
TABLE 1-continued
Examples of the Moiety R¹—E—A—
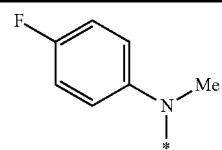 A37
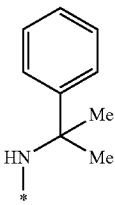 A38
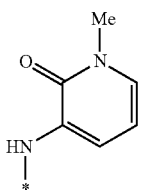 A39
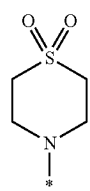 [SMILES: *N1CCS(=O)(=O)CC1] A40
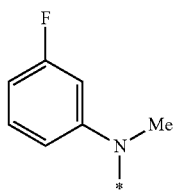 [SMILES: *N(C)c1cccc(F)c1] A41
 A42
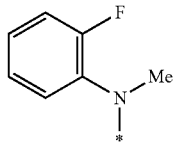 [SMILES: *N(C)c1ccccc1F] A43
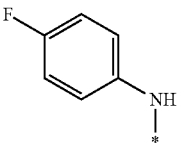 A44
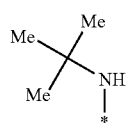 A45

TABLE 1-continued

Examples of the Moiety R¹—E—A—

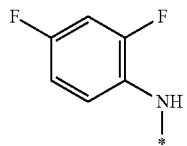 A46

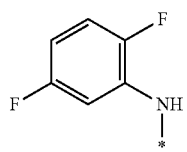 A47

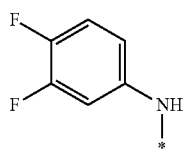 A48

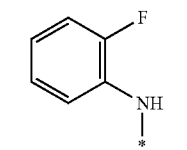 [SMILES: *Nc1ccccc1F] A49

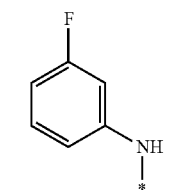 A50

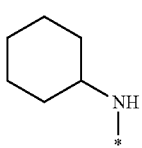 A51

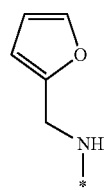 A52

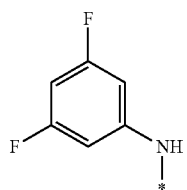 A53

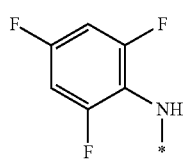 A54

TABLE 1-continued

Examples of the Moiety R¹—E—A—

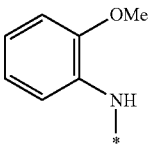 A55

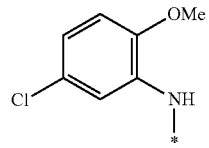 [SMILES: *Nc1cc(Cl)ccc1OC] A56

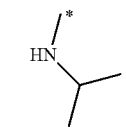 A57

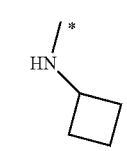 A58

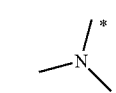 A59

In Table 1, preferred groups R¹-E-A- include A1, A4, A10, A11, A13, A20, A22, A23, A24, A29, A30, A31, A32, A38, A42, A43, A44, A46, A47, A49, A54 and A56.

In another embodiment the group R^-E-A is A57, A58 or A59.

A preferred sub-set of groups R^-E-A- includes A1, A4, A20, A24, A30, A44, A46 and A54. Within this sub-set, one particular group R*-A- is the group A24.

One sub-group of compounds of the invention is represented by the formula (II):

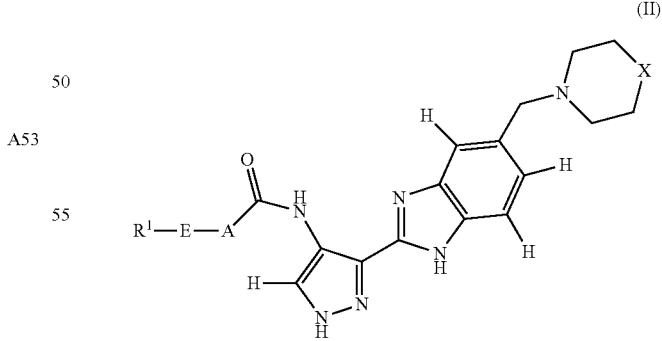

(II)

wherein R¹, E, A and X are as defined herein.

Within formula (II), one subset of compounds is the subset wherein X is O.

One sub-group of compounds of the formula (II) can be represented by the formula (III):

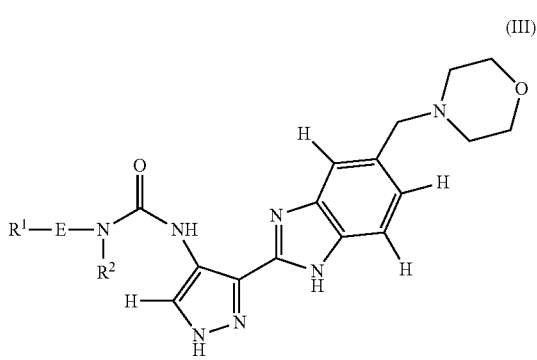

(III)

and salts thereof, in particular the lactate salt.

Within formula (III), one sub-set of compounds is the sub-set wherein E is a bond.

Another sub-set of compounds within formula (III) is the sub-set wherein E is $CH_2$ or $C(CH_3)_2$.

In one particularly preferred embodiment within formula (III), F is a bond, $R^2$ is H and $R^1$ is a cycloalkyl group (i) as defined herein. In one embodiment the cycloalkyl group can be cyclopropyl or cyclobutyl. More preferably $R^1$ is a cyclopropyl group.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^5$ and/or $R^6$ and/or $R^7$ and/or $R^8$ and/or $R^9$ and/or $R^{10}$ and/or $R^{11}$ and/or D1 and/or D2 and/or A and/or E and/or X and/or $X^a$ and any sub-groups thereof as defined herein, unless the context indicates otherwise, and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below.

One preferred compound of the invention is 1-cyclopropyl-3-[3-(5-morpholin-4-ylmethyl-1H-benzoimidazol-2-yl)-1H-pyrazol-4-yl]-urea and salts, solvates and tautomers thereof. Salts, Solvates, Tautomers, Isomers, N-Oxides, Esters, Prodrugs and Isotopes of Compounds of Sub-Groups (A) and (B) of Formula (I) and Sub-Groups and Embodiments Thereof Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. As in the preceding sections of this application, all references to Formula (I) shall be taken to refer to formulae (II), (III) and sub¬groups thereof as defined herein unless the context indicates otherwise.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, 1>-toluenesulphonic, undecylenic and valeric acids, as well as acylated amino acids and cation exchange resins.

The acid addition salts may also be selected from aspartic (e.g. D-aspartic), carbonic, dodecanoate, isobutyric, laurylsulphonic, mucic, naphthalenesulphonic (e.g. naphthalene-2-sulphonic), toluenesulphonic (e.g. j?-toluenesulphonic), and xinafoic acids.

One particular group of salts consists of salts formed from hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

One sub-group of salts consists of salts formed from hydrochloric, acetic, adipic, L-aspartic and DL-lactic acids.

Another sub-group of salts consists of the acetate, mesylate, ethanesulphonate, DL-lactate, adipate, D-glucuronate, D-gluconate and hydrochloride salts.

Salts such as acid addition salts have a number of advantages over the corresponding free base. For example, the salts will enjoy one or more of the following advantages over the free base in that they will:

be more soluble and hence will be better for i.v. administration (e.g. by infusion) and will have improved pharmacokinetics;
have better stability (e.g. improved shelf life);
have better thermal stability;
be less basic and therefore better for i.v. administration;
have advantages for production;
have improved metabolic properties; and
exhibit less clinical variation between patients.

Preferred salts for use in the preparation of liquid (e.g. aqueous) compositions of the compounds of formulae (I), (II), (III), (XXX) and sub-groups and examples thereof as described herein are salts having a solubility in a given liquid carrier (e.g. water) of greater than 25 mg/ml of the liquid carrier (e.g. water), more typically greater than 50 mg/ml and preferably greater than 100 mg/ml.

In another embodiment preferred salts for use in the preparation of liquid (e.g. aqueous) compositions the compounds of formulae (I), (II), (III), (XXX) and sub¬ groups and examples thereof as described herein are salts having a solubility in a given liquid carrier (e.g. water or buffer systems) greater than 1 mg/ml, typically greater than 5 mg/ml of the liquid carrier (e.g. water), more typically greater than 15 mg/ml, more typically greater than 20 mg/ml and preferably greater than 25 mg/ml.

In another embodiment the preferred acid addition salts are mesylate, ethanesulphonate, D- or L-lactate, and hydrochloride salts. In one particular embodiment the acid addition salt is the lactate salt, in particular L-lactate or D-lactate, preferably L-lactate.

In one embodiment of the invention, there is provided a pharmaceutical composition comprising an aqueous solution containing a compound of the formula (I), (II), (III), (XXX) and sub-groups and examples thereof as described herein in the form of a salt in a concentration of greater than 25 mg/ml, typically greater than 50 mg/ml and preferably greater than 100 mg/ml.

In another embodiment of the invention, there is provided a pharmaceutical composition comprising an aqueous solution containing a compound of the formula (I), (II), (III), (XXX) and sub-groups and examples thereof as described herein in the form of a salt in a concentration of greater than 1 mg/ml, typically greater than 5 mg/ml of the liquid carrier (e.g. water), more typically greater than 15 mg/ml, more typically greater than 20 mg/ml and preferably greater than 25 mg/ml.

If the compound is anionic, or has a functional group which may be anionic (e.g., —COOH may be —COO⁻) then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al, 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I) the benzoimidazole group may take either of the following two tautomeric forms A, A', B and B'. For simplicity, the general formula (I) illustrates forms A and A' but the formula is to be taken as embracing all four tautomeric forms.

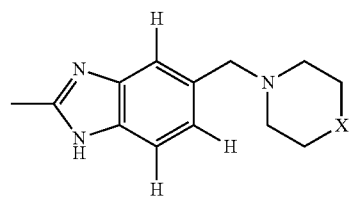

A

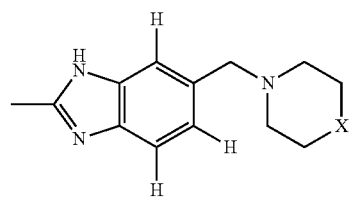

B

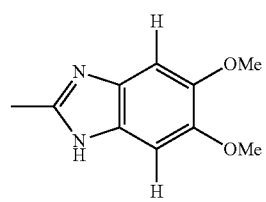

A'

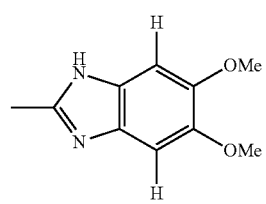

B'

The pyrazole ring may also exhibit tautomerism and can exist in the two tautomeric forms C and D below.

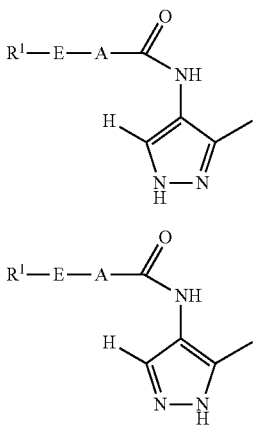

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

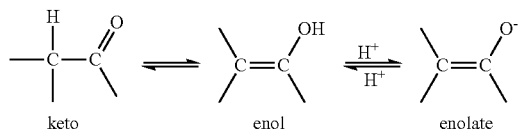

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

For example, the group A can include one or more chiral centres. Thus, when E and $R^1$ are both attached to the same carbon atom on the linker group A, the said carbon atom is typically chiral and hence the compound of the formula (I) will exist as a pair of enantiomers (or more than one pair of enantiomers where more than one chiral centre is present in the compound).

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluloyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(O)CH$_3$ (acetoxy), —OC(=O)CH$_2$CH$_3$, —OC(=O)C(CH$_3$)$_3$, —OC(=O)Ph, and —OCC=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (~C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
Ci.yalkyl
(e.g., -Me, -Et, -nPr, -iPr, -nBu, -sBu, -iBu, -tBu);
$C_{1-7}$-aminoalkyl
(e.g., aminoethyl; 2-(N,N-diethylamino)ethyl; 2-(4-morpholino)ethyl); and acyloxy-$C_{1-7}$ alkyl (e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

1-Cyclopropyl-3-[3-r5-morpholin-4-ylmethyl-1H-benzoimidazol-2-yl)-1H-pyrazol-4-yll-urea and salts thereof One particular compound of Formula (I), Sub-Group (A) is 1-cyclopropyl-3-[3-(5-morpholin-4-ylmethyl-1H-benzoimidazol-2-yl)-1H-pyrazol-4-yl]-urea.

Accordingly, in one preferred embodiment, the invention provides a free base or an acid addition salt of 1-cyclopropyl-3-[3-(5-morpholin-4-ylmethyl-1II-benzoimidazol-2-yl)-1H-pyrazol-4-yl]-urea The free base of 1-cyclopropyl-3-[3-(5-morpholin-4-ylmethyl-1H-benzoimidazol-2-yl)-1H-pyrazol-4-yl]-urea from which the salts are derived has the formula (XXX):

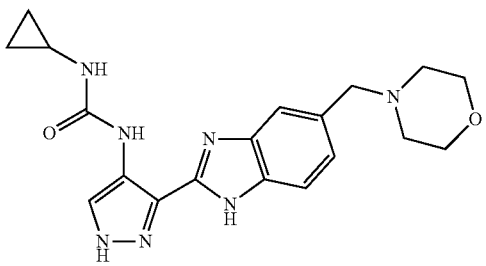

(XXX)

The compound of the formula (XXX) may be referred to in this application by its chemical name, 1-cyclopropyl-3-[3-(5-morpholin-4-ylmethyl-1H-benzoimidazol-2-yl)-1H-pyrazol-4-yl]-urea, or, for convenience, as "the compound XXX", "the compound of formula (XXX)" or the compound of Example 24. Each of these synonyms refers to the compound shown in formula (XXX) above and having the chemical name 1-cyclopropyl-3-[3-(5-morpholin-4-ylmethyl-1H-benzoimidazol-2-yl)-1H-pyrazol-4-yl]-urea.

References to the compound 1-cyclopropyl-3-[3-(5-morpholin-4-ylmethyl-1H-benzoimidazol-2-yl)-1H-pyrazol-4-yl]-urea free base and its acid addition salts include within their scope all solvates, tautomers and isotopes thereof and, where the context admits, N-oxides, other ionic forms and prodrugs. Therefore a reference to the alternative tautomer of formula (XXX), 1-cyclopropyl-3-[3-(6-morpholin-4-ylmethyl-1II-benzoimidazol-2-yl)-1H-pyrazol-4-yl]-urea is to be understood to refer to compound (XXX).

The acid addition salt of formula (XXX) may be selected from salts formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), aspartic (e.g. L-aspartic), benzenesulphonic, benzoic, 4-acetamidobenzoic, butanoic, (+) camphoric (e.g. (+) camphoric), camphor-sulphonic, (+)-(1<S)-camphor-10-sulphonic, capric, caproic, caprylic, carbonic, cinnamic, citric, cyclamic, dodecanoate, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, isobutyric, lactic (e.g. (+)-L-lactic and, (−)-D-lactic), lactobionic, laurylsulphonic, maleic, malic, (−)-L-malic, malonic, (±)-DL-mandelic, methanesulphonic, mucic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, toluenesulphonic (e.g. p-toluenesulphonic), undecylenic and valeric and xinafoic acids, as well as acylated amino acids and cation exchange resins.

One particular group of salts consists of salts formed from hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

One sub-group of salts consists of salts formed from hydrochloric, acetic, adipic, L-aspartic and D- or L-lactic acids.

Another sub-group of salts consists of the acetate, mesylate, ethanesulphonate, D- or L-lactate, adipate, D-glucuronate, D-gluconate and hydrochloride salts. In another embodiment the preferred acid addition salts are mesylate, ethanesulphonate, D- or L-lactate, and hydrochloride salts.

In one particular embodiment the acid addition salt is the DL-lactate, in particular the L-lactate or D-lactate, preferably the L-lactate.

In another embodiment the free base or salt of the compound of Formula (XXX) is selected from the L-lactate salt, free base dehydrate, esylate salt, free base and hydrochloride salt.

In a further and preferred embodiment, the salt of the compound of Formula (XXX) is selected from the lactate and citrate salts and mixtures thereof, and more preferably is selected from the L-lactate and citrate salts and mixtures thereof, with the L-lactate salt being particularly preferred. Particular and preferred embodiments of the invention relating to the L-lactate and citrate salts of 1-cyclopropyl-3-[3-(5-morpholin-4-ylmethyl-1H-benzoimidazol-2-yl)-1H-pyrazol-4-yl]-urea are set out and described in more detail below.

In another embodiment, the compound of Formula (XXX) is a free base.

The salts of the present invention, such as the lactate (e.g. L-lactate) and citrate salts, can be synthesized from the parent compound 1-cyclopropyl-3-[3-(5-morpholin-4-ylmethyl-1H-benzoimidazol-2-yl)-1H-pyrazol-4-yl]-urea by conventional chemical methods such as methods described in *Pharmaceutical Salts: Properties, Selection, and Use*, P. Hemrich Stahl (Editor), Camille G. Wermuth (Editor), ISBN: 3-90639-

026-8, Hardcover, 388 pages, August 2002. Generally, such salts can be prepared by reacting the parent compound 1-cyclopropyl-3-[3-(5-morpholin-4-ylmethyl-1H-benzoimidazol-2-yl)-1H-pyrazol-4-yl]-urea with the appropriate acid in water or in an organic solvent, or in a mixture of the two; generally, non-aqueous media such as ether, ethyl acetate, ethanol, isopropanol, or acetonitrile are used.

In another aspect, the invention provides a method of preparing an acid addition salt of 1-cyclopropyl-3-[3-(5-morpholin-4-ylmethyl-1H-benzoimidazol-2-yl)-1H-pyrazol-4-yl]-urea, such as the lactate (e.g. L-lactate) and citrate salts, which method comprises forming a solution of 1-cyclopropyl-3-[3-(5-morpholin-4-ylmethyl-1H-benzoimidazol-2-yl)-1H-pyrazol-4-yl]-urea free base in a solvent (typically an organic solvent) or mixture of solvents, and treating the solution with an acid to form a precipitate of the acid addition salt.

The acid may be added as a solution in a solvent which is miscible with the solvent in which the free base is dissolved. The solvent in which the free base is initially dissolved may be one in which the acid addition salt thereof is insoluble.

Alternatively, the solvent in which the free base is initially dissolved may be one in which the acid addition salt is at least partially soluble, a different solvent in which the acid addition salt is less soluble subsequently being added such that the salt precipitates out of solution.

In an alternative method of forming an acid addition salt, such as the lactate (e.g. L-lactate) and citrate salts, 1-cyclopropyl-3-[3-(5-morpholin-4-ylmethyl-1H-benzoimidazol-2-yl)-1H-pyrazol-4-yl]-urea is dissolved in a solvent comprising a volatile acid and optionally a co-solvent, thereby to form a solution of the acid addition salt with the volatile acid, and the resulting solution is then concentrated or evaporated to isolate the salt. A further example of an acid addition salt that can be made in this way is the acetate salt.

In another aspect, the invention provides a method of forming an acid addition salt of 1-cyclopropyl-3-[3-(5-morpholin-4-ylmethyl-1H-benzoimidazol-2-yl)-1H-pyrazol-4-yl]-urea as defined herein, such as the lactate (e.g. L-lactate) and citrate salts, which method comprises treating a compound of the formula (XXX):

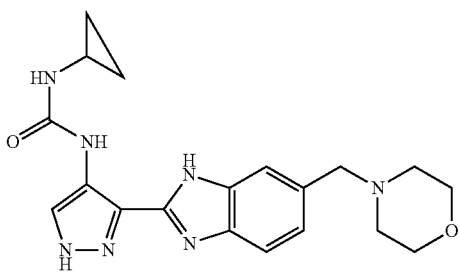

(XXX)

with an organic or inorganic acid as defined herein in an organic solvent to an acid addition salt of 1-cyclopropyl-3-[3-(5-moφholin-4-ylmethyl-1H-benzoimidazol-2-yl)-1H-pyrazol-4-yl]-urea with the organic or inorganic acid, and optionally isolating the acid addition salt thus formed.

The salt is typically precipitated from the organic solvent as it is formed and hence can be isolated by separation of the solid from the solution, e.g. by filtration.

One salt form of the invention can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid by one of the methods described above or elsewhere herein.

The preferred salts such as acid addition salts e.g. the lactate (e.g. L-lactate) and citrate salts, have a number of advantages. For example, the salts will enjoy one or more of the following advantages in that they:

will be more soluble in particular they will have improved solubility in aqueous solution and hence will be better for i.v. administration (e.g. by infusion)

will allow control of solution pH and are therefore better for i.v. administration;

may have improved anti-cancer activity; and may have an improved therapeutic index.

Further advantages of the salts are that they:

will have better stability for example thermal stability (e.g. improved shelf life);

will have advantages for production; and will have better physicochemical properties.

The lactate (e.g. L-lactate) salt of the invention is particularly advantageous as it has good solubility in water, and gives better solubility in buffer systems.

Preferred salts for use in the preparation of liquid (e.g. aqueous) pharmaceutical compositions are acid addition salts (such as the lactates) having a solubility in a given liquid carrier (e.g. water) of greater than 1 mg/ml, typically greater than 5 mg/ml of the liquid carrier (e.g. water), more typically greater than 15 mg/ml, more typically greater than 20 mg/ml and preferably greater than 25 mg/ml.

Aqueous solutions of the salts (e.g. in the form of pharmaceutical compositions) represent a further aspect of the invention. Such solutions may be buffered or unbuffered. In solution, the salts will typically dissociate to form 1-cyclopropyl-3-[3-(5-morpholin-4-ylmethyl-1H-benzoimidazol-2-yl)-1H-pyrazol-4-yl]-urea in protonated form together with one or more counter ions. In another aspect, therefore, the invention also provides an aqueous solution of 1-cyclopropyl-3-[3-(5-morpholin-4-ylmethyl-1H-benzoimidazol-2-yl)-1H-pyrazol-4-yl]-urea in protonated form together with one or more counter ions and optionally one or more further counter ions (for example counter ions derived from other salts such as sodium chloride or buffering agents).

The salts of 1-cyclopropyl-3-[3-(5-morpholin-4-ylmethyl-1H-benzoimidazol-2-yl)-1H-pyrazol-4-yl]-urea are typically pharmaceutically acceptable salts, and examples of pharmaceutically acceptable salts are discussed in Berge et ah, 1977, "Pharmaceutically Acceptable Salts,"*J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms therefore also form part of the invention.

The compound 1-cyclopropyl-3-[3-(5-morpholin-4-ylm-ethyl-1H-benzoimidazol-2-yl)-1H-pyrazol-4-yl]-urea may also form N-oxides. N-Oxides can be formed by the methods described above.

As with other compounds of this invention, the compound 1-cyclopropyl-3-[3-(5-morpholin-4-ylmethyl-1H-benzoimidazol-2-yl)-1H-pyrazol-4-yl]-urea and its acid addition salts may exist in a number of different tautomeric forms and references in this application to the compound include all such forms.

More particularly, in 1-cyclopropyl-3-[3-(5-morpholin-4-ylmethyl-1H-benzoimidazol-2-yl)-1H-pyrazol-4-yl]-urea and its salts, the benzoimidazole group may take either of the two tautomeric forms A" and B" identified below. For simplicity, the general formula (I) illustrates forms A" but the formula is to be taken as embracing all tautomeric forms.

A"

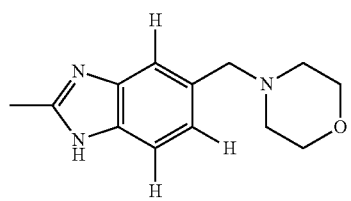

B"

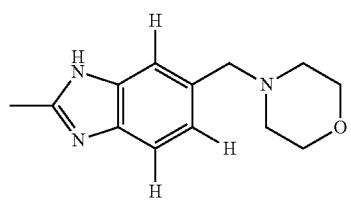

Therefore references to the alternative tautomer, 1-cyclopropyl-3-[3-(6-morpholin-4-ylmethyl-1H-benzoimidazol-2-yl)-1H-pyrazol-4-yl]-urea are clearly references to the same compound as 1-cyclopropyl-3-[3-(5-morpholin-4-ylmethyl-1H-benzoimidazol-2-yl)-1H-pyrazol-4-yl]-urea.

The pyrazole ring may also exhibit tautomerism and can exist in the two tautomeric forms C" and D" below.

C"

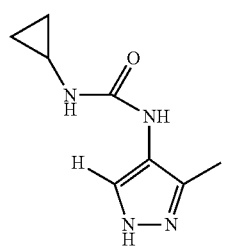

D"

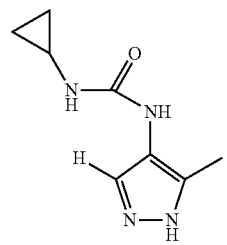

In addition cis and trans conformations of the urea are possible as illustrated below.

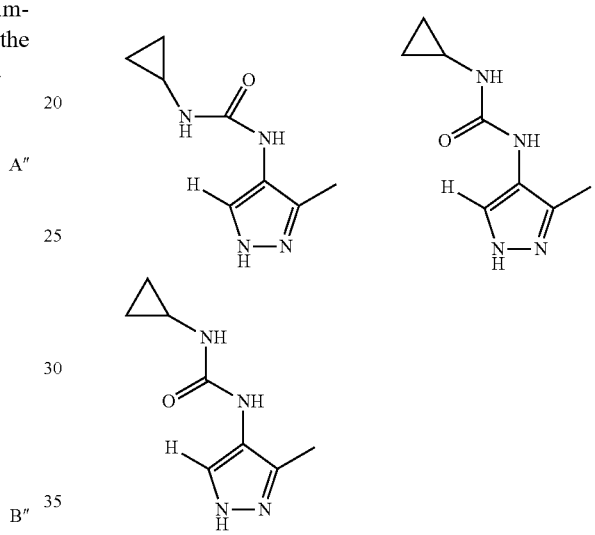

References to 1-cyclopropyl-3-[3-(5-morpholin-4-ylmethyl-1H-benzoimidazol-2-yl)-1H-pyrazol-4-yl]-urea and its salts also include variants with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by references to 1-cyclopropyl-3-[3-(5-morpholin-4-ylmethyl-1H-benzoimidazol-2-yl)-1H-pyrazol-4-yl]-urea and its salts are any polymorphic forms, solvates (e.g. hydrates), complexes (e.g. inclusion complexes or clathrates with compounds such as cyclodextrins, or complexes with metals) thereof.

Lactate and Citrate Salts, Mixtures and Crystals Thereof

As will be apparent from the foregoing sections of the this application, preferred salts of 1-cyclopropyl-3-[3-(5-morpholin-4-ylmethyl-1H-benzoimidazol-2-yl)-1H-pyrazol-4-yl]-urea are the acid addition salts formed with lactic acid (more preferably L-lactic acid), citric acid or mixtures thereof.

For convenience the salts formed from lactic acid, L-lactic acid and citric acid may be referred to herein as the lactate, L-lactate and citrate salts respectively.

In one particular embodiment the salt is the L-lactate or D-lactate, preferably L-lactate.

In another embodiment, the salt is a salt formed with citric acid.

More particularly the salts are a mixture of the L-lactate salts and citrate salts.

In the solid state, the lactate (particularly the L-lactate) or citrate salts of the invention can be crystalline or amorphous or a mixture thereof.

In one embodiment, the lactate (particularly the L-lactate) or citrate salts are amorphous.

In an amorphous solid, the three dimensional structure that normally exists in a crystalline form does not exist and the positions of the molecules relative to one another in the amorphous form are essentially random, see for example Hancock et al. *J. Pharm. Set.* (1997), 86, 1).

In another embodiment, the lactate (particularly the L-lactate) or citrate salts are substantially crystalline i.e. they may be from 50% to 100% crystalline, and more particularly they may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

In a further embodiment, the lactate (particularly the L-lactate) or citrate salts are selected from the group consisting of lactate (particularly the L-lactate) or citrate salts that are from 50% to 100% crystalline, for example at least 50% crystalline, at least 60% crystalline, at least 70% crystalline, at least 80% crystalline, at least 90% crystalline, at least 95% crystalline, at least 98% crystalline, at least 99% crystalline, at least 99.5% crystalline, and at least 99.9% crystalline, for example 100% crystalline.

More preferably the lactate (particularly the L-lactate) or citrate salts may be those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

One example of a substantially crystalline salt is a crystalline salt formed with L-lactic acid.

Another example of a substantially crystalline salt is a crystalline salt formed with citric acid.

The salts of the invention, in the solid state, can be solvated (e.g. hydrated) or non-solvated (e.g. anhydrous).

In one embodiment, the salts are non-solvated (e.g. anhydrous).

A further example of a non-solvated salt is the crystalline salt formed with lactic acid (particularly the L-lactic acid) as defined herein.

The term "anhydrous" as used herein does not exclude the possibility of the presence of some water on or in the salt (e.g. a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the lactate (particularly the L-lactate) or citrate salts are solvated. Where the salts are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

In one embodiment, the lactic acid salt (particularly the L-lactic acid salt) is solvated for example with water and/or ethanol.

The L-lactate salts and citrate salts can be prepared according to the methods described in the preceding sections of this application and elsewhere herein.

The advantages of the L-lactate and citrate salts include the general advantages set out above in the preceding section of the application. However, the crystalline lactate salt of the invention is particularly advantageous in that it:

is non-hygroscopic;
is anhydrous and does not form hydrates;
exists in a single crystalline form and is believed not to exhibit polymorphism
is crystalline;
is stable to storage
has a sharp melting point and exhibits no form changes in when analysed by DSC;
has good solubility in water; and
gives better solubility in buffer systems.

Thus, the L-lactate salt exists in a stable crystalline form that does not form hydrates and does not undergo changes in form under typical handling, processing and storage conditions.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

The L-lactate salt and the citrate salt and mixtures thereof have good aqueous solubility and can therefore be used to prepare aqueous solutions containing relatively high concentrations of the salts. Accordingly, in another embodiment, there is provided an aqueous solution (e.g. in the form of a pharmaceutical composition) containing the L-lactate salt or citrate salt or mixtures thereof of 1-cyclopropyl-3-[3-(5-morpholin-4-ylmethyl-1H-benzoimidazol-2-yl)-1H-pyrazol-4-yl]-urea in a concentration of greater than 1 mg/ml, typically greater than 5 mg/ml of the liquid carrier (e.g. water or buffered systems), more typically greater than 15 mg/ml, more typically greater than 20 mg/ml and preferably greater than 25 mg/ml. Within this embodiment, aqueous solutions (e.g. in the form of a pharmaceutical composition) containing (i) the L-lactate salt or (ii) mixtures of the L-lactate and citrate salts are particularly preferred.

The aqueous solutions of the L-lactate salt or citrate salt or mixtures thereof may be presented as aqueous solutions having a pH in the range 2 to 6, for example 2 to 5, and more particularly 4 to 6, such as 4 to 5.

The aqueous solutions of the L-lactate salt or citrate salt or mixtures thereof may be buffered or unbuffered but, in one embodiment, are buffered, for example to a pH in a range as set out above.

Preferred buffers are those that are capable of buffering the solution to a pH of approximately 4.5 and which are not volatile under conditions used to lyophilize the solution.

In the context of the salt formed with L-lactic acid, a preferred buffer is a buffer formed from citric acid and corrected with NaOH or HCl to the correct pH, for example at a solution pH of approximately 4.5. At this pH and in the citrate buffer, the free base has a solubility of about 80 mg/ml.

Aqueous solutions of the L-lactate or citrate salts or mixtures thereof will contain 1-cyclopropyl-3-[3-(5-morpholin-4-ylmethyl-1H-benzoimidazol-2-yl)-1H-pyrazol-4-yl]-urea in protonated form together with L-lactate and/or citrate counter ions. Other counter ions may also be present and these may be derived, for example, from tonicity adjusting agents such as saline (i.e. chloride counter ions) and/or buffering agents such as citrate buffers. For example, where the L-lactate salt is mixed in aqueous solution with a citrate buffer, both L-lactate and citrate counter ions will be present, the nature of the citrate counter ion depending upon the pH of the solution. In addition, aqueous solutions of the L-lactate or citrate salts of mixtures thereof may contain one or more other excipients typically found in LV. formulations such as tonicity adjusting agents, examples of which are detailed in the United States Pharmacopeia and the National Formulary and include hexose sugars such as glucose, e.g. dextrose (D-glucose).

In a further embodiment, therefore, the invention provides an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate and mixtures thereof; and optionally (i) one or more further counter ions such as a chloride ions and/or (ii) one or more LV. excipients such as tonicity adjusting agents (e.g. hexose sugars such as glucose, preferably D-glucose).

The aqueous solutions can be formed inter alia by dissolving a lactate salt in a solution of citrate ions (e.g. a citrate buffer) or by dissolving a citrate salt in a solution of lactate ions. The lactate and citrate ions may be present in the solution in a lactate:citrate ratio of from 10:1 or less, for example 10:1 to 1:10, more preferably less then 8:1, or less than 7:1, or less than 6:1, or less than 5:1 or less than 4:1 or less than 3:1 or less than 2:1 or less than 1:1, more particularly from 1:1 to 1:10. In one embodiment, the lactate and citrate ions are present in the solution in a lactate:citrate ratio of from 1:1 to 1:10, for example 1:1 to 1:8, or 1:1 to 1:7 or 1:1 to 1:6 or 1:1 to 1:5, e.g. approximately 1:4.4.

Each of the aqueous solutions described in this section of the application and elsewhere herein can be subjected to lyophilisation to provide a solid formulation that can readily be reconstituted to give an aqueous solution (preferably a sterile solution) when required by the addition of water (preferably sterile water) or an aqueous medium containing an LV. excipient such as saline and/or dextrose.

Accordingly, the invention also provides a lyophilized formulation (e.g. in the form of a pharmaceutical composition) comprising the L-lactate salt or citrate salt or mixtures thereof as defined herein, for example wherein the formulation, when dissolved in water, has a pH of 2 to 6, for example 2 to 5, and more particularly 4 to 6 such as 4 to 5.

In another embodiment, the invention provides a lyophilized formulation (e.g. in the form of a pharmaceutical composition) comprising 1-cyclopropyl-3-[3-(5-moφholin-4-ylmethyl-1H-benzoimidazol-2-yl)-1H-pyrazol-4-yl]-urea in protonated form together with one or more counter ions selected from L-lactate and citrate and mixtures thereof; and optionally (i) one or more further counter ions such as a chloride ions and/or (ii) one or more LV. excipients such as tonicity adjusting agents (e.g. hexose sugars such as glucose, preferably D-glucose).

The ratios of L-lactate to citrate ions in each of the lyophilized formulations may be as set out above in respect of the aqueous solutions.

Crystal Structures of 1-Cyclopropyl-3-[3-(5-morpholin-4-ylmethyl-1H-benzoimidazol-2-yl)-1H-pyrazol-4-yl]-urea and its salts As described above, the lactate (in particular the L-lactate) or citrate salts of 1-cyclopropyl-3-[3-(5-morpholin-4-ylmethyl-1H-benzoimidazol-2-yl)-1H-pyrazol-4-yl]-urea can be amorphous or substantially crystalline. In one particular embodiment, the lactate (particularly the L-lactate) or citrate salts are substantially crystalline, the term "substantially crystalline" having the meaning defined above. In particular the lactate salt (particularly the L-lactate) of 1-cyclopropyl-3-[3-(5-morpholin-4-ylmethyl-1H-benzoimidazol-2-yl)-1H-pyrazol-4-yl]-urea is substantially crystalline.

The free base of 1-cyclopropyl-3-[3-(5-morpholin-4-ylmethyl-1H-benzoimidazol-2-yl)-1H-pyrazol-4-yl]-urea can also be amorphous or substantially crystalline. In one particular embodiment, the free base is substantially crystalline, the term "substantially crystalline" having the meaning defined above. In one embodiment, the free base of 1-cyclopropyl-3-[3-(5-moi-pholin-4-ylmethyl-1H-benzoimidazol-2-yl)-1H-pyrazol-4-yl]-urea exists in a dihydrate crystalline form.

The crystals described herein and the crystal structures form further aspects of the invention.

As indicated above, the lactate salt of the invention is believed to exist in a single crystalline form having the characteristics set out herein. This crystalline form represents a preferred embodiment of the invention. However, in the event that other crystalline forms do exist, these are not excluded from the scope of the present invention.

Thus, where the lactate salt (particularly the L-lactate) of 1-cyclopropyl-3-[3-(5-morpholin-4-ylmethyl-1H-benzoimidazol-2-yl)-1H-pyrazol-4-yl]-urea is substantially crystalline, one single crystalline form (e.g. the crystalline form defined and characterised herein) may predominate, although other crystalline forms may be present in minor and preferably negligible amounts.

The crystalline forms (e.g. the crystalline forms defined and characterised herein) of 1-cyclopropyl-3-[3-(5-morpholin-4-ylmethyl-1H-benzoimidazol-2-yl)-1H-pyrazol-4-yl]-urea (or salts thereof) contain less than or equal to about 5% by weight of other crystalline forms of 1-cyclopropyl-3-[3-(5-moφholin-4-ylmethyl-1H-benzoimidazol-2-yl)-1H-pyrazol-4-yl]-urea (or salts thereof), in particular containing less than or equal to about 1% by weight of other crystalline forms (or salts thereof).

In a preferred embodiment, the invention provides a substantially crystalline salt (e.g. a lactate salt such as the L-lactate as defined herein) of 1-cyclopropyl-3-[3-(5-morpholin-4-ylmethyl-1H-benzoimidazol-2-yl)-1H-pyrazol-4-yl]-urea containing a single crystalline form (e.g. the crystalline form defined and characterised herein) of the salt and no more than 5% by weight of any other crystalline forms of the salt.

Preferably, the single crystalline form (e.g. the crystalline forms defined and characterised herein) is accompanied by less than 4%, or less than 3%, or less than 2% of other crystalline forms, and in particular contains less than or equal to about 1% by weight of other crystalline forms. More preferably, the single crystalline form (e.g. the crystalline form defined and characterised herein) is accompanied by less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, by weight of other crystalline forms, for example 0% by weight of other crystalline forms.

The crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (international Union of Crystallography/Oxford University Press, 1992 ISBN 0-19-855578-4 (h/b), 0-19-85579-2 (h/b)). This technique involves the analysis and interpretation of the X-ray diffraction of single crystal.

The crystal structure of the free base dihydrate and the L-lactate salt of 1-cyclopropyl-3-[3-(5-morpholin-4-ylmethyl-1H-benzoimidazol-2-yl)-1H-pyrazol-4-yl]-urea have been determined by X-ray crystallography—see Examples 69 and 71 respectively below.

Tables 2 and 4 in Examples 69 and 71 respectively give coordinate data for crystals of 1-cyclopropyl-3-[3-(5-morpholin-4-ylmethyl-1H-benzoimidazol-2-yl)-1H-pyrazol-4-yl]-urea and its L-lactate salt in Crystallographic Information File (CIF) Format (see Hall, Allen and Brown, Acta Cryst. (1991). A47, 655-685; http://www.iucr.ac.uk/iucr-top/cif/home.html). Alternative file formats such as a PDB file format (e.g. format consistent with that of the EBI Macromolecular Structure Database (Hinxton, UK)) may be used or preferred by others of skill in the art. However it will be apparent that the use of a different file format to present or manipulate the coordinates of the Tables is within the scope of the present invention. The numbers in brackets in the Tables represents the deviation (s.u., standard uncertainty). The crystal structure of the lactate salt is illustrated in FIGS. 4 and 5.

In one embodiment, the invention provides the dihydrate free base of 1-cyclopropyl-3-[3-(5-morpholin-4-ylmethyl-1H-benzoimidazol-2-yl)-1H-pyrazol-4-yl]-urea which is crystalline and (i) has a crystal structure as defined by the coordinates in Table 2 herein; and/or (ii) wherein the crystals belong to a monclinic space group P2/7 (#14) with crystal lattice parameters α=7.66(10), 0=15.18(10), c=17.71(10) A, β=198.53(2)°, α=γ=90°.

In another embodiment the invention provides the L-lactate salt of 1-cyclopropyl-3-[3-(5-morpholin-4-ylmethyl-1H-benzoimidazol-2-yl)-1H-pyrazol-4-yl]-urea which is crystalline and has a crystal structure as defined by the coordinates in Table 4 herein.

In another embodiment the invention provides an L-lactate salt of 1-cyclopropyl-3-[3-(5-morpholin-4-ylmethyl-1H-benzoimidazol-2-yl)-1H-pyrazol-4-yl]-urea which is crystalline and has a crystal structure as set out in FIGS. 4 and 5.

In another embodiment the invention provides an L-lactate salt of 1-cyclopropyl-3-[3-(5-morpholin-4-ylmethyl-1H-benzoimidazol-2-yl)-1H-pyrazol-4-yl]-urea which is crystalline and has a crystal structure that belongs belong to an orthorhombic space group P2; 2/2/(#19) and has crystal lattice parameters at 97(2) K a=9.94(10), 6=15.03(10), c=1 6.18 (10) A, α=β=γ=90°.

In another embodiment the invention provides an L-lactate salt of 1-cyclopropyl-3-[3-(5-morpholin-4-ylmethyl-1H-benzoimidazol-2-yl)-1H-pyrazol-4-yl]-ui ea which is crystalline and has crystal lattice parameters at room temperature a=10.08(10), 6=15.22(10), c=16.22(10) A, α=β=γ=90°.

Accordingly, in another embodiment, the invention provides an L-lactate salt of 1-cyclopropyl-3-[3-(5-morpholin-4-ylmethyl-1H-benzoimidazol-2-yl)-1H-pyrazol-4-yl]-urea which is crystalline and:
  (a) has a crystal structure as set out in FIGS. 4 and 5; and/or
  (b) has a crystal structure as defined by the coordinates in Table 4 herein; and/or
  (c) has crystal lattice parameters at 97(2) K a=9.94(10), 6=15.03(10), c=1 6.18(10) A, α=β=γ=90°; and/or
  (d) has crystal lattice parameters at room temperature a=10.08(10), 6=15.22(10), c=16.22(10) A, α=β=γ=90°; and/or
  (e) has a crystal structure that belongs belong to an orthorhombic space group $P2_12_12_1$ (#19).

Alternatively, the crystalline structure of a compound can be analysed by the solid state technique of X-ray Powder Diffraction (XRPD). XRPD can be carried out according to conventional methods such as those described herein (see Examples 70 and 72) and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle (2θ) and interplanar spacing (d) parameters of an X-ray diffraction spectrum. These are related by Bragg's equation, nλ=2d Sin θ, (where 11=1; λ=wavelength of the cathode used; cHnterplanar spacing; and θ=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of 2θ±0.2°. The peaks mean main peaks and include peaks not larger than medium at diffraction angles other than those stated above.

Both the L-lactate salt and free base forms of 1-cyclopropyl-3-[3-(5-morpholin-4-ylmethyl-1H-benzoimidazol-2-yl)-1H-pyrazol-4-yl]-urea have been characterised by XRPD. In each case, the powder X-ray diffraction patterns are expressed in terms of the diffraction angle (2Θ), inter planar spacing (d) and/or relative intensities. Tables 3, 5 and 6 in Examples 70 ands 72 show the interplanar spacing (d) values of the X-ray diffraction spectrum that correspond to the diffraction angle values of the free base, L-lactate salt and dihydrate free base forms of 1-cyclopropyl-3-[3-(5-morpholin-4-ylmethyl-1H-benzoimidazol-2-yl)-1H-pyrazol-4-yl]-urea.

Therefore 1-cyclopropyl-3-[3-(5-morpholin-4-ylmethyl-1H-benzoimidazol-2-yl)-1H-pyrazol-4-yl]-urea and its salts have X-ray powder diffraction patterns essentialfy as shown in FIG. 3, 6, 7 or 8 and/or Tables 3, 5 or 6 in Examples 70 and 72.

Accordingly, in one embodiment, the invention provides crystals of 1-cyclopropyl-3-[3-(5-morpholin-4-ylmethyl-1H-benzoimidazol-2-yl)-1H-pyrazol-4-yl]-urea free base or an L-lactate salt thereof exhibiting X-ray powder diffraction patterns containing peaks at the same diffraction angles as those of the X-ray powder diffraction pattern shown in FIG. 3, 6, 7 or 8 and/or Table 3 and/or Table 5 and/or Table 6 and wherein the peaks optionally have the same relative intensity. More particularly, the crystals of the salts are those that have X-ray powder diffraction pattern substantially as shown in FIG. 3, 6, 7 or 8.

In a preferred embodiment, the invention provides a crystal of 1-cyclopropyl-3-[3-(5-morpholin-4-ylmethyl-1H-benzoimidazol-2-yl)-1H-pyrazol-4-yl]-urea L-lactic acid salt which has an X-ray powder diffraction pattern essentially as shown in FIG. 6.

In another embodiment, the invention provides a substantially crystalline L-lactate salt of 1-cyclopropyl-3-[3-(5-morpholin-4-ylmethyl-1H-benzoimidazol-2-yl)-1H-pyrazol-4-yl]-urea which exhibits peaks at the same diffraction angles as those of the X-ray powder diffraction pattern shown in FIG. 6. Preferably the peaks have the same relative intensity as the peaks in FIG. 6.

The invention also provides a substantially crystalline L-lactic acid salt of 1-cyclopropyl-3-[3-(5-morpholin-4-ylmethyl-1H-benzoimidazol-2-yl)-1H-pyrazol-4-yl]-urea having an X-ray powder diffraction pattern substantially as shown in FIG. 6.

The X-ray powder diffraction pattern of the L-lactate salt may be characterised by the presence of peaks at the diffraction angles (2Θ) and interplanar spacings (d), and preferably the intensities shown in Table 5 in Example 72.

Therefore the invention provides a crystal of cyclopropyl-3-[3-(6-morpholin-4-ylmethyl-1H-benzoimidazol-2-yl)-1H-pyrazol-4-yl]-urea L-lactate, which shows an X-ray powder diffraction pattern having characteristic peaks at a diffraction angle (2θ±1.0 degree such as ±0.2 degree, in particular ±0.1 degree) of Table 5 in Example 72.

The invention also provides crystals of cyclopropyl-3-[3-(6-morpholin-4-ylmethyl-1H-benzoimidazol-2-yl)-1H-pyrazol-4-yl]-urea L-lactate salt having an X-ray powder diffraction pattern showing major peaks of diffraction angles 2Θ of 17.50, 18.30, 19.30, 19.60, and 21.85±1.0 degree such as ±0.2 degree, in particular ±0.1 degree. The crystals may be further characterised by peaks in the X-ray diffraction pattern at 12.40, 15.20, 15.60, 17.50, 18.30, 18.50, 19.30, 19.60, 21.85, and 27.30±1.0 degrees two-theta.

The crystal of cyclopropyl-3-[3-(6-morpholin-4-ylmethyl-1H-benzoimidazol-2-yl)-1H-pyrazol-4-yl]-urea L-lactate salt is also characterised in that the characteristic X-ray powder diffraction pattern is represented by the spacings between lattice planes d (Å) of Table 5 in Example 72.

In a further embodiment the invention provides a crystal of cyclopropyl-3-[3-(6-morpholin-4-ylmethyl-1H-benzoimidazol-2-yl)-1H-pyrazol-4-yl]-urea lactate salt, which possess an X-ray powder diffraction pattern comprising characteristic peaks appearing as the lattice spacing (d) of the powder X-ray diffraction at 5.06, 4.85, 4.60, 4.53, and 4.07, and more particularly comprising further characteristic peaks appearing as the lattice spacing (d) of the powder X-ray diffraction at 7.13, 5.83, 5.68, 5.06, 4.85, 4.79, 4.60, 4.53, 4.07, and 3.26 angstrom.

In another embodiment, the invention provides a substantially crystalline L-lactate salt of 1-cyclopropyl-3-[3-(5-morpholin-4-ylmethyl-1H-benzoimidazol-2-yl)-1H-pyrazol-4-yl]-urea having an X-ray powder diffraction pattern characterised by the presence of major peaks at the diffraction angles (2Θ) of 17.50, 18.30, 19.30, 19.60, and 21.85 degrees, more particularly 12.40, 15.20, 15.60, 17.50, 18.30, 18.50, 19.30, 19.60, 21.85, and 27.30 degrees, and interplanar spacings (d) of 5.06, 4.85, 4.60, 4.53, and 4.07, more particularly 7.13, 5.83, 5.68, 5.06, 4.85, 4.79, 4.60, 4.53, 4.07, and 3.26 angstrom.

In a further embodiment, the invention provides a substantially crystalline L-lactate salt of 1-cyclopropyl-3-[3-(5-moipholm-4-ylmethyl-1H-benzoimidazol-2-yl)-1H-pyrazol-4-yl]-urea having an X-ray powder diffraction pattern characterised by the presence of peaks at the diffraction angles (2Θ) and interplanar spacings (d), and preferably the intensities shown in Table 5 in Example 72.

The invention also provides a crystal of 1-cyclopropyl-3-[3-(5-morpholin-4-ylmethyl-1H-benzoimidazol-2-yl)-1H-pyrazol-4-yl]-urea free base, which shows an X-ray powder diffraction pattern having characteristic peaks at a diffraction angle (2θ±1.0 degree such as ±0.2 degree, in particular ±0.1 degree) of Table 2.

In a further embodiment the invention provides a crystal of 1-cyclopropyl-3-[3-(5-morpholin-4-ylmethyl-1H-benzoimidazol-2-yl)-1H-pyrazol-4-yl]-urea free base, which possess an X-ray powder diffraction pattern whose characteristic peaks appear as the lattice spacing (d) of Table 2.

The crystalline salts of the invention can also be characterised by differential scanning calorimetry (DSC).

The L-lactate salt has been analysed by DSC and exhibits a peak (melting point and decomposition) at 190° C.

Accordingly, in another aspect, the invention provides an L-lactate salt of 1-cyclopropyl-3-[3-(5-morpholin-4-ylmethyl-1H-benzoimidazol-2-yl)-1H-pyrazol-4-yl]-urea which is anhydrous and exhibits an endothermic peak at 190° C. when subjected to DSC.

A further aspect of the invention is the L-lactate salt of 1-cyclopropyl-3-[3-(5-morpholin-4-ylmethyl-1H-benzoimidazol-2-yl)-1H-pyrazol-4-yl]-urea which exhibits peaks at the same diffraction angles as those of the X-ray powder diffraction pattern shown in FIG. 6, 7 or 8 and further exhibits an endothermic peak accompanying decomposition in the vicinity of 190° C. according to thermal analysis (DSC).

The free base of 1-cyclopropyl-3-[3-(5-morpholin-4-ylmethyl-1H-benzoimidazol-2-yl)-1H-pyrazol-4-yl]-urea exhibits peaks at the same diffraction angles as those of the X-ray powder diffraction pattern shown in FIG. 3 and/or Table 2 and further exhibits an exothermic peak accompanying decomposition in the vicinity of 193° C. according to thermal analysis (DSC).

The behaviour of the salts of the invention in conditions of high humidity can be analysed by standard gravimetric vapour sorption (GVS) methods, for example as described in Section E of Example 68.

The L-lactate salt can exist in a stable anhydrous crystalline form in conditions of high relative humidity and does not undergo changes in crystal structure under such conditions.

The salts of 1-cyclopropyl-3-[3-(5-morpholin-4-ylmethyl-1H-benzoimidazol-2-yl)-1H-pyrazol-4-yl]-urea can be further characterised by infra-red spectroscopy, e.g. FTIR. The infra-red spectrum of the L-lactate salt (KBr disc method) contains characteristic peaks at 3229, 2972 and 1660 cm$^{-1}$.

Accordingly, in a further embodiment, the invention provides a (preferably substantially crystalline) L-lactic acid salt of 1-cyclopropyl-3-[3-(5-morpholin-4-ylmethyl-1H-benzoimidazo 1-2-yl)-1H-pyrazol-4-yl]-urea that exhibits an infra-red spectrum, when analysed using the KBr disc method, that contains characteristic peaks at 3229, 2972 and 1660 cm$^{-1}$.

As will be evident from the foregoing paragraphs, the L-lactate salt of the invention can be characterised by a number of different physicochemical parameters. Accordingly, in a preferred embodiment, the invention provides an L-lactate salt of 1-cyclopropyl-3-[3-(5-morpholin-4-ylmethyl-1H-benzoimidazol-2-yl)-1H-pyrazol-4-yl]-urea which is crystalline and is characterised by any one or more (in any combination) or all of the following parameters, namely that the salt:

(a) has a crystal structure as set out in FIGS. 4 and 5; and/or
(b) has a crystal structure as defined by the coordinates in Table 4 in Example 71 herein; and/or
(c) has crystal lattice parameters at 97(2) K<<=9.94(10), &=15.03(10), c=16.18(10) A, α=β=γ=90°; and/or
(d) has crystal lattice parameters at room temperature a=\ 0.08(10), 6=15.22(10), c=16.22(10) A, α=β=γ=90°; and/or
(e) has a crystal structure that belongs belong to an orthorhombic space group P2$_1$2; 2$_1$ (#19); and/or
(f) has an X-ray powder diffraction pattern characterised by the presence of major peaks at the diffraction angles (2Θ) of 17.50, 18.30, 19.30, 19.60, and 21.85 degrees, and more particularly additionally at 12.40, 15.20, 15.60, 17.50, 18.30, 18.50, 19.30, 19.60, 21.85, and 27.30 degrees, and/or interplanar spacings (d) of 5.06, 4.85, 4.60, 4.53, and 4.07, and more particularly additionally at 7.13, 5.83, 5.68, 5.06, 4.85, 4.79, 4.60, 4.53, 4.07, and 3.26 angstrom; and/or
(g) exhibits peaks at the same diffraction angles as those of the X-ray powder diffraction pattern shown in FIG. 6 or Table 5 of Example 72 and optionally wherein the peaks have the same relative intensity as the peaks in FIG. 6; or Table 5 and/or
(h) has an X-ray powder diffraction pattern substantially as shown in FIG. 6; and/or
(i) is anhydrous and exhibits an endothermic peak at 190° C. when subjected to DSC; and/or
(j) exhibits an infra-red spectrum, when analysed using the KBr disc method, that contains characteristic peaks at 3229, 2972 and 1660 cm$^{-1}$.

Compounds of sub-group (C) of Formula (T)

In one sub-group of compounds of the formula (I) (i.e. sub-group (C) of formula (I)), M is a group D1; X is O; A is a group NR$^2$ where R$^2$ is hydrogen; E is a bond; R$^1$ is 2,6-difluorophenyl; and the compound is an acid addition salt formed from a selected group of acids.

Accordingly, in one embodiment, the invention provides an acid addition salt of 1-(2,6-difluorophenye-N-[3-(5-morpholin-4-ylmethyl-1H-benzimidazol-2-yl)-1H-pyrazol-4-yl]-urea which is a salt formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), c-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methancsulphonic, mucic, naphthalcncsulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. /?-toluenesulphonic), valeric and xinafoic acids.

In one embodiment, the acid addition salt is formed from an acid selected from the group consisting of adipic, alginic, ascorbic (e.g. L-ascorbic), aspartic (e.g. L-aspartic), benzoic, camphoric (e.g. (+) camphoric), capric, caprylic, carbonic, cyclamic, dodecanoate, dodecylsulphuric, ethane-1,2-disulphonic, galactaric, gentisic, glucoheptonic, D-gluconic, glutamic (e.g. L-glutamic), α-oxoglutaric, glycolic, hippuric, isobutyric, laurylsulphonic, mucic, naphthalene-1,5-disulphonic, nicotinic, oleic, orotic, oxalic, palmitic, pamoic, sebacic, stearic, tartaric (e.g. (+)-L-tartaric), thiocyanic and xinafoic acids.

In another embodiment, the acid addition salt is formed from an acid selected from the group consisting of acetic, adipic, ascorbic, aspartic, citric, DL-lactic, fumaric, gluconic, glucuronic, hippuric, hydrochloric, glutamic, DL-malic, p-toluenesulphonic, methanesulphonic (mesylate), ethanesulphonic (esylate), sebacic, stearic, succinic and tartaric acids.

In a further embodiment, the acid addition salt is formed from an acid selected from the group consisting of adipic, ascorbic, aspartic, gluconic, hippuric, glutamic, sebacic, stearic and tartaric acids.

In another particular embodiment, the compound is an acid addition salt formed with hydrochloric acid.

Preferred salts are salts having a solubility in a given liquid carrier (e.g. water) of greater than 25 mg/ml of the liquid carrier (e.g. water), more typically greater than 50 mg/ml and preferably greater than 100 mg/ml. Such salts are particularly advantageous for administration in a liquid form, for example by injection or infusion.

In another aspect of the invention, there is provided a composition (e.g. a pharmaceutical composition) comprising an aqueous solution containing a salt as described herein in a concentration of greater than 25 mg/ml, typically greater than 50 mg/ml and preferably greater than 100 mg/ml.

Salts of the invention that have a solubility of greater than 25 mg/ml include the D-glucuronate, mesylate, esylate and DL-lactate salts, the latter three of which have solubilities in excess of 100 mg/ml.

Accordingly, in one particular embodiment, there is provided a mesylate salt of 1-(2,6-difluorophenyl)-N-[3-(5-morpholin-4-ylmethyl-1H-benzimidazol-2-yl)-1H-pyrazol-4-yl]-urea.

In another particular embodiment, there is provided an esylate (ethanesulphonate) salt of 1-(2,6-difluorophenyl)-N-[3-(5-morpholin-4-ylmethyl-N-[3-(5-benzimidazol-2-yl)-1H-pyrazol-4-yl]-urea.

In a further particular embodiment, there is provided a DL lactate salt of 1-(2,6-difluorophenyl)-N-[3-(5-morpholin-4-ylmethyl-1H-benzimidazol-2-yl)-1H-pyrazol-4-yl]-urea. In one embodiment, the lactate salt is the L-lactate.

The free base or parent compound from which the compounds (i.e. acid addition salts) of sub-group (C) of Formula (I) of the invention are derived has the formula (IA):

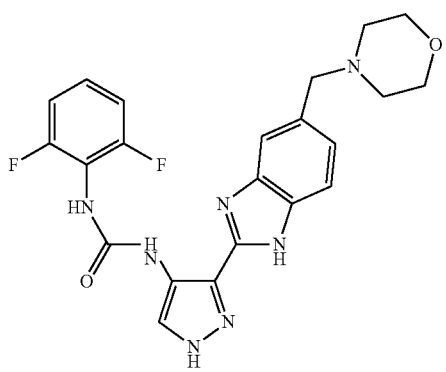

(IA)

The salts of compound (IA) can be amorphous or crystalline.

In one embodiment, the salt is an amorphous form.

In another embodiment, the compound is in a crystalline form.

The compound can be non-solvated (e.g. anhydrous) or solvated.

In one embodiment, the salts are non-solvated.

In another embodiment, the salts are solvated, e.g. hydrated.

Where the compounds are hydrated, they can contain, for example, up to three molecules of water of crystallisation, more usually up to two molecules of water, e.g. one molecule of water or two molecules of water.

The salts of the invention have advantages over the free base form of 1-(2,6-difluorophenyl)-N-[3-(5-morpholin-4-ylmethyl-1H-benzimidazol-2-yl)-1H-pyrazol-4-yl]-urea.

For example, the salts have greater solubility in water and are therefore better for use in preparing parenteral formulations for injection or infusion (e.g. i.v. infusion). Salts of the invention also have one or more other advantages selected from:
 improved pharmacokinetics;
 better stability, for example improved shelf life;
 lower basicity making them better for i.v. use;
 advantages for production;
 improved metabolic properties; and
 less clinical variation between patients.

The salts may be prepared by any of the methods set out in the preceding section of this application describing salts of compounds of sub-groups (A) and (B) of formula (I)—

The compounds of sub-group (C) of formula (I) are typically pharmaceutically acceptable salts. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The compounds of sub-group (C) of formula (I) may exist in a number of different tautomeric forms and references to the compounds of the invention include all such forms. For the avoidance of doubt, where a compound can exist in one of several geometric isomeric or tautomeric forms and only one is specifically described or shown, all others are nevertheless embraced by this application.

For example, in compounds of the invention the benzimidazole group may take either of the following two tautomeric forms A" and B" set out above.

The pyrazole ring may also exhibit tautomerism and can exist in the two tautomeric forms C" and D" below.

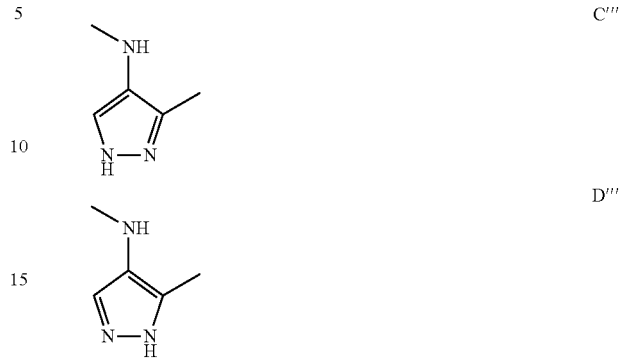

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by the invention are any polymorphic forms of the compounds as well as complexes (e.g. inclusion complexes or clathrates with substances such as cyclodextrins, or complexes with metals) of the compounds, and prodrugs of the compounds. By "prodrugs" is meant for example any compound that is converted in vivo into a biologically active compound of the invention.

Biological Activity

The compounds of the invention have cyclin dependent kinase inhibiting or modulating activity and glycogen synthase kinase-3 (GSK3) inhibiting or modulating activity, and/or Aurora kinase inhibiting or modulating activity, and which it is envisaged will be useful in preventing or treating disease states or conditions mediated by the kinases.

Thus, for example, it is envisaged that the compounds of the invention will be useful in alleviating or reducing the incidence of cancer.

More particularly, the compounds of the formulae (I) and sub-groups thereof are inhibitors of cyclin dependent kinases. For example, compounds of the invention have activity against CDK1, CDK2, CDK3, CDK4, CDK5, CDK6 and CDK7 kinases, and in particular cyclin dependent kinases selected from CDK1, CDK2, CDK3, CDK4, CDK5 and CDK6.

Preferred compounds are compounds that inhibit one or more CDK kinases selected from CDK1, CDK2, CDK4 and CDK5, for example CDK1 and/or CDK2.

In addition, CDK4, CDK8 and/or CDK9 may be of interest.

The lactate or citrate salts of 1-cyclo-propyl-3-[3-(5-morpholin-4-ylmethyl-1H-benzoimidazol-2-yl)-1H-pyrazol-4-yl]-urea have activity against CDK2, CDK4, CDK5, CDK6 and CDK 9 kinases, and in particular CDK2.

Compounds of the invention also have activity against glycogen synthase kinase-3 (GSK-3).

Compounds of the invention also have activity against Aurora kinases. Preferred compounds of the invention are those having $IC_{50}$ values of less than 0.1 µM.

In particular, the lactate or citrate salts of 1-cyclo-propyl-3-[3-(5-morpholin-4-ylmethyl-1H-benzoimidazol-2-yl)-1H-pyrazol-4-yl]-urea are inhibitors of aurora kinase and, for example, inhibit Aurora A and/or Aurora B.

Many of the compounds of the invention exhibit selectivity for the Aurora A kinase compared to CDK1 and CDK2 and such compounds represent one preferred embodiment of the invention. For example, many compounds of the invention have $IC_{50}$ values against Aurora A that are between a tenth and a hundredth of the $IC_{50}$ against CDK1 and CDK2.

As a consequence of their activity in modulating or inhibiting CDK and Aurora kinases and glycogen synthase kinase, they are expected to be useful in providing a means of arresting, or recovering control of, the cell cycle in abnormally dividing cells. It is therefore anticipated that the compounds will prove useful in treating or preventing proliferative disorders such as cancers. It is also envisaged that the compounds of the invention will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB-ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocyte leukemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases selected from CDK1, CDK2, CDK3, CDK4, CDK5 and CDK6, for example, one or more CDK kinases selected from CDK1, CDK2, CDK4 and CDK5, e.g. CDK1 and/or CDK2.

Whether or not a particular cancer is one which is sensitive to inhibition by a cyclin dependent kinase or an aurora kinase may be determined by means of a cell growth assay as set out in Examples 79 and 80 below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Ban-virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anti-cancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes breast cancer, ovarian cancer, colon cancer, prostate cancer, oesophageal cancer, squamous cancer and non-small cell lung carcinomas.

In the case of compounds having activity against Aurora kinase, particular examples of cancers where it is envisaged that the Aurora kinase inhibiting compounds of the invention will be useful include:
human breast cancers (e.g. primary breast tumours, node-negative breast cancer, invasive duct adenocarcinomas of the breast, non-endometrioid breast cancers);
ovarian cancers (e.g. primary ovarian tumours);
pancreatic cancers;
human bladder cancers;
colorectal cancers (e.g. primary colorectal cancers);
gastric tumours;
renal cancers;
cervical cancers:
neuroblastomas;
melanomas;
lymphomas;
prostate cancers;
leukemia;
non-endometrioid endometrial carcinomas;
gliomas; and
non-Hodgkin's lymphoma.

Cancers which may be particularly amenable to Aurora inhibitors include breast, bladder, colorectal, pancreatic, ovarian, non-Hodgkin's lymphoma, gliomas and nonendometrioid endometrial carcinomas.

A particular sub-set of cancers which may be particularly amenable to Aurora inhibitors consist of breast, ovarian, colon, liver, gastric and prostate cancers.

Another subset of cancers that Aurora inhibitors may be particularly amenable to treat consists of hematological cancers, in particular leukemia. Therefore, in a further embodiment the compounds of formula (I) are used to treat hematological cancers, in particular leukemia. Particular leukemias are selected from Acute Myelogenous Leukemia (AML), chronic myelogenous leukaemia (CML), B-cell lymphoma (Mantle cell), and Acute Lymphoblastic Leukaemia (ALL) (alternatively known as acute lymphocytic leukaemia). In one embodiment the leukemias are selected from relapsed or refractory acute myelogenous leukemia, myelodysplastic syndrome, and chronic myelogenous leukemia.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.

Another particular cancer is mantle cell lymphoma.

Another particular cancer is diffuse large B cell lymphoma.

It is further envisaged that the compounds of the invention, and in particular those compounds having aurora kinase inhibitory activity, will be particularly useful in the treatment or prevention of cancers of a type associated with or characterised by the presence of elevated levels of aurora kinases, for example the cancers referred to in this context in the introductory section of this application.

The activity of the compounds of the invention as inhibitors of cyclin dependent kinases, Aurora kinases and glycogen synthase kinase-3 can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

Advantages of the Compounds of the Invention

Compounds of the invention (for example the compounds of Examples 24, 62, 63 and 64) have a number of advantages over prior art compounds. For example, the compounds of the invention (see Table A) demonstrate enhanced selectivity for and potency against Aurora A and B kinases in particular.

TABLE A

Inhibition of Aurora kinases in vitro by 1-cyclopropyl-3-[3-('5-moφ holin-4-ylmethyl-1H-benzoimidazol-2-yl)-1H-pyrazol-4-yll-urea

| Aurora Kinase | $IC_{50}$ (nM) |
|---|---|
| Aurora-A | 52% at 3 nM |
| Aurora-B | 58% at 3 nM |

Kinase activities in vifro were determined according to the protocols described in Examples 75 and 76.

Compounds of the invention are also advantageous over prior art compounds in that they have different susceptibilities to P450 enzymes (see Table B below and Example 81).

TABLE B

Inhibition of expressed cytochrome P45Q isoforms by 1-cyclopropyl-3-r3-(5-morpholin-4-ylmethyl-1H-benzoimidazol-2-yl)-1H-pyrazol-4-yll-urea in vitro

| P450 isoform | IC50 (µM) |
|---|---|
| CYP1A2 | >10 |
| CYP2D6 | >10 |
| CYP3A4 | >10 |
| CYP2C9 | >10 |
| CYP2C19 | >10 |

In addition, compounds of the invention are also advantageous over prior art compounds in that they exhibit improvements with regard to drug metabolism and pharmacokinetic properties. In particular the compounds of the invention have reduced plasma protein binding. The binding of the compound of Examples 24, 62, 63 and 64 to plasma proteins was comparably moderate across all species tested, ranging from 61% in rat to 82% in mouse plasma. This could confer the advantage of having more free drug available in the systemic circulation to reach the appropriate site of action to exert its therapeutic effect. Increased free fraction to exert pharmacological action in tumours potentially leads to improved efficacy which thereby allows reduced dosages to be administered.

Compounds of the invention (for example Examples 24, 62, 63 and 64) also demonstrate improved cell activity in proliferation and clonogenic assays (for example in the assays described in Example 79 and 80) against a wider range of solid tumour cell lines, thereby indicating improved anticancer activity (Table C). Data indicates that compound-treatment has different effects on tumour cells compared with normal cells. In checkpoint compromised tumour cells compound treatment leads to multinucleation, due to disruption of mitosis, inhibition of cytokinesis and bypass of the spindle checkpoint through Aurora kinase inhibition. It is this multinucleation that appears to lead to cell death. In contrast, in normal checkpoint competent cells treated with compound, fewer cells become multinucleated or die after 24 h compound treatment, instead the greater proportion undergo reversible G2/M arrest and then re-enter the cell cycle once the compound is removed. These differences in effects could reflect the fact that normal cells have checkpoints in place to halt the cell cycle if accurate chromosomal segregation does not take place, such as the post-mitotic p53-dependent checkpoint. In tumour cells these checkpoints are absent allowing mitosis to proceed and multinucleation to occur.

TABLE 3

Inhibitory effect of 1-cyclopropyl-B-B-fS-niorpholin^-ylmethyl-1H-benzoimidazol-2-yl)-1H-pyrazol-4-vH-urea on tumour cell colony formation

| Origin | Origin | IC50 (nM) | p53 Status* |
|---|---|---|---|
| Colon | HCT 116 | 13 | + |
| | HCT 116 N7 | 14 | − |
| | HT-29 | 11 | − |
| | SW620 | 14 | + |
| Ovarian | A2780 | 7.7 | + |
| Lung | A549 | 12 | + |

TABLE 3-continued

Inhibitory effect of 1-cyclopropyl-B-B-fS-niorpholin´-ylmethyl-1H-benzoimidazol-2-yl)-1H-pyrazol-4-vH-urea on tumour cell colony formation

| Origin | Origin | IC50 (nM) | p53 Status* |
|---|---|---|---|
| Breast | MCF7 | 20 | + |
| Pancreatic | MIA-Pa-Ca-2 | 7.8 | − |

*+ indicates expression of wild type p53; − indicates no expression of p53 or that p53 is non-functional.

Furthermore, salt forms of the compounds of the invention demonstrate improved solubility in aqueous solution and better physicochemical properties, e.g. a lower logD.

Methods for the Preparation of Compounds of the Formula (I)

In this section, as in all other sections of this application unless the context indicates otherwise, references to Formula (I) also include Formulae (II), (III), (XXX) and all other sub-groups and examples thereof as defined herein.

Compounds of the formula (I) can be prepared in accordance with synthetic methods well known to the skilled person.

For example, compounds of the formula (I) wherein A is a bond (i.e. where A and the carbonyl group form an amide bond), can be prepared by the reaction of a compound of the formula (X):

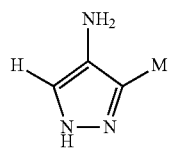

(X)

with a carboxylic acid R^-E-CO$_2$H or a reactive derivative thereof under standard amide forming conditions.

The coupling reaction between the carboxylic acid and the amine (X) can be carried out in the presence of a reagent of the type commonly used in the formation of peptide linkages. Examples of such reagents include 1,3-dicyclohexylcarbodiimide (DCC) (Sheehan et al, *J. Amer. Chem. Soc.* 1955, 77, 1067), 1-ethyl-3-(3'-dimethylaminopropyl)-carbodiimide (EDC) (Sheehan et al, *J. Org. Chem.,* 1961, 26, 2525), uronium-based coupling agents such as <9-(7-azabenzotriazol-1-yl)-N,N,N',N'-tetramethyluronium hexafluorophosphate (HATU) (L. A. Carpino, *J. Amer. Chem. Soc,* 1993, 115, 4397) and phosphonium-based coupling agents such as 1-benzotriazolyloxytris(pyrrolidino)phosphonium hexafluorophosphate (PyBOP) (Castro et al, *Tetrahedron Letters,* 1990, 31__, 205). Carbodiimide-based coupling agents are advantageously used in combination with 1-hydroxyazabenzotriazole (HOAt) or 1-hydroxybenzotriazole (HOBt) (Konig et al, *Chem. Ber.,* 103, 708, 2024-2034). Preferred coupling reagents include EDC and DCC in combination with HOAt or HOBt.

The coupling reaction is typically carried out in a non-aqueous, non-protic solvent such as acetonitrile, dioxane, dimethylsulphoxide, dichloromethane, dimethylformamide or N-methylpyrrolidone, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,iV-diisopropylethylamine.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

Amines of the formula (X) can be prepared by reduction of the corresponding nitro¬compound of the formula (XI) under Standard conditions. The reduction may be effected, for example by catalytic hydrogenation in the presence of a catalyst such as palladium on carbon in a polar solvent such as ethanol or dimethylformamide at room temperature.

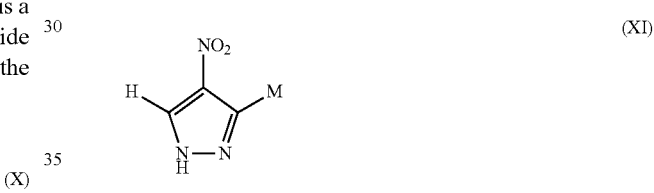

(XI)

The nitro-compounds of the formula (XI) can be prepared by reaction of the nitro-pyrazole carboxylic acid of the formula (XII):

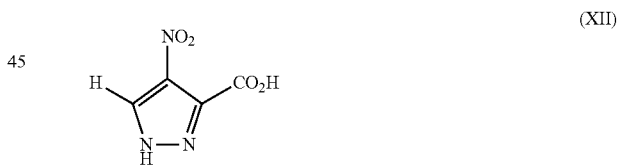

(XII)

with either 4-morpholin-4-ylmethyl-benzene-1,2-diamine (to form compounds where M is D1) or 4,5-dimethoxy-benzene-1,2-diamine (to form compounds wherein M is D2).

The reaction between the diamine and the carboxylic acid (XII) can be carried out in the presence of a reagent such as DCC or EDC in the presence of HOBt as described above, under amide coupling conditions as described previously, to give an intermediate ϕ/t/70-aminophenylamide (not shown) which is then cyclised to form the benzimidazole ring. The final cyclisation step is typically carried out by heating under reflux in the presence of acetic acid.

An illustrative reaction scheme, showing the preparation of compounds of the formula (X) where M is a group D1 is set out in Scheme 1.

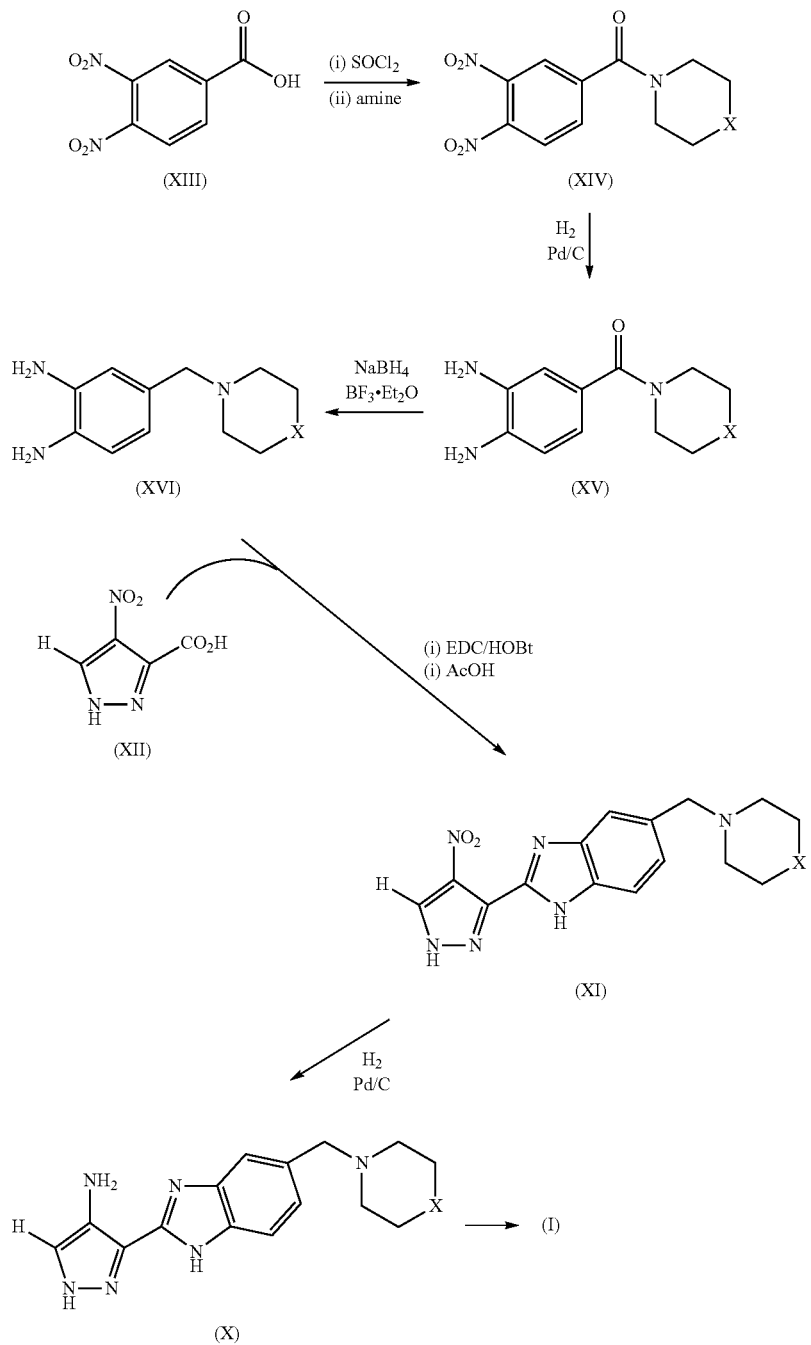

Typical conditions for each step in Scheme 1 may be found in the Examples section below.

Compounds wherein M is a group D2 can be made in an analogous manner but using 4,5-dimethoxy-benzene-1,2-diamine instead of the diamine (XVI) in Scheme 1.

In an alternative synthesis of compounds of the formula (I) wherein A is a bond, the diamines 4-morpholin-4-ylmethyl-benzene-1,2-diamine and 4,5-dimethoxy-benzene-1,2-diamine can also be reacted with carboxylic acids of the formula (XVII) where A is a bond to give compounds of the formula (I).

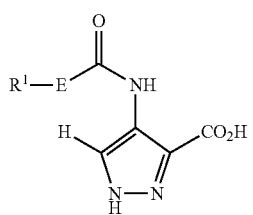

The reaction of the diamine with the carboxylic acid (XVII) can be carried out under conditions analogous to those described above for preparing the nitro¬compounds (XI). Carboxylic acids of the formula (XVII) can be prepared by the sequence of reactions shown in Scheme 2.

As shown in Scheme 2, a substituted or unsubstituted 4-nitro-3-pyrazole carboxylic acid (XVIII) can be esterified by reaction with thionyl chloride to give the acid chloride intermediate followed by reaction with ethanol to form the ethyl ester (XIX). Alternatively, the esterification can be carried out by reacting the alcohol and carboxylic acid in the presence of an acidic catalyst, one example of which is thionyl chloride. The reaction is typically earned out at room temperature using the esterifying alcohol (e.g. ethanol) as the solvent. The nitro group can then be reduced using palladium on carbon according to standard methods to give the amine (XX). The amine (XX) is coupled with an appropriate carboxylic acid R^E-CO$_2$H under amide forming conditions the same as or analogous to those described above to give the amide (XXI). The ester group of the amide (XXI) can then be hydrolysed using an alkali metal hydroxide such as sodium hydroxide in a polar water miscible solvent such as methanol, typically at room temperature.

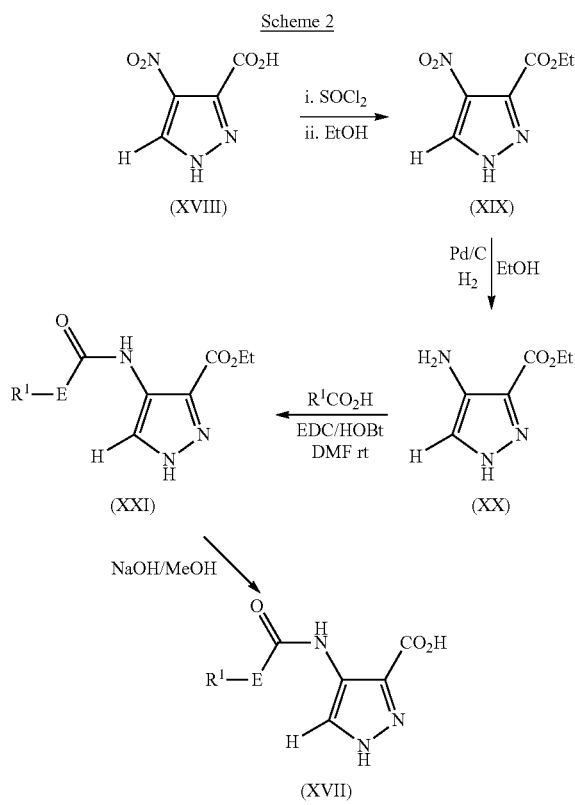

Compounds of the formula (I) in which A is NR$^2$ can be prepared using standard methods for the synthesis of ureas. For example, such compounds can be prepared by reacting an aminopyrazole compound of the formula (X) with a suitably substituted isocyanate of the formula R^-E-N=C=O in a polar solvent such as DMF. The reaction is conveniently carried out at room temperature.

Alternatively, ureas of the formula (I) can be prepared by reacting an amine of the formula (X) with an amine of the formula R$^1$-E-NH$_2$ in the presence of carbonyl diimidazole (CDI). The reaction is typically carried out in a polar solvent such as THF with heating (for example using a microwave heater) to a temperature of up to about 150° C.

Instead of using CDI, the coupling of the two amines to form the urea can be effected using triphosgene (bis(trichloromethyl)carbonate) in the presence of a non-interfering base such as triethylamine in a solvent such as dichloromethane at room temperature or below.

As a further alternative to CDI, phosgene may be used instead of triphosgene.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999). A hydroxy group may be protected, for example, as an ether (—OR) or an ester (—OC(=O)R), for example, as: a t-butyl ether; a benzyl, benzhydryl(diphenylmethyl), or trityl(triphenylmethyl) ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRC0-R) or a urethane (—NRC0-0R), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH—Bpoc), as a 9-fluorenylmethoxy amide (—NII-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-mcthoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

The acid addition salts constituting sub-group (C) of formula (I) can be formed during the synthesis of the parent compound 1-(2,6-difluorophenyl)-N-[3-(5-morpholin-4-yl-methyl-1H-benzimidazol-2-yl)-1H-pyrazol-4-yl]-urea, or by conversion of the free base of the parent compound to a desired salt, or by conversion of one salt of the parent compound to another desired salt of the parent compound. The parent compound 1-(2,6-difluoiOphenyl)-N-[3-(5-mo϶ho-lin-4-ylmethyl-1H-benzimidazol-2-yl)-1H-pyrazol-4-yl]-urea (the compound of formula (IA)) can be prepared by the method illustrated in Scheme 3 below.

As shown in Scheme 3, the 3,4-dinitrocarboxylic acid (XIII), a commercially available compound, is converted to the morpholide (XXI). Formation of the amide can be accomplished by converting the acid (XIII) to an active derivative such as an acid chloride using standard methods. For example, the acid chloride can be formed by heating with excess thionyl chloride at the reflux temperature of the thionyl chloride and then removing excess thionyl chloride by azeotrope with toluene.

The morpholide (XXI) can be reduced to the dinitrobenzyl morpholine (XXIII) by treatment with a suitable reducing agent such as sodium borohydride in combination with boron trifluoride. The reduction reaction is typically carried out in an anhydrous solvent such as tetrahydrofuran at a reduced temperature, for example a temperature of 0-5° C. The dinitrobenzylmorpholine (XXIII) can then be reduced to the diaminobenzylmorpholine (XXIV) under standard conditions, for example by catalytic hydrogenation in the presence of a catalyst such as palladium on carbon in a polar solvent such as ethanol at room temperature.

The diaminobenzyl morpholine (XXIV) is then reacted with the commercially available 4-nitropyrazole-3-carboxylic acid to form the nitropyrazolyl-benzimidazole (XXV). The formation of the nitropyrazolyl-benzimidazole (XXV) may be achieved by first forming an amide bond between the carboxylic acid and the diaminobenzyl compound (XXIV) using a peptide coupling reagent such as O-(benzotriazol-1-yl)-N,N,N',N'-tetramethyluronium tetrafluoroborate (TBTU) capable of promoting amide bond formation with an aromatic amine group. The intermediate amide (not shown) is then cyclised to the nitro-pyrazolyl-benzimidazole (XXV) by heating in excess glacial acetic acid, for example at a temperature of approximately 65° C.

The nitropyrazolyl-benzimidazole (XXV) can be reduced to the corresponding amine (XXVI) under standard conditions. The reduction may be effected, for example by catalytic hydrogenation in the presence of a catalyst such as palladium on carbon in a polar solvent such as ethanol or dimethylformamide at room temperature.

The amine (XXVI) can in turn be converted to the urea (IA) using standard methods for the synthesis of ureas, for example by reacting the amine (XXVI) with 2,6-difluorophenyl-isocyanate in a polar solvent such as THF at room temperature or below, for example at a temperature of 0-5° C.

The free base form of the urea (IA) can be used to prepare the acid addition salts of the invention.

Scheme 3

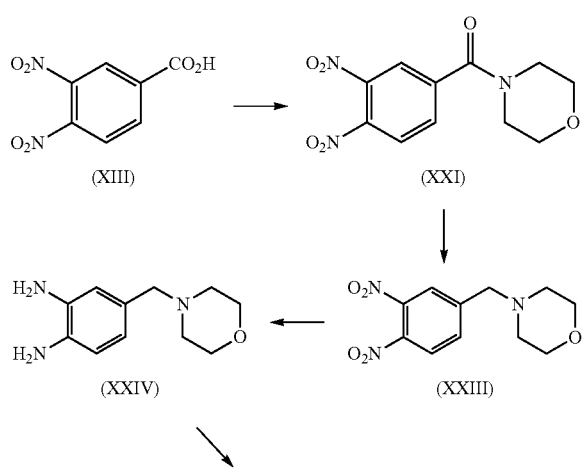

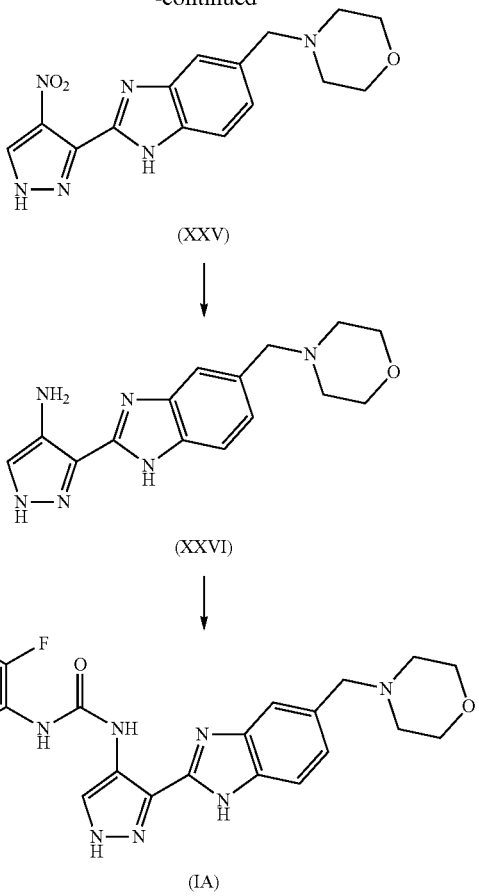

The salts of the present invention can be prepared from the free base by conventional methods such as the methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. For example, the salts can be prepared by reacting the free base with the appropriate acid in water or in an organic solvent, or in a mixture of the two; generally, nonaqueous media such as ether, ethyl acetate, methanol, ethanol, isopropanol, or acetonitrile are used.

In another aspect, the invention provides a method of preparing an acid addition salt of 1-(2,6-difluorophenyl)-N-[3-(5-morpholin-4-ylmethyl-1H-benzimidazol-2-yl)-1H-pyrazol-4-yl]-urea, which method comprises forming a solution of 1-(2,6-difluorophenyl)-N-[3-(5-morpholin-4-ylmethyl-1H-benzimidazol-2-yl)-1H-pyrazol-4-yl]-urea free base in a solvent (typically an organic solvent) or mixture of solvents, and treating the solution with an acid to form a precipitate of the acid addition salt.

The acid is typically added as a solution in a solvent which is miscible with the solvent in which the free base is dissolved.

The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

For example, in one method of preparing the salts of the invention, the free base is dissolved in a first solvent (which can be ethyl acetate or a mixture of ethyl acetate and an alcohol such as methanol) and a solution (e.g. a concentrated or saturated solution) of an acid such as hydrochloric acid in a second solvent (which can be an ether such as diethyl ether or dioxin) is then added such that a precipitate of the acid addition salt is formed, and the precipitate is then collected, for example by filtration.

Processes for Preparing 1-Cyclopropyl-3-r3-(5-morpholin-4-ylmethyl-1H-benzoimit.azol-2-vD-1H-pyrazol-4-vH-urea In the examples of our earlier application WO 2005/002552 and in Schemes 1 and 3 above, it is disclosed that a [3-(5-moφholin-4-ylmethyl-1H-benzimidazol-2-yl)-1H-pyrazol-4-yl]-amide can be prepared by a sequence of steps including:
(i) reacting 4-morpholin-4-ylmethyl-benzene-1,2-diamine with 4-nitro-1H-pyrazole-3-carboxylic acid in the presence of 1-ethyl-3-(3'-dimethylaminopropyl)-carbodiimide (EDC) and 1-hydroxybenzotriazole (IIOBt) in N,N-dimethyl formamide (DMF) to give 5-morpholin-4-ylmethyl-2-(4-nitro-1H-pyrazol-3-yl) 1H-benzimidazole; and
(ii) reducing the nitro group by treatment with palladium on carbon under a hydrogen atmosphere;
or
(i) reacting the 4-amino-1H-pyrazole-3-carboxylic ester with the appropriate carboxylic acid in the presence of 1-ethyl-3-(3'-dimethylaminopropyl)-carbodiimide (EDC) and 1-hydroxybenzotriazole (HOBt) in N,N-dimethyl formamide (DMF) or with the appropriate acid chloride in the presence of triethylamine to form the 4-amide-1H-pyrazole carboxylic acid; and
(ii) reacting 4-morpholin-4-ylmethyl-benzene-1,2-diamine with the appropriate 4-amide-1H-pyrazole carboxylic acid in the presence of 1-ethyl-3-(3'-dimethylaminopropyl)-carbodiimide (EDC) and 1-hydroxybenzotriazole (HOBt) in dimethyl formamide (DMF) to give the [3-(5-morpholin-4-ylmethyl-1H-benzimidazol-2-yl)-1H-pyrazol-4-yl]-amide.

It has now been found that instead of reacting the nitro-pyrazole compound with the diamine and then reducing the nitro group to the amine, or reacting the amide-pyrazole with the diamine, the amino-pyrazole may be reacted with the diamine provided that the amino group of the aminopyrazole is appropriately protected. The product of the reaction can then be cyclised to form the benzimidazole. In addition, it has been found that removal of the amine protecting group and cyclisation to the benzimidazole can be performed in one step.

Accordingly, in another aspect, the invention provides a process for preparing a compound of the formula (XXVII) or (XXVIII) or a salt thereof:

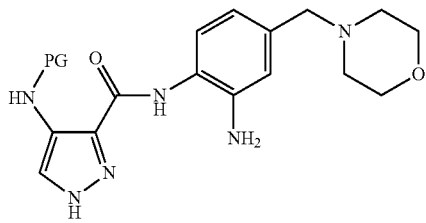

(XXVII)

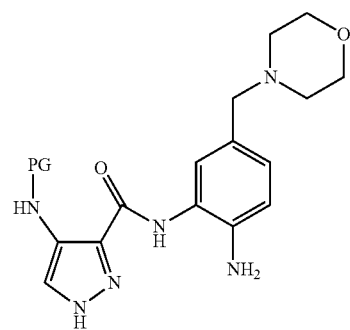

(XXVIII)

which process comprises:
(i) the reaction of a compound of the formula (XXIX):

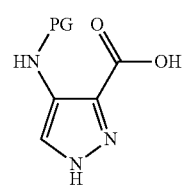

(XXIX)

where PG is an amine-protecting group:
(ii) with a compound of the formula (XXXI):

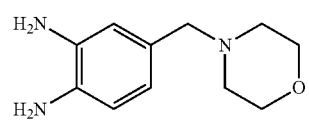

(XXXI)

in an organic solvent in the presence of a coupling agent such as EDC and HOBt:

Formula (XXVIII) is a regioisomer of (XXVII).

The amine-protecting group PG can be any protecting group known for use in protecting amine groups under the conditions used in the above process, see for example Green et al. referred to above. Thus, for example, the nitrogen may be protected as an amide (NCO—R) or a urethane (NCO—OR), for example, as: a methyl amide (NCO—CH$_3$); a benzyloxy amide (NCO—OCH$_2$C$_6$H$_5$, —NH-Cbz); as a tert-butoxy amide (—NCO—OC(CH$_3$)$_3$, N-Boc); a 2-biphenyl-2-propoxy amide (NCO—OC(CH$_3$)$_2$C$_6$H$_4$C$_6$H$_5$, N-Bpoc), as a 9-fluorenylmethoxy amide (N-Fmoc), as a 6-nitroveratryloxy amide (N-Nvoc), as a 2-trimethylsilylethyloxy amide (N—. Teoc), as a 2,2,2-trichloroethyloxy amide (N-Troc), as an allyloxy amide (N-AUoc), or as a 2-(phenylsulphonyl) ethyloxy amide (—N-Psec). Other protecting groups for amines include benzyl groups such as a parø-methoxybenzyl (PMB) group. Preferred amine protecting groups are a urethane (NCO—OR), for example, a benzyloxy amide (NCO—OCII$_2$C$_6$II$_5$, —NII-Cbz), or a tert-butoxy amide (—NCO—OC(CH$_3$)$_3$, N-Boc); or an allyloxy amide (N-Alloc). In one embodiment, the protecting group PG is a protecting group APG, which is an amine protecting group that may be removed under acidic conditions. Such groups include the urethanes. A particularly preferred urethane protecting group is tert-butyloxycarbonyl which may be removed under acidic conditions.

In one embodiment, the protecting group PG is then removed from the compound of formula (XXVII) or (XXVIII) and replaced with a protecting group, APG, to form a compound of formula (XXVIIa) or (XXVIIIa).

One particularly preferred compound of formula (XXIX) is the compound of the formula (XXXII) below:

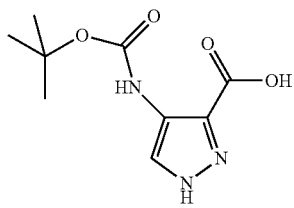
(XXXII)

The invention further provides a novel chemical intermediate per se of the formula (XXXII).

The invention also provides novel chemical intermediates per se of formula (XXVII) or (XXVIII), for example novel chemical intermediates of formula (XXVIIa) or (XXVIIIa) below. Therefore the invention provides 4-amino-1H-pyrazole-3-carboxylic acid (2-amino-4-morpholin-4-ylmethyl-phenyl)-amide or 4-amino-1H-pyrazole-3-carboxylic acid (2-amino-5-morpholin-4-ylmethyl-phenyl)-amide and protected forms thereof as a novel chemical intermediates. One particular preferred novel chemical intermediate of formula ((XXVII) is [3-(2-amino-4-morpholin-4-ylmethyl-phenylcarbamoyl)-1H-pyrazol-4-yl]-carbamic acid tert-butyl ester. One particularly preferred novel chemical intermediate of Formula (XXVIII) is [3-(2-amino-5-morpholin-4-ylmethylphenylcarbamoyl)-1H-pyrazol-4-yl]-carbamic acid tert-butyl ester.

When the protecting group PG is a tert-butyloxycarbonyl group, the overall yield from the process is in excess of 85%. Furthermore, the process is advantageous in that it makes use of relatively simple and inexpensive reagents and solvents and is also advantageous with respect to the ease of purification of the products.

In another aspect, the invention provides a process for preparing 3-(5-morpholin-4-ylmethyl-1H-benzoimidazol-2-yl)-1H-pyrazol-4-ylamine or a salt thereof, which process comprises:

(i) treating a compound of the formula (XXVIIa) or (XXVIIIa):

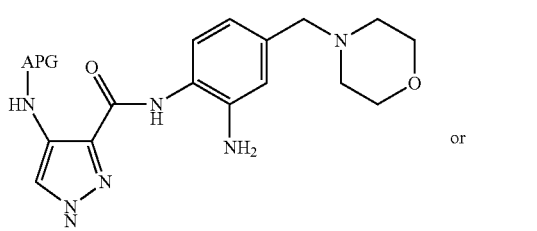
(XXVIIa)

or

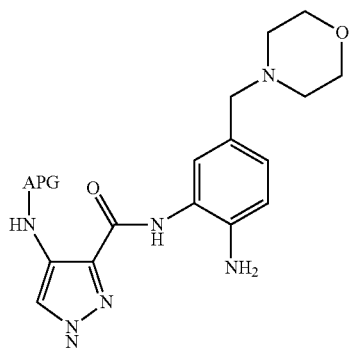
(XXVIIIa)

with an acid in a solvent, optionally with heating; and
(ii) neutralizing the reaction.

The amine-protecting group APG can be any protecting group known for use in protecting amine groups as defined above in relation to the compounds of the formulae (XXVII) or (XXVIII), and which is removable under the conditions used in the above process.

In step (i), the reaction with acid may be carried out with heating, for example to a temperature in the range 80 to 100° C. The solvent in which step (i) is carried out is an alcohol solvent, and it may be, for example, ethanol.

In step (i), the protecting group is preferably one such as the Boc group that can be removed by treatment with acid, the acid being selected so as be appropriate for protonation of the intermediate to activate the carbonyl group for the cyclisation reaction. Suitable acids include strong acids such as sulphuric acid, methanesulphonic acid or hydrochloric acid, and one particular acid is hydrochloric acid.

Following completion of the reaction in step (i), as judged for example by the disappearance of starting material (XIIIa), the reaction can be neutralized.

In step (ii), a non-interfering base is used. The term "non-interfering base" in the present context means a base such as sodium carbonate which will not react with compound produced. Step (ii) is typically carried out at room temperature.

In step (ii), the reaction is neutralized for example until the reaction is saturated with neutralizing agent and at pH 8.5.

Following step (ii), the compound can be reacted with carbonylating reagent such as 1,1'-carbonyldiimidazole (CDI) or a phosgene equivalent and then treated with cyclopropylamine. Phosgene equivalents include triphosgene or phosgene. A preferred carbonylating reagent is 1,1'-carbonyldiimidazole (CDI).

Alternatively, the urea can be prepared by reacting the aminopyrazole, 3-(5-morpholin-4-ylmethyl-1H-benzoimidazol-2-yl)-1H-pyrazol-4-ylamine, with phenyl chloroformate in the presence of a base such as pyridine in solvent e.g. THF to give the cyclic urea and then treating with cyclopropylamine, or by reacting the aminopyrazole with cyclopropylisocyanate which can be made from the Curtius rearrangement of cyclopropanecarboxylic acid azide (as described in U.S. Pat. No. 4,313,755 and U.S. Pat. No. 4,299,778).

Thus, a further aspect of the invention is a process for preparing 1-cyclopropyl-3-[3-(5-morpholin-4-ylmethyl-1H-benzoimidazol-2-yl)-1H-pyrazol-4-yl]-urea or a salt thereof, which process comprises:
(i) treating a compound of the formula ((XXVIIa) with an acid in a solvent, optionally with heating;
(ii) neutralizing the reaction;

(iii) reacting the product of step (ii) with carbonylating reagent;
(iv) reacting the product of step (iii) with cyclopropylamine.

Step (iii) is typically carried out under reflux, for example to a temperature of up to about 100° C., more typically up to 70-75° C. In step (iii), the reaction may be carried out in a polar aprotic solvent such as tetrahydrofuran. A carbonylating reagent can be a compound such as 1,1'-carbonyldiimidazole (CDI) or a phosgene equivalent such as triphosgene or phosgene. A preferred carbonylating reagent is 1,1'-carbonyldiimidazole (CDI).

Step (iv) is typically carried out with heating, for example to a temperature of up to about 100° C.

Following step (iv), the product may subjected to salt conversion or recrystallisation (e.g. using 2-propanol or ethanol as the solvent) to increase the purity and to give a crystalline form.

Step (iii) above gives rise to an intermediate compound of the formula (XXXIII) and/or its regioisomer (XXXIIIa):

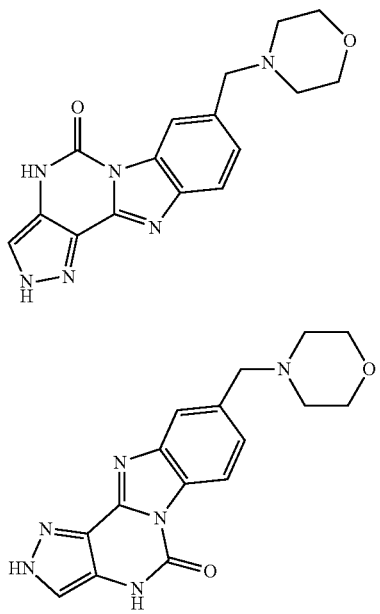

The intermediates of formulae (XXXIII) and (XXXIIIa), which can be isolated if required, are then reacted with cyclopropylamine to give a compound of the formula (XXX).

Accordingly, in another aspect, the invention provides a process for the preparation of a compound of the formula (XXX) as defined herein, which process comprises reacting a compound of the formula (XXXIII) or (XXXIIIa) with cyclopropylamine, and thereafter optionally forming an acid addition salt of the compound of the formula (XXX). The reaction is typically carried out in a polar aprotic solvent such as N-methylpyrrolidone, preferably at an elevated temperature such as a temperature in excess of 80° C., more typically in excess of 90° C., for example 95° C. to 105° C.

The foregoing process may also be used to prepare other compounds of the formula (I) and sub-groups thereof as defined herein where the moiety A in formula (I) is a group NH.

Accordingly, in a further aspect, the invention provides a process for preparing a compound of the formula (I) as defined herein, wherein the moiety A in formula (I) is a group NH; which process comprises the reaction of (i) a compound of the formula (XXXIII) and/or its regioisomer (XXXIIIa), or (ii) a compound of the formula (XXXIV) and/or its regioisomer (XXXIVa):

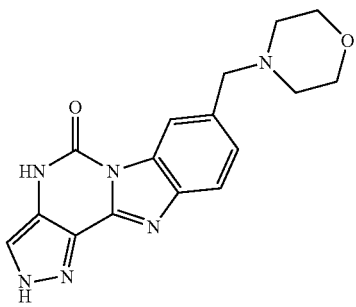

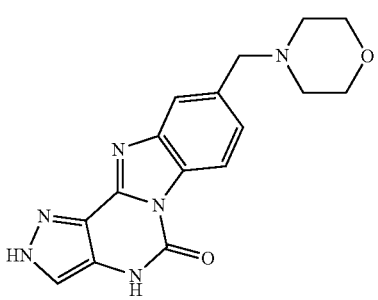

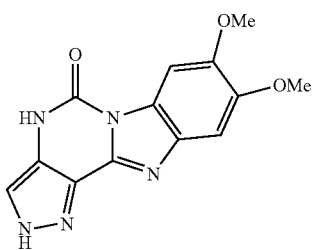

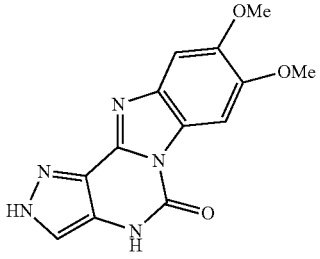

with a compound of the formula R^-E-NH$_2$, preferably in a polar aprotic solvent such as N-methylpyrrolidone, preferably at an elevated temperature such as a temperature in excess of 80° C., more typically in excess of 90° C., for example 95° C. to 105° C., and thereafter optionally forming an acid addition salt of the compound of formula (I).

The invention further provides novel chemical intermediates of the formulae (XXXIII), (XXXIIIa), (XXXIV) and (XXXIVa).

In further embodiments, the compound of formula ((XXVIIa) in the process for preparing 3-(5-morpholin-4-ylmethyl-1H-benzoimidazol-2-yl)-1H-pyrazol-4-ylamine or a salt thereof or process for preparing 1-cyclopropyl-3-[3-(5-morpholin-4-ylmethyl-1H-benzoimidazol-2-yl)-1H-pyrazol-4-yl]-urea or a salt thereof above, can be prepared by a process which comprises:

(i) reaction of a compound of the formula (XXIX), where PG is an amine-protecting group which is removable with acid, APG;

(ii) with a compound of the formula (XXXI) in an organic solvent in the presence of a coupling agent such as EDC and HOBt.

Optionally the processes described herein have the further step of recrystallising the salt to give a crystalline form, e.g. a crystalline form as defined herein.

Methods of Purification

The compounds of the invention may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C, Development of a custom high-throughput preparative liquid chromatography/mass spectrometer platform for the preparative purification and analytical analysis of compound libraries; *J Comb Chem.;* 2003; 5(3); 322-9.

One such system for purifying compounds via preparative LC-MS is described in the experimental section below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Recrystallisation

Methods of recrystallisation of compounds of formula (I) and salt thereof, in particular 1-cyclopropyl-3-[3-(5-morpholin-4-ylmethyl-1H-benzoimidazol-2-yl)-1H-pyrazol-4-yl]-urea and its salts can be carried out by methods well known to the skilled person—see for example (P. Heinrich Stahl (Editor), Camille G. Wermuth (Editor), ISBN: 3-90639-026-8, Handbook of Pharmaceutical Salts: *Properties, Selection, and Use*, Chapter 8, Publisher Wiley-VCH). Products obtained from an organic reaction are seldom pure when isolated directly from the reaction mixture. If the compound (or a salt thereof) is solid, it may be purified and/or crystallized by recrystallization from a suitable solvent. A good recrystallization solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallizing solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for crystallization include crystallization from a vapor, which includes an evaporation step for example in a sealed tube or an air stream, and crystallization from melt (Crystallization Technology Handbook 2nd Edition, edited by A. Mersmann, 2001).

In particular the compound of formula (I) may subjected to recrystallisation (e.g. using 2-propanol or ethanol as the solvent) to increase the purity and to give a crystalline form.

Generally, the crystals obtained are analysed by an X-ray diffraction method such as X-ray powder diffraction (XRPD) or X-ray crystal diffraction.

Pharmaceutical Formulations

While it is possible for the active compound or salt thereof to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents; for example agents that reduce or alleviate some of the side effects associated with chemotherapy. Particular examples of such agents include anti-, emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compounds of the formula (I) and sub-groups thereof such as formulae (II) and (III) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intra-peritoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Examples of these are described in R. G. Strickly, Solubilizing Excipients in oral and injectable formulations, Pharmaceutical Research, Vol 21(2) 2004, p 201-230. In addition, they may contain co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

A drug molecule that is ionizable can be solubilized to the desired concentration by pH adjustment if the drug's pKa is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to rV bolus or IV infusion.

Alternatively increased water solubility can be achieved through molecular complexation with cyclodextrins Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at ~5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (I) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediamietetraacetic acid salts. Preservatives may include benzoic acid and its salts, sorbic acid and its salts, alkyl esters ofpara-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

Pharmaceutical compositions of the present invention for parenteral injection can also comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If a compound is not stable in aqueous media or has low solubility in aqueous media, it can be formulated as a concentrate in organic solvents. The concentrate can then be diluted to a lower concentration in an aqueous system, and can be sufficiently stable for the short period of time during dosing. Therefore in another aspect, there is provided a pharmaceutical composition comprising a non aqueous solution composed entirely of one or more organic solvents, which can be dosed as is or more commonly diluted with a suitable IV excipient (saline, dextrose; buffered or not buffered) before administration (Solubilizing excipients in oral and injectable formulations, Pharmaceutical Research, 21(2), 2004, p 201-230). Examples of solvents and surfactants are propylene glycol, PEG300, PEG400, ethanol, dimethylacetamide (DMA), N-methyl-2-pyrrolidone (NMP, Pharmasolve), Glycerin, Cremophor EL, Cremophor RH 60 and polysorbate. Particular non aqueous solutions are composed of 70-80% propylene glycol, and 20-30% ethanol. One particular non aqueous solution is composed of 70% propylene glycol, and 30% ethanol. Another is 80% propylene glycol and 20% ethanol. Normally these solvents are used in combination and usually diluted at least 2-fold before IV bolus or IV infusion. The typical amounts for bolus IV formulations are ~50% for Glycerin, propylene glycol, PEG300, PEG400, and ~20% for ethanol. The typical amounts for IV infusion formulations are ~15% for Glycerin, 3% for DMA, and ~10% for propylene glycol, PEG300, PEG400 and ethanol.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a nialeic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, e.g. from 1 nanogram to 2 milligrams of active ingredient. Within this range, particular sub-¬ ranges of compound are 0.1 milligrams to 2 grams of active ingredient (more usually from 10 milligrams to 1 gram, for example, 50 milligrams to 500 milligrams or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the formulae (I), (II), (III), (XXX) and sub-¬ groups as defined herein will be useful in the prophylaxis or treatment of a range of disease states or conditions mediated by cyclin dependent kinases, glycogen synthase kinase-3 and Aurora kinases. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, such as 1 microgram to 10 milligrams) per kilogram of bodyweight although higher or lower doses may be administered where required.

The compounds (e.g. the compound 1-cyclopropyl-3-[3-(5-morpholin-4-ylmethyl-1H-benzoimidazol-2-yl)-1H-pyrazol-4-yl]-urea or a salt thereof such as the lactate or citrate salt) can be administered on a daily basis or on a repeat basis every 2, or 3, or 4, or 5, or 6, or 7, or 10 or 14, or 21, or 28 days for example. Ultimately, however, the quantity of compound administered and the type of composition used will be commensurate with the nature of the disease or physiological condition being treated and will be at the discretion of the physician.

An example of a daily dosage regimen for the compound 1-cyclopropyl-3-[3-(5-morpholin-4-ylmethyl-1H-benzoimidazol-2-yl)-1H-pyrazol-4-yl]-urea or a salt thereof such as the lactate (particularly the L-lactate) or citrate salt comprises administering the said compound (e.g. in the form of the L-lactate salt) at a starting dosage of 1 mg/ni$^2$/day-100 mg/m$^2$/day, in particular 1 mg/m$^2$/day-10 mg/m$^2$/day more particularly 3-6 mg/m$^2$/day (equivalent to 2.5-5 mg free base/m$^2$/day) or at an efficacious dose of the lactate salt of 2.5 mg/ni$^2$/day-1.5 g/m$^2$/day, in particular 25 mg/m$^2$/day-600 mg/ni$^2$/day, more particularly 200-500 mg/m$^2$/day such as 250 mg/m$^2$/day or 45-200 mg/m$^2$/day such as 45-150 mg/m$^2$/day or 56-185 mg/m$^2$/day (equivalent to 45-150 mg free base/m$^2$/day) although higher or lower doses may be administered where required.

In one particular dosing schedule, a patient will be given accontinuous IV infusion of 1-cyclopropyl-3-[3-(5-morpholin-4-ylmethyl-1H-benzoimidazol-2-yl)-1H-pyrazol-4-yl]-urea or a salt thereof such as the lactate (particularly the L-lactate) or citrate salt, for periods of 2 hour to 120 hour, for example 2 to 96 hour in particular for 24 to 72 hour and the treatment repeated at a desired interval such as every one to three weeks.

More particularly, a patient may be given a continuous IV infusion of 1-cyclopropyl-3-[3-(5-morpholin-4-ylmethyl-1H-benzoimidazol-2-yl)-1H-pyrazol-4-yl]-urea or a salt thereof such as the lactate (particularly the L-lactate) or citrate salt for periods of 24 hour daily for 5 days and the treatment repeated every week, or for periods of 48 hour and the treatment repeated every two weeks or for periods of 72 hour and the treatment repeated every three weeks.

In another particular dosing schedule, a patient is given an infusion of 1-cyclopropyl-3-[3-(5-morpholin-4-ylmethyl-1H-benzoimidazol-2-yl)-1H-pyrazol-4-yl]-urea or a salt thereof such as the lactate (particularly the L-lactate) or citrate salt as an IV bolus over 2 hour once a day for a week every 1, 2, or 3 weeks or over 2 hour once every 1, 2, or 3 weeks.

Higher doses such as 1.5 g/m$^2$/day could be administered using a dosing regimen with frequent off-treatment periods such as 24 to 48 hour continuous IV fusion every one to two weeks. Lower dosages such could be administered using a dosing regimens with more sustained dosing (but still cyclical on/off) such as 48 to 72 hour continuous IV fusion every two to three weeks.

In particular, compounds of the formula (F) or 1-cyclopropyl-3-[3-(5-morpholin-4-ylmethyl-1H-benzoimidazol-2-yl)-1H-pyrazol-4-yl]-urea or all salts thereof such as the lactate or citrate salt in particular the lactate salt could be administered to a patient at 250 mg/m$^2$/day for 72 hours by continuous IV infusion every 3 weeks.

In another embodiment, compounds of the formula (F) or 1-cyclopropyl-3-[3-(5-morpholin-4-ylmethyl-1H-benzoimidazol-2-yl)-1H-pyrazol-4-yl]-urea or all salts thereof such as the lactate or citrate salt in particular the lactate salt could be administered to a patient over a five day treatment cycle.

Ultimately, the quantity of compound administered and the type of composition used will be commensurate with the nature of the disease or physiological condition being treated and will be at the discretion of the physician.

The compounds of formulae (I), (II), (III), (XXX) and sub-groups as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or therapies that may be administered or used together (whether concurrently or at different time intervals) with the compounds of the invention include but are not limited to topoisomerase inhibitors, alkylating agents, antimetabolites, DNA binders, microtubule inhibitors (tubulin targeting agents), particular examples being cisplatin, cyclophosphamide, doxorubicin, irinotecan, fludarabine, 5FU, taxanes, mitomycin C and radiotherapy.

Other examples of therapeutic agents that may be administered together (whether concurrently or at different time intervals) with the compounds of the formulae (I), (II), (III), (XXX) and sub-groups as defined herein include monoclonal antibodies and signal transduction inhibitors.

For the case of CDK or Aurora inhibitors combined with other therapies, the two or more treatments may be given in individually varying dose schedules and via different routes.

Where the compound of the formula (I) is administered in combination therapy with one, two, three, four or more other therapeutic agents (preferably one or two, more preferably one), the compounds can be administered simultaneously (either in the same or different pharmaceutical formulation) or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against Aurora and/or cyclin dependent kinases.

For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol. Chem. 2004 Mar. 26; 279(13):12695-705) or loss of p21 or p27, or presence of CDC4 variants (Rajagopalan H, Jallepalli P V, Rago C, Velculescu V E, Kinzler K W, Vogelstein B, Lengauer C; Nature. 2004 Mar. 4; 428(6978):77-81). Tumours with mutants of CDC4 or up-regulation, in particular over-expression, of cyclin E or loss of p21 or p27 may be particularly sensitive to CDK inhibitors. Alternatively or in addition, a biological sample taken from a patient may be analysed to determine whether a condition or disease, such as cancer, that the patient is or may be suffering from is one which is characterised by upregulation of Aurora kinase and thus may be particularly to Aurora inhibitors. The term up-regulation includes elevated expression or over-expression, including gene amplification (i.e. multiple gene copies) and increased expression by a transcriptional effect, and hyperactivity and activation, including activation by mutations.

Thus, the patient may be subjected to a diagnostic test to detect a marker characteristic of over-expression, up-regulation or activation of Aurora kinase or the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of Aurora or CDC4. The term marker also includes markers which are characteristic of up regulation of Aurora or cyclin E, including enzyme-activity, enzyme levels, enzyme state (e.g. phosphorylated or not) and mRNA levels of the aforementioned proteins. Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, see Ewart-Toland et al., (Nat. Genet. 2003 August; 34(4):403-12), that individuals forming part of the sub-population possessing the Ile31 variant of the STK gene (the gene for Aurora kinase A) may have an increased susceptibility to certain forms of cancer. It is envisaged therefore that such individuals suffering from cancer will benefit from the administration of compounds having Aurora kinase inhibiting activity. A patient suffering from, or suspected of suffering from, a cancer may therefore be screened to determine whether he or she forms part of the He31 variant sub-population. In addition, it has been found, Rajagopalan et al (Nature. 2004 Mar. 4; 428(6978):77-81), that there were mutations present in CDC4 (also known as Fbw7 or Archipelago) in human colorectal cancers and endometrial cancers (Spruck et al, Cancer Res. 2002 Aug. 15; 62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Tumours with activating mutants of Aurora or up-regulation of Aurora including any of the isoforms thereof, may be particularly sensitive to Aurora inhibitors. Tumours may preferentially be screened for up-regulation of Aurora or for Aurora possessing the Ile31 variant prior to treatment (Ewart-Toland et al., Nat. Genet. 2003 August; 34(4):403-12). Ewart-Toland et al identified a common genetic variant in STK1 5 (resulting in the amino acid substitution F311) that is preferentially amplified and associated with the degree of aneuploidy in human colon tumors. These results are consistent with an important role for the Ile31 variant of STK1 5 in human cancer susceptibility. In particular, this polymorphism in Aurora A has been suggested to be a genetic modifier fir developing breast carcinoma (Sun et al, Carcinogenesis, 2004, 25(11), 2225-2230).

The aurora A gene maps to the chromosome 2Oq13 region that is frequently amplified in many cancers e.g. breast, bladder, colon, ovarian, pancreatic. Patients with a tumour that has this gene amplification might be particularly sensitive to treatments targeting aurora kinase inhibition Methods of identification and analysis of mutations and up-regulation of protein e.g. Aurora isoforms and chromosome 20q13 amplification are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al, eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272, 057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants, Aurora up-regulation and mutants of Aurora could be applicable in the present case.

Therefore, all of these techniques could also be used to identify tumours particularly suitable for treatment with the compounds of the invention.

Tumours with mutants of CDC4 or up-regulation, in particular over-expression, of cyclin E or loss of p21 or p27 may be particularly sensitive to CDK inhibitors. Tumours may preferentially be screened for up-regulation, in particular over-expression, of cyclin E (Harwell R M, Mull B B, Porter D C, Keyomarsi K.; J Biol Chem. 2004 Mar. 26; 279(13): 12695-705) or loss of p21 or p27 or for CDC4 variants prior to treatment (Rajagopalan H, Jallepalli P V, Rago C, Velculescu V E, Kinzler K W, Vogelstein B, Lengauer C; Nature. 2004 Mar. 4; 428(6978):77-81).

Patients with mantle cell lymphoma (MCL) could be selected for treatment with a compound of the invention using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11; 14)(q13; q32) translocation. Over-expression of cyclin D1 mRNA, found in mantle cell lymphoma (MCL), is a critical diagnostic marker. Yatabe et al (Blood. 2000 Apr. 1; 95(7):2253-61) proposed that cyclin D1-positively should be included as one of the standard criteria for MCL, and that innovative therapies for this incurable disease should be explored on the basis of the new criteria. Jones et al (J MoI Diagn. 2004 May; 6(2):84-9) developed a real-time, quantitative, reverse transcription PCR assay for cyclin D1 (CCND1) expression to aid in the diagnosis of mantle cell lymphoma (MC1). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD 19 mRNA can be used in the diagnosis of MCL in blood, marrow, and tissue. Alternatively, patients with breast cancer could be selected for treatment with a CDK inhibitor using diagnostic tests outline above. Tumour cells commonly overexpress cyclin E and it has been shown that cyclin E is overexpressed in breast cancer (Harwell et al, Cancer Res, 2000, 60, 481-489). Therefore breast cancer may in particular be treated with a CDK inhibitor as provided herein.

Antifungal Use

In a further aspect, the invention provides the use of the compounds of the formula (I), (II), (III), (XXX) and sub-groups thereof as defined herein as antifungal agents.

The compounds of the formula (I), (II), (III), (XXX) and sub-groups thereof as defined herein may be used in animal medicine (for example in the treatment of mammals such as humans), or in the treatment of plants (e.g. in agriculture and horticulture), or as general antifungal agents, for example as preservatives and disinfectants.

In one embodiment, the invention provides a compound of the formula (I), (II), (III), (XXX) and sub-groups thereof as defined herein for use in the prophylaxis or treatment of a fungal infection in a mammal such as a human.

Also provided is the use of a compound of the formula (I), (II), (III), and sub-¬ groups thereof as defined herein for the manufacture of a medicament for use in the prophylaxis or treatment of a fungal infection in a mammal such as a human.

For example, compounds of the invention may be administered to human patients suffering from, or at risk of infection by, topical fungal infections caused by among other organisms, species of *Candida, Trichophyton, Microsporum* or *Epidermophyton*, or in mucosal infections caused by *Candida albicans* (e.g. thrush and vaginal candidiasis). The compounds of the invention can also be administered for the treatment or prophylaxis of systemic fungal infections caused by, for example, *Candida albicans, Cryptococcus neoformans, Aspergillus flavus, Aspergillus fumigatus, Coccidiodies, Paracoccidioides, Histoplasma* or *Blastomyces*.

In another aspect, the invention provides an antifungal composition for agricultural (including horticultural) use, comprising a compound of the formulae (I), (II), (III), (XXX) and sub-groups thereof as defined herein together with an agriculturally acceptable diluent or carrier.

The invention further provides a method of treating an animal (including a mammal such as a human), plant or seed having a fungal infection, which comprises treating said animal, plant or seed, or the locus of said plant or seed, with an effective amount of a compound of the formula (I), (II), (III), (XXX) and sub-groups thereof as defined herein.

The invention also provides a method of treating a fungal infection in a plant or seed which comprises treating the plant or seed with an antifungally effective amount of a fungicidal composition containing a compound of the formula (I), (II), (III), (XXX), and sub-groups thereof as defined herein.

Differential screening assays may be used to select for those compounds of the present invention with specificity for non-human CDK enzymes. Compounds which act specifically on the CDK enzymes of eukaryotic pathogens can be used as anti-¬ fungal or anti-parasitic agents Inhibitors of the *Candida* CDK kinase, CKSI, can be used in the treatment of candidiasis. Antifungal agents can be used against infections of the type hereinbefore defined, or opportunistic infections that commonly occur in debilitated and immunosuppressed patients such as patients with leukemias and lymphomas, people who are receiving immunosuppressive therapy, and patients with predisposing conditions such as diabetes mellitus or AIDS, as well as for non-immunosuppressed patients.

Assays described in the art can be used to screen for agents which may be useful for inhibiting at least one fungus implicated in mycosis such as candidiasis, aspergillosis, *mucormycosis, blastomycosis, geotrichosis, cryptococcosis, chromoblastomycosis, coccidiodomycosis, conidiosporosis, histoplasmosis, maduromycosis, rhinosporidosis, nocardiosis, para-actinomycosis, penicilliosis, monoliasis*, or *sporotrichosis*. The differential screening assays can be used to identify anti-fungal agents which may have therapeutic value in the treatment of aspergillosis by making use of the CDK genes cloned from yeast such as *Aspergillus fumigatus, Aspergillus flavus, Aspergillus niger, Aspergillus nidulans*, or *Aspergillus terreus*, or where the mycotic infection is muconnycosis, the CDK assay can be derived from yeast such as *Rhizopus arrhizus, Rhizopus oryzae, Absidia corymbifera, Absidia ramosa*, or *Mucor pusillus*. Sources of other CDK enzymes include the pathogen *Pneumocystis carinii*.

By way of example, in vitro evaluation of the antifungal activity of the compounds can be performed by determining the minimum inhibitory concentration (M.I.C.) which is the concentration of the test compounds, in a suitable medium, at which growth of the particular microorganism fails to occur. In practice, a series of agar plates, each having the test compound incorporated at a particular concentration is inoculated with a standard culture of, for example, *Candida albicans* and each plate is then incubated for an appropriate period at 37° C. The plates are then examined for the presence or absence of growth of the fungus and the appropriate M.I.C. value is noted. Alternatively, a turbidity assay in liquid cultures can be performed and a protocol outlining an example of this assay can be found in Example 64.

The in vivo evaluation of the compounds can be carried out at a series of dose levels by intraperitoneal or intravenous injection or by oral administration, to mice that have been inoculated with a fungus, e.g., a strain of *Candida albicans* or *Aspergillus flavus*. The activity of the compounds can be assessed by monitoring the growth of the fungal infection in groups of treated and untreated mice (by histology or by retrieving fungi from the infection). The activity may be measured in terms of the dose level at which the compound provides 50% protection against the lethal effect of the infection ($PD_{50}$).

For human antifungal use, the compounds of the formula (I), (II), (III), (XXX) and sub-groups thereof as defined herein can be administered alone or in admixture with a pharmaceutical carrier selected in accordance with the intended route of administration and standard pharmaceutical practice. Thus, for example, they may be administered orally, parenterally, intravenously, intramuscularly or subcutaneously by means of the formulations described above in the section headed "Pharmaceutical Formulations".

For oral and parenteral administration to human patients, the daily dosage level of the antifungal compounds of the invention can be from 0.01 to 10 mg/kg (in divided doses), depending on inter alia the potency of the compounds when administered by either the oral or parenteral route. Tablets or capsules of the compounds may contain, for example, from 5 mg to 0.5 g of active compound for administration singly or two or more at a time as appropriate. The physician in any event will determine the actual dosage (effective amount)

which will be most suitable for an individual patient and it will vary with the age, weight and response of the particular patient.

Alternatively, the antifungal compounds can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

In addition to the therapeutic uses described above, antifungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms. In similar fashion, side by side comparison of inhibition of a mammalian CDK and an insect CDK, such as the Drosophilia CDK5 gene (Heimlich et al. (1994) FEBS Lett 356:317-21), will permit selection amongst the compounds herein of inhibitors which discriminate between the human/mammalian and insect enzymes. Accordingly, the present invention expressly contemplates the use and formulation of the compounds of the invention in insecticides, such as for use in management of insects like the fruit fly.

In yet another embodiment, certain of the subject CDK inhibitors can be selected on the basis of inhibitory specificity for plant CDK's relative to the mammalian enzyme. For example, a plant CDK can be disposed in a differential screen with one or more of the human enzymes to select those compounds of greatest selectivity for inhibiting the plant enzyme. Thus, the present invention specifically contemplates formulations of the subject CDK inhibitors for agricultural applications, such as in the form of a defoliant or the like.

For agricultural and horticultural purposes the compounds of the invention may be used in the form of a composition formulated as appropriate to the particular use and intended purpose. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they can be manufactured in accordance with conventional procedures. The compositions may also incorporate other active ingredients, for example, compounds having licrbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack. By way of example, the compositions may contain from 0.01 to 1 wt. % of the active ingredient. For field use, likely application rates of the active ingredient may be from 50 to 5000 g/hectare.

The invention also contemplates the use of the compounds of the formula (I), (II), (III), (XXX) and sub-groups thereof as defined herein in the control of wood decaying fungi and in the treatment of soil where plants grow, paddy fields for seedlings, or water for perfusion. Also contemplated by the invention is the use of the compounds of the formula (I), (II), (III), (XXX) and sub-groups thereof as defined herein to protect stored grain and other non-plant loci from fungal infestation.

EXAMPLES

Figure 1:
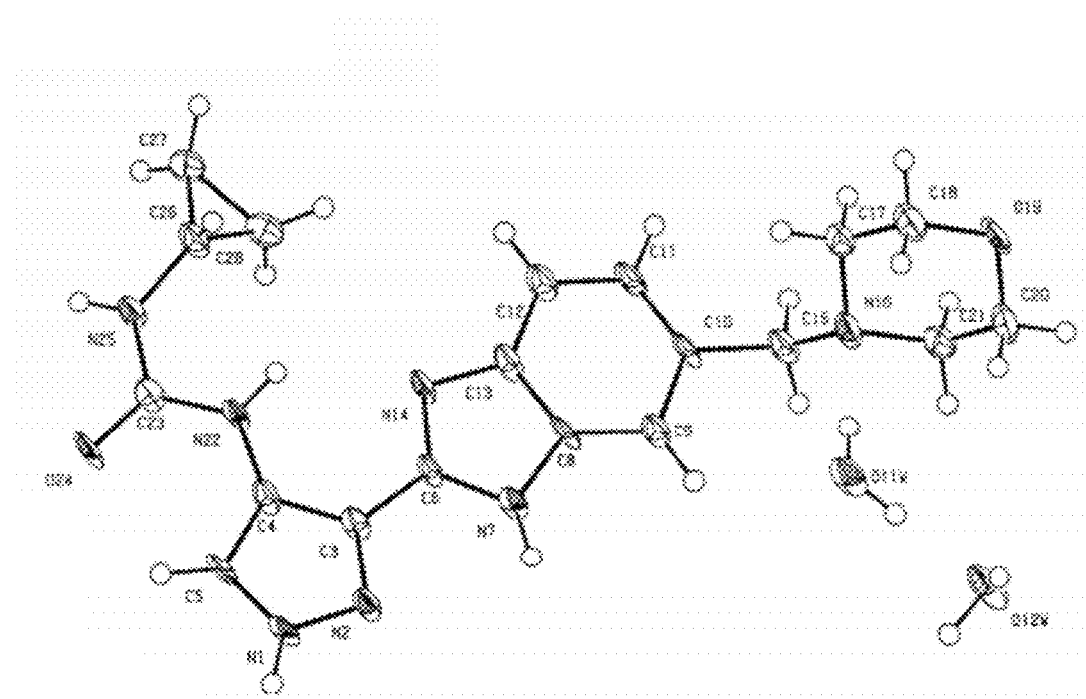
FIG. 1 is a thermal ellipsoid plot of the free base dihydrate of 1-cyclopropyl-3-[3-(5-morpholin-4-ylmethyl-1H-benzoimidazol-2-yl)-1H-pyrazol-4-yl]-urea as described in Example 69 below.

The invention will now be illustrated, but not limited, by reference to the specific embodiments described in the following examples.

In the examples, the following abbreviations are used.
AcOH acetic acid
BOC te/Y-hutyloxycarhonyl
CDI 1,1-carbonyldiimidazole
DMAW90 Solvent mixture: DCM: MeOH, AcOH, $H_2O$ (90:18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
$Et_3N$ triethylamine
EtOAc ethyl acetate
$Et_2O$ diethyl ether
HOBt 1-hydroxyazabenzotriazole
HOBt 1-hydroxybenzotriazole
MeCN acetonitrile
MeOH methanol
SiO, silica TBTU N,N,N^N'-tetramethyl-O-(benzotriazol-1-yl)uronium tetrafluoroborate
THF tetrahydrofuran Analytical LC-MS System and Method Description In the examples, the compounds prepared were characterised by liquid chromatography and mass spectroscopy using the systems and operating conditions set out below. Where atoms with different isotopes are present, and a single mass quoted, the mass quoted for the compound is the monoisotopic mass (i.e. $^{35}$Cl; $^{79}$Br etc.). Several systems were used, as described below, and these were equipped with, and were set up to run under, closely similar operating conditions. The operating conditions used are also described below.

Waters Platform LC-MS System:
HPLC System: Waters 2795
Mass Spec Detector: Micromass Platform LC
PDA Detector: Waters 2996 PDA
Analytical Acidic Conditions:
Eluent A: $H_2O$ (0.1% Formic Acid)
Eluent B: $CH_3CN$ (0.1% Formic Acid)
Gradient: 5-95% eluent B over 3.5 minutes
Flow: 0.8 ml/min
Column: Phenomenex Synergi 4μ MAX-RP 8OA, 2.0×50 mm
Analytical Basic Conditions:
Eluent A: $H_2O$ (1O mM $NH_4HCO_3$ buffer adjusted to pH=9.2 with $NH_4OH$)
Eluent B: $CH_3CN$
Gradient: 05-95% eluent B over 3.5 minutes
Flow: 0.8 ml/min
Column: Phenomenex Luna C18(2) 5 μm 2.0×50 mm
Analytical Polar Conditions:
Eluent A: $H_2O$ (0.1% Formic Acid)
Eluent B: $CH_3CN$ (0.1% Formic Acid)
Gradient: 00-50% eluent B over 3 minutes
Flow: 0.8 ml/min
Column: Phenomenex Synergi 4μ MAX-RP 80A, 2.0×50 mm
Analytical Lipophilic Conditions:
Eluent A: $H_2O$ (0.1% Formic Acid)
Eluent B: $CH_3CN$ (0.1% Formic Acid)
Gradient: 55-95% eluent B over 3.5 minutes
Flow: 0.8 ml/min
Column: Phenomenex Synergi 4μ MAX-RP 80A, 2.0×50 mm
Analytical Long Acidic Conditions:
Eluent A: $H_2O$ (0.1% Formic Acid)
Eluent B: $CH_3CN$ (0.1% Formic Acid)
Gradient: 05-95% eluent B over 15 minutes
Flow: 0.4 ml/min
Column: Phenomenex Synergi 4μ MAX-RP 8OA, 2.0×150 mm
Analytical Long Basic Conditions:
Eluent A: $H_2O$ (1O mM $NH_4HCO_3$ buffer adjusted to pH=9.2 with $NH_4OH$)
Eluent B: $CH_3CN$
Gradient: 05-95% eluent B over 15 minutes
Flow: 0.8 ml/min
Column: Phenomenex Lima C18(2) 5 μm 2.0×50 mm
Platform MS Conditions:
Capillary voltage: 3.6 kV (3.40 kV on ES negative)
Cone voltage: 25 V
Source Temperature: 120° C.
Scan Range: 100-800 amu
Ionisation Mode: ElectroSpray Positive or
  ElectroSpray Negative or
  ElectroSpray Positive & Negative Waters Fractionlynx LC-MS system:
HPLC System: 2767 autosampler—2525 binary gradient pump
Mass Spec Detector: Waters ZQ
PDA Detector: Waters 2996 PDA
Analytical Acidic Conditions:
Eluent A: $H_2O$ (0.1% Formic Acid)
Eluent B: $CH_3CN$ (0.1% Formic Acid)
Gradient: 5-95% eluent B over 4 minutes
Flow: 2.0 ml/min
Column: Phenomenex Synergi 4μ MAX-RP 80A, 4.6×50 mm
Analytical Polar Conditions:
Eluent A: $H_2O$ (0.1% Formic Acid)
Eluent B: $CH_3CN$ (0.1% Formic Acid)
Gradient: 00-50% eluent B over 4 minutes
Flow: 2.0 ml/min
Column: Phenomenex Synergi 4μ MAX-RP $80A_S$ 4.6×50 mm
Analytical Lipophilic Conditions:
Eluent A: $H_2O$ (0.1% Formic Acid)
Eluent B: $CH_3CN$ (0.1% Formic Acid)
Gradient: 55-95% eluent B over 4 minutes
Flow: 2.0 ml/min
Column: Phenomenex Synergi 4μ MAX-RP 8OA, 4.6×50 mm
Fractionlynx Ms Conditions:
Capillary voltage: 3.5 kV (3.2 kV on ES negative)
Cone voltage: 25 V (30 V on ES negative)
Source Temperature: 120° C.
Scan Range: 100-800 amu
Ionisation Mode: ElectroSpray Positive or
  Electro Spray Negative or
  ElectroSpray Positive & Negative Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C, Development of a custom high-throughput preparative liquid chromatography/mass spectrometer platform for the preparative purification and analytical analysis of compound libraries; *J Comb Chem.*; 2003; 5(3); 322-9.

One such system for purifying compounds via preparative LC-MS is described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS Systems:
Waters Fractionlynx System:
  Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
  Software:
Masslynx 4.0
  Waters MS running conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode ElectroSpray Positive or
  ElectroSpray Negative
Agilent 1100 LC-MS Preparative System:
  Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter
  Software:
Chemstation: Chem32
  Agilent MS running conditions:
Capillary voltage: 4000 V (3500 V on ES Negative)
Fragmentor/Gain: 150/1
Drying gas flow: 13.0 L/min
Gas Temperature: 350° C.
Nebuliser Pressure: 50 psig
Scan Range: 125-800 amu
Ionisation Mode ElectroSpray Positive or
  ElectroSpray Negative
Chromatographic Conditions:
  Columns:
1. Low pH Chromatography:
Phenomenex Synergy MAX-RP, 10μ, 100×21.2 mm
(alternatively used Thermo Hypersil-Keystone HyPurity Aquastar, 100×21.2 mm for more polar compounds)
2. High pH Chromatography:
Phenomenex Luna C18 (2), 10μ, 100×21.2 mm
(alternatively used Phenomenex Gemini, 5μ, 100×21.2 mm)
  Eluents:
1. Low pH Chromatography:
Solvent A: $H_2O$+0.1% Formic Acid, pH-1.5
Solvent B: $CH_3CN$+0.1% Formic Acid
2. High pH Chromatography:
Solvent A: $H_2O$+10 mM $NH_4HCO_3$+$NH_4OH$, pH=9.2
Solvent B: $CH_3CN$
3. Make Up Solvent:
MeOH+0.2% Formic Acid (for both chromatography type)

Methods:

According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen. Typical running condition for both low and high pH chromatography methods were:

Flow rate: 24 ml/min

Gradient: Generally all gradients had an initial 0.4 min step with 95% A+5% B. Then according to analytical trace a 3.6 min gradient was chosen in order to achieve good separation (e.g. from 5% to 50% B for early retaining compounds; from 35% to 80% B for middle retaining compounds and so on)

Wash: 1.2 minute wash step was performed at the end of the gradient

Re-equilibration: 2.1 minutes re-equilibration step was ran to prepare the system for the next run Make Up flow rate: 1 ml/min Solvent:

All compounds were usually dissolved in 100% MeOH or 100% DMSO

From the information provided someone skilled in the art could purify the compounds described herein by preparative LC-MS.

The starting materials for each of the Examples are commercially available unless otherwise specified.

Example 1

Synthesis of 5-cyano-2-methoxy-N-[3-(5-morpholin-4-ylmethyl-1H-benzoimidazol-2-yl')-1H-pyrazol-4-yl]-benzamide IA. Synthesis of (3,4-Dinitro-phenyl)-morpholin-4-yl-methan one

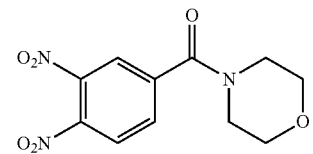 [SMILES: O=C(c1ccc([N+](=O)[O-])c([N+](=O)[O-])c1)N1CCOCC1]

A mixture of 3,4-dinitrobenzoic acid (10.0 g) and thionyl chloride (30 ml) was heated at reflux for 2 hours, cooled to ambient temperature and excess thionyl chloride removed through azeotrope with toluene. The residue was taken up in THF (100 ml) and morpholine (4.1 ml) and $Et_3N$ (7.2 ml) added concurrently to the mixture at 0° C. The mixture was stirred for 3 hours, water (100 ml) added and then extracted with EtOAc. The organic portion was washed with brine, dried ($MgSO_4$) and reduced in vacuo. Recrystallisation of the residue from MeOH gave (3,4-dinitro-phenyl)-morpholin-4- yl-methanone (8.23 g) as a yellow solid. (¹H NMR (300 MHz, DMSO-d₆) δ 8.3 (d, IH), 8.3 (s, IH), 8.0 (d, IH), 3.7-3.5 (m, 8H)).

IB. Synthesis of (3,4-Diamino-phenyl)-morpholin-4-yl-methanone

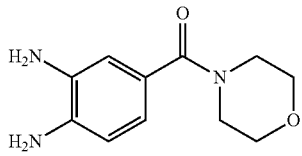

A mixture of (3,4-dinitro-phenyl)-morpholin-4-yl-methanone (1.0 g) and 10% Pd/C (150 mg) in MeOH (30 ml) was shaken under a hydrogen atmosphere at ambient temperature for 10 hours, then filtered through a plug of Celite and reduced in vacuo to give (3,4-diamino-phenyl)-morpholin-4-yl-methanone (900 mg). (¹H NMR (300 MHz, DMS (W₆) δ 6.6 (s, IH), 6.5 (s, 2H), 4.8 (s, 1.5H), 4.6 (s, 1.5H), 4.1 (s, IH), 3.6 (m, 4H), 3.4 (m, 4H)).

1C. Synthesis of 4-Morpholin-4-ylmethyl-benzene-1,2-diamine

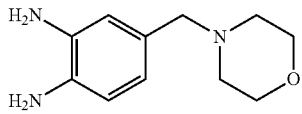

To a mixture of (3,4-dinitro-phenyl)-moφholin-4-yl-methanone (2.84 g) in dry THF (50 ml) was added NaBH₄ (954 mg) followed drop-wise by BF₃-Et₂O (3.2 ml). The mixture was stirred at ambient temperature for 3 hours and then quenched though addition of MeOH. The mixture was reduced in vacuo, partitioned between EtOAc and water and the organic portion washed with brine, dried (MgSO₄) and reduced in vacuo. The residue was purified via flash column chromatography eluting with EtOAc to give 4-(3,4-dinitro-benzyl)-morpholine (1.08 g).

A mixture of 4-(3,4-dinitro-benzyl)-morpholine (550 mg) and 10% Pd/C (75 mg) in MeOH (10 ml) was shaken under a hydrogen atmosphere at ambient temperature for 4 hours, then filtered through a plug of Celite and reduced in vacuo to give 4-morpholin-4-ylmethyl-benzene-1,2-diamine (483 mg) as the major component of a mixture.

ID. Synthesis of 5-morpholin-4-ylmethyl-2-f4-nitro-1H-pyrazol-3-yl)IH-benzimidazole

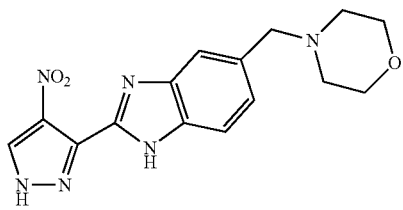

A mixture of 4-morpholin-4-ylmethyl-benzene-1,2-diamine (2.30 g, 11.1 mmol), 4-nitro-1H-pyrazole-3-carboxylic acid (1.57 g, 10.0 mmol), EDC (2.13 g, 11.1 mmol) and HOBt (1.50 g, 11.1 mmol) in dry DMF (25 ml) was stirred at ambient temperature for 24 hours. The mixture was reduced in vacuo and the crude residue dissolved in AcOH (40 ml) and heated at reflux for 3 h. The solvent was removed in vacuo and the residue was purified by flash column chromatography eluting with 0-20% MeOH in EtOAc to give 5-morpholin-4-ylmethyl-2-(4-nitro-1H-pyrazol-3-yl)IH-benzimidazole as a yellow solid. (1.0 g, 61%). (LC/MS: R, 1.83, [M+H]+329).

IE. Synthesis of 3-r5-morpholin-4-ylmethyl-1H-benzimidazol-2-yl)-1H-pyrazol-4-ylamine

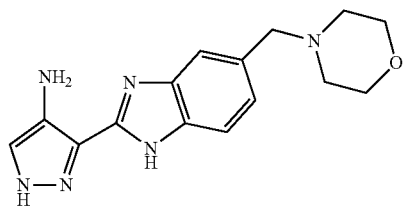

Palladium on carbon (10%, 0.08 g) was added to solution of 5-morpholin-4-ylmethyl-2-4-nitro-1II-pyrazol-3-yl) 1II-benzimidazole (0.82 g, 2.5 mmol) in DMF (30 ml) under an atmosphere of nitrogen. The mixture was shaken under a hydrogen atmosphere for 4 hours then filtered through Celite, washing with MeOH. The filtrate was concentrated in vacuo to give 3-(5-morpholin-4-ylmethyl-1H-benzimidazol-2-yl)-1H-pyrazol-4-ylamine as a brown solid (530 mg, 71%).

(LC/MS: R, 1.94, [M+H]+ 299).

IF. Synthesis of 5-cyano-2-methoxy-benzoic acid

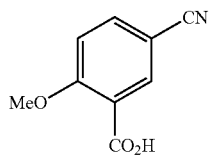 [SMILES: COc1ccc(C#N)cc1C(=O)O]

To a mixture of methyl-2-hydroxy-5-cyano-benzoate (2 g, 5.6 mmol), K₂CO₃ (4.68 g, 16.8 mmol) in acetone (50 ml) was added methyl iodide (0.7 ml, 5.6 mmol). The reaction was then heated at 65° C. overnight resulting in formation of a solid which was filtered off whilst hot and washed with acetone to give 5-cyano-2-methoxy-benzoic acid methyl ester (0.45 g). The crude product was dissolved in THF (5 ml) and then treated with LiOH (0.108 g 0.26 mmol) in water (5 ml) and stirred at room temperature overnight. The reaction was acidified with 2M HCl and extracted EtOAc (×2). The organic portion dried (MgSO₄) and reduced in vacuo to give 5-cyano-2-methoxy-benzoic acid (0.277 g). (LC/MS Acidic: R, 2.92, [MH–H]⁺ 178).

IG Synthesis of 5 cyano-2-methoxy-N-[3-{5-morpholin-4-ylmethyl-1H-benzoimidazol-2-yl)-1H-pyrazol-4-yn-benzamide (Acid chloride method)

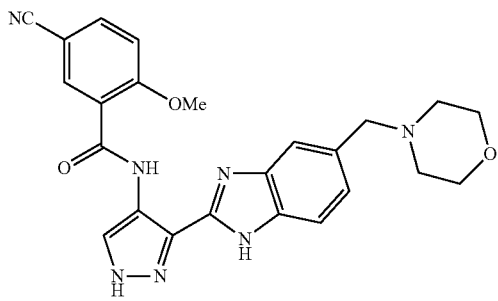 [SMILES: COc1ccc(C#N)cc1C(=O)Nc1c[nH]nc1-c1nc2cc(CN3CCOCC3)ccc2[nH]1]

5-Cyano-2-methoxy-benzoic acid (Example IF) (40 mg, 0.22 mmol) was dissolved in DCM (5 ml) and oxalyl chloride (34.4 mg, 0.264 mmol) was then added drop wise followed by DMF (1 drop). The reaction mixture was stirred at ambient temperature for 1 hour, reduced in vacuo, then re-evaporated using toluene (×2). A mixture of 3-(5-morpholin-4-ylmethyl-1H-benzimidazol-2-3' 1)-1H-pyrazol-4-ylamine (100 mg, 0.33 mmol), 5-cyano-2-methoxy-benzoyl chloride and diisopropylethylamine (1.83 µl, 0.9 mmol) in THF (5 ml) was stirred at 0° C. and then allowed to warm to room temperature over 2 hours. The reaction mixture was then concentrated in vacuo. The residue was purified by flash column chromatography SiO$_2$, 5-7% MeOH-DCM] to give 5-cyano-2-methoxy-N-[3-(5-morpholin-4-ylmethyl-1H-benzimidazol-2-yl)-1H-pyrazol-4-yl]-benzamide (12 mg). (LC/MS Acidic: R$_t$ 2.02 min [M−H]+ 458).

Example 2

Synthesis of 6-methyl-imadazol[2.1-b]thiazole-5-carboxylic acid [3-(5-morpholin-4-ylmethyl-1H-benzoimidazol-2-yl)-1H-pyrazol-4-yli-amide

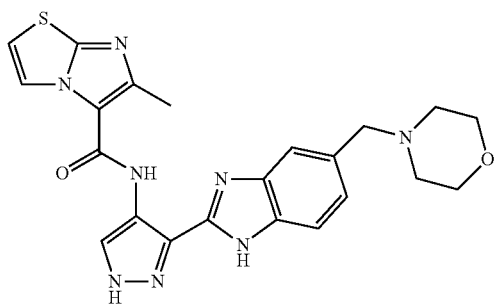 [SMILES: Cc1nc2sccn2c1C(=O)Nc1c[nH]nc1-c1nc2cc(CN3CCOCC3)ccc2[nH]1]

A mixture of 6-methyl-imidazo[2.1-b]thiazole-5-carboxylic acid (Bionet) (61 mg, 0.33 mmol), 3-(5-morpholin-4-ylmethyl-1H-benzoimidazol-2-yl)-1H-pyrazol-4-ylamine (100 mg, (133 mmol), EDC (77 mg 0.39 mmol) and IIOAt (54 mg, 0.39 mmol) was stirred in DMF (3 ml) at 80° C. for 1 h then at ambient temperature for 20 h. The mixture was reduced in vacuo and the residue was partitioned between EtOAc and saturated NaHCO. The organic portion was washed with brine, dried (MgSO$_4$) and reduced in vacuo. The residue was purified by preparative LC/MS to give 6-methyl-imidazo[2.1-b]thiazole-5-carboxylic acid [3-(5-morpholin-4-ylmethyl-1H-benzoimidazol-2-yl)-1H-pyrazol-4-yl]-amide (29 mg). (LC/MS Basic: R$_t$ 2.56 [M+H]$^+$ 463).

Example 3

Synthesis of 2-cyano-N-[3-(5-moφholin-4-ylmethyl-1H-benzoimidazol-2-yl)-1H-pyrazol-4-yll-acetamide

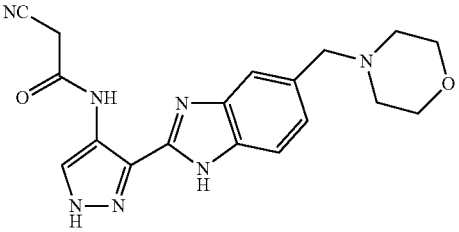 [SMILES: N#CCC(=O)Nc1c[nH]nc1-c1nc2cc(CN3CCOCC3)ccc2[nH]1]

A mixture of cyano-acetic acid (23 mg, 0.28 mmol), 3-(5-morpholin-4-ylmethyl-1H-benzoimidazol-2-yl)-1H-pyrazol-4-ylamine (70%, 100 mg, 0.23 mmol), TBTU (89 mg, 0.28 mmol) and DMF (2 ml) was stirred at 25° C. overnight. The mixture was then evaporated in vacuo. Flash chromatography, eluting with DCM—6% MeOH/DCM afforded 2-cyano-N-[3-(5-morpholin-4-ylmethyl-1H-benzoimidazol-2-yl)-1H-pyrazol-4-yl]-acetamide as a yellow solid (65 mg, 77%). (LC/MS (acidic method/final compound): R$_t$ 4.61, [M+H]$^+$ 366).

Example 4

2-Cyano-2-cyclopropyl-N-[3-(5-moφholin-4-ylmethyl-1H-benzoimidazol-2-yl)-1H-pyrazol-4-yll-acetamide 4A. Synthesis of cyano-cyclopropyl-acetic acid

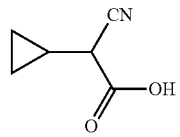

IN NaOH (3.26 ml, 3.26 mmol) was added to a solution of cyano-cyclopropyl-acetic acid ethyl ester (0.5 g, 3.26 mmol) in THF (15 ml). After 4 hours stirring at 25° C., the reaction mixture was evaporated in vacuo, re-dissolved in water (20 ml) and neutralized by the addition of IN IICl solution (3.26 ml). This mixture was then extracted with EtOAc (3×20 ml) and the combined, dried (Na$_2$SO$_4$) organics evaporated in vacuo to give impure cyano-cyclopropyl-acetic acid as a clear oil. This material was used without any further purification in the preparation of Example 4B.

4B. 2-Cyano-2-cyclopropyl-N-[3-(5-morpholin-4-ylmethyl-1H-benzoimidazol-2-vD-1H-pyrazol-4-vH-acetamide

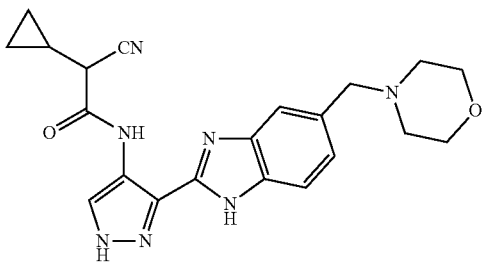 [SMILES: N#CC(C(=O)Nc1c[nH]nc1-c1nc2cc(CN3CCOCC3)ccc2[nH]1)C1CC1]

The product of Example 4A was reacted with 3-(5-morpholin-4-ylmethyl-1H-benzimidazol-2-yl)-1H-pyrazol-4-ylamine according to the method described in Example 3, except that the crude product was partitioned between DCM and saturated aqueous $NaHCO_3$ and was then purified by trituration with $Et_2O$. LC/MS (acidic method) $R_t$ 1.79 $[M+H]^+$ 406.

Examples 5-14

By following the methods of Examples $I_5$2 and 3, modified where indicated in the Table below, the compounds of Examples 5 to 14 were prepared.

| Example | Structure | General Method of Preparation | Differences to General Method | LC/MS |
|---|---|---|---|---|
| 5 | 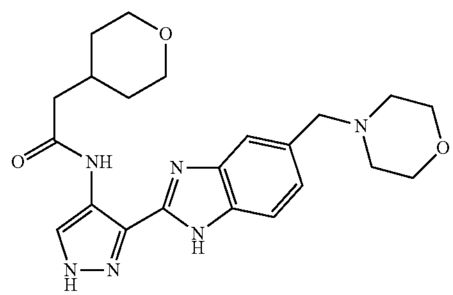 [SMILES: O=C(CC1CCOCC1)Nc1c[nH]nc1-c1nc2cc(CN3CCOCC3)ccc2[nH]1] | Ex. 1G | | $[M + H]^+$ 425 $R_t$ 1.77 Acidic |
| 6 | 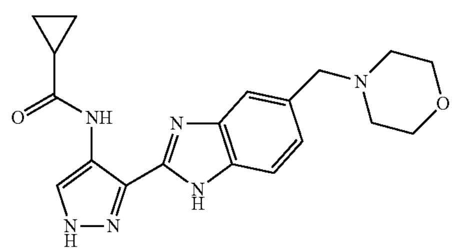 [SMILES: O=C(Nc1c[nH]nc1-c1nc2cc(CN3CCOCC3)ccc2[nH]1)C1CC1] | Ex. 1G | Purified by preparative LC/MS | $[M + H]^+$ 365 $R_t$ 2.45 Basic |
| 7 | 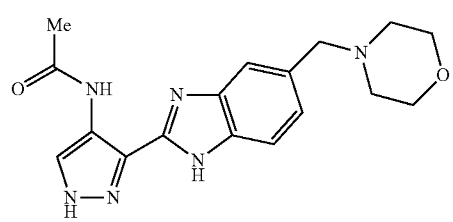 [SMILES: CC(=O)Nc1c[nH]nc1-c1nc2cc(CN3CCOCC3)ccc2[nH]1] | Ex. 1G | Purified by preparative LC/MS | $[M + H]^+$ 339 $R_t$ 2.21 Basic |
| 8 | 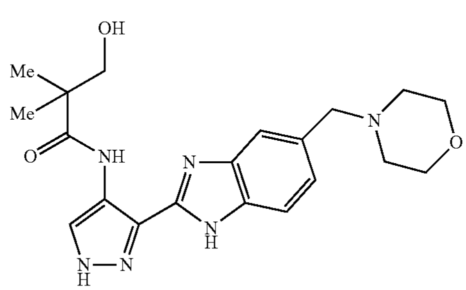 [SMILES: CC(C)(CO)C(=O)Nc1c[nH]nc1-c1nc2cc(CN3CCOCC3)ccc2[nH]1] | Ex. 2 | Purified by preparative LC/MS | $[M + H]^+$ 399 $R_t$ 1.74 Acidic |

-continued

| Example | Structure | General Method of Preparation | Differences to General Method | LC/MS |
|---------|-----------|-------------------------------|-------------------------------|-------|
| 9 | 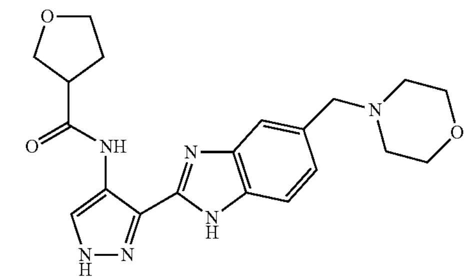 [SMILES: O=C(Nc1c[nH]nc1-c1nc2cc(CN3CCOCC3)ccc2[nH]1)C1CCOC1] | Ex. 2 | Purified by preparative LC/MS | [M + H]⁺ 397 R$_t$ 1.64 Acidic |
| 10 | 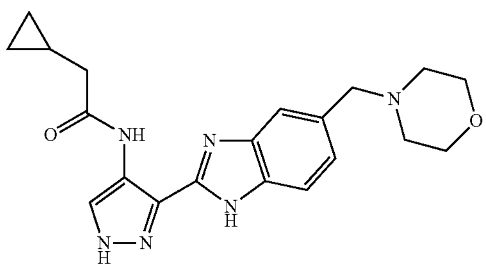 [SMILES: O=C(CC1CC1)Nc1c[nH]nc1-c1nc2cc(CN3CCOCC3)ccc2[nH]1] | Ex. 3 | Purified by column chromatography [SiO₂ eluting with DMAW 240-120] | [M + H]⁺ 381 R$_t$ 1.85 Acidic |
| 11 | 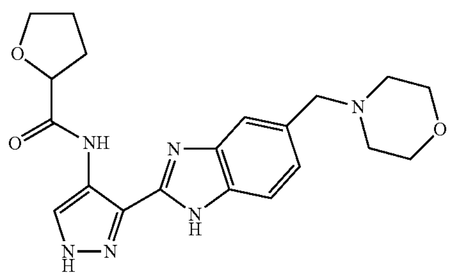 [SMILES: O=C(Nc1c[nH]nc1-c1nc2cc(CN3CCOCC3)ccc2[nH]1)C1CCCO1] | Ex. 3 | Purified by column chromatography [SiO₂ eluting with DMAW 240-120] | [M + H]⁺ 397 R$_t$ 1.76 Acidic |
| 12 | 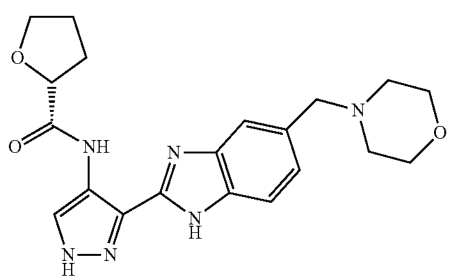 | Ex. 3 | Purified by column chromatography [SiO₂ eluting with DMAW 240-120] | [M + H]⁺ 397 R$_t$ 1.76 Acidic |
| 13 | 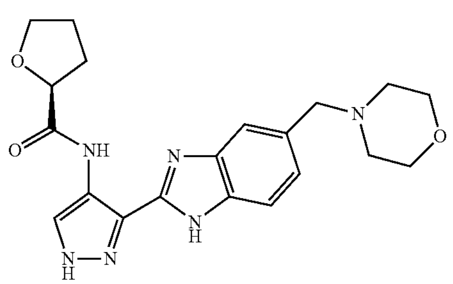 [SMILES: O=C(Nc1c[nH]nc1-c1nc2cc(CN3CCOCC3)ccc2[nH]1)[C@@H]1CCCO1] | Ex. 3 | Purified by column chromatography [SiO₂ eluting with DMAW 240-120] | [M + H]⁺ 397.24 R$_t$ 1.79 Acidic |

| Example | Structure | General Method of Preparation | Differences to General Method | LC/MS |
|---|---|---|---|---|
| 14 | (structure) | Ex. 3 | Purified by column chromatography [SiO₂ eluting with DMAW 240-120] | [M + H]⁺ 465.3 R$_t$ 1.99 Acidic |

Example 15

Synthesis of N-[3-(5,6-dimethoxy-1H-benzimidazol-2-yl)-1H-pyrazol-4-yl]-rac-2-morpholine carboxamide-trifluoroacetate salt

15A. Synthesis of 5,6-dimethoxy-2-(4-nitro-1H-pyrazol-3-yl)-1H-benzimidazole

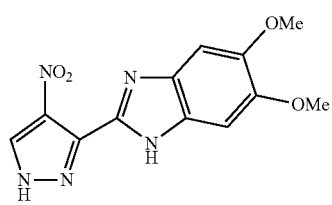 [SMILES: COc1cc2nc(-c3n[nH]cc3[N+](=O)[O-])[nH]c2cc1OC]

To a solution of EDC (4.81 g 25 mmol), HOBt (3.40 g, 25 mmol) and triethylamine (4.67 g, 46 mmol) in DMF (100 ml) was added 4-nitro-1H-pyrazole-3-carboxylic acid (3.63 g, 23.09 mmol) and 4,5-dimethoxy-benzene-1,2-diamine dihydrochloride (5.06 g, 20.99 mmol) and the mixture was stirred at room temperature overnight. The solvent was removed in vacuo and the resulting solid partitioned between EtOAc (50 ml) and saturated aqueous NaHCO₃ (50 ml). A precipitate was formed and removed by filtration. The filtrate was washed with water followed by diethyl ether and then azeotroped with MeOH and toluene to yield 4-nitro-1H-pyrazole-3-carboxylic acid (2-amino-4,5-dimethoxy-phenyl)-amide (2.35 g, 36%). 4-Nitro-1H-pyrazole-3-carboxylic acid (2-amino-4,5-dimethoxy-phenyl)-amide (2.35 g, 7.65 mmol) was dissolved in acetic acid (150 ml) and refluxed at 140° C. for 5 hours. The solution was left to cool and the solvent removed in vacuo. The resulting solid was partitioned between EtOAc (25 ml) and brine (25 ml). The organic layer was separated, dried (MgSO₄), filtered and the solvent removed in vacuo to yield 5,6-dimethoxy-2-(4-nitro-1H-pyrazol-3-yl)-1H-benzimidazol (2.08 g, 94%).

15B. Synthesis of 3-(5,6-dimethoxy-1H-benzimidazol-2-yl)-1H-pyrazol-4-ylamine A mixture of 5,6-dimethoxy-2-(4-nitro-1H-pyrazol-3-yl)-1H-benzimidazole (2.08 g, 7.2 mmol) and 10% palladium on carbon (200 mg) in ethanol (150 ml) and DMF (50 ml) was hydrogenated at room temperature and pressure overnight. The reaction mixture was filtered through Celite and the solvent removed in vacuo. The resulting solid was azeotroped with methanol and toluene and the solvent removed in vacuo. The crude material was purified by flash chromatography, eluting with DCM:MeOH:acetic acid:water (120:18:3:2) [DMAW120] followed by DCM:MeOH:acetic acid:water (90:18:3:2) (DMAW90). Product fractions were combined and the solvent removed in vacuo to yield 3-(5,6-dimethoxy-1H-benzimidazol-2-yl)-1H-pyrazol-4-ylamine (~1g, 53%).

15C. Synthesis of N-[3-(5,6-dimethoxy-1H-benzimidazol-2-ylV1H-pyrazol-4-yr[-røc-4-BOC-2-morpholine carboxamide

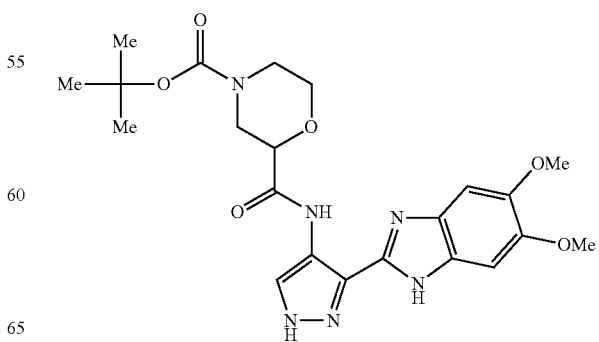

To a solution of EDC (125 mg, 0.54 mmol) and HOAt (74 mg, 0.54 mmol) in DMF (2 ml) was added 3-(5,6-dimethoxy-1H-benzimidazol-2-yl)-1H-pyrazol-4-ylamine (117 mg, 0.45 mmol) (Example 15B) and (rac>BOC-2-carboxymorpholine (125 mg, 0.54 mmol) and the mixture stirred at room temperature overnight. The mixture was then partitioned between EtOAc and water. The organic layer was then washed successively with saturated aqueous sodium bicarbonate, brine and then dried (MgSO$_4$). The solution was evaporated to dryness in vacuo and the residue purified by flash column chromatography [SiO$_2$, gradient elution: EtOAc-hexanes (1:1)-EtOAc-MeOH (80:20)] to give N-[3-(5,6-dimethoxy-1H-benzimidazol-2-yl)-1H-pyrazol-4-yl]-7-αc-4-BOC-2-morpholine carboxamide (65 mg) as a colourless solid. (LC/MS (acidic method): R$_t$ 2.65 min, [M+H]$^+$ 473).

15D. Synthesis of N-[3-(5,6-dimethoxy-1H-benziniadazol-2-ylV1H-pyrazol-4-yl]-mc-2-morpholine carboxamide-trifluoroacetate salt

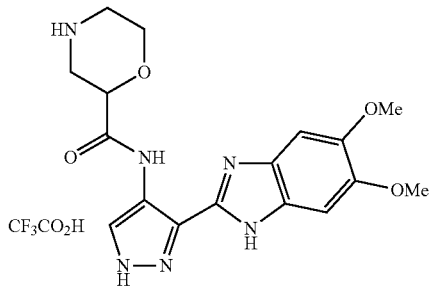 [SMILES: "CF3CO2H" ; COc1cc2nc(-c3n[nH]cc3NC(=O)C3CNCCO3)[nH]c2cc1OC]

N-[3-(5,6-dimethoxy-1H-benzimmidazol-2-yl)-1H-pyrazol-4-yl]-rac-4-BOC-2-morpholine carboxamide (65 mg, 0.14 mmol) and anisole (60 μl, 0.56 mmol) were dissolved in a mixture of trifluoroacetic acid and dicliloromethane (1:1; 2 ml). After 3 hours at room temperature, the mixture was evaporated to dryness to give N-[3-(5,6-dimethoxy-1H-benzimidazol-2-yl]-1H-pyrazol-4-yl]-rαc-2-morpholine carboxamide-trifluoroacetic acid salt (73 mg) as a colourless solid (LC/MS (acidic method): R$_t$ 1.42 min, [M–H$^+$]$^-$ 371.

Example 16

Synthesis of N-[3-(5,6-dimethoxγ-1H-benzimidazol-2-yl)-1H-pyrazol-4-yl]-rac-4 isopropyl-2-morpholine carboxamide

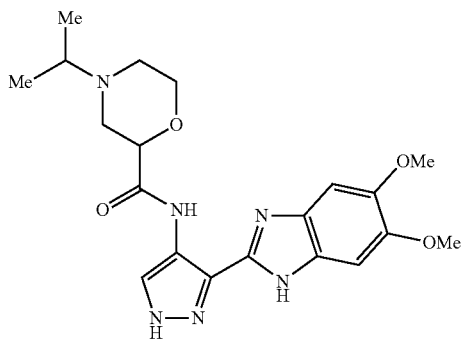 [SMILES: COc1cc2nc(-c3n[nH]cc3NC(=O)C3CN(C(C)C)CCO3)[nH]c2cc1OC]

To N-[3-(5,6-dimethoxy-1H-benzimidazol-2-yl)-1H-pyrazol-4-yl]-røc-2-morpholine carboxamide-trifluoroacetic acid salt (Example 15D) (34 mg, 0.07 mmol) and K$_2$CO$_3$ (20 mg, 0.14 mmol), in McCN (1 ml) was added 2-iodopropanc (17 μl, 0.15 mmol). The mixture was stirred at 80° C. for approximately 48 hours after which the mixture was concentrated and the residue purified by flash chromatography [SiO$_2$ gradient elution: DCM:MeOH (98:2) to DCM:MeOH: conc. aq. NH$_3$ (90:10:1) to give N-[3-(5,6 dimethoxy-1H-benximidazol-2-yl)-1H-pyrazol-4-yl]-røc-4-isopropyl-2-morpholine carboxamide (12 mg) as a colourless gum (LC/MS (basic method): R$_t$ 2.52 min [M+H]$^+$ 415).

Example 17

Synthesis of N-[3-(5,6-dimethoxy-H-benzimidazol-2-ylV1H-pyrazol-4-yl]-rctc-l-methyl-piperidine 3-carboxamide

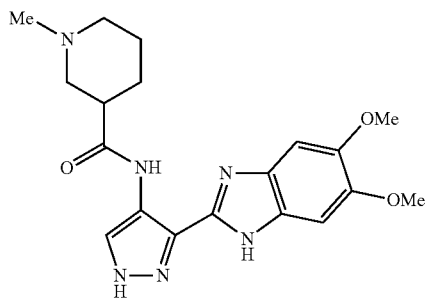 [SMILES: COc1cc2nc(-c3n[nH]cc3NC(=O)C3CCCN(C)C3)[nH]c2cc1OC]

To a solution of 3-(5,6-dimethoxy-1H-benzimidazol-2-yl)-1H-pyrazol-4-ylamine (65 mg, 0.25 mmol) (Example 15B) (røcH-methyl-piperidine-5-carboxylic acid-hydrocholoride salt (50 mg, 0.27 mmol) and disopropylethylamine (50 μl, 0.27 mmol) in DMF (1 ml) was added TBTU (97 mg, 0.30 mmol). The mixture was stirred at room temperature for approximately 16 hours after which 1N aqueous NaOH (1 ml) was added and the mixture stirred for a further 1 hours. The mixture was then evaporated to dryness in vacuo and the residue purified by flash column chromatography (SiO$_2$, eluting with a gradient of DCM:McOH (98:2) to DCM:MeOH; cone. Aq. NH$_3$ (70:30:3) to give N-[3-(5,6-dimethoxy-1H-benzimidazol-2-yl)-1H-pyrazol-4-yl]-røc-1-methyl-piperidine 3-carboxamide (20 mg) as a colourless gum (LC/MS (basic method): R$_t$ 2.35 min, (M+H)+385).

Example 18

Synthesis of 3-chloro-N-(5,6-dimethoxy-1H-benzoimidazol-2-yl)-1H-pyrazol-4-yl-5-(4-methyl-piperazin-1-vD-benzamide 18A. Synthesis of 3-Chloro-5-(4-methyl-piperazin-1-ylVbenzonitrile

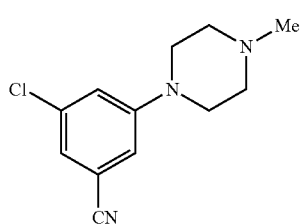 [SMILES: CN1CCN(c2cc(Cl)cc(C#N)c2)CC1]

5-Fluoro-3-chloro-benzonitrile (Ig, 6.4 mmol) was dissolved in DMSO (20 ml) followed by addition OfK₂CO₃ (1.3 g, 9.6 mmol) and 1-methyl piperazine (1.4 ml, 12.8 mmol). The reaction mixture was heated at 80° C. for 20 hours. Diethyl ether was added to the crude material (10 ml) then acidified with IN HCl. A precipitate was filtered off from the crude reaction mixture to give 3-chloro-5-(4-methyl-piperazin-1-yl)-benzonitrile (1.4 g, 93% yield) as a white solid (LC/MS: $R_t$ 1.83 [M+H]⁺ 236, acidic method).

18B. Synthesis of 3-Chloro-5-C4-methyl-piperazin-1-viybenzoic acid

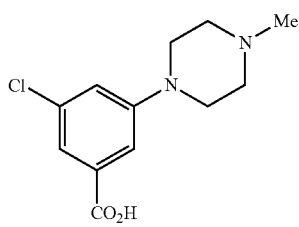 [SMILES: CN1CCN(c2cc(Cl)cc(C(=O)O)c2)CC1]

To 3-chloro-5-(4-methyl-piperazin-1-yl)-benzonitrile (1.4 g, 5.9 mmol) dissolved in ethanol (10 ml) was added 2M NaOH (20 ml) and reaction mixture was heated at reflux for 20 hours. The mixture was reduced in vacuo and the crude product was acidified in IN IICl to pII 6 and partitioned between EtOAc and II₂O. The organic layer was evaporated to dryness in vacuo to give 0.7 g of the title compound as a white solid (LC/MS: $R_t$ 1.67, [M+H]⁺ 256, acidic method).

18C. Synthesis of [3-chloro-N-_r3-(5,6-dimethoxy-1H-Benzoimidaxol-2-ylV1H-pyrazol-4-yll-5-(4-methyl-piperazin-1-yl)-benzamide

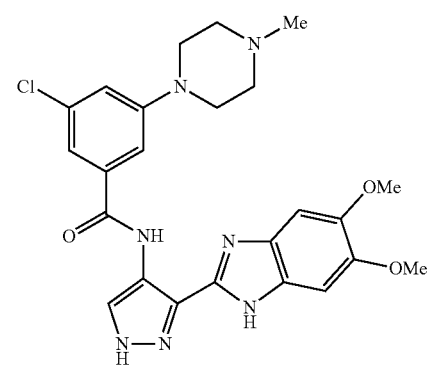 [SMILES: COc1cc2nc(-c3n[nH]cc3NC(=O)c3cc(Cl)cc(N4CCN(C)CC4)c3)[nH]c2cc1OC]

The compound was prepared in a manner analogous to Example 15C but using 3-chloro-5-(4-methyl-piperazin-1-yl)-benzoic acid (200 mg, 0.78 mmol) as a reagent in 15C in place of (røc)-BOC-2-carboxymorpholine. The crude product was purified by flash column chromatography [SiO₂ eluting with DMAW240-90 to give 92 mg (25% yield) of the title compound as a light brown solid (LC/MS: $R_t$ 2.07 [M+H]⁺ 496).

Examples 19-21

By following the procedures set out in Example 15, modified where indicated, the compounds of Examples 19 to 21 were prepared.

| Example | Structure | General Method of Preparation | Differences to General Method | LC/MS |
|---------|-----------|-------------------------------|-------------------------------|-------|
| 19 | 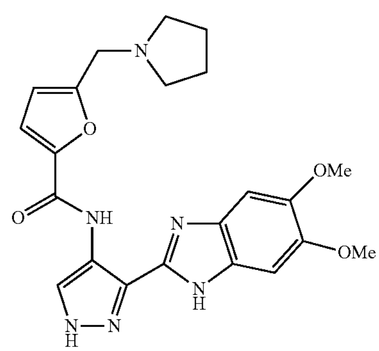 [SMILES: COc1cc2nc(-c3n[nH]cc3NC(=O)c3ccc(CN4CCCC4)o3)[nH]c2cc1OC] | Ex. 15C | Using 5-pyrrolidin-1-ylmethyl furan-2-carboxylic acid | [M + H]⁺ 437 $R_t$ 2.62 Basic |
| 20 | 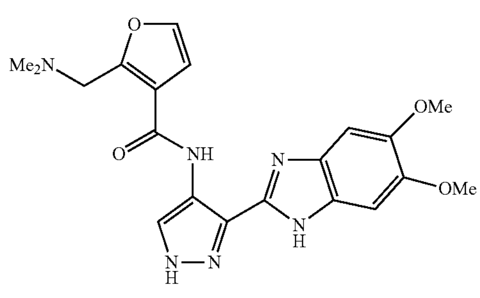 [SMILES: COc1cc2nc(-c3n[nH]cc3NC(=O)c3ccoc3CN(C)C)[nH]c2cc1OC] | Ex. 15C | Using 2-dimethylaminomethyl-furan-3-carboxylic acid Purified by preparative LC/MS | [M + H]⁺ 411 $R_t$ 1.6 Acidic |

| Example | Structure | General Method of Preparation | Differences to General Method | LC/MS |
|---|---|---|---|---|
| 21 | 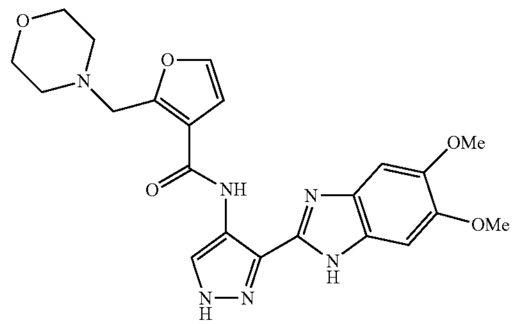 [SMILES: COc1cc2nc(-c3n[nH]cc3NC(=O)c3ccoc3CN3CCOCC3)[nH]c2cc1OC] | Ex 15C | No aqueous work up-purified by column chromatography [SiO₂ eluting with DMAW 240] Further purified by preparative LC/MS | [M + H]⁺ 453.17 R, 1.75 Acidic |

Example 22

Synthesis of S-chloiOˆ-methoxy-N—IS-fS-ˆ-methyl-piperazin-1-ylmethv π-1H-benzoimidazol-2-yl]-1H-pyrazol-4-yl)-benzamide

22A. Synthesis of (3,4-dinitrophenyl)-(4-methylpiperazin-1-yl)-methanone

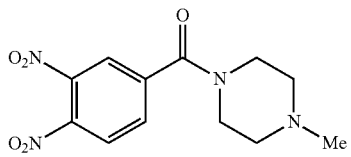 [SMILES: CN1CCN(C(=O)c2ccc([N+](=O)[O-])c([N+](=O)[O-])c2)CC1]

3,4-Dinitrobenzoic acid (50 g, (124 mol) was heated at reflux in SOCl₂ (160 ml) for 6 hours. The mixture was then evaporated to dryness in vacuo. The product was dissolved in THF and cooled to 5° C. To this solution, N-methylpiperazine (26.2 ml, 0.24 mol) and Et₃N (42 ml) were added dropwise as a solution in THF (50 ml). After stirring overnight at room temperature, the solution was poured into water (1.5 L) and stirred at approximately 5° C. for 0.5 hours. The solid precipitate which formed was collected and dried to give (3,4-dinitrophenyl)-(4-methylpiperazin-1-yl)-methanone (40 g) as a yellow solid.

22B. Synthesis of 1-C3.4 diaminobenzylV4-methylpiperazine

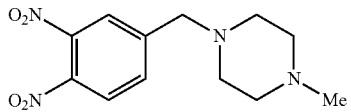 [SMILES: CN1CCN(Cc2ccc([N+](=O)[O-])c([N+](=O)[O-])c2)CC1]

To a cooled solution (5° C.) of (3,4-dinitrophenyl)-(4-methylpiperazin-1-yl)-methanone 12.2 g, 0.041 mol) in THF, was added powdered NaBH₄, followed by the dropwise addition of BF₃OEt₂, while keeping the temperature below 5° C. The mixture was allowed to come to room temperature over 2 hours and then stirred for a further 2 hours at room temperature. MeOH was then added cautiously to the mixture (causing effervescence), the stirring was continued for 10 minutes and then the mixture concentrated. The residue was partitioned between EtOAc and saturated aqueous NaHCO₃. The organic layer was washed with water, brine and then dried (MgSO₄). The solution was evaporated in vacuo and the residue purified by flash chromatography on SiO₂ eluting with gradient DCM: MeOH (98:2) to DCM: MeOII: concentrated aqueous NII₃ (90:10:1) to give an orange crystalline solid (3.7 g). Recrystallisation from MeOH gave 1-(3,4-dinitrobenzyl)-4-methypiperazine (1 g) as an orange crystalline solid.

22C. Synthesis of 1-(3,4-diaminobenzyl)-4-methylpiperazine

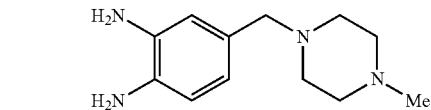

1-(3,4-dinitrobenzyl)-4-methylpiperazine (1 g) was dissolved in DMF:MeOH (1:1, 20 ml) and agitated with 10% Pd/C (50 mg) under an atmosphere of H, for 6 hours. The mixture was then filtered and evaporated to give a dark solid which was used immediately without any further purification.

22D. Synthesis of 5-chloro-2-methoxy-N-(3-[5-4-methyl-piperazin-1-ylmethylV 1H-benzoimidazol-2-yll-1H-pyrazol-4-yll-benzamide

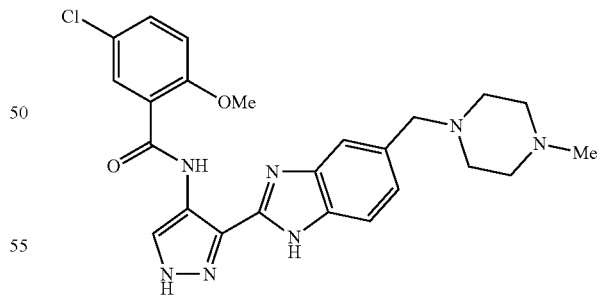

4-(5-chloro-2-methoxy-benzoylamino)-1H-pyrazole-3-carboxylic (1.17 g), the crude diamine, 1-(3,4-diaminobenzyl)-4-methylpiperazine (0.87 g), and TBTU (1.52 g) were dissolved in DMF (15 ml) and stilted for approximately 16 hours. The mixture was then evaporated to dryness to give a dark solid. The dark solid (100 mg) was dissolved in AcOH (4 ml) the mixture heated at 80° C. for 3 hours. The reaction mixture was evaporated in vacuo and the residue purified by flash chromatography (SiO₂, eluting with DMAW 120) to give 5-chloro-2-methoxy-N-{3-[5-(4-methyl-piperazin-1-ylmethyl)-1H-benzoimidazol-2-yl]-1H-pyrazol-4-yl}-benzamide as the di-acetic acid salt (35 mg). (LC/MS (acidic method/final compound): R$_t$ 6.63 [M+H]$^+$ 480).

Example 23

Synthesis of 1-(2,6-Difluoro-benzyl-3-[3-(5-morpholin-4-ylmethyl-1H-benzoimidazol-2-yl)-1H-pyrazol-4-yl]-urea

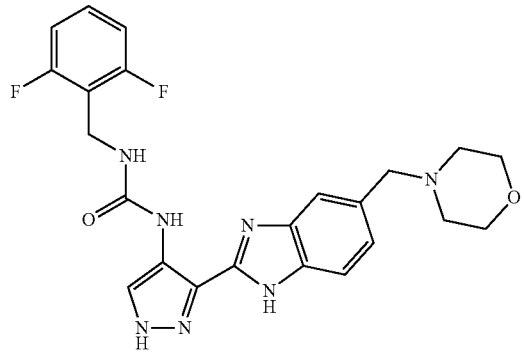 [SMILES: O=C(NCc1c(F)cccc1F)Nc1c[nH]nc1-c1nc2cc(CN3CCOCC3)ccc2[nH]1]

A mixture of 3-(5-morpholin-4-ylmethyl-1H-benzimidazol-2-yl)-1H-pyrazol-4-ylamine (Example IE.), (100 mg, 0.33 mmol), and CDI (217 mg, 1.34 mmol) in THF (2 ml) was subjected to microwave irradiation (150° C., 150 W) for 15 minutes. 2,6-Difluoro-benzylamine (384 mg, 2.68 mmol) was then added and the reaction mixture irradiated again under identical conditions for a further 15 minutes. After cooling, the heterogeneous mixture was filtered, the filtrate was concentrated and the residue purified by column chromatography (SiO$_2$ eluting with gradient—DCM:MeOH:AcOH:H$_2$O (240:20:3:2) (DMAW240 to (120:18:3:2) (DMAW120) to give 1-(2,6-difluoro-benzyl)-[3-(5-morpholin-4-ylmethyl-1H-benzimidazol-2-yl)-1H-pyrazol-4-yl]-urea (30 mg 19%). (LC/MS Acidic: R$_1$ 1.84 [M+H]$^+$ 468).

Examples 24-34

By following the general method set out in Example 23, but modified where indicated in the Table below, the compounds of Examples 24 to 34 were prepared.

| Example | Structure | Differences to General Method | LC/MS |
|---|---|---|---|
| 24 | 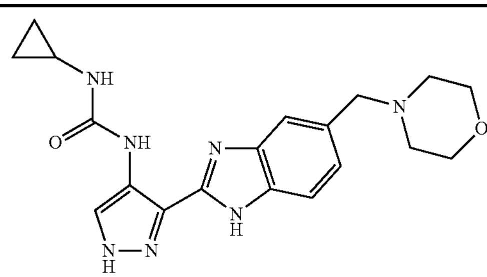 | Cyclopropylamine used as the amine | [M + H]$^+$ 382.24 R$_t$ 1.59 Acidic |
| 25 | 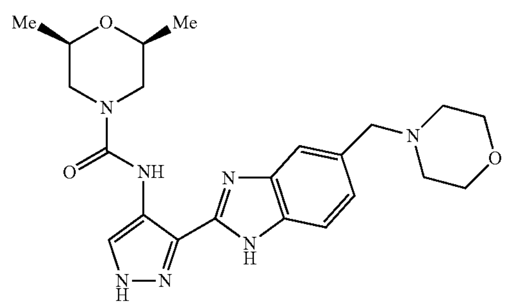 [SMILES: C[C@@H]1CN(C(=O)Nc2c[nH]nc2-c2nc3cc(CN4CCOCC4)ccc3[nH]2)C[C@H](C)O1] | | [M + H]$^+$ 440.31 R$_t$ 1.84 Acidic |
| 26 | 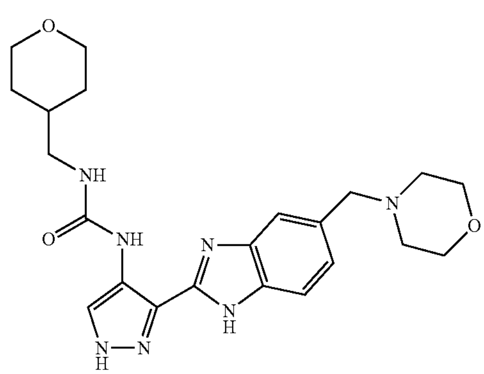 [SMILES: O=C(NCC1CCOCC1)Nc1c[nH]nc1-c1nc2cc(CN3CCOCC3)ccc2[nH]1] | Purified by preparative LC/MS | [M + H]$^+$ 440.34 R$_t$ 2.20 Polar |

-continued

| Example | Structure | Differences to General Method | LC/MS |
|---------|-----------|-------------------------------|-------|
| 27 | 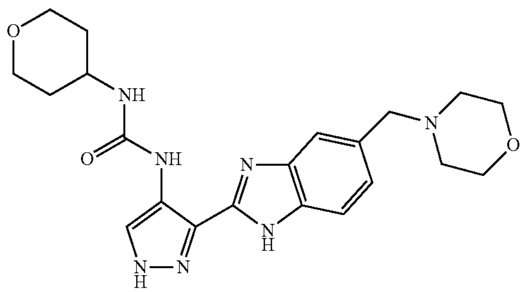 | Purified by preparative LC/MS | [M + H]⁺ 426.27 R$_t$ 1.57 Acidic |
| 28 | 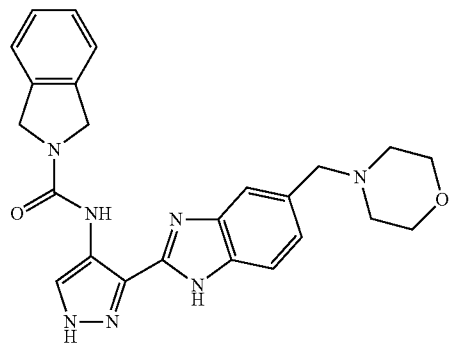 [SMILES: O=C(Nc1c[nH]nc1-c1nc2cc(CN3CCOCC3)ccc2[nH]1)N1Cc2ccccc2C1] | Crude product partitioned between EtOAc and sat. NaHCO$_3$. Purified by flash column chromatography on silica eluting with 100% EtOAc to 10% MeOH | [M + H]⁺ 444 R$_t$ 6.67 Acidic |
| 29 | 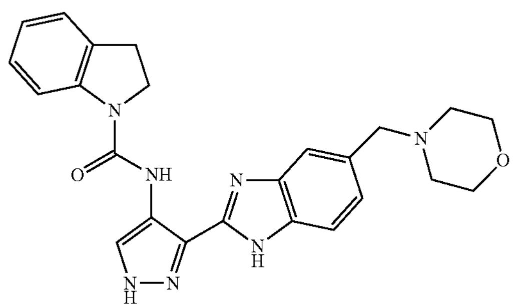 [SMILES: O=C(Nc1c[nH]nc1-c1nc2cc(CN3CCOCC3)ccc2[nH]1)N1CCc2ccccc21] | Crude product partitioned between EtOAc and sat. NaHCO$_3$. Purified by flash column chromatography on silica eluting with 100% EtOAc to 10% MeOH | [M + H]⁺ 444 R$_t$ 6.98 Acidic |
| 30 | 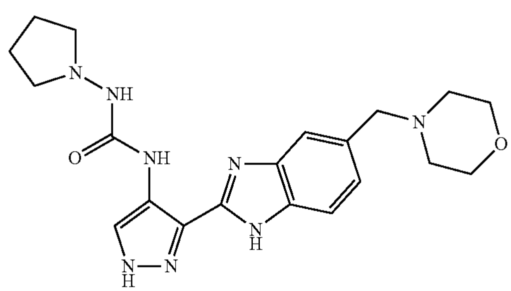 [SMILES: O=C(Nc1c[nH]nc1-c1nc2cc(CN3CCOCC3)ccc2[nH]1)NN1CCCC1] | 2.68 mmol DIPEA added. Work up - mixture stirred with 2M NaOH and extracted with DCM. Purified by flash column chromatography 2-5% MeOH—DCM, then LC/MS | [M + H]⁺ 411 R$_t$ 2.45 Basic |
| 31 | 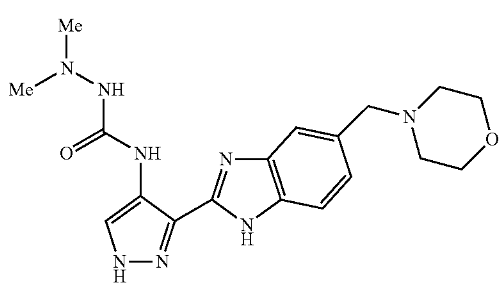 [SMILES: CN(C)NC(=O)Nc1c[nH]nc1-c1nc2cc(CN3CCOCC3)ccc2[nH]1] | 2.68 mmol DIPEA added. Purified by preparative LC/MS | [M + H]⁺ 385 R$_t$ 1.60 Acidic |

| Example | Structure | Differences to General Method | LC/MS |
|---|---|---|---|
| 32 | 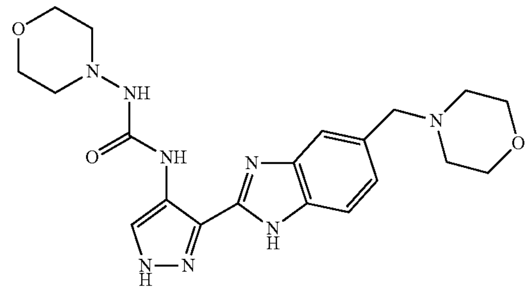 [SMILES: O=C(Nc1c[nH]nc1-c1nc2cc(CN3CCOCC3)ccc2[nH]1)NN1CCOCC1] | 2.68 mmol DIPEA added. Purified by preparative LC/MS | [M + H]+ 427 $R_t$ 1.69 Acidic |
| 33 | 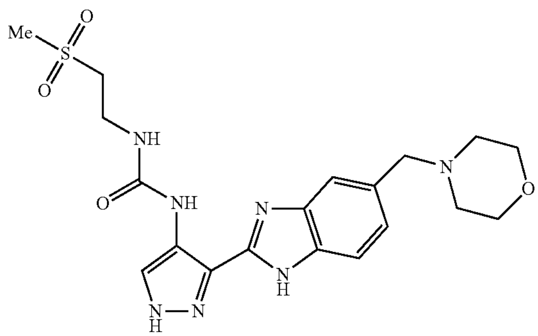 [SMILES: CS(=O)(=O)CCNC(=O)Nc1c[nH]nc1-c1nc2cc(CN3CCOCC3)ccc2[nH]1] | 2.68 mmol DIPEA added. Work up by partitioning between EtOAc and sat. NaHCO₃. Purified by column chromatography on silica (DMAW240-120) then preprarative LC/MS | [M + H]+ 448 $R_t$ 2.07 Basic |
| 34 | 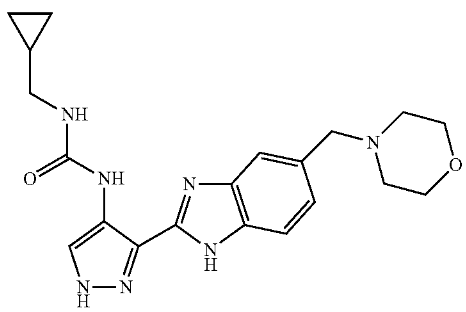 [SMILES: O=C(NCC1CC1)Nc1c[nH]nc1-c1nc2cc(CN3CCOCC3)ccc2[nH]1] | 2.68 mmol DIPEA added. Work up by partitioning between EtOAc and sat. NaHCO₃. Purified by preprarative LC/MS | [M + H]+ 396 $R_t$ 1.74 Basic |

Example 35

Synthesis of 1-[3-(5 morpholin-4-ylmethyl-1H-benzoimidazol-2-yl)-1H-pyrazol-4-yl]-3-pyridin-3-yl-urea

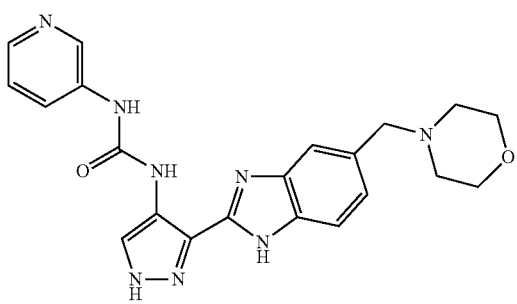 [SMILES: O=C(Nc1cccnc1)Nc1c[nH]nc1-c1nc2cc(CN3CCOCC3)ccc2[nH]1]

A mixture of 3-aminopyridine (31.5 mg, 0.33 mmol), Et₃N (0.195 ml, 1.32 mmol) in DCM (3 ml) was cooled to 0° C. and then treated with triphosgene (85 mg, 0.28 mmol). The reaction was stirred at ambient temperature for 1 hour, then 3-(5-morpholin-4-ylmethyl-1H-benzimidazol-2-yl)-1H-pyrazol-4-ylamine (100 mg, 0.33 mmol) was added and stirred at ambient temperature until the reaction was complete. The mixture was treated with 2M NaOH in MeOH for 30 minutes and then reduced in vacuo. The residue was purified by flash column chromatography [SiO₂, 2-20% MeOH/DCM] and then trituration with DCM followed by diethyl-ether to give 1-[3-(5-morpholin-4-ylmethyl-1H-benzoimidazol-2-yl)-1H-pyrazol-4-yl]-3-pyridin-3-yl-urea (20 mg). (LC/MS Basic: $R_1$ 2.29, [M+H]+ 419).

Example 36

Synthesis of thiomorpholine-4-carboxylic acid [3-(5-morpholin-4-ylmethyl-1H-benzoimidazol-2-yl)-1H-pyrazol-4-vH-amide

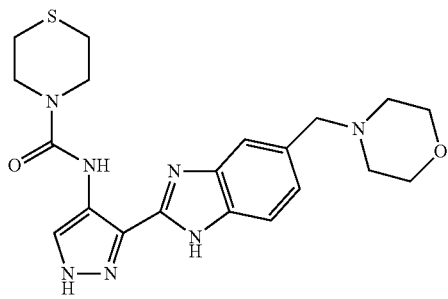 [SMILES: O=C(Nc1c[nH]nc1-c1nc2cc(CN3CCOCC3)ccc2[nH]1)N1CCSCC1]

Phosgene (20% in toluene) (0.3 ml) was added at 0° C. to a solution of 3-(5-morpholin-4-ylmethyl-1H-benzimidazol-2-yl)-1H-pyrazol-4-ylamine (100 mg, 0.33 mmol) in a mixture of toluene/DCM (1:1). The reaction was stirred at ambient temperature for 1 hour then the excess phosgene was blown off by a stream of nitrogen. Thiomorpholine (35 mg, 0.33 mmol) was added and the reaction was stirred at ambient temperature for 1 hour then at 60° C. for 1 hour. The mixture was then concentrated in vacuo and the residue purified by preparative LC/MS to give thiomorpholine-4-carboxylic acid [3-(5-morpholin-4-ylmethyl-1H-benzoimidazol-2-yl)-1H-pyrazol-4-yl]-amide (LC/MS Polar: $R_t$ 2.58, [M+H]+428).

Example 37

Synthesis of 1-(4-fluorophenyl)-1-methyl-3-[3-(5-morpholin-4-ylmethyl-1H-benzimidazol-2-ylV 1H-pyrazol-4-vH-urea

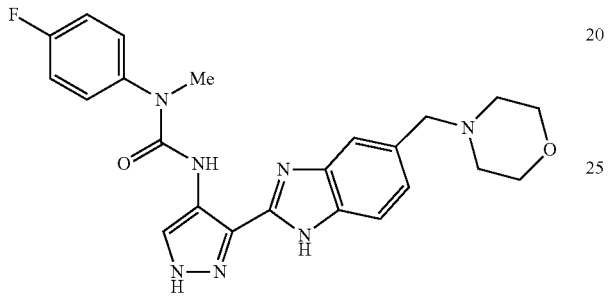

The procedure used to prepare the title compound was analogous to that described for Example 35 but using 4-fluoro-N-methylaniline instead of 3-aminopyridine, and conducting the reaction at 50° C. for 2 hours. The crude product was isolated as a precipitate from the cooled reaction mixture and was then purified by flash column chromatography [SiO$_2$ eluting with DCM:MeOH:AcOH:water (240:20:3:2)]. The resulting product was triturated with diethyl ether to give 1-(4-fluorophenyl)-1-methyl-3-[3-(5-morpholin-4-ylmethyl-1H-benzimidazol-2-yl)-1H-pyrazol-4-yl]-urea (3 mg) as a colourless solid. (LC/MS Acidic: $R_t$ 2.12, [M+H]$^+$ 450).

Examples 38-43

By following the methods described in Examples 35 and 37, modified where indicated in the Table below, the compounds of Examples 38 to 43 were prepared.

| Example | Structure | General Method of Preparation | Differences to General Method | LC/MS |
|---|---|---|---|---|
| 38 | 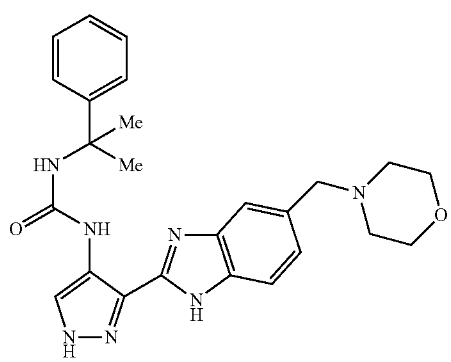 [SMILES: CC(C)(NC(=O)Nc1c[nH]nc1-c1nc2cc(CN3CCOCC3)ccc2[nH]1)c1ccccc1] | Ex. 35 | Work up by partitioning between EtOAc and sat. NaHCO$_3$. Purified by preparative LC/MS | [M + H]$^+$ 460 $R_t$ 2.03 Acidic |
| 39 | 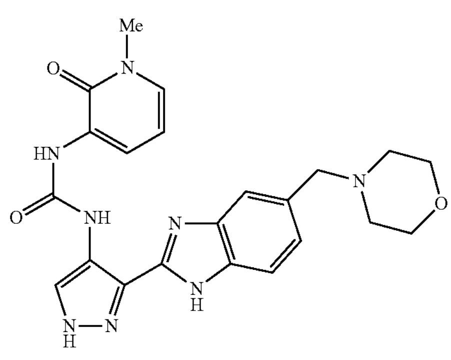 [SMILES: Cn1cccc(NC(=O)Nc2c[nH]nc2-c2nc3cc(CN4CCOCC4)ccc3[nH]2)c1=O] | Ex. 35 | Work up by partitioning between EtOAc and sat. NaHCO$_3$. Purified by preparative LC/MS | [M + H]$^+$ 449 $R_t$ 2.32 Polar |

| Example | Structure | General Method of Preparation | Differences to General Method | LC/MS |
|---|---|---|---|---|
| 40 | 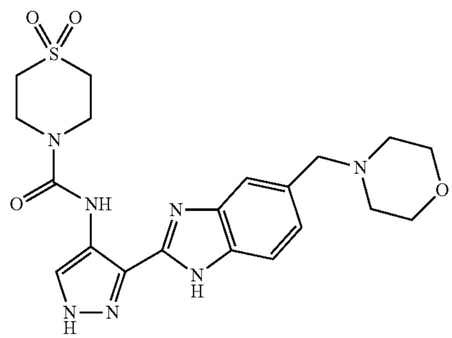 [SMILES: O=C(Nc1c[nH]nc1-c1nc2cc(CN3CCOCC3)ccc2[nH]1)N1CCS(=O)(=O)CC1] | Ex. 35 | Reaction heated to 60° C. Work up by partitioning between EtOAc and sat. NaHCO₃. Purified by preparative LC/MS | [M + H]⁺ 460 R$_t$ 2.22 Basic |
| 41 | 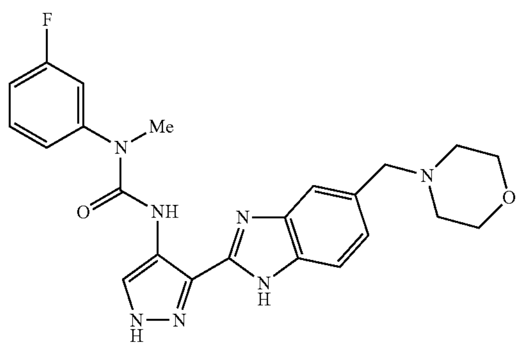 [SMILES: CN(C(=O)Nc1c[nH]nc1-c1nc2cc(CN3CCOCC3)ccc2[nH]1)c1cccc(F)c1] | Ex. 37 | | [M + H]⁺ 450.24 R$_t$ 2.09 Basic |
| 42 | 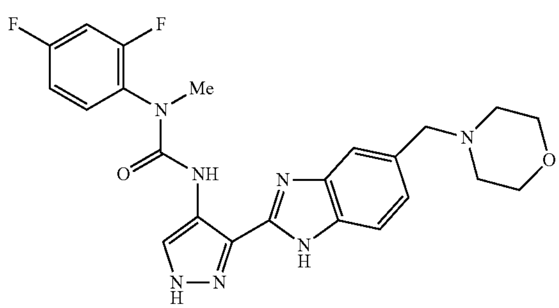 [SMILES: CN(C(=O)Nc1c[nH]nc1-c1nc2cc(CN3CCOCC3)ccc2[nH]1)c1ccc(F)cc1F] | Ex. 37 | | [M + H]⁺ 468.38 R$_t$ 1.99 Acidic |
| 43 | 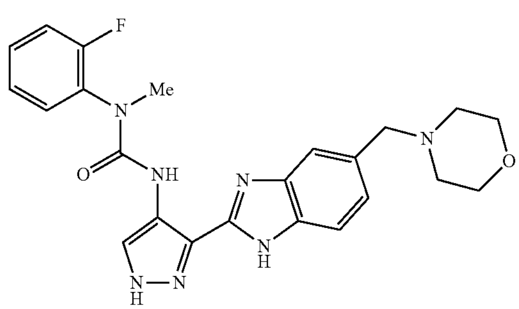 [SMILES: CN(C(=O)Nc1c[nH]nc1-c1nc2cc(CN3CCOCC3)ccc2[nH]1)c1ccccc1F] | Ex. 37 | Crude product isolated from the filtrate rather than the precipitate. Further purified by preparative LC/MS | [M + H]⁺ 450.41 R$_t$ 2.68 Basic |

Example 44

Synthesis of 1-(4-fluorophenyl)-N-r3-('5-morpholin-4-ylmethyl-1H-benzimidazol-2-vD-1H-pyrazol-4-yli-urea

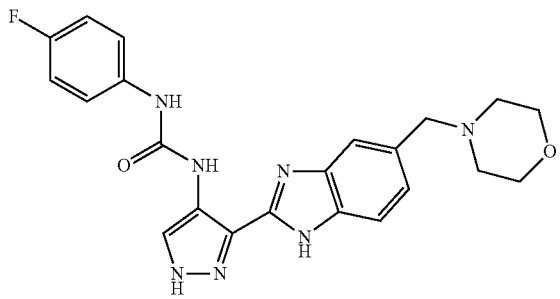

To 3-(5-morpholin-4-ylmethyl-1H-benzimidazol-2-yl)-1H-pyrazol-ylamine (Example IE) (100 mg, 0.33 mmol), in THF (2 ml), was added 4-fluorophenyl isocyanate and the mixture was stirred for about 16 hours at room temperature. Resin-supported tris-amine (800 mg, 4 mmol/g) was added and the mixture agitated for a further 4 hours. The resin was removed by filtration, the filtrate was treated with 1N KOH (2 ml, MeOH:THF; 1:3) and the solution stirred for approximately 16 hours. The mixture was then partitioned between EtOAc and $H_2O$. The aqueous layer was further extracted with EtOAc and then the combined organic fractions washed with brine, dried ($MgSO_4$) and evaporated to dryness. The crude solid was dissolved in DCM and triturated with hexanes to give a solid which was collected by filtration. The solid was purified by flash column chromatography [$SiO_2$, EtOAc-MeOH (90:10)] to give 1-(4-fluorophenyl)-N-[3-(5-morpholin-4-ylmethyl-1H-benzimidazol-2-yl)-1H-pyrazol-4-yl]-urea (30 mg, 20%) as a yellow solid (LC/MS (acidic method): $R_t$ 2.01 min, $[M-H^+]^-$ 434).

Examples 45-56

By following the method described in Example 44, but modifying the conditions where indicated in the Table below, the compounds of Examples 45 to 56 were prepared.

| Example | Structure | Differences to General Method | LC/MS |
|---|---|---|---|
| 45 | 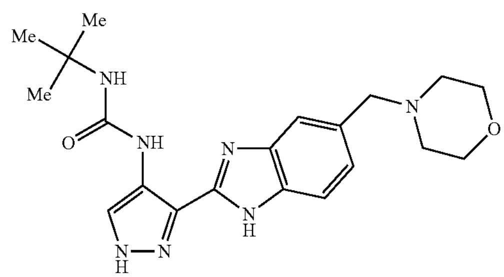 [SMILES: CC(C)(C)NC(=O)Nc1c[nH]nc1-c1nc2cc(CN3CCOCC3)ccc2[nH]1] | Reaction required heating (80°, 4 h)<br>No chromatography required | $[M + H]^+$ 398<br>$R_t$ 1.79<br>Acidic |
| 46 | 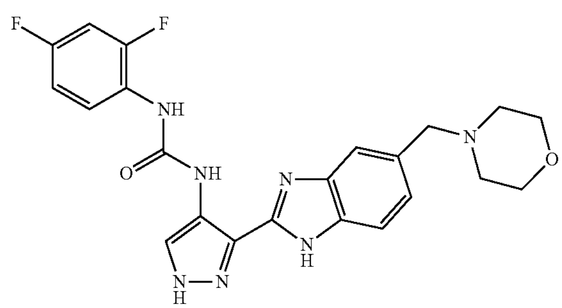 [SMILES: O=C(Nc1ccc(F)cc1F)Nc1c[nH]nc1-c1nc2cc(CN3CCOCC3)ccc2[nH]1] | | $[M + H]^+$ 454<br>$R_t$ 1.95<br>Acidic |
| 47 | 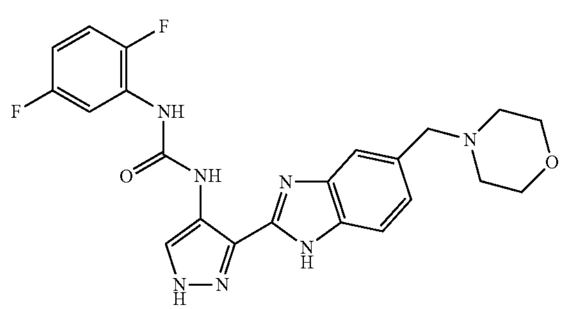 [SMILES: O=C(Nc1cc(F)ccc1F)Nc1c[nH]nc1-c1nc2cc(CN3CCOCC3)ccc2[nH]1] | | |

-continued

| Example | Structure | Differences to General Method | LC/MS |
|---|---|---|---|
| 48 | 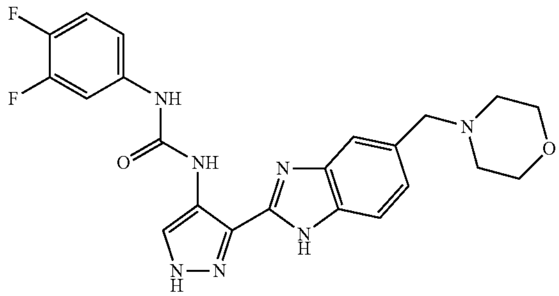 [SMILES: O=C(Nc1ccc(F)c(F)c1)Nc1c[nH]nc1-c1nc2cc(CN3CCOCC3)ccc2[nH]1] | Following chromatography on silica, impurity removed by precipitation from MeOH solution. | [M + H]+ 452 R$_t$ 2.09 Acidic |
| 49 | 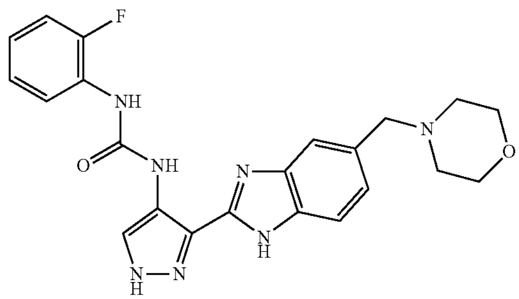 [SMILES: O=C(Nc1ccccc1F)Nc1c[nH]nc1-c1nc2cc(CN3CCOCC3)ccc2[nH]1] | Purified by preparative LC/MS | [M + H]+ 436 R$_t$ 2.68 Basic |
| 50 | 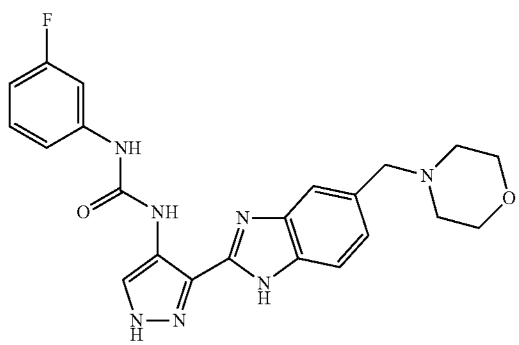 [SMILES: O=C(Nc1cccc(F)c1)Nc1c[nH]nc1-c1nc2cc(CN3CCOCC3)ccc2[nH]1] | Purified by preparative LC/MS | [M + H]+ 436 R$_t$ 2.77 Basic |
| 51 | 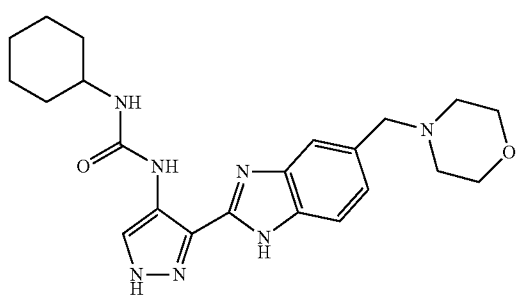 [SMILES: O=C(Nc1c[nH]nc1-c1nc2cc(CN3CCOCC3)ccc2[nH]1)NC1CCCCC1] | | [M + H]+ 422 R$_t$ 1.89 Acidic |
| 52 | 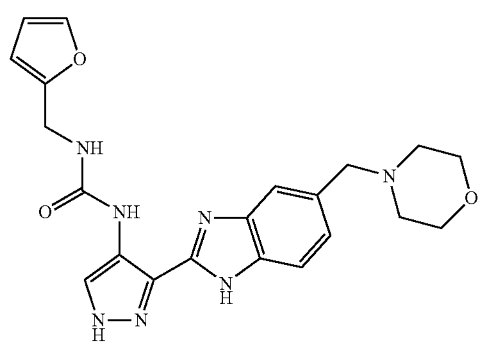 [SMILES: O=C(NCc1ccco1)Nc1c[nH]nc1-c1nc2cc(CN3CCOCC3)ccc2[nH]1] | | [M + H]+ 422 R$_t$ 1.65 Acidic |

-continued

| Example | Structure | Differences to General Method | LC/MS |
|---|---|---|---|
| 53 | 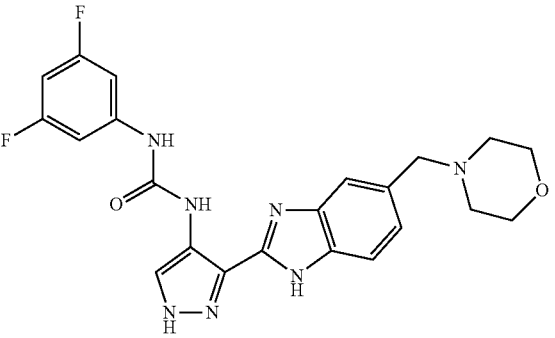 [SMILES: O=C(Nc1cc(F)cc(F)c1)Nc1c[nH]nc1-c1nc2cc(CN3CCOCC3)ccc2[nH]1] | Following chromatography on silica, impurity removed by precipitation from MeOH solution. | [M + H]⁺ 452 R$_t$ 2.21 Acidic |
| 54 | 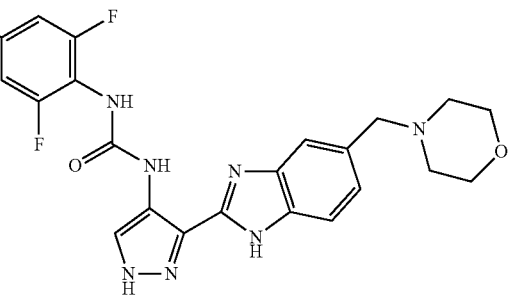 | No tris-amine required. Purified by preparative LC/MS | [M + H]⁺ 472 R$_t$ 1.89 Acidic |
| 55 | 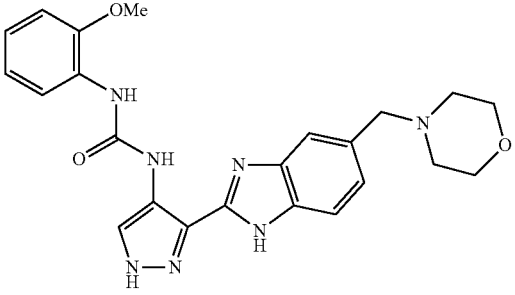 [SMILES: COc1ccccc1NC(=O)Nc1c[nH]nc1-c1nc2cc(CN3CCOCC3)ccc2[nH]1] | Reaction run for 1.5 hours at 0° C. Mixture concentrated and purified directly by preparative LC/MS. | [M + H]⁺ 448 R$_t$ 6.28 Acidic |
| 56 | 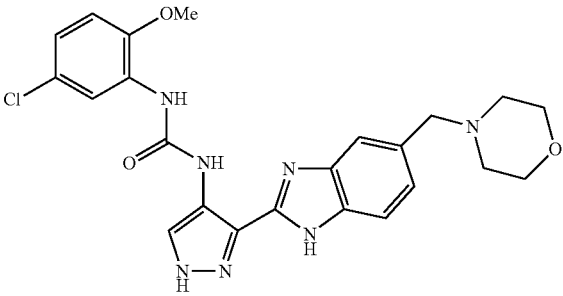 [SMILES: COc1ccc(Cl)cc1NC(=O)Nc1c[nH]nc1-c1nc2cc(CN3CCOCC3)ccc2[nH]1] | Reaction run for 1.5 hours at 0° C. Mixture concentrated and purified directly by preparative LC/MS. | [M + H]⁺ 482 R$_t$ 7.28 Acidic |

Examples 57-59

By following the general method set out in Example 23, but modified where indicated in the Table below, the compounds of Examples 57 to 59 were prepared.

| Example | Structure | Procedure from Example | Differences to General Method | LC/MS |
|---|---|---|---|---|
| 57 | 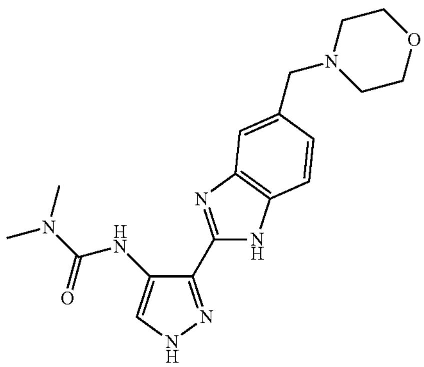 [SMILES: CN(C)C(=O)Nc1c[nH]nc1-c1nc2cc(CN3CCOCC3)ccc2[nH]1] | Example 23 using dimethyl-amine | | [M + H]⁻ 368 R$_t$ 2.39 (Basic method) |
| 58 | 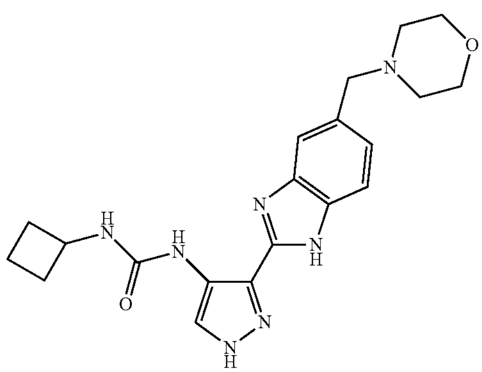 [SMILES: O=C(Nc1c[nH]nc1-c1nc2cc(CN3CCOCC3)ccc2[nH]1)NC1CCC1] | Example 23 using cyclobutyl-amine | | [M + H]⁺ 396 R$_t$ 2.48 (Basic method) |
| 59 | 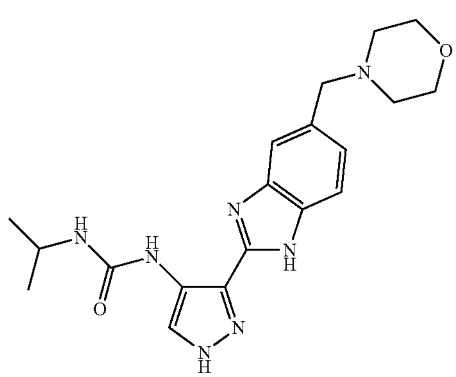 [SMILES: CC(C)NC(=O)Nc1c[nH]nc1-c1nc2cc(CN3CCOCC3)ccc2[nH]1] | Example 23 using iso-propylamine | | [M + H]⁺ 384 R$_t$ 2.40 (Basic method) |

Example 60

Synthesis of 1-(2,6-difluorophenyl)-N-[3-(5-morpholin-4-ylmethyl-1H-benzimidazol-2-yl)-1H-pyrazol-4-yl]-urea-hydrochloride salt

60A. Synthesis of (3,4-Dinitro-phenyl)-morpholin-4-yl-methanone

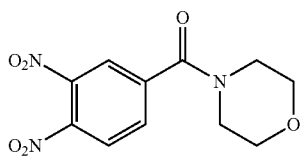 [SMILES: O=C(c1ccc([N+](=O)[O-])c([N+](=O)[O-])c1)N1CCOCC1]

A mixture of 3,4-dinitrobenzoic acid (1 mol. eq.) and thionyl chloride (9.2 mol. eq.) was heated at reflux for 6 hours, cooled to ambient temperature and excess thionyl chloride removed through azeotrope with toluene. The residue was taken up in THF (8 vol.) and then morpholine (1.0 mol. eq.) and Et$_3$N (1.1 mol. eq.) were added concurrently to the mixture at 0-5° C. The mixture was stirred for 1 hour at ambient temperature before being poured into water (25 vol.). The mixture was cooled to 3-7° C. and allowed to stand for 0.5 hours during which time the product appeared as a precipitate. The precipitate was collected by filtration, washed with water and dried to give 3,4-dinitro-phenyl)-morpholin-4-yl-methanone (75%) as a yellow solid. ($^1$H NMR (300 MHz, DMSO-$d_6$) δ 8.3 (d, 1H), 8.3 (s, 1H), 8.0 (d, 1H), 3.7-3.5 (m, 8H).

60B. Synthesis of 4-f3,4-Dinitro-benzylVmorpholine

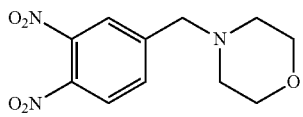 [SMILES: O=[N+]([O-])c1ccc(CN2CCOCC2)cc1[N+](=O)[O-]]

To a mixture of (3,4-dinitro-phenyl)-morpholin-4-ylmethanone (1 mol. eq.) in dry tetrahydrofuran (THF) (25 vol.), at 0-5° C., was added NaBH$_4$ (2 mol. eq.) followed drop-wise by BF$_3$-Et$_2$O (1.01 mol. eq.) so as to maintain the temperature at 0-5° C. The mixture was then stirred at ambient temperature for 3 hours and then quenched through addition of methanol. The mixture was then reduced in vacuo, partitioned between ethyl acetate and saturated aqueous NaHCO$_3$. The mixture was stirred rapidly for 30 minutes before separating the layers. The organic layer was washed successively with water and brine before being reduced in vacuo. The product was crystallised from methanol to give 4-(3,4-dinitro-benzyl)-morpholine (85%).

(LC/MS (basic method): $R_t$ 2.80, [M+H]$^+$ 268).

60C. Synthesis of 4-Morpholin-4-ylmethyl-benzene-1,2-diamine

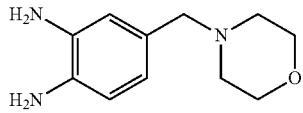

A mixture of 4-(3,4-dinitro-benzyl)-morpholine (1 mol. eq.) and 5% Pd/C (0.05 wt. eq.) in IMS (33 vol.) was stirred at 0-5° C. while the vessel was charged with hydrogen. The mixture was carefully warmed to 15-20° C. with stirring until the reaction was complete (<24 hours). The mixture was filtered and the filtrate evaporated to dryness to give 4-morpholin-4-ylmethyl-benzene-1,2-diamine (90%). The material was used immediately in the next step. (LC/MS (basic method): $R_t$ 1.64, [M—N(CH$_2$CH$_2$)$_2$O—]$^+$ 121).

60D. Synthesis of 5-Morpholin-4-ylmethyl-2-(4-nitro-1H-pyrazol-3-vnill-benzimidazole

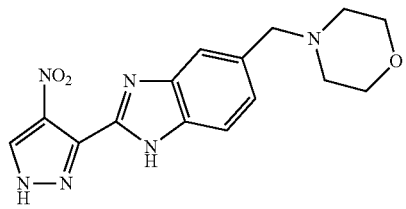 [SMILES: O=[N+]([O-])c1c[nH]nc1-c1nc2cc(CN3CCOCC3)ccc2[nH]1]

4-Morpholin-4-ylmethyl-benzene-1,2-diamine (1 mol. eq.) and 4-nitro-1H-pyrazole-3-carboxylic acid (1 mol. eq.) were dissolved in dimethylformamide (DMF) (10 vol.). O-(Benzot πazol-1-yl)-N,N,N',N$^1$-tetramethyluronium tetrafluoroborate (TBTU) (1.2 mol. eq.) was added and the mixture was stiffed at ambient temperature for 24 hours. The mixture was concentrated in vacuo until no further solvent was seen to distil. The residue was then dissolved in glacial acetic acid (10 vol.) and heated at 65° C. for ~12 hours. The mixture was concentrated in vacuo and then dissolved in water (6 vol.) at 75° C. The black solution was cooled to 0-5° C. over 2 hours during which time a solid was formed. The solid was removed by filtration and the aqueous filtrate was diluted with ethyl acetate (4 vol.) and tetrahydrofuran (2 vol.). Solid NaHCO$_3$ was added slowly to the stirred mixture until no further effervescence was observed and a pH of 6.8 was reached. The mixture was then stirred until a precipitation was observed. After standing the mixture at 0-5° C. for 2 hours, the solid was collected by filtration and washed with water (2 vol.) and ethyl acetate (2 vol.) and dried to give 5-morpholin-4-ylmethyl-2-(4-nitro-1H-pyrazol-3-yl)1H-benzimidazole as a brown solid (40%). (LC/MS (basic method): $R_t$ 1.93, [M–H$^+$]$^-$ 327).

6OE. Synthesis of 3-(5-morpholin-4-ylmethyl-1H-benzimidazol-2-yl)-1H-pyrazol-ylamine

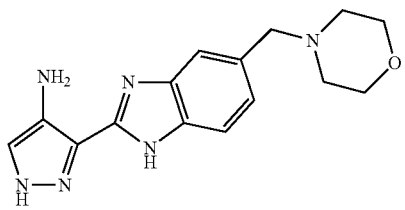

To 5-morpholin-4-ylmethyl-2-(4-nitro-1H-pyrazol-3-yl) 1H-benzimidazole (1 mol. eq.) in DMF (36 vol.) under an atmosphere of nitrogen, was added 5% Pd/C (0.1 wt. eq.). The reaction vessel was charged with hydrogen and stirred at ambient temperature for 24 hours. The mixture was then filtered through celite, washing with methanol. The filtrate was concentrated in vacuo to give 3-(5-morpholin-4-ylmethyl-1H-benzimidazol-2-yl)-1H-pyrazol-4-ylamine as a brown solid (90%). (LC/MS (basic method): $R_t$ 1.94, $[M-H^+]^-$ 297. The product was used without any further purification.

6OF. Synthesis of 1-(2,6-difluorophenylVN-r3-(5-morpholia-4-ylmethyl-1H-benzimidazol-2-yl)-1H-pyrazol-4-yll-urea-hydrochloride salt

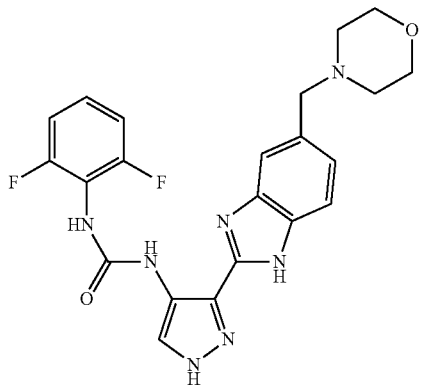 [SMILES: O=C(Nc1c[nH]nc1-c1nc2cc(CN3CCOCC3)ccc2[nH]1)Nc1c(F)cccc1F]

To a mixture of 3-(5-morpholin-4-ylmethyl-1H-benzimidazol-2-yl)-1H-pyrazol-4-ylamine (1 mol. eq.) in THF (10 vol.) was added 2,6-difluorophenyl isocyanate (1.3 mol. eq.) while stirring at 0-5° C. The mixture was then stirred for 16 hours at ambient temperature after which time the mixture was treated with 1M aq. KOH (4 vol.). After stirring for a further 2 hours the mixture was then concentrated in vacuo and partitioned between ethyl acetate and saturated aqueous NaHCO$_3$. The organic layer was washed with saturated brine, dried (MgSO$_4$), evaporated to dryness and then the residue purified by flash column chromatography [SiO$_2$, eluting with a gradient CH$_2$Cl$_2$-MeOH (98:2)-(90:10)] to give 1-(2,6-difluorophenyl)-N-[3-(5-morpholin-4-ylmethyl-1H-benzimidazol-2-yl)-1H-pyrazol-4-yl]-urea.

6OG. Recrystallisation and characterization of the Free Base

Following chromatography on silica as described in Example 6OE, the product was dissolved in a minimum amount of hot ethyl acetate, filtered and allowed to cool. The free base was thus obtained as a fine crystalline solid.

The compound 1-(2,6-difluorophenyl)-N-[3-(5-morpholin-4-ylmethyl-1H-benzimidazol-2-yl)-1H-pyrazol-4-yl]-urea has the following physicochemical parameters.
pKa values—3.42, 6.92 & 10.97
logP—3.24
logPion—0.36
logD (pH=6) 2.27
(pH=6.5) 2.68
(pH=7.4) 3.11

6OH. Formation of Hydrochloride Salt

The product was dissolved in ethyl acetate and treated with excess saturated HCl in diethyl ether. The resulting precipitate was collected by filtration, washed with diethyl ether and dried to give 1-(2,6-difluorophenye-N-[3-(5-morpholin-4-ylmethyl-1H-benzimidazol-2-yl)-1H-pyrazol-4-yl]-urea-hydrochloride salt (59%) as a colourless solid. (LC/MS (acidic method): $R_L$ 1.80, $[M+H]^+$ 454).

By replacing the hydrogen chloride with other acids (e.g. DL lactic acid, ethane sulphonic acid and methane sulphonic acid) and changing the make up of the solvents as required, other salts of 1-(2,6-difluorophenyl)-N-[3-(5-morpholin-4-ylmethyl-1H-benzimidazol-2-yl)-1H-pyrazol-4-yl]-urea may be prepared.

6OJ. Comparison of the Solubilities of the Free Base and Hydrochloride salt

The solubilities of the free base and hydrochloride salt were measured and compared. The solubility of the free base at pH 7.4 (buffered aqueous solution) was found to be <0.001 mg/ml whereas the solubility of the hydrochloride salt at pH 7.1 (in buffered aqueous solution) was found to be 0.093 mg/ml. Thus, the hydrochloride salt has significant advantages in terms of solubility with respect to the free base.

Example 61

Determination of the Solubilities of Acid Addition Salts of 1-(2,6-difluorophenyl')-N-|3-(5-morpliolin-4-ylmethyl-1H-benzimidazol-2-ylV 1H-pyrazol-4-yll-urea The free base form of 1-(2,6-difluorophenyl)-N-[3-(5-morpholin-4-ylmethyl-1H-benzimidazol-2-yl)-1H-pyrazol-4-yl]-urea was combined with various acids by the procedure set out below in order to assess the solubilities of the resulting acid addition salts.

Procedure

Into an 8 ml vial was added the free base (59 mg, 0.13 mmol) and water (0.59 ml). To the vial was added the appropriate acid (1 eq., 0.13 mmol) and the vial was shaken at ambient temperature for 16 hours. After this time the vials were visually inspected. If a homogenous solution was observed, then the experiment was terminated, and it was concluded that the salt thus formed has a solubility greater than 100 mg/ml.

If solid remained, then a further 0.59 ml of water was added and the vial was shaken for 4 hours. If a homogenous solution was formed by this stage, it was concluded that the salt has a solubility of greater than 50 mg/ml.

If solid remained at this juncture, then a further 1.18 ml of water was added and the vial was shaken at ambient temperature. If this resulted in a homogenous solution, then it was concluded that the solubility is greater than 25 mg/ml. If solid still remained, it was concluded that the solubility of the salt is less than 25 mg/ml.

The free base was regenerated by passing the salt solution through a Strata-NH., column.

The results of the experiments are set out in the Table below.

| Solubilities of salts of 1-f2.6-difluoro ühenyl)-N-r3-(5-morpholin-4-ylmethyl-1H-benzimidazol-2-yl)-1H-pyrazol-4-yll-urea | | | |
|---|---|---|---|
| >100 mg/ml | >50 mg/ml | >25 mg/ml | <25 mg/ml |
| Mesylate | | D-Glucuronate | Acetate |
| Ethanesulphonate | | | Adipate |
| DL-Lactate | | | L-(+)-Aspartate |
| | | | D-Gluconate |
| | | | L-Glutamate |
| | | | Hydrochloride |
| | | | Tosylate |
| | | | Free base |

On the basis of the results shown in the Table, it may be concluded that the mesylate, ethanesulphonate and DL-Lactate salts should prove to be particularly useful for preparing aqueous liquid compositions, for example for parenteral administration.

Example 62

Free Base and Salts of 1-Cyclopropyl-S—P-fS-morpholm^-ylmethyl-1H-benzoimidazol-2-vD-1H-pyrazol-4-yl]-urea The compound of Example 24, 1-cyclopropyl-3-[3-(5-morpholin-4-ylmethyl-1H-benzoimidazol-2-yl)-1H-pyrazol-4-yl]-urea, can be isolated in free base or acid addition salt form by the methods set out below or methods analogous thereto.

Free Base

Following chromatography on silica (see Example 24), the product of Example 24 was dissolved in a minimum volume of hot MeOH, filtered and allowed to cool. After ~16 h, the product was collected as a colourless crystalline solid.

Hydrochloride Salt (Generic Procedure)

Following chromatography on silica, the product (2.05 g) was dissolved in MeOH:EtOAc (1:10; 100 ml) and treated with 4N HCl in dioxane (1.1 mol. eq.). The resulting precipitate was collected by filtration and dried to give 1-cyclopropyl-3-[3-(5-morpholin-4-ylmethyl-1H-benzoimidazol-2-yl)-1H-pyrazol-4-yl]-urea hydrochloride (1.5 g). The product was dissolved in a minimum volume of MeOH and then triturated with Et₂O, until a cloudiness persisted for several seconds. After cooling overnight, the product was collected as a colourless crystalline solid.

Mesylate Salt

The product was collected as a colourless crystalline solid using the generic procedure described above but using methanesulphonic acid instead of hydrochloric acid.

Other Salts

It is anticipated other salts of interest could be prepared using the generic procedure described above.

Example 63

Determination of the Solubilities of the Free Base and Salts of 1-Cyclopropyl-3-[3-(5-morpholm-4-ylmethyl-1H-benzoimidazol-2-yl)-1H-pyrazol-4-yl]-urea The compound of Example 24, 1-cyclopropyl-3-[3-(5-morpholin-4-ylmethyl-1H-benzoimidazol-2-yl)-1H-pyrazol-4-yl]-urea was combined with various acids by the procedure set out below in order to assess the solubilities of the resulting acid addition salts.

Procedure

Into an 8 ml vial was added the free base (50 mg, 0.131 mmol) of the compound of Example 24 and water (0.5 ml). To the vial was added the appropriate acid (1 eq., 0.131 mmol) and the vial was shaken at ambient temperature for 14-16 hours. After this time the vials were visually inspected. If a homogenous solution was observed, then the experiment was terminated, and it was concluded that the salt thus formed has a solubility greater than 100 mg/ml.

If solid remained, then a further 0.5 ml of water was added and the vial was shaken for 6 hours. If a homogenous solution was formed by this stage, it was concluded that the salt has a solubility of greater than 50 mg/ml.

If solid remained at this juncture, then a further 1 ml of water was added and the vial was shaken at ambient temperature. If this resulted in a homogenous solution, then it was concluded that the solubility is greater than 25 mg/ml. If solid still remained, it was concluded that the solubility of the salt is less than 25 mg/ml.

The free base was regenerated by passing the salt solution through a Strata-NII₂ column.

The results of the experiments are set out in the Table below.

| Solubilities of salts of 1-cyclopropyl-3-[3-(5-morpholin-4-ylmethyl-1H-benzoimidazol-2-yl)-1H-pyrazol-4-yl]-urea | | | |
|---|---|---|---|
| >100 mg/ml | >50 mg/ml | >25 mg/ml | <25 mg/ml |
| Acetate | | Tosylate | L-(+)-Aspartate |
| Mesylate | | | L-Glutamate |
| Ethanesulphonate | | | Free base |
| DL-Lactate | | | |
| Adipate | | | |
| D-Glucuronate | | | |
| D-Gluconate | | | |
| Hydrochloride | | | |

On the basis of the results shown in the Table, it may be concluded that the acetate, mesylate, ethanesulphonate, DL-lactate, adipate, D-glucuronate, D-gluconate and hydrochloride salts should prove to be particularly useful for preparing aqueous liquid compositions, for example for parenteral administration.

From data gathered to date, it is envisaged that the compounds of the invention, and in particular the free base and salts of 1-cyclopropyl-3-[3-(5-morpholin-4-ylmethyl-1H-benzoimidazol-2-yl)-1H-pyrazol-4-yl]-urea (in particular the L-lactate), will have a number of advantages over prior art compounds. In particular, such advantages include one or more of the following:

Improved solubility in aqueous solution;
Better physicochemical properties in particular lower logD;
Differences in susceptibility to P450 enzymes;
Improvement in drug metabolism and pharmacokinetic properties;
Improved stability, e.g. improved shelf life and/or improved thermal stability;
Reduced dosage requirements;
Improved potency versus therapeutic targets and in particular Aurora A and B;
Improved cell activity in proliferation and clonogenic assays;
Improved anti-cancer activity; and
Improved therapeutic index.

Example 64

Preparation of 1-Cyclopropyl-3-[3-(5-Morpholin-4-ylmethyl-1H-Benzoimidazol-2-yl]V1H-Pyrazol-4-yll-Urea lactate salt To a solution of 1-cyclopropyl-3-[3-(5-morpholin-4-ylmethyl-1H-benzoimidazol-2-yl)-1H-pyrazol-4-yl]-urea (0.7 g, 1.83 mmol) in EtOAc-MeOH was added L-lactic acid (166 mg, 1.85 mmol). The mixture was stirred at ambient temperature then reduced in vacuo. This solid was purified by recrystallisation from boiling EtOH (20 niL) to give after drying 1-cyclopropyl-3-[3-(5-morpholin-4-ylmethyl-1H-benzoimidazol-2-yl)-1H-pyrazol-4-yl]-urea, L-lactate salt (0.48 g).

Example 65

Synthesis of the L-lactate salt of 1-cyclopropyl-3-[3-(5-morpholin-4-ylmethyl-1H-benzoimidazol-2-yl)-1H-pyrazol-4-yl]-urea The L-lactate salt of 1-cyclopropyl-3-[3-(5-morpholin-4-ylmethyl-1H-benzoimidazol-2-yl)-1H-pyrazol-4-yl]-urea may be prepared by the synthetic route shown in the Scheme below.

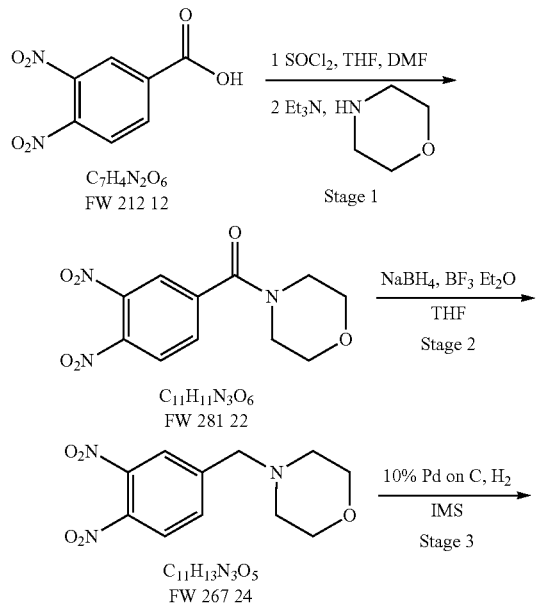

-continued

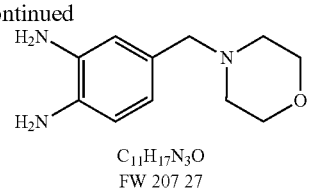

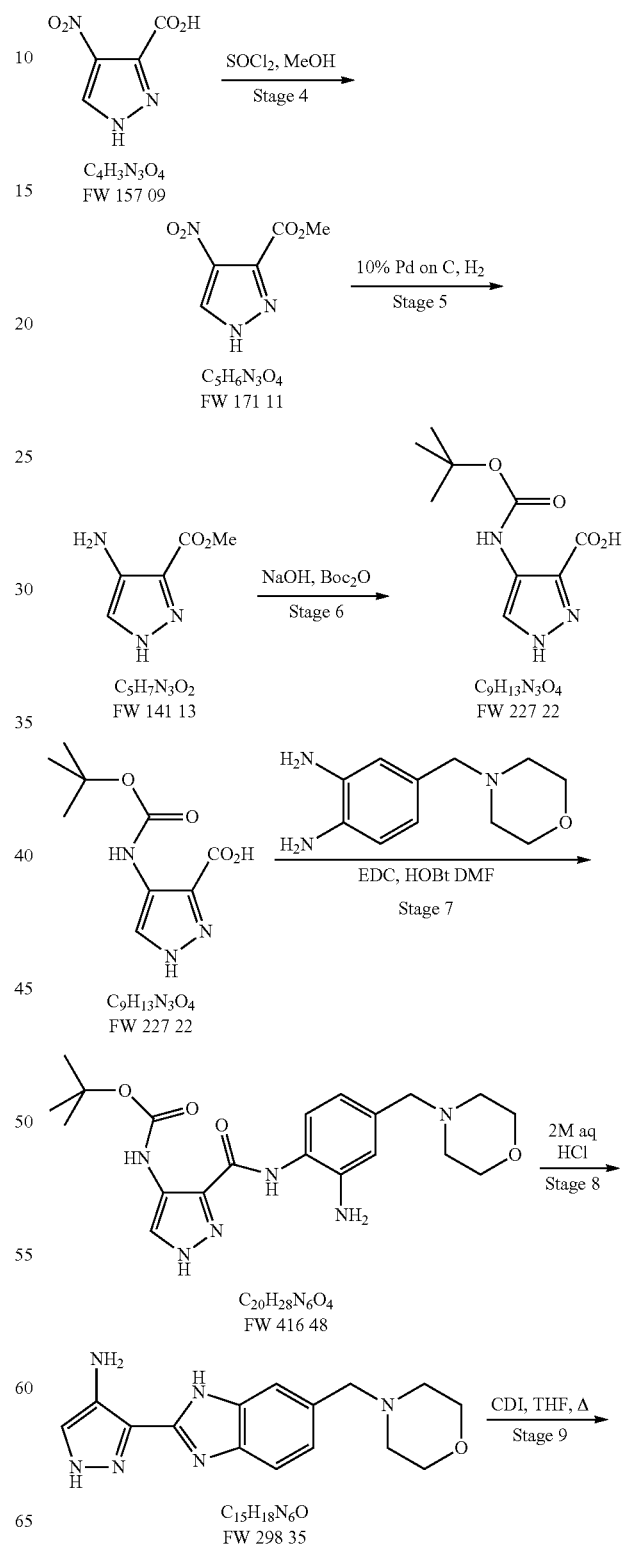

-continued

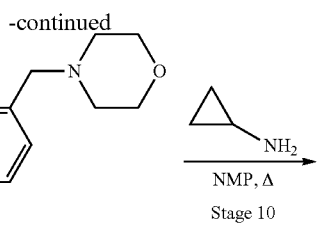

C$_{16}$H$_{16}$N$_6$O$_2$
FW 324 34

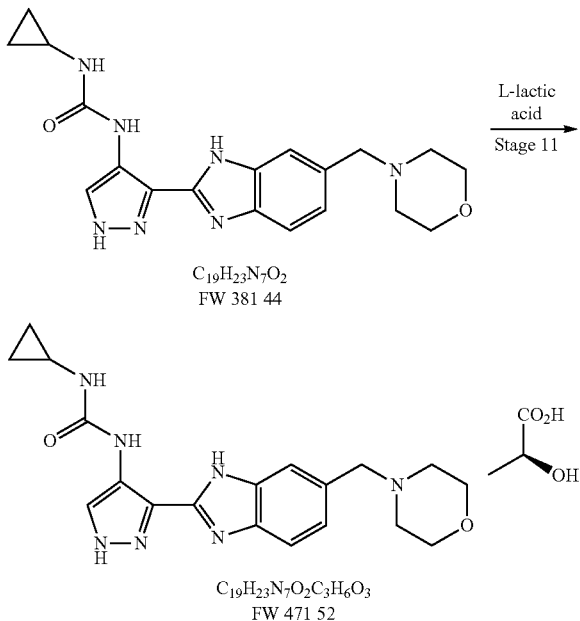

C$_{19}$H$_{23}$N$_7$O$_2$
FW 381 44

C$_{19}$H$_{23}$N$_7$O$_2$C$_3$H$_6$O$_3$
FW 471 52

Stage 1: Synthesis of
(3,4-dinitro-phenyl)-morpholin-4-yl-methanone

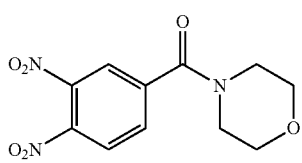

A solution of 3,4-dinitrobenzoic acid (10 g, 47 mmol, 1 eq.) and DMF (0.1 mL) in THF (100 mL) was treated with thionyl chloride (4.5 mL, 62 mmol, 1.3 eq.) then heated to reflux for 2.5 h. The mixture was cooled in ice then triethylamine (10 mL, 71 mmol, 1.1 eq.) was added over 20 min, keeping internal temperature <5° C. Morpholine (6.2 mL, 71 mmol, 1.5 eq) was added to the resulting thick yellow suspension over 15 min, keeping internal temperature <10° C. The ice-bath was removed and the mixture allowed to warm to r.t. After 15 min, a further portion of morpholine (1 mL, 11 mmol, 0.24 eq.) was added and the mixture stirred overnight. The mixture was diluted with water (250 mL) and cooled in ice. A beige solid was filtered off under suction, washed with a further portion of cold water (25 mL) and dried in vacuo to afford the title compound (12.7 g, 96%).

Stage 2: Synthesis of
4-(3,4-dinitro-benzyl)-morpholine

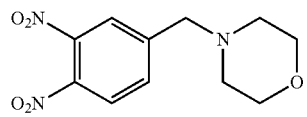 [SMILES: O=[N+]([O-])c1ccc(CN2CCOCC2)cc1[N+](=O)[O-]]

Sodium borohydride (3.36 g, 89 mmol, 2.1 eq.) was ground, placed in a nitrogen-flushed flask and suspended in TFIF (120 mL). After cooling to ~0° C., boron trifluoride etherate (11.3 mL, 89 mmol, 2.1 eq.) was added via syringe. This reaction is mildly exothermic and some hydrogen evolution was noted. 4-(3,4-Dinitrobenzoyl)morpholine (11.91 g, 42 mmol, 1.0 eq.) was added as a solid in one portion, the vessel being rinsed with an additional portion of THF (20 mL). The ice-bath was removed and the suspension stirred at r.t. for 3 h before cooling again in ice. Methanol (100 mL) was added cautiously (hydrogen evolution) then the mixture was brought to reflux for 1 h. The mixture was concentrated in vacuo then the residue was partitioned between ethyl acetate (100 mL) and 1:1 saturated sodium bicarbonate solution/water (100 mL). The organic phase was separated, washed with water (50 mL) then brine (100 mL) and dried (MgSO$_4$). The initial bicarbonate wash was extracted a second time with ethyl acetate (50 mL), this extract then being washed with the same aqueous washes used for the first extract before drying (MgSO$_4$), combination and concentration to afford 10.97 g of crude material. Recrystallisation from methanol (45 mL, 10 mL wash) gave the title compound (9.34 g, 83%).

Stage 3: Synthesis of
4-morpholin-4-ylmethyl-benzene-1,2-diamine

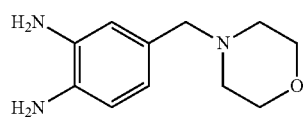

4-(3,4-Dinitrobenzyl)morpholine (21 g, 101 mmol) was suspended in ethanol (0.9 L) and the vessel purged with nitrogen. 10% Palladium on charcoal (1.05 g) was suspended in ethanol (25 mL) and added to the substrate. The mixture was cooled in ice then the atmosphere exchanged for hydrogen. The mixture was allowed to warm to 15-20° C. and hydrogenation continued at ambient pressure for 2 days. The vessel was purged with nitrogen then the mixture was filtered through Celite, rinsing with ethanol (0.3 L) in portions. Concentration afforded the title compound (15.8 g, 97%).

Stage 4: Synthesis of 4-nitro-1H-pyrazole-3-carboxylic acid methyl ester

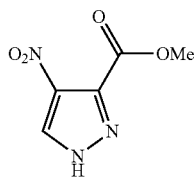 [SMILES: COC(=O)c1n[nH]cc1[N+](=O)[O-]]

A 20 L reaction vessel equipped with a digital thermometer and stirrer was charged with 4-nitro-17f-pyrazole-3-carboxylic acid (1.117 Kg, 7.11 mol, 1 wt) and methanol (8.950 L, 8 vol). The reaction mixture was stirred under nitrogen, cooled to 0 to 5° C., thionyl chloride (0.581 L, 8.0 mol, 0.52 vol) added over 180 minutes and the resultant mixture allowed to warm to and stir at 18 to 22° C. overnight after which time $^1$ NMR analysis ($d_6$-DMSO) indicated reaction completion. The reaction mixture was concentrated under reduced pressure at 40 to 45° C., the residue treated with toluene and re-concentrated (3×2.250 L, 3×2 vol) under reduced pressure at 40 to 45° C. to give 4-nitro-1H-pyrazole-3-carboxylic acid methyl ester as an off-white solid (1.210 Kg, 99.5% th).

Stage 5: Synthesis of 4-amino-1H-pyrazole-3-carboxylic acid methyl ester

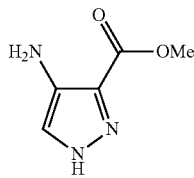

A 2O L, reaction vessel equipped with a digital thermometer and stirrer was charged with palladium on carbon (10% wet paste, 0.170 Kg, 0.14 wt) under nitrogen. In a separate vessel, a slurry of 4-nitro-1H-pyrazole-3-carboxylic acid methyl ester (1.210 Kg, 7.07 mol, 1 wt) in ethanol (12.10 L, 1O vol) was warmed to 30 to 35° C. to effect dissolution and the solution added to the catalyst under nitrogen. Following a nitrogen-hydrogen purge sequence an atmosphere of hydrogen was introduced and the reaction mixture maintained at 28 to 3O° C. until reaction completion (5 to 10 hours) was noted by $^1$H NMR analysis ($d_6$-DMSO). Following a purge cycle, the reaction mixture under nitrogen was filtered and the liquors concentrated under reduced pressure to give 4-amino-1H-pyrazole-3-carboxylic acid methyl ester (0.987 Kg, 98.9% th).

Stage 6: Synthesis of 4-tert-butoxycarbonylamino-1H-pyrazole-3-carboxylic acid

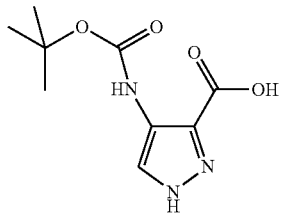 [SMILES: CC(C)(C)OC(=O)Nc1c[nH]nc1C(=O)O]

To a mixture of 4-amino-1H-pyrazole-3-carboxylic acid methyl ester (50.0 g, 355 mmol) in dioxane (500 mL) was added 2M aqueous NaOH solution (213 mL, 426 mmol), the mixture heated to 50° C. and stirred for 5 h. To this mixture was then added (BOC)$_2$O (81.4 g, 373 mmol), using a dioxane rinse (100 mL) and the mixture heated at 50° C. for a further 5 h, then stirred at ambient for 14 h. The dioxane was removed in vacuo and water (1 L) added. The mixture was taken to pH ~2 using cone. aqueous HCl solution and the solid formed collected by filtration and dried on the filter. The solid was dried further through azeotrope with toluene (×3) and in the vacuum oven to give 4-tert-butoxycarbonylamino-1H-pyrazole-3-carboxylic acid (70.0 g, 87%) as a violet solid.

Stage 7: Synthesis of r3-(2-amine-4-morpholin-4-ylmethyl-phenylcarbamoylV1H-pyrazol-4-yl]-carbamic acid tert-butyl ester

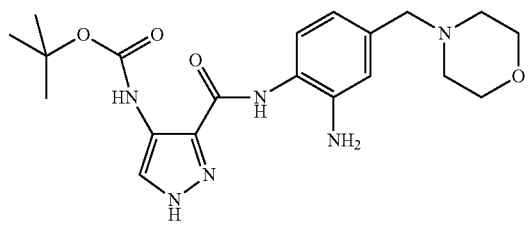 [SMILES: CC(C)(C)OC(=O)Nc1c[nH]nc1C(=O)Nc1ccc(CN2CCOCC2)cc1N]

A mixture of 4-tert-butoxycarbonylamino-1H-pyrazole-3-carboxylic acid (10.0 g, 44.1 mmol), 4-morpholin-4-yl methyl-benzene-1,2-diamine (10.0 g, 48.5 mmol), EDC (10.14 g, 52.9 mmol) and HOBt (7.15 g, 52.9 mmol) in DMF (150 mL) was stirred at ambient temperature for 20 h and then the majority of the solvent removed in vacuo. The residue was partitioned between EtOAc (150 mL) and saturated aqueous NaHCO$_3$ (150 mL), the layers separated and the organic portion washed with brine, dried over MgSO$_4$ and reduced in vacuo to give [3-(2-amino-4-morpholin-4-ylmethyl-phenylcarbamoyl)-1H-pyrazol-4-yl]-carbamic acid tert-butyl ester (17.6 g, 96%) as a brown solid. LC/MS analysis indicates product contains ~15% of the di-amide. This shows at approx. 5% level in $^1$H NMR. Di-amide is cleaved in subsequent step.

Stage 8: Synthesis of 3-(5-morpholin-4-ylmethyl-1H-benzoimidazol-2-yl)-1H-pyrazol-4-ylamine

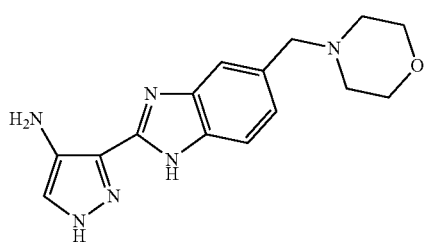 [SMILES: Nc1c[nH]nc1-c1nc2cc(CN3CCOCC3)ccc2[nH]1]

A mixture of [3-(2-amino-4-morpholin-4-ylmethyl-phenylcarbamoyl)-1H-pyrazol-4-yl]-carbamic acid tert-butyl ester (12.0 g, 28.8 mmol) and 2M aqueous HCl solution (50 mL) was heated at 85° C. for 14 h, then allowed to cool to ambient temperature. Solid Na$_2$CO$_3$ was carefully added until mixture was pH ~8.5 and solution was saturated. A dark coloured gummy liquid was formed. The mixture was allowed to settle and the solvent decanted. To the remaining residue was added EtOH (60 mL), the mixture heated at reflux for 1 h and then hot filtered, washing with EtOH (2×20 mL), to remove inorganic residues. The filtrate was reduced in vacuo to give a glassy solid which was then stirred in Et$_2$O (60 mL) for 1 h and the resultant purple coloured powder collected by filtration and dried in vacuo to give 3-(5-morpholin-4-ylmethyl-1H-benzoimidazol-2-yl)-1H-pyrazol-4-ylamine (6.8 g, 80%, ~90% purity).

Stage 9: Synthesis of 7-morpholin-4-ylmethyl-2,4-dihydiO-1,2,4,5a,10-pentaaza-cyclopentaralfluoren-5-one

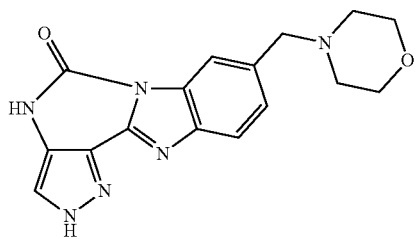 [SMILES: O=c1[nH]c2c[nH]nc2c2nc3ccc(CN4CCOCC4)cc3n12]

To a mixture of 3-(5-morphomi-4-ylmethyl-1H-benzoimidazol-2-yl)-1H-pyrazol-4-ylamine (3.2 g, 10.7 mmol) in anhydrous THF (50 mL) stirring at ambient temperature was added 1,1'-carbonyldiimidazole (1.78 g, 11 mmol). The mixture was heated at reflux for 14 h and then cooled to ambient. The solid formed was collected by filtration, washed with THF (20 mL) and dried in vacuo to give 7-morpholin-4-ylmethyl-2,4-dihydro-1,2,4,5a,10-pentaaza-cyclopenta[a]fluoren-5-one (2.34 g, 67%) as a pink solid.

Stage 10: Synthesis of 1-cyclopropyl-3-[3-(5-morpholin-4-ylmethyl-1II-benzoimidazol-2-ylV 1H-pyrazol-4-yli-urea,

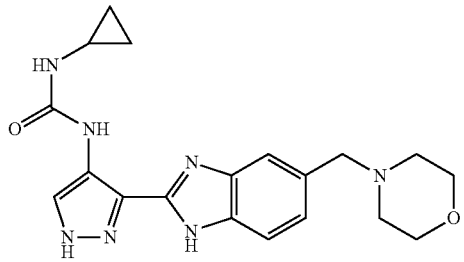 [SMILES: O=C(Nc1c[nH]nc1-c1nc2cc(CN3CCOCC3)ccc2[nH]1)NC1CC1]

To a mixture of 7-morpholin-4-ylmethyl-2,4-dihydro-1,2,4,5a,10-pentaaza-cyclopenta[a]fluoren-5-one (10.7 g, 32.9 mmol) in NMP (65 mL) was added cyclopropylamine (6.9 mL, 99 mmol). The mixture was heated at 100° C. for 5 h. LC/MS analysis indicated ~75% conversion to product, therefore a further portion of cyclopropylamine (2.3 mL, 33 mmol) was added, the mixture heated at 100° C. for 4 h and then cooled to ambient. The mixture was diluted with water (100 mL) and extracted with EtOAc (100 mL). The organic portion was washed with sat. aq. NH$_4$Cl (2×50 mL) and brine (50 mL) and then the aqueous portions re-extracted with EtOAc (3×100 mL). The combined organic portions were dried over MgSO$_4$ and reduced in vacuo to give 1-cyclopropyl-3-[3-(5-morpholin-4-ylmethyl-1H-benzoimidazol-2-yl)-1H-pyrazol-4-yl]-urea as an orange glassy solid (9.10 g).

Stage 11: Synthesis of 1-cyclopropyl-S—P-fS-morpholin^-ylmethyl-1H-benzoimidazol-2-yl)-1H-pyrazol-4-yll-urea, L-lactate salt

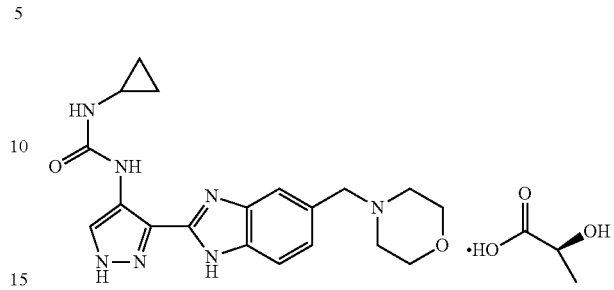

To a solution of 1-cyclopropyl-3-[3-(5-morpholin-4-ylmethyl-1H-benzoimidazol-2-yl)-1H-pyrazol-4-yl]-urea (9.10 g, 24 mmol) in EtOAc-iPrOH (1:1, 90 mL) was added L-lactic acid (2.25 g, 25 mmol). The mixture was stirred at ambient temperature for 24 h then reduced in vacuo. The residue was given consecutive slurries using toluene (100 mL) and Et$_2$O (100 mL) and the resultant solid collected and dried (8.04 g).

This solid was purified by recrystallisation from boiling iPrOH (200 mL) to give after drying 1-cyclopropyl-3-[3-(5-morpholin-4-ylmethyl-1H-benzoimidazol-2-yl)-1II-pyrazol-4-yl]-urea, L-lactate salt (5.7 g) as a beige solid.

Example 66

Stage 1: Preparation of (3,4-dinitrophenyl)-morpholin-4-yl-methanone

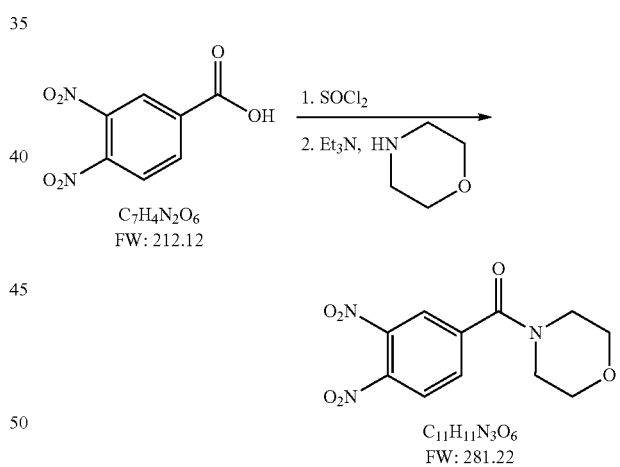

3,4-Dinitrobenzoic acid (1.000 Kg, 4.71 mol, 1.O wt), tetrahydrofuran (10.00 L, 1O.O vol), and dimethylformamide (0.010 L, O.O1 vol) were charged to a flask under nitrogen. Thionyl chloride (0.450 L, 6.16 mol, 0.45 vol) was added at 20 to 3O° C. and the reaction mixture was heated to 65 to 7O° C. Reaction completion was determined by $^1$H NMR analysis (d$_6$-DMSO), typically in 3 hours. The reaction mixture was cooled to 0 to 5° C. and triethylamine (1.25 L, 8.97 mol, 1.25 vol) was added at 0 to 10° C. Morpholine (0.62 L, 7.07 mol, 0.62 vol) was charged to the reaction mixture at 0 to 10° C. and the slurry was stirred for 30 minutes at 0 to 10° C. Reaction completion was determined by $^1$H NMR analysis (d$_6$-DMSO). The reaction mixture was warmed to 15 to 2O° C. and water (4.00 L, 4.0 vol) was added. This mixture was then charged to a 40 L flange flask containing water (21.00 L, 21.0 vol) at 15 to 25° C. to precipitate the product. The flask contents were cooled to and aged at 0 to 5° C. for 1 hour and the solids were collected by filtration. The filter-cake was washed with water (4×5.00 L, 4×5.0 vol) and the pH of the final wash was found to be pH 7. The wet filter-cake was analysed by $^1$H NMR for the presence of triethylamine hydrochloride. The filter-cake was dried at 40 to 45° C. under vacuum until the water content by KF<0.2% w/w, to yield (3,4-dinitrophenyl)-morpholin-4-yl-methanone (1.286 Kg, 97.0%, KF 0.069% w/w) as a yellow solid.

Stage 2: Preparation of 4-(3,4-dinitro-benzyl)-morpholine

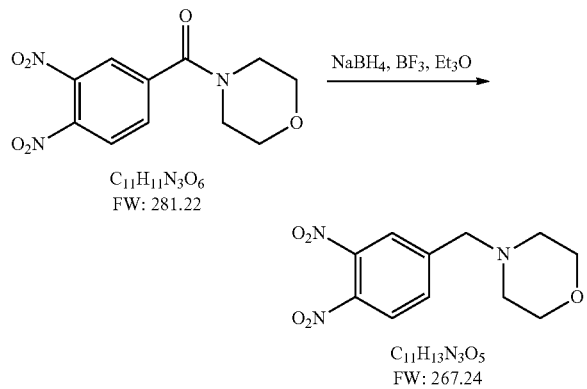

(3,4-Dinitrophenyl)-morpholin-4-yl-methanone (0.750 Kg, 2.67 mol, 1.0 wt) and tetrahydrofuran (7.50 L, 10.0 vol) were charged to a flask under nitrogen and cooled to 0 to 5° C. Borontrifluoride etherate (0.713 L, 5.63 mol, 0.95 vol) was added at 0 to 5° C. and the suspension was stirred at this temperature for 15 to 30 minutes. Sodium borohydride (0.212 Kg, 5.60 mol, 0.282 wt) was added in 6 equal portions over 90 to 120 minutes. (A delayed exotherm was noted 10 to 15 minutes after addition of the first portion. Once this had started and the reaction mixture had been re-cooled, further portions were added at 10 to 15 minute intervals, allowing the reaction to cool between additions). The reaction mixture was stirred at 0 to 5° C. for 30 minutes. Reaction completion was determined by $^1$H NMR analysis (d$_6$-DMSO). Methanol (6.30 L, 8.4 vol) was added dropwise at 0 to 10° C. to quench the reaction mixture (rapid gas evolution, some foaming). The quenched reaction mixture was stirred at 0 to 10° C. for 25 to 35 minutes then warmed to and stirred at 20 to 30° C. (exotherm, gas/ether evolution on dissolution of solid) until gas evolution had slowed. The mixture was heated to and stirred at 65 to 70° C. for 1 hour. The mixture was cooled to 30 to 40° C. and concentrated under vacuum at 40 to 45° C. to give crude 4-(3,4-dinitro-benzyl)-morpholine (0.702 Kg, 98.4%) as a yellow/orange solid.

4-(3,4-Dinitro-benzyl)-niorpholme (2.815 kg, 10.53 mol, 1.0 wt) and methanol (12.00 L, 4.3 vol) were charged to a flask under nitrogen and heated to 65 to 70° C. The temperature was maintained until complete dissolution. The mixture was then cooled to and aged at 0 to 5° C. for 1 hour. The solids were isolated by filtration. The filter-cake was washed with methanol (2×1.50 L, 2×0.5 vol) and dried under vacuum at 35 to 45° C. to give 4-(3,4-dinitro-benzyl)-morpholine (2.353 Kg, 83.5% based on input Stage 2, 82.5% overall yield based on total input Stage 1 material) as a yellow solid.

Stage 3: Preparation of 4-morpholin-4-yl-methyl-benzene-L2-diamine

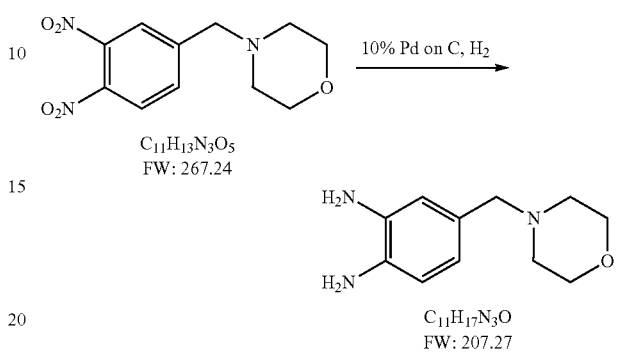

4-(3,4-Dinitro-benzyl)-morpholine (0.800 Kg, 2.99 mol, 1.0 wt), and ethanol (11.20 L, 14.0 vol) were charged to a suitable flask and stirred at 15 to 25° C. and a vacuum/nitrogen purge cycle was performed three times. 10% Palladium on carbon (10% Pd/C, 50% wet paste, 0.040 Kg, 0.05 wt wet weight) was slurried in ethanol (0.80 L, 1.0 vol) and added to the reaction. The mixture was cooled to 10 to 20° C. and a vacuum/nitrogen purge cycle was performed three times. A vacuum/hydrogen purge cycle was performed three times and the reaction was stirred under a hydrogen atmosphere at 10 to 20° C. Reaction completion was determined by $^1$H NMR analysis (d$_6$-DMSO), typically 14 to 20 hours. A vacuum/nitrogen purge cycle was performed three times and the reaction mixture was filtered through glass microfibre paper under nitrogen. The filter-cake was washed with ethanol (3×0.80 L, 3×1.0 vol) and the combined filtrate and washes were concentrated to dryness under vacuum at 35 to 45° C. to give 4-morpholin-4-yl-methyl-benzene-1,2-diamine (0.61 IKg 98.6%) as a brown solid.

Stage 4: Preparation of 4-nitro-1H-pyrazole-3-carboxylic acid methyl ester

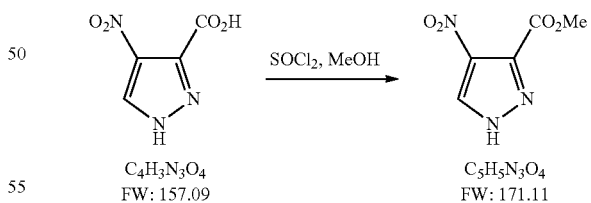

4-Nitro-1H-pyrazole-3-carboxylic acid (1.00 kg, 6.37 mol, 1.0 wt) and methanol (8.00 L, 8.0 vol) were charged to a flange flask equipped with a mechanical stirrer, condenser and thermometer. The suspension was cooled to 0 to 5° C. under nitrogen and thionyl chloride (0.52 L, 7.12 mol, 0.52 vol) was added at this temperature. The mixture was warmed to 15 to 25° C. over 16 to 24 hours. Reaction completion was determined by $^1$H NMR analysis (d$_6$-DMSO). The mixture was concentrated under vacuum at 35 to 45° C. Toluene (2.00 L, 2.0 vol) was charged to the residue and removed under vacuum at 35 to 45° C. The azeotrope was repeated twice using toluene (2.00 L, 2.0 vol) to give 4-nitro-1H-pyrazole-3-carboxylic acid methyl ester (1.071 Kg, 98.3%) as an off white solid.

Stage 5: Preparation of 4-amino-1H-pyrazole-3-carboxylic acid methyl ester.

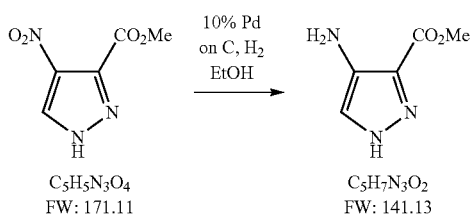 [SMILES: COC(=O)c1n[nH]cc1[N+](=O)[O-] ; COC(=O)c1n[nH]cc1N]

A suspension of 4-nitro-1H-pyrazole-3-carboxylic acid methyl ester (1.084 Kg, 6.33 mol, 1.O wt) and ethanol (10.84 L, 1O.O vol) was heated to and maintained at 30 to 35° C. until complete dissolution occurred. 10% Palladium on carbon (10% Pd/C wet paste, 0.152 Kg, 0.14 wt) was charged to a separate flask under nitrogen and a vacuum/nitrogen purge cycle was performed three times. The solution of 4-nitro-1H-pyrazole-3-carboxylic acid methyl ester in ethanol was charged to the catalyst and a vacuum/nitrogen purge cycle was performed three times. A vacuum/hydrogen purge cycle was performed three times and the reaction was placed under an atmosphere of hydrogen. The reaction mixture was stirred at 28 to 30° C. until deemed complete by ¹H NMR analysis (d₆-DMSO). The mixture was filtered under nitrogen and concentrated under vacuum at 35 to 45° C. to give 4-amino-1H-pyrazole-3-carboxylic acid methyl ester (0.883 Kg, 98.9%) as a purple solid.

Stage 6: Preparation of 4-tert-butoxycarbonylamino-1H-pyrazole-3-carboxylic acid

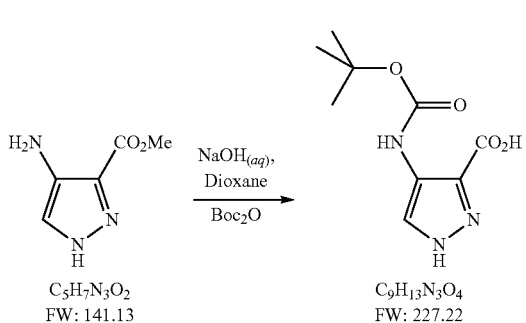 [SMILES: "Boc2O" ; COC(=O)c1n[nH]cc1N ; CC(C)(C)OC(=O)Nc1c[nH]nc1C(=O)O]

4-Amino-1H-pyrazole-3-carboxylic acid methyl ester (1.024 Kg, 7.16 mol, 1.O wt) and dioxane (10.24 L, 1O.O vol) were charged to a flange flask equipped with a mechanical stirrer, condenser and thermometer. 2M aq. Sodium hydroxide solution (4.36 L, 8.72 mol, 4.26 vol) was charged at 15 to 25° C. and the mixture was heated to 45 to 55° C. The temperature was maintained at 45 to 55° C. until reaction completion, as determined by ¹H NMR analysis (d₆-DMSO). Di-te/Y-butyl dicarbonate (Boc anhydride, 1.667 Kg, 7.64 mol, 1.628 wt) was added at 45 to 55° C. and the mixture was stirred for 55 to 65 minutes. ¹H NMR IPC analysis (d₆-DMSO) indicated the presence of 9% unreacted intermediate. Additional di-tert-butyl dicarbonate (Boc anhydride, 0.141 Kg, 0.64 mol, 0.14 wt) was added at 55° C. and the mixture was stirred for 55 to 65 minutes. Reaction completion was determined by ¹H NMR analysis (d₆-DMSO). The dioxane was removed under vacuum at 35 to 45° C. and water (17.60 L, 20.0 vol) was added to the residue. The pH was adjusted to pH 2 with 2M aq. hydrochloric acid (4.30 L, 4.20 vol) and the mixture was filtered. The filter-cake was slurried with water (10.00 L₃ 9.7 vol) for 20 to 30 minutes and the mixture was filtered. The filter-cake was washed with heptanes (4.10 L, 4.0 vol) and pulled dry on the pad for 16 to 20 hours. The solid was azeodried with toluene (5×4.00 L, 5×4.6 vol) then dried under vacuum at 35 to 45° C. to give 4-tert-butoxycarbonylamino-1H-pyrazole-3-carboxylic acid (1.389 Kg, 85.4%) as a purple solid.

Stage 7: Preparation of [3-(2-amino-4-morpholin-4-ylmethyl-phenylcarbamoviy 1H-pyrazol-4-yl]-carbamic acid tert-butyl ester

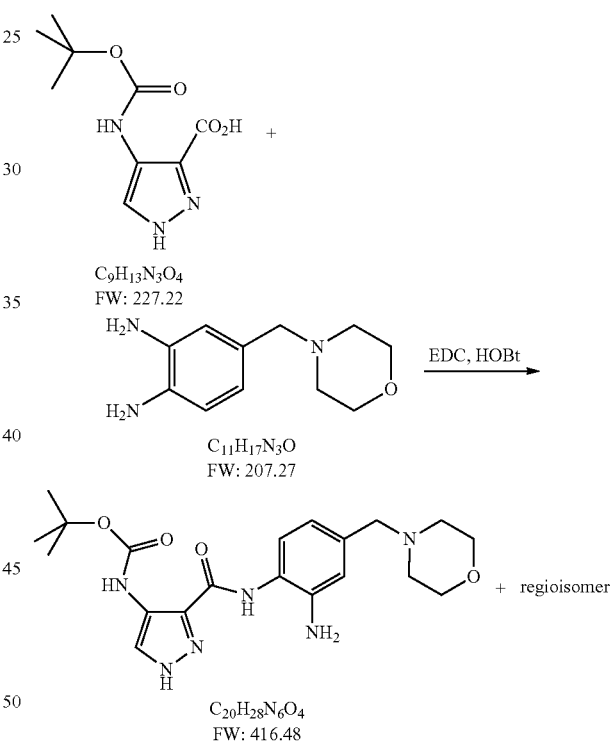

4-førf-Butoxycarbonylamino-1H-pyrazole-3-carboxylic acid (0.750 Kg, 3.30 mol, 1.O wt), 4-morpholin-4-yl-methyl-benzene-1,2-diamine (0.752 Kg, 3.63 mol, 1.O wt) and N,N'-dimethylformamide (11.25 L, 15.0 vol) were charged under nitrogen to a flange flask equipped with a mechanical stirrer and thermometer. 1-Hydroxybenzotriazole (HOBT, 0.540 Kg, 3.96 mol, 0.72 wt) was added at 15 to 25° C. N-(3-Dimethylaminopropyl)-N'-ethylcarbodiimide (EDC, 0.759 Kg, 3.96 mol, 1.01 wt) was added at 15 to 25° C. and the mixture was stirred at this temperature for 16 to 24 hours. Reaction completion was determined by ¹H NMR analysis. The reaction mixture was concentrated under vacuum at 35 to 45° C. The residue was partitioned between ethyl acetate (7.50 L, 1O.O vol) and sat. aq. sodium hydrogen carbonate solution (8.03 L, 10.7 vol) and the layers were separated. The organic phase was washed with brine (3.75 L, 5.0 vol), dried over magnesium sulfate (1.00 Kg, 1.33 wt) and filtered. The filter-cake was washed with ethyl acetate (1.50 L, 2.0 vol). The combined filtrate and wash were concentrated under vacuum at 35 to 45° C. to give [3-(2-amino-4-morpholin-4-ylmethyl-phenylcarbamoyl)-1H-pyrazol-4-yl]-carbamic acid tert-butyl ester (1.217 Kg, 88.6%) as a dark brown solid.

Stage 8: Preparation of 3-f5-morpholin-4-ylmethyl-1H-benzoimidazol-2-ylV 1H-pyrazol-4-ylamine stirred until gas evolution ceased and was then filtered. The filter-cake was washed with ethanol (1.35 L, 1.O vol) and the filtrates retained. The filter-cake was slurried with ethanol (4.00 L, 3.0 vol) at 15 to 25° C. for 20 to 40 minutes and the mixture was filtered. The filter-cake was washed with ethanol (1.35 $L_3$ 1.O vol) and the total combined filtrates were concentrated under vacuum at 35 to 4.5° C. Ethanol (4.00 L, 3.O vol) was charged to the residue and removed under vacuum at 35 to 45° C. Tetrahydrofuran (5.90 L, 4.4 vol) was added to the residue and stirred for 10 to 20 minutes at 15 to 25° C. The resulting solution was filtered, the filter-cake was washed with tetrahydrofuran (1.35 L, 1.O vol) and the combined

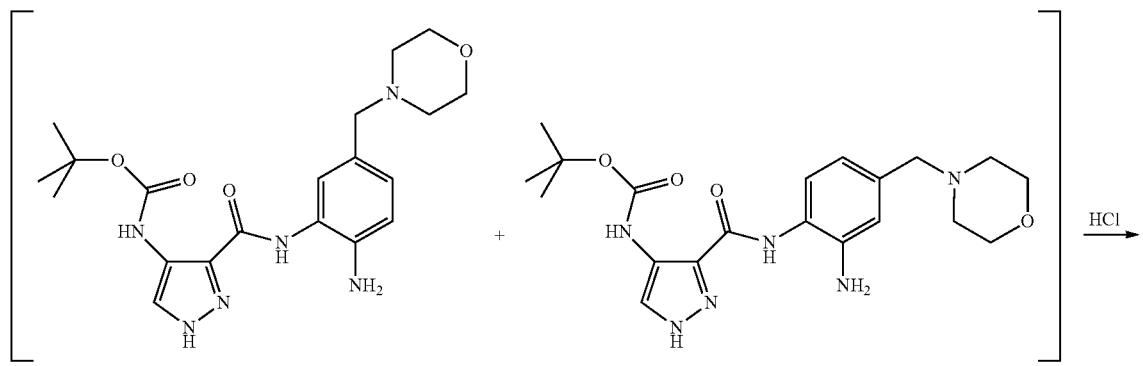

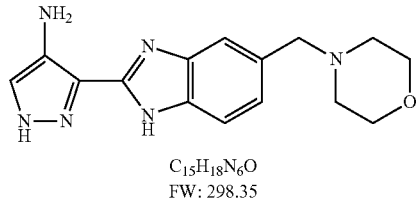

[3-(2-Amino-4-morpholin-4-ylmethyl-phenylcarbamoyl)-1II-pyrazol-4-yl]-carbamic acid tert-butyl ester (1.350 Kg, 3.24 mol, 1.O wt) and ethanol (6.751, 5.0 vol) were charged to a flange flask equipped with a mechanical stirrer, condenser and thermometer. Cone. aq. hydrochloric acid (1.10 L, 13.2 mol, 0.80 vol) was added at 15 to 3O° C. under nitrogen and the contents were then heated to 70 to 8O° C. and maintained at this temperature for 16 to 24 hours. A second portion of hydrochloric acid (0.1 IL, 1.32 mol, O.OSO vol) was added at 70 to 8O° C. and the reaction was heated for a further 4 hours. Reaction completion was determined by HPLC analysis. The reaction mixture was cooled to 10 to 20° C. and potassium carbonate (1.355 Kg, 9.08 mol, 1.O wt) was charged portionwise at this temperature. The suspension was filtrates were concentrated under vacuum at 35 to 45° C. Tetrahydrofuran (5.40 L, 4.O vol) was charged to the concentrate and removed under vacuum at 35 to 45° C. Tetrahydrofuran (5.40 L, 4.O vol) was charged to the concentrate and removed under vacuum at 35 to 45° C. to give the desired product, 3-(5-morpholin-4-ylmethyl-1H-benzoimidazol-2-yl)-1II-pyrazol-4-ylamine (0.924 Kg, 95.5%, 82.84% by HPLC area) as a purple foam.

Stage 9: Preparation of 7-morpholin-4-ylmethyl-2,4-dihydro-1,2,4,5a,10-pentaaza-cyclopentaFalfluoren-5-one

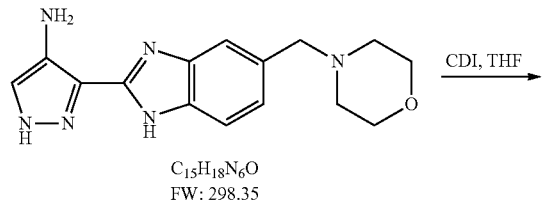

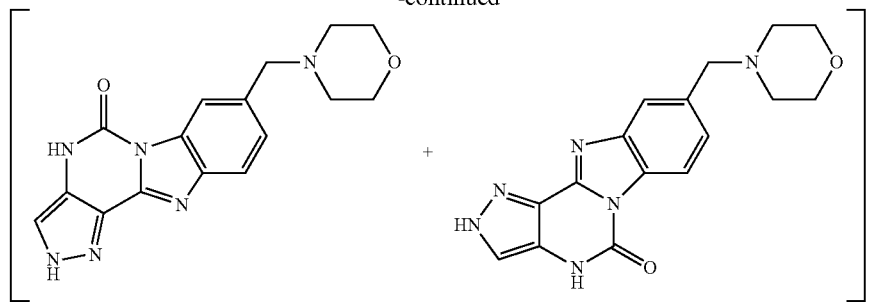

C₁₆H₁₆N₆O₂
FW: 324.34
As a mixture of two regioisomers 3-(5-Morpholin-4-ylmethyl-1H-benzoimidazol-2-yl)-1H-pyrazol-4-ylamine (0.993 Kg, 3.33 mol, 1.O wt) and tetrahydrofuran (14.0 L, 15.0 vol) were charged to a flange flask equipped with a mechanical stirrer, condenser and thermometer. The contents were stirred under nitrogen at 15 to 25° C. and 1,1'-carbonyldiimidazole (0.596 Kg, 3.67 mol, 0.6O wt) was added. The contents were then heated to 60 to 70° C. and stirred at this temperature for 16 to 24 hours. Reaction completion was determined by TLC analysis. The mixture was cooled to 15 to 20° C. and filtered. The filter-cake was washed with tetrahydrofuran (4.00 L, 4.O vol) and pulled dry for 15 to 30 minutes. The solid was dried under vacuum at 35 to 45° C. to yield 7-morpholin-4-ylmethyl-2,4-dihydro-1,2,4,5a,10-pentaaza-cyclopenta[a]fluoren-5-one (0.810 Kg, 75.0% th, 92.19% by HPLC area) as a purple solid.

Stage 10: Preparation of 1-cyclopropyl-3-[3-(5-morpholin-4-ylmethyl-1H-benzoimidazol-2-vD-1H-pyrazol-4-yll-urea

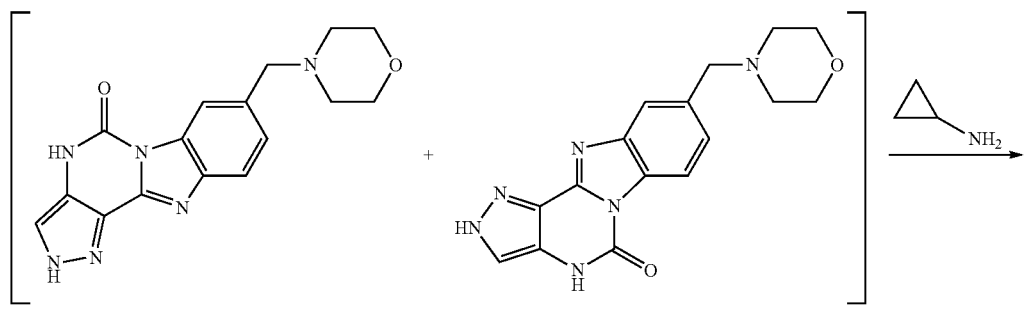

C₁₆H₁₆N₆O₂
FW: 324.34
As a mixture of two regioisomers

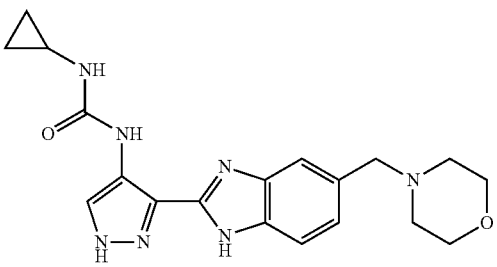

C₁₉H₂₃N₇O₂
FW: 381.44

7-Morpholin-4-ylmethyl-2,5,4-dihydro-1,2,4,5a,10-pentaaza-cyclopental[a]fluoren-5-one (0.797 Kg, 2.46 mol, 1.O wt) and 1-methyl-2-pyrrolidinone (2.40 L, 3.0 vol) were charged to a flange flask equipped with a mechanical stirrer, condenser and thermometer. Cyclopropylamine (0.279 Kg, 4.88 mol, 0.35 l wt) was added at 15 to 30° C. under nitrogen. The contents were heated to 95 to 105° C. and stirred at this temperature for 16 to 24 hours. Reaction completion was determined by ¹H NMR analysis. The reaction mixture was cooled to 10 to 20° C. and ethyl acetate (8.00 L, 1.O.O vol) and sat. aq. sodium chloride (2.50 L, 3.0 vol) were charged, the mixture was stirred for 2 to 5 minutes and the layers separated. The organic phase was stirred with sat. aq. sodium chloride (5.00 L, 6.O vol) for 25 to 35 minutes, the mixture filtered and the filter-cake washed with ethyl acetate (0.40 L, 0.5 vol). The filter-cake was retained and the filtrates were transferred to a separating funnel and the layers separated. The procedure was repeated a further 3 times and the retained solids were combined with the organic phase and the mixture concentrated to dryness under vacuum at 35 to 45° C. The concentrate was dissolved in propan-2-ol (8.00 L, 1O.O vol) at 45 to 55° C. and activated carbon (0.080 Kg₅ O.1 wt) was charged. The mixture was stirred at 45 to 55° C. for 30 to 40 minutes and then hot filtered at 45 to 55° C. The filter-cake was washed with propan-2-ol (0.40 L, 0.5 vol). Activated carbon (0.080 L, O.1 wt) was charged to the combined filtrates and wash and the mixture stirred at 45 to 55° C. for 30 to 40 minutes. The mixture was hot filtered at 45 to 55° C. and the filter-cake washed with propan-2-ol (0.40 L, 0.5 vol). The filtrates and wash were concentrated under vacuum at 35 to 45° C. Ethyl acetate (8.00, 1O.O vol) and water (2.20 L, 3.0 vol) were charged to the concentrate at 25 to 35° C.' and the mixture stirred for 1 to 2 minutes. The layers were separated and the organic phase was concentrated under vacuum at 35 to 45° C. Ethyl acetate (4.00 L, 5.0 vol) was charged to the residue and concentrated under vacuum at 35 to 45° C. Ethyl acetate (4.00 L, 5.0 vol) was charged to the residue and the mixture was stirred for 2 to 20 hours at 15 to 25° C. The mixture was cooled to and aged at 0 to 5° C. for 90 to 120 minutes and then filtered. The filter-cake was washed with ethyl acetate (0.80 L, 1.O vol) and pulled dry for 15 to 30 minutes. The solid was dried under vacuum at 35 to 45° C. to yield 1-cyclopropyl-3-[3-(5-morpholin-4-ylmethyl-1H-benzoimidazol-2-yl)-1H-pyrazol-4-yl]-urea (0.533 Kg, 56.8%, 93.20% by HPLC area) as a brown solid.

Several batches of Stage 9 product were processed in this way and the details of the quantities of starting material and product for each batch are set out in Table IA.

Stage 11: Preparation of 1-cyclopropyl-3-r3-(5-morpholin-4-ylmethyl-1H-benzoimidazol-2-ylˢ)-1H-pyrazol-4-yll-urea £-lactic acid salt

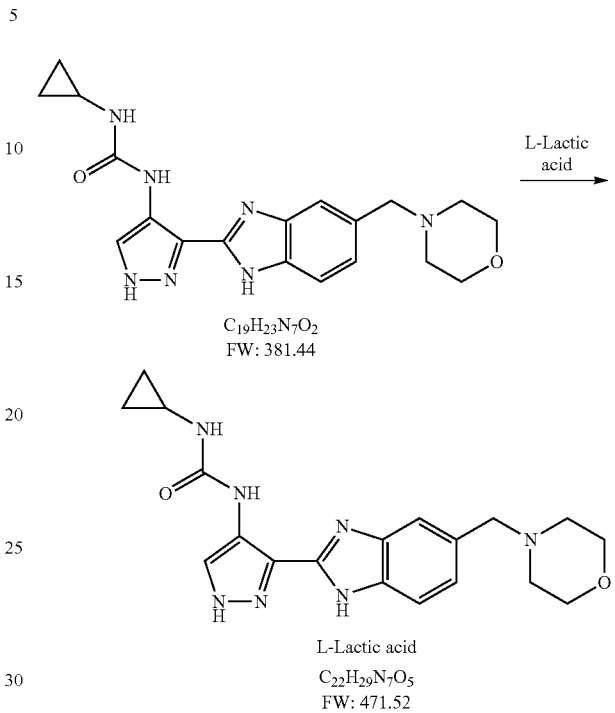

1-Cyclopropyl-3-[3-(5-morpholin-4-ylmethyl-1H-benzoimidazol-2-yl)-1H-pyrazol-4-yl]-urea (1.859 Kg, 4.872 mol, 1.O wt), propan-2-ol (9.00 L₅ 5.0 vol) and ethyl acetate (8.OO L, 4.5 vol) were charged to a flange flask equipped with a mechanical stirrer and thermometer. The contents were stirred under nitrogen and L-lactic acid (0.504 Kg, 5.59 mol, 0.269 wt) was added at 15 to 25° C. followed by a line rinse of ethyl acetate (0.90 L, 0.5 vol). The mixture was stirred at 15 to 25° C. for 120 to 140 minutes. The solid was isolated by filtration, the filter-cake washed with ethyl acetate (2×2.00 L, 2×1.O vol) and pulled dry for 20 to 40 minutes. The filter-cake was dissolved in ethanol (33.00 L, 17.7 vol) at 75 to 85° C.,

TABLE IA

Yields from urea formation step—Stage 10

| Batch | Input (g) of 7-Morpholin-4-ylmethyl-2,4-dihydro-1,2,4,5a,10-pentaaza-cyclopenta[a]fluoren-5-one | Input (g) of 1-cyclopropyl-3-[3-(5-morpholin-4-ylmethyl-1H-benzoimidazol-2-yl)-1H-pyrazol-4-yl]-urea | Chemical purity by HPLC area |
|---|---|---|---|
| 1 | 680 | 442 | 91.80 |
|   |   | 55.2% th, 64.9% w/w |   |
| 2 | 882 | 487 | 91.21 |
|   |   | 47.0% th, 56.6% w/w |   |
| 3 | 879 | 445 | 91.66 |
|   |   | 43.0% th, 50.6% w/w |   |
| 4 | 797 | 533 | 93.20 |
|   |   | 56.8% th, 66.8% w/w |   | cooled to 65 to 70° C. and the solution clarified through glass microfibre paper. The filtrates were cooled to and aged at 15 to 25° C. for 2 to 3 hours. The crystallised solid was isolated by filtration, the filter-cake washed with ethanol (2×1.00 L, 2×0.5 vol) and pulled dry for at least 30 minutes. The solid was dried under vacuum at 35 to 45° C. to yield 1-cyclopropyl-3-[3-(5-morpholin-4-ylmethyl-1H-benzoimidazol-2-yl)-1H-pyrazol-4-yl]-ureal-lactic acid salt (1.386 Kg, 58.7% th, 99.47% by HPLC area) as a dark pink uniform solid.

The infra-red spectrum of the lactate salt (KBr disc method) included characteristic peaks at 3229, 2972 and 1660 cm$^{-1}$.

Without wishing to be bound by any theory, it is believed that the infra red peaks can be assigned to structural components of the salt as follow:

| Peak: | Due to: |
|---|---|
| 3229 cm$^{-1}$ | N—H |
| 2972 cm$^{-1}$ | aliphatic C—H |
| 1660 cm$^{-1}$ | urea C=O |

Example 67

Synthesis of Crystalline Free Base And Crystalline Salt Forms Of 1-Cyclopropyl-3-[3-(5-Morpholin-4-ylmethyl-1H-Benzoimidazol-2-v π-1H-Pyrazol-4-yl]-Urea A. Preparation of 1-Cyclopropyl-3-[3-f5-Morpholin-4-ylmethyl-1H-Benzoimidazol-2-yl)-1H-Pyrazol-4-yl]-Urea free base A sample of crude 1-cyclopropyl-3-[3-(5-morpholin-4-ylmethyl-1H-benzoimidazol-2-yl)-1H-pyrazol-4-yl]-urea free base was prepared as outlined in Example 60 and initially purified by column chromatography on silica gel, eluting with EtOAc-MeOH (98:2-80:20). A sample of the free base obtained was then recrystallised from hot methanol to give crystalline material of 1-cyclopropyl-3-[3-(5-morpholin-4-ylmethyl-1H-benzoimidazol-2-yl)-1H-pyrazol-4-yl]-urea free base.

B. Preparation of 1-Cyclopropyl-S-rS-fS-Morpholin^-ylmethyl-1H-Benzoimidazol-2-yl)-1H-Pyrazol-4-yl]-Urea free base dihydrate A sample of crude 1-cyclopropyl-3-[3-(5-moφholin-4-yl-methyl-1H-benzoimidazol-2-yl)-1II-pyrazol-4-yl]-urea free base was dissolved in THF and then concentrated in vacuo to a minimum volume (~4 volumes). To the solution was added water dropwise (2-4 volumes) until the solution became turbid. A small amount of THF was added to re-establish solution clarity and the mixture left to stand overnight to give a crystalline material which was air-dried to give 1-cyclopropyl-3-[3-(5-morpholin-4-ylmethyl-1H-benzoimidazol-2-yl)-1H-pyrazol-4-yl]-urea free base dihydrate.

C. Preparation of 1-Cyclopl^pyl-3-[3-(5-Morpholin-4-ylmethyl-1H-Benzoimidazol-2-ylVlH-Pyrazol-4-yl]-Urea hydrochloride salt A sample of crude 1-cyclopropyl-3-[3-(5-moφholin-4-yl-methyl-1H-benzoimidazol-2-yl)-1H-pyrazol-4-yl]-urea free base was dissolved in the minimum amount of MeOH and then diluted with EtOAc. To the solution at 0° C. was slowly added 1.1 equivalents of HCl (4M solution in dioxane). Following addition, solid precipitated from solution which was collected by filtration. To the solid was added MeOH and the mixture reduced in vacuo. To remove traces of residual MeOH the residue was evaporated from water and then dried at 60° C./0.1 mbar to give the hydrochloride salt.

D. Preparation of 1-Cyclopropyl-3-[3-(5-Morpholin-4-ylmethyl-1H-Benzoimidazol-2-yiyiH-Pyrazol-4-yl1-Urea ethanesulfonate salt To a solution of 1-cyclopropyl-3-[3-(5-morpholin-4-ylm-ethyl-1H-benzoimidazol-2-yl)-1H-pyrazol-4-yl]-urea free base in MeOH-EtOAc was added 1 equivalent of ethanesulfonic acid. The mixture was stirred at ambient temperature and then reduced in vacuo. The residue was taken up in MeOH and to the solution was added Et$_2$O. Mixture left to stand for 72 h and the solid formed collected by filtration and dried to give 1-cyclopropyl-3-[3-(5-morpholin-4-ylmethyl-1H-benzoimidazol-2-yl)-1H-pyrazol-4-yl]-urea ethanesulfonate salt.

E. Preparation of 1-Cyclopropyl-3-[3-(5-Morpholin-4-ylmethyl-1H-Benzoimidazol-2-yl)-1II-Pyrazol-4-yl]Urea methanesulfonate salt To a solution of 1-cyclopropyl-3-[3-(5-morpholin-4-ylm-ethyl-1H-benzoimidazol-2-yl)-1H-pyrazol-4-yl]-urea free base (394 mg) in MeOH-EtOAc was added 1 equivalent of methanesulfonic acid (67 µl). A solid was formed which was collected by filtration, washing with EtOAc. The solid was dissolved in the minimum amount of hot MeOH, allowed to cool and then triturated with Et$_2$O. The solid was left to stand for 72 h and then collected by filtration, washing with MeOH, to give 1-cyclopropyl-3-[3-(5-morpholin-4-ylmethyl-1H-benzoimidazol-2-yl)-1H-pyrazol-4-yl]-urea methanesulfonate salt.

Example 68

Characterisation of 1-Cyclopropyl-3-[3-(5-Morpholin-4-ylmethyl-1H-Benzoimidazol-2-yl)-1H-Pyrazol-4-yl]-UreaFree Base and Salts Various forms of 1-cyclopropyl-3-[3-(5-morpholin-4-ylm-ethyl-1H-benzoimidazol-2-yl)-1H-pyrazol-4-yl]-urea were characterised. The forms selected for characterisation were identified from studies which primarily investigated extent of polymorphism and salt stability. The salts selected for further characterisation were the L-lactate salt, Free base dihydrate, Esylate salt, Free base and Hydrochloride salt.

A. Differential Scanning Calorimetry (DSC):

Thermograms were collected on a TA instrument Q1OOO equipped with a 50 position auto-sampler. The energy and temperature calibration standard was indium. Samples were heated at a rate of 10° C./minute from 10 to 250° C. A nitrogen purge of 30 ml/min was maintained over the sample. Between 2 and 10 mg of sample was used (unless otherwise stated) and all samples were enclosed in an aluminium pan with a pinhole in the lid.

| Identity | Melting Point (° C.) |
|---|---|
| L-lactate salt | 190° C. |
| Free base dihydrate | Desolvates (peaking at 110° C.) |

| Identity | Melting Point (° C.) |
|---|---|
| Esylate salt | None seen (up to 350° C.) |
| Free base | 193° C. |
| Hydrochloride salt | 190° C. |

B. Thermogravimetric Analysis (TGA):

Thermograms were collected on a TA Instruments Q500. Samples were heated at a rate of 10° C./minute. A nitrogen purge of 100 ml/minute was maintained over the sample. Typically 5-20 mg of sample was loaded into a tared, open aluminium pan.

| Identity | Observation |
|---|---|
| L-lactate salt | Loss of 1.7% unbound solvent, melt with degradation at 190° C. |
| Free base dihydrate | Weight loss (prior to degradation) of 4.1% w/w (corresponds to 1 equivalent of water) |
| Esylate salt | Loss of 4% unbound solvent, no other clearly identifiable features. |
| Free base | Loss of 1.7% unbound solvent, melt with degradation at 193° C. |
| Hydrochloride salt | Loss of 5.4% unbound solvent, melt with degradation at 190° C. |

C. Polarised Light Microscopy

Samples were studied on a Leica LM/DM microscope with a digital camera for image capture. A small amount of sample was mounted in immersion oil on a glass slide and covered with a glass cover slip. The individual particles were separated as well as possible and viewed with 50-500× magnification and partially crossed polars, coupled to a λ wave-plate.

| Identity | Observation |
|---|---|
| L-lactate salt | Irregular crystalline particles |
| Free base dihydrate | Irregular crystalline particles |
| Esylate salt | Irregular crystalline particles |
| Free base | Acicular crystalline particles |
| Hydrochloride salt | Irregular crystalline particles |

D. XRPD (X-Ray Powder Diffraction)
D5000

An XRPD study was carried out on a Siemens D5000 diffractometer using CuKa radiation (4O kV, 4O mA), θ-θ goniometer, automatic divergence and receiving slits, a graphite secondary monochromator and a scintillation counter. The data were collected over an angular range of 2° to 30° 2θ in continuous scan mode using a step size of either 0.02° 2Θ or 0.005° 2Θ and a step time of 1 second.

Samples, run under ambient conditions, were prepared as flat plate specimens using powder as received without grinding. Approximately 25-50 mg of the sample was gently packed into 12 mm diameter, 0.5 mm deep cavity cut into a polished, zero-background (510) silicon wafer (The Gem Dugout, 1652 Princeton Drive, Pennsylvania State College, Pa. 16803, USA).

All XRPD analyses were performed using the Diffrac Plus XRD Commander software v2.3.1.
Bruker AXS C2 GADDS Diffractometer (Used for Samples Recovered from GVS)

X-ray powder diffraction patterns for the samples were acquired on a Bruker AXS C2 GADDS diffractometer using CuKa radiation (4O kV, 4O mA), automated XYZ stage, laser video microscope for auto-sample positioning and a HiStar 2-dimensional area detector. X-ray optics consists of a single Göbel multilayer mirror coupled with a pinhole collimator of 0.3 mm.

Beam divergence, i.e. the effective size of the X-ray beam on the sample, was approximately 4 mm A θ-θ continuous scan mode was employed with a sample to detector distance of 20 cm which gives an effective 2θ range of 3.2-29.8°. A typical exposure time of a sample would be 120s.

Samples were prepared as flat plate specimens using powder as received without grinding. Approximately 1-2 mg of the sample was lightly pressed on a glass slide to obtain a flat surface.

The XRPD trace was recorded for the L-lactate salt and the free base. The traces show good signal to noise ratio, and indicate crystalline material.

E. Gravimetric Vapour Sorption (GVS):

All samples were run on a Hiden IGASorp moisture sorption analyser running CFRSorp software. The sample size was ca. 10-25 mg. A moisture adsorption/desorption isotherm was performed as outlined below. The sample was loaded and unloaded at room humidity and temperature (ca. 40% RH, 25° C.) and analysed afterwards by XRPD (using a Bruker AXS C2 GADDS system).

The standard isotherm run was a single cycle starting at 40% RH.
The humidity was stepped as follows:
40, 50, 60, 70, 80, 90
85, 75, 65, 55, 45, 35, 25, 15, 5, 0
10, 20, 30, 40

(i) L-Lactate Salt

The GVS isotherm for the L-lactate salt indicates that the sample does not display hygroscopic behaviour and does not form a hydrate. The XRPD trace for the sample following the GVS experiment is concordant with that of the input material, indicating that no phase change occurred during the experiment.

(ii) Free Base

During the experiment the sample weight differs by approximately 9% between 0% R.H and 95% R.H. This indicates that the sample is hygroscopic in nature.

Example 69

Determination of the crystal structure of 1-Cyclopropyl-3-r3-('5-Morpholin-4-ylmethyl-1H-Benzoimidazol-2-yl)-1H-Pyrazol-4-yll-Urea dihydrate free base by X-ray diffraction The crystal used for the diffraction experiment was colourless and of irregular shape with dimensions 0.2×0.2×0.2 mm$^3$. It was obtained by precipitation of water solution of esylate salt with THF in a liquid-liquid diffusion experiment. The equivalence of such sample and the same crystal form prepared from free base (using water as anti-solvent with a range of solvents such as alcohols e.g. ethanol, ketones such as methyl ethyl ketone and ethers such as THF and dioxane) was established by comparison of X-ray powder diffraction pattern of both samples. Crystallographic data were collected at 101(2) K using CuKa radiation (λ=1.5418 A) from a Rigaku rotating anode RU3HR, Osmic blue confocal optics, AFC9 $^1$A χ goniometer and a Rigaku Jupiter CCD detector. Images were collected in four ω scans, one at 2θ=30° and three scans at 2θ=90° with a detector to crystal distance of 67 mm. Data collection was controlled by CrystalClear software and images were processed and scaled by Dtrek. Although absorption coefficient was moderate (μ=0.82 mm$^{-1}$) data were corrected using $4^{th}$ order Fourier absorption correction to compensate for glue and crystal holder (micromount) absorption. It was found that the crystals belong to a monclinic space group ?2$_1$/n (#14) with crystal lattice parameters α=7.66(10), 6=15.18(10), c=17.71(10) A₅β=98.53(2)°, α=γ=90°. The numbers in brackets represents the deviation (s.u., standard uncertainty).

The crystal structure was solved using direct methods implemented in SHELXS-97. Intensity data for a total of 2822 unique reflections in a resolution range from 11.5-0.89 A (3.85<θ<60.01) were used in the refinement of 274 crystallographic parameters by SHELXL-97. Final statistical parameters were: wR2=0.2416 (all data), R$_F$=0.0866 (data with I>2σ(I)) and goodness of fit S=I. 145.

One molecule of free base and two water molecules were found in the asymmetric unit. The elemental composition of the asymmetric unit was C$_{19}$H$_{26}$N$_7$O$_4$ and the calculated density of the crystals is 1.36 Mg/m$^3$. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropic thermal factors (see FIG. 1).

The crystal structure contains one intramolecular (N22-H . . . N14 2.898 A) and seven intermolecular hydrogen bonds (see FIG. 2). 1-Cyclopropyl-3-[3-(5-morpholin-4-yl-methyl-1H-benzoimidazol-2-yl)-1H-pyrazol-4-yl]-urea molecules are linked together into chains along crystallographic b axis by two H-bonds: N7-H . . . O24 2.761 A and N25-H . . . N2 3.310 A. Benzimidazole moieties from two chains stack together at distance of 3.5-3.6 A. The network of 1-cyclopropyl-3-[3-(5-morpholin-4-ylmethyl-1H-benzoimidazol-2-yl)-1H-pyrazol-4-yf]-urea molecules form pockets occupied by four water molecules, two and two being related by the centre of symmetry. Three H-bonds link 1-cyclopropyl-3-[3-(5-morpholin-4-ylmethyl-1H-benzoimidazol-2-yl)-1II-pyrazol-4-yl]-urea molecules with water molecules, one to 1$^{st}$ water molecule (O1 W1-H . . . N16 2.845 A) and remaining two to 2$^{nd}$ water molecule (N1-H . . . O1W2 2.875 A and O1W2-H . . . O19 2.746 A). Water molecules are involved in mutual interaction through another two H-bonds: O1W1-H . . . O1W2 2.884 A and O1W2-H . . . O1W1 2.771 A.

Figure 2:
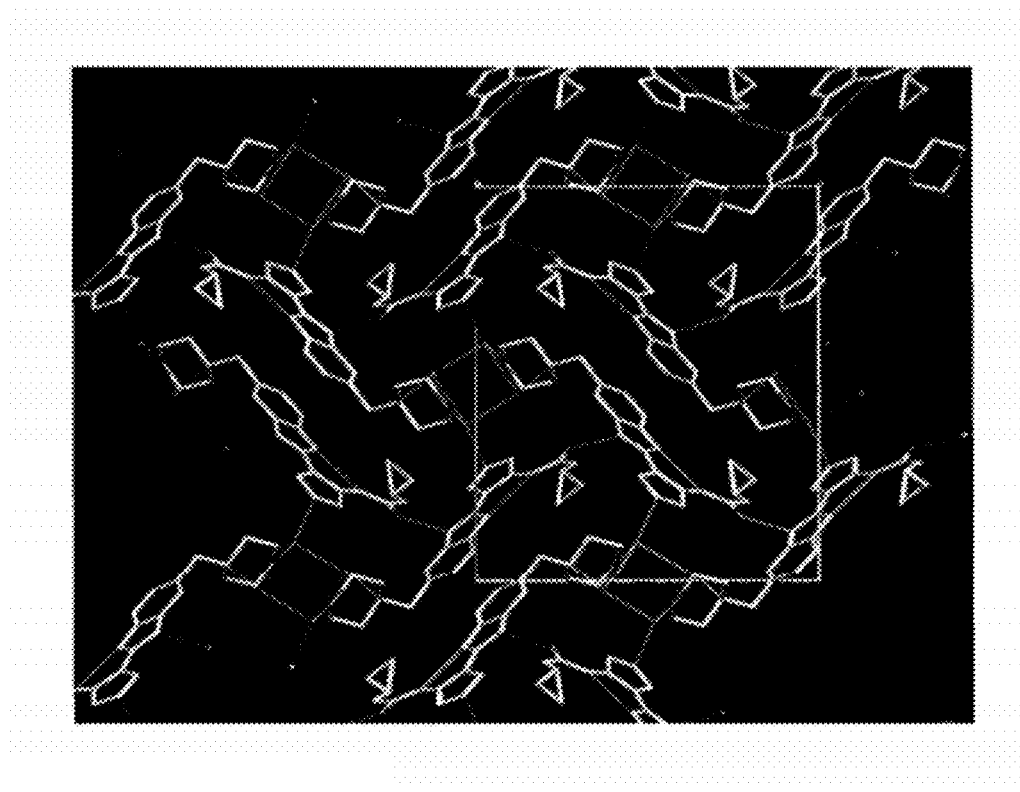
FIG. 2 shows a packing diagram of the free base dihydrate of 1-cyclopropyl-3-[3-(5-morpholin-4-ylmethyl-1H-benzoimidazol-2-yl)-1H-pyrazol-4-yl]-urea as described in Example 69 below.

A thermal ellipsoid representation of the structure generated by the X-ray diffraction study is provided in FIG. 1 and packing diagram is in FIG. 2.

The coordinates for the atoms making up the structure of the 1-cyclopropyl-3-[3-(5-morpholin-4-ylmethyl-1H-benzoimidazol-2-yl)-1H-pyrazol-4-yl]-urea free base dihydrate are as set out in Table 2. The numbers in brackets represents the deviation (s.u., standard uncertainty).

TABLE 2

| _cell_length_a | 7.662 (10) |
|---|---|
| _cell_length_b | 15.184 (10) |
| _cell_length_c | 17.711 (10) |
| _cell_angle_alpha | 90.00 |
| _cell_angle_beta | 98.53 (2) |
| _cell_angle_gamma | 90.00 |
| _cell_measurement_temperature | 101 (2) | loop_
_atom_s ite_l abe 1
_atom_site_type_symbol
_atom_site_f ract_x
_atom_site_f ract_y
_atom_site_fract_z
_atom_site_U__iso_or_equiv
_atom_site_adp_type
_atom_site_occupancy
_atom_site_symmetry_multiplicity
_atom_site_calc_f lag

| NÏ | N | 0.4468 (4) | 0.0332 (2) | 0.71441 (19) | 0.0274 (9) | Uani | 1 | i | d |
|---|---|---|---|---|---|---|---|---|---|
| HI | H | 0.5453 | 0.0189 | 0.6973 | 0.033 | Uiso | 1 | 1 | calc |
| N2 | N | 0.3749 (4) | −0.01642 (19) | 0.76559 (19) | 0.0253 (8) | Uani | 1 | i | d |
| C3 | C | 0.2277 (5) | 0.0286 (2) | 0.7751 (2) | 0.0237 (9) | Uani | 1 | i | d |
| C4 | C | 0.2074 (6) | 0.1060 (2) | 0.7308 (2) | 0.0246 (9) | Uani | 1 | i | d |
| C5 | C | 0.3539 (5) | 0.1058 (3) | 0.6923 (2) | 0.0254 (10) | Uani | 1 | i | d |
| H5 | H | 0.3822 | 0.1490 | 0.6572 | 0.030 | Uiso | 1 | 1 | calc |
| C6 | C | 0.1101 (5) | −0.0035 (2) | 0.8265 (2) | 0.0213 (9) | Uani | 1 | i | d |
| N7 | N | 0.1457 (5) | −0.0752 (2) | 0.87205 (19) | 0.0268 (9) | Uani | 1 | i | d |
| H7 | H | 0.2403 | −0.1087 | 0.8758 | 0.032 | Uiso | 1 | 1 | calc |
| C8 | C | 0.0015 (6) | −0.0852 (2) | 0.9119 (2) | 0.0251 (10) | Uani | 1 | i | d |
| C9 | C | −0.0262 (6) | −0.1443 (2) | 0.9695 (2) | 0.0266 (10) | Uani | 1 | i | d |
| H9 | H | 0.0553 | −0.1898 | 0.9865 | 0.032 | Uiso | 1 | 1 | calc |
| ClO | C | −0.1833 (5) | −0.1319 (2) | 1.0008 (2) | 0.0258 (10) | Uani | 1 | i | d |
| CIl | C | −0.3006 (6) | −0.0649 (3) | 0.9758 (2) | 0.0295 (10) | Uani | 1 | i | d |
| HIl | H | −0.4052 | −0.0590 | 0.9982 | 0.035 | Uiso | 1 | 1 | calc |
| C12 | C | −0.2704 (6) | −0.0064 (3) | 0.9194 (2) | 0.0321 (11) | Uani | 1 | i | d |
| H12 | H | −0.3527 | 0.0387 | 0.9023 | 0.039 | Uiso | 1 | 1 | calc |
| C13 | C | −0.1115 (6) | −0.0163 (2) | 0.8878 (2) | 0.0261 (10) | Uani | 1 | i | d |
| N14 | N | −0.0434 (4) | 0.03474 (19) | 0.83324 (19) | 0.0254 (8) | Uani | 1 | i | d |
| C15 | C | −0.2143 (5) | −0.1900 (2) | 1.0676 (2) | 0.0263 (10) | Uani | 1 | i | d |
| H15A | H | −0.1009 | −0.1979 | 1.1018 | 0.032 | Uiso | 1 | 1 | calc |
| H15B | H | −0.2963 | −0.1593 | 1.0970 | 0.032 | Uiso | 1 | 1 | calc |
| N16 | N | −0.2871 (5) | −0.2772 (2) | 1.04532 (18) | 0.0268 (8) | üani | 1 | i | d |
| C17 | C | −0.4708 (6) | −0.2702 (3) | 1.0075 (2) | 0.0303 (10) | Uani | 1 | i | d |
| H17A | H | −0.4749 | −0.2350 | 0.9602 | 0.036 | Uiso | 1 | 1 | calc |
| H17B | H | −0.5421 | −0.2395 | 1.0416 | 0.036 | Uiso | 1 | 1 | calc |
| C18 | C | −0.5484 (6) | −0.3603 (3) | 0.9879 (2) | 0.0344 (11) | Uani | 1 | i | d |
| H18A | H | −0.6723 | −0.3540 | 0.9631 | 0.041 | Uiso | 1 | 1 | calc |

TABLE 2-continued

| | | | | | | | | | |
|---|---|---|---|---|---|---|---|---|---|
| H18B | H | −0.4814 | −0.3896 | 0.9513 | 0.041 | Uiso | 1 | 1 | calc |
| O19 | O | −0.5428 (4) | −0.41359 (18) | 1.05435 (16) | 0.0343 (8) | Uani | 1 | i | d |
| C20 | C | −0.3636 (6) | −0.4216 (3) | 1.0925 (3) | 0.0344 (11) | Uani | 1 | i | d |
| H20A | H | −0.2914 | −0.4518 | 1.0584 | 0.041 | Uiso | 1 | 1 | calc |
| H20B | H | −0.3617 | −0.4580 | 1.1390 | 0.041 | Uiso | 1 | 1 | calc |
| C21 | C | −0.2855 (6) | −0.3338 (3) | 1.1140 (2) | 0.0287 (10) | Uani | 1 | i | d |
| H21A | H | −0.3537 | −0.3048 | 1.1503 | 0.034 | Uiso | 1 | 1 | calc |
| H21B | H | −0.1626 | −0.3413 | 1.1397 | 0.034 | Uiso | 1 | 1 | calc |
| N22 | N | 0.0659(4) | 0.16310 (19) | 0.72860 (18) | 0.0242 (8) | Uani | 1 | i | d |
| H22 | H | −0.0267 | 0.1453 | 0.7484 | 0.029 | Uiso | 1 | 1 | calc |
| C23 | C | 0.0617 (5) | 0.2451 (2) | 0.6976 (2) | 0.0247 (9) | Uani | 1 | i | d |
| O24 | O | 0.1870 (4) | 0.27405 (17) | 0.66702 (16) | 0.0304 (8) | Uani | 1 | i | d |
| N25 | N | −0.0851(4) | 0.2937 (2) | 0.70242 (19) | 0.0270 (8) | Uani | 1 | i | d |
| H25 | H | −0.0807 | 0.3509 | 0.6948 | 0.032 | Uiso | 1 | 1 | calc |
| C26 | C | −0.2479 (6) | 0.2563 (3) | 0.7194 (3) | 0.0320 (11) | Uani | 1 | i | d |
| H26 | H | −0.3061 | 0.2121 | 0.6820 | 0.038 | Uiso | 1 | 1 | calc |
| C27 | C | −0.3687 (6) | 0.3144 (3) | 0.7561 (2) | 0.0346 (11) | Uani | 1 | i | d |
| H27A | H | −0.4974 | 0.3069 | 0.7404 | 0.041 | Uiso | 1 | 1 | calc |
| H27B | H | −0.3304 | 0.3757 | 0.7681 | 0.041 | Uiso | 1 | 1 | calc |
| C28 | C | −0.2705 (6) | 0.2417 (3) | 0.8022 (3) | 0.0370 (11) | Uani | 1 | i | d |
| H28A | H | −0.3387 | 0.1896 | 0.8144 | 0.044 | Uiso | 1 | 1 | calc |
| H28B | H | −0.1716 | 0.2585 | 0.8421 | 0.044 | Uiso | 1 | 1 | calc |
| O1W1 | O | −0.0371 (4) | −0.37444 (18) | 0.97522 (18) | 0.0392 (8) | Uani | 1 | i | d |
| H1W1 | H | 0.0243 | −0.4072 | 1.0168 | 0.047 | Uiso | 1 | i | d |
| H2W1 | H | −0.1218 | −0.3425 | 0.9983 | 0.047 | Uiso | 1 | i | d |
| O1W2 | O | 0.1516 (4) | −0.4721 (2) | 1.1013 (2) | 0.0421 (9) | Uani | 1 | i | d |
| H1W2 | H | 0.113 (7) | −0.509 (4) | 1.067 (3) | 0.051 | Uiso | 1 | i | d |
| H2W2 | H | 0.2534 | −0.4527 | 1.0856 | 0.051 | Uiso | 1 | i | d |

Example 70

Determination of the XRPD pattern of 1-cyclopropyl-S—P-fS-morphorinˆ-ylmethyl-1H-benzoimidazol-2-ylVlH-pyrazol-4-yll-urea free base Samples for X-ray powder diffraction (XRPD) data collection were gently ground by marble mortar and loaded into a crystallographic capillary (from Hampton Research, Quartz or Glass Type 10, 0.4 or 0.7 mm diameter). Diffraction patterns were collected at room temperature using CuKa radiation (λ=1.5418 A) from a Rigaku rotating anode RU3HR, Osniic blue confocal optics, $^1$A % goniometer and a Rigaku HTC image plate detector. 2D Images were collected while spinning φ axis with a detector to crystal distance of 250 mm. Data collection was controlled by CrystalClear software and 2D images were converted to ID plot (2Θ vs. Intensity) by Datasqueeze (intensity averaged over the azimuthal angle 0<%<360° for 2Θ range 3-30° in 0.01° or 0.02° steps). In house program AstexXRPD was used for manipulation and visualisation of ID XRPD patterns.

The XRPD pattern and relative intensity of peaks do not change between different crystallisation batches which is consistent with the presence of only one crystal form.

Figure 3:
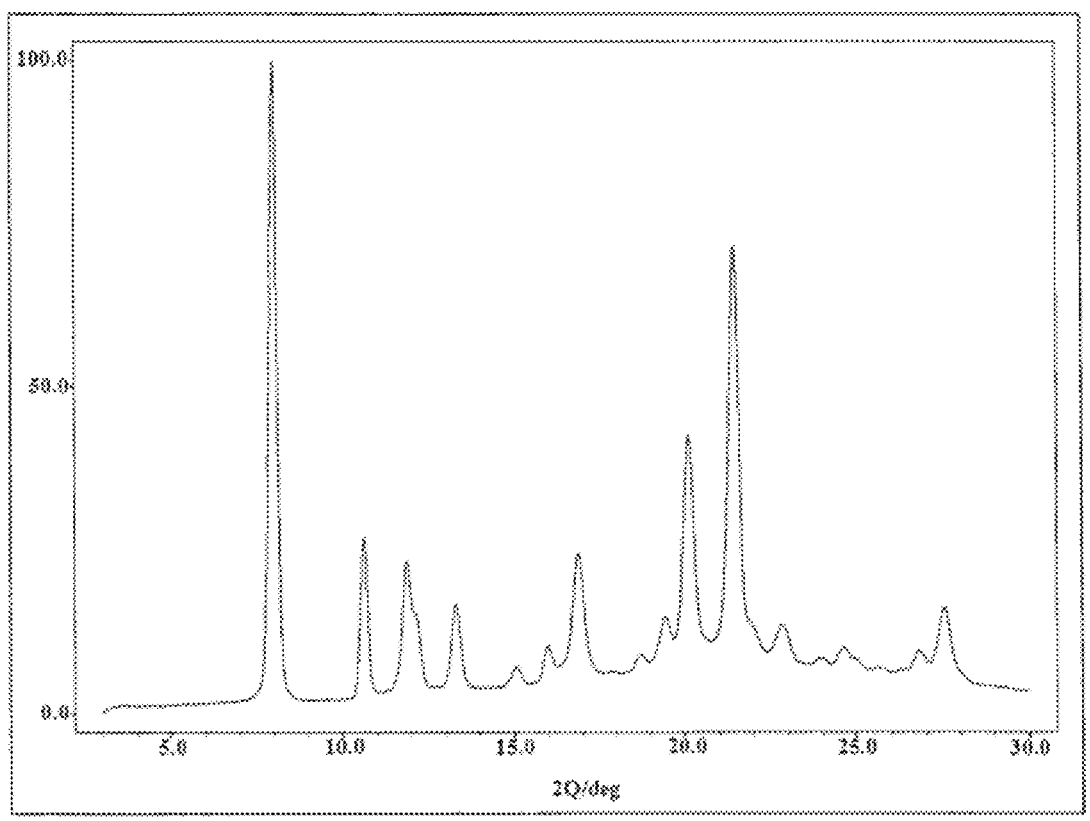
FIG. 3 shows the XRPD pattern of the free base of 1-cyclopropyl-3-[3-(5-morpholin-4-ylmethyl-1H-benzoimidazol-2-yl)-1H-pyrazol-4-yl]-urea as described in Example 70 below.

The XRPD pattern for the FBI form of 1-cyclopropyl-3-[3-(5-morpholin-4-ylmethyl-1H-benzoimidazol-2-yl)-1H-pyrazol-4-yl]-urea free base is provided in FIG. 3 and details of the main peaks are listed in Table 3.

TABLE 3

| 2Θ, d-spacing and relative intensity of main peaks. | | |
|---|---|---|
| 2θ/° | d/Å | I |
| 7.97 | 11.09 | 100 |
| 10.60 | 8.35 | 26 |
| 11.87 | 7.46 | 23 |
| 12.13 | 7.30 | 15 |
| 13.30 | 6.66 | 16 |
| 15.04 | 5.89 | 6 |

TABLE 3-continued

| 2Θ, d-spacing and relative intensity of main peaks. | | |
|---|---|---|
| 2θ/° | d/Å | I |
| 15.97 | 5.55 | 9 |
| 16.85 | 5.26 | 24 |
| 18.68 | 4.75 | 8 |
| 19.40 | 4.58 | 14 |
| 20.10 | 4.42 | 42 |
| 21.40 | 4.15 | 72 |
| 21.92 | 4.05 | 13 |
| 22.81 | 3.90 | 13 |
| 23.92 | 3.72 | 8 |
| 24.62 | 3.62 | 9 |
| 24.98 | 3.56 | 8 |
| 26.78 | 3.33 | 9 |
| 27.52 | 3.24 | 15 |

Example 71

Determination of the crystal structure of 1-Cyclopropyl-3-[3-(5-Morpholin-4-ylmethyl-1H-Benzoimidazol-2-yD-1H-Pyrazol-4-yli-Urea lactate salt A single crystal form of 1-cyclopropyl-3-[3-(5-moφholin-4-ylmethyl-1H-benzoimidazol-2-yl)-1H-pyrazol-4-yl]-urea L-lactate salt has been identified. The crystal used for the diffraction experiment was a colourless prism with dimensions 0.1×0.1×0.1 mm³ obtained by evaporation from ethanol. Crystallographic data were collected at 97 K using CuKa radiation (λ=1.5418 A) from a Rigaku rotating anode RU3HR, Osmic blue confocal optics, AFC9 $^1$A χ goniometer and a Rigaku Jupiter CCD detector. Images were collected in five (0 scans, one at 2Θ=15° and four scans at 2Θ=90° with a detector to crystal distance of 67 mm Data collection was controlled by CrystalClear software and images were processed and scaled by Dtrek. Although absorption coefficient was moderate (μ=0.78 mm$^{-1}$) data were corrected using 4$^{th}$ order Fourier absorption correction to compensate for glue and crystal holder (micromount) absorption. It was found that the crystals belong to an orthorhombic space group $P2_12_12_1$ (#19) with crystal lattice parameters a=9.94(10), b=15.03 (10), c=16.18(10) Å, α=β=γ=90°. The numbers in brackets represents the deviation (s.u., standard uncertainty). One short room temperature scan was taken to check crystal lattice parameters and symmetry. It was found that symmetry is the same as at 97 (2) K and crystal lattice parameters are similar (room temperature a=10.08, 6=15.22, c=16.22 A).

The crystal structure was solved using direct methods implemented in SHELXS-97. Absolute configuration was selected to match L-lactate configuration used in crystallisation experiment. Intensity data for a total of 3417 unique reflections in a resolution range from 11-0.9 A (4.01<θ<58.92) were used in the refinement of 308 crystallographic parameters by SHELXL-97. Final statistical parameters were: wR2=0.2275 (all data), $R_F$=0.0817 (data with I>2σ (I)) and goodness of fit S=1.076.

One molecule of protonated free base and one L-lactate anion were found in the asymmetric unit. The elemental composition of the asymmetric unit was $C_{22}H_{29}N_7O_5$ and the calculated density of the crystals is 1.30 $Mg/m^3$. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropic thermal factors (see FIG. 4).

The crystal structure contains one intramolecular (N22-H . . . N14 2.852 A) and seven intermolecular hydrogen bonds forming complex 3D network (see FIG. 5). Two of intermolecular H-bonds, N7-H . . . O24 2.800 A and N25-H . . . N2 3.004 A, link 1-cyclopropyl-3-[3-(5-morpholin-4-ylmethyl-1H-benzoimidazol-2-yl)-1H-pyrazol-4-yl]-urea molecules into chains along crystallographic c axis. L-lactate anions are linked into chains along crystallographic a axis by H-bond O3L-H . . . O1L 2.626 A. Two bifurcated H-bonds join 1-cyclopropyl-3-[3-(5-morpholin-4-ylmethyl-1H-benzoimidazol-2-yl)-1H-pyrazol-4-yl]-urea cations and L-lactate anions. Protonated morpholine nitrogen atom interacts with both carboxyloxygen atoms (N16-H . . . O1L 3.125 A and N16-H . . . O2L 2.625 A), while pyrazole N1 nitrogen is H donor to O2L and O3L (N1-H . . . O2L 2.882 A, N1-H . . . 03L 2.740 A).

Figure 4:
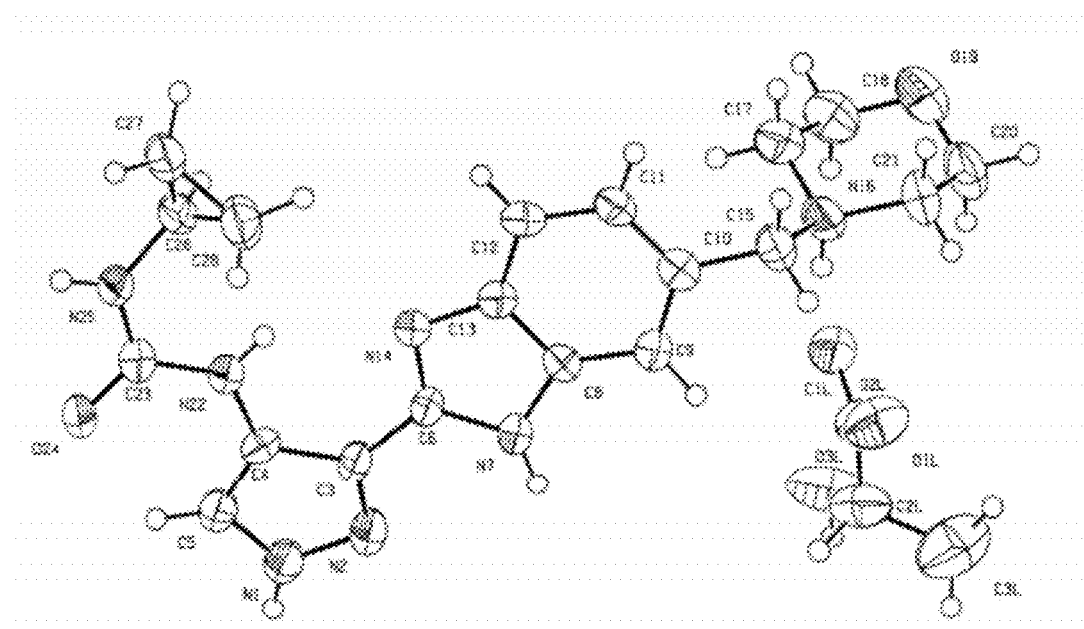
FIG. 4 shows a thermal ellipsoid plot of the L-lactate salt of 1-cyclopropyl-3-[3-(5-morpholin-4-ylmethyl-1H-benzoimidazol-2-yl)-1H-pyrazol-4-yl]-urea as described in Example 71 below.
Figure 5:
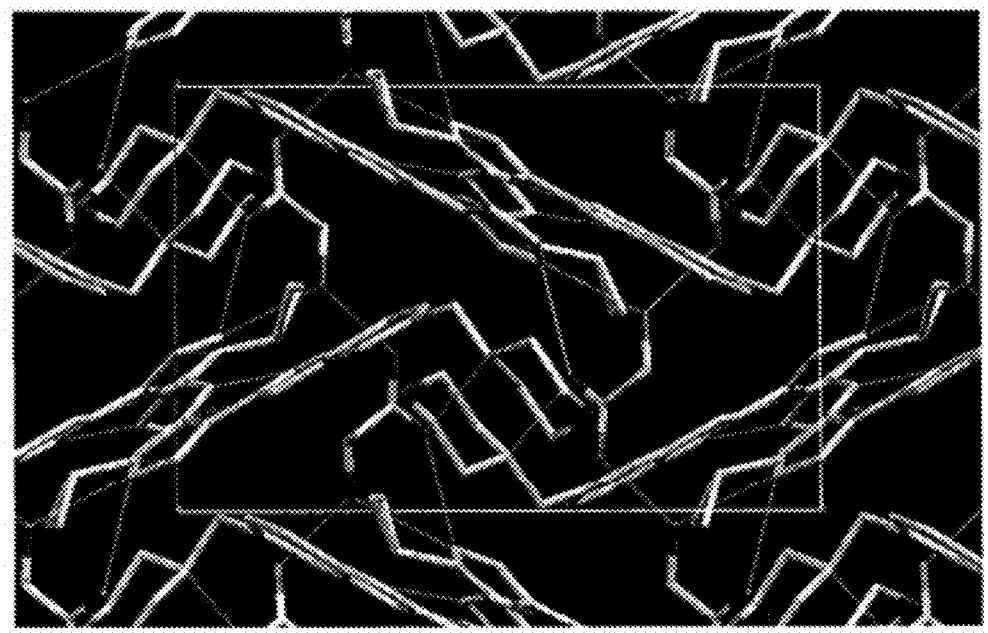
FIG. 5 shows a packing diagram of the L-lactate salt of 1-cyclopropyl-3-[3-(5-morpholin-4-ylmethyl-1H-benzoimidazol-2-yl)-1H-pyrazol-4-yl]-urea as described in Example 71 below.

A thermal ellipsoid representation of the structure generated by the X-ray diffraction study is provided in FIG. 4 and packing diagram is in FIG. 5.

The coordinates for the atoms making up the structure of 1-cyclopropyl-3-[3-(5-morpholin-4-ylmethyl-1H-benzoimidazol-2-yl)-1H-pyrazol-4-yl]-urea lactate salt are as set out in Table 4. The numbers in brackets represents the deviation (s.u., standard uncertainty).

TABLE 4

| _cell_length_a | | | 9.941 (10) | | | |
|---|---|---|---|---|---|---|
| _cell_length_b | | | 15.034 (10) | | | |
| _cell_length_c | | | 16.175 (10) | | | |
| _cell_angle_alpha | | | 90.00 | | | |
| _cell_angle_beta | | | 90.00 | | | |
| _cell_angle_gamma | | | 90.00 | | | |
| _cell_measurement_temperature | | | 97 (2) | | | |
| loop_ | | | | | | |
| _atom_site_label | | | | | | |
| _atom_site_type_symbol | | | | | | |
| _atom_site__fract_x | | | | | | |
| _atom_site_fract_y | | | | | | |
| _atom_site_fract_z | | | | | | |
| _atom__site_U_iso_or_equiv | | | | | | |
| _atom__site_adp_type | | | | | | |
| _atom__site_occupancy | | | | | | |
| _atom__site_symmetry_multiplicity | | | | | | |
| _atom_site_calc_flag | | | | | | |
| N1 | N | 0.9111 (5) | 0.4310 (3) | 0.5668 (2) | 0.0509 (12) | Uani 1 i d |
| H1 | H | 0.9653 | 0.3878 | 0.5824 | 0.061 | Uiso 1 1 calc |
| N2 | N | 0.8702 (5) | 0.4971 (3) | 0.6177 (2) | 0.0503 (12) | Uani 1 i d |
| C3 | C | 0.7902 (5) | 0.5479 (3) | 0.5704 (3) | 0.0395 (11) | Uani 1 i d |
| C4 | C | 0.7795 (6) | 0.5130 (3) | 0.4891 (3) | 0.0431 (12) | Uani 1 i d |
| C5 | C | 0.8601 (5) | 0.4380 (3) | 0.4893 (3) | 0.0449 (12) | Uani 1 i d |
| H5 | H | 0.8766 | 0.3991 | 0.4441 | 0.054 | Uiso 1 1 calc |
| C6 | C | 0.7254 (5) | 0.6280 (3) | 0.6003 (3) | 0.0404 (12) | Uani 1 i d |
| N7 | N | 0.7166 (4) | 0.6504 (3) | 0.6825 (2) | 0.0428 (10) | Uani 1 i d |
| H7 | H | 0.7473 | 0.6201 | 0.7250 | 0.051 | Uiso 1 1 calc |
| C8 | C | 0.6485 (5) | 0.7316 (3) | 0.6840 (3) | 0.0413 (11) | Uani 1 i d |
| C9 | C | 0.6136 (5) | 0.7875 (3) | 0.7496 (3) | 0.0443 (12) | Uani 1 i d |
| H9 | H | 0.6337 | 0.7722 | 0.8052 | 0.053 | Uiso 1 1 calc |
| C10 | C | 0.5477 (6) | 0.8667 (3) | 0.7300 (3) | 0.0482 (12) | Uani 1 i d |
| C11 | C | 0.5166 (6) | 0.8863 (3) | 0.6481 (3) | 0.0495 (13) | Uani 1 i d |
| H11 | H | 0.4708 | 0.9403 | 0.6364 | 0.059 | Uiso 1 1 calc |
| C12 | C | 0.5495 (6) | 0.8304 (3) | 0.5826 (3) | 0.0508 (13) | Uani 1 i d |
| H12 | H | 0.5264 | 0.8449 | 0.5272 | 0.061 | Uiso 1 1 calc |
| C13 | C | 0.6186 (5) | 0.7510 (3) | 0.6021 (3) | 0.0428 (12) | Uani 1 i d |
| N14 | N | 0.6671 (4) | 0.6851 (3) | 0.5497 (2) | 0.0434 (10) | Uani 1 i d |
| C15 | C | 0.5154 (6) | 0.9337 (3) | 0.7949 (3) | 0.0529 (14) | Uani 1 i d |
| H15A | H | 0.4767 | 0.9027 | 0.8434 | 0.064 | Uiso 1 1 calc |
| H15B | H | 0.4462 | 0.9749 | 0.7733 | 0.064 | Uiso 1 1 calc |
| N16 | N | 0.6353 (5) | 0.9869 (3) | 0.8225 (3) | 0.0504 (11) | Uani 1 i d |
| H16 | H | 0.6962 | 0.9472 | 0.8458 | 0.060 | Uiso 1 1 calc |
| C17 | C | 0.7050 (7) | 1.0325 (4) | 0.7543 (4) | 0.0652 (16) | Uani 1 i d |
| H17A | H | 0.6420 | 1.0734 | 0.7260 | 0.078 | Uiso 1 1 calc |
| H17B | H | 0.7370 | 0.9882 | 0.7135 | 0.078 | Uiso 1 1 calc |

TABLE 4-continued

| | | | | | | | | | |
|---|---|---|---|---|---|---|---|---|---|
| C18 | C | 0.8234 (7) | 1.0844 (4) | 0.7881 (4) | 0.0732 (18) | Uani | 1 | i | d |
| H18A | H | 0.8887 | 1.0426 | 0.8130 | 0.088 | Uiso | 1 | 1 | calc |
| H18B | H | 0.8689 | 1.1157 | 0.7421 | 0.088 | Uiso | 1 | 1 | calc |
| O19 | O | 0.7835 (5) | 1.1470 (3) | 0.8481 (3) | 0.0804 (14) | Uani | 1 | i | d |
| C20 | C | 0.7191 (8) | 1.1040 (4) | 0.9155 (4) | 0.0724 (19) | Uani | 1 | i | d |
| H20A | H | 0.6921 | 1.1492 | 0.9568 | 0.087 | Uiso | 1 | 1 | calc |
| H20B | H | 0.7835 | 1.0629 | 0.9423 | 0.087 | Uiso | 1 | 1 | calc |
| C21 | C | 0.5984 (6) | 1.0533 (4) | 0.8886 (4) | 0.0619 (16) | Uani | 1 | i | d |
| H21A | H | 0.5299 | 1.0950 | 0.8668 | 0.074 | Uiso | 1 | 1 | calc |
| H21B | H | 0.5591 | 1.0218 | 0.9366 | 0.074 | Uiso | 1 | 1 | calc |
| N22 | N | 0.7055 (5) | 0.5524 (3) | 0.4260 (2) | 0.0455 (10) | Uani | 1 | i | d |
| H22 | H | 0.6642 | 0.6028 | 0.4368 | 0.055 | Uiso | 1 | 1 | calc |
| C23 | C | 0.6930 (6) | 0.5175 (3) | 0.3483 (3) | 0.0475 (13) | Uani | 1 | i | d |
| O24 | O | 0.7394 (4) | 0.4431 (2) | 0.32976 (19) | 0.0524 (10) | Uani | 1 | i | d |
| N25 | N | 0.6245 (5) | 0.5675 (3) | 0.2934 (2) | 0.0506 (11) | Uani | 1 | i | d |
| H25 | H | 0.5979 | 0.5428 | 0.2468 | 0.061 | Uiso | 1 | 1 | calc |
| C26 | C | 0.5929 (6) | 0.6602 (3) | 0.3080 (3) | 0.0512 (13) | Uani | 1 | i | d |
| H26 | H | 0.6709 | 0.7017 | 0.3144 | 0.061 | Uiso | 1 | 1 | calc |
| C27 | C | 0.4712 (6) | 0.6964 (4) | 0.2675 (3) | 0.0580 (15) | Uani | 1 | i | d |
| H27A | H | 0.4182 | 0.6557 | 0.2321 | 0.070 | Uiso | 1 | 1 | calc |
| H27B | H | 0.4743 | 0.7589 | 0.2481 | 0.070 | Uiso | 1 | 1 | calc |
| C28 | C | 0.4692 (7) | 0.6806 (4) | 0.3585 (3) | 0.0642 (17) | Uani | 1 | i | d |
| H28A | H | 0.4156 | 0.6298 | 0.3794 | 0.077 | Uiso | 1 | 1 | calc |
| H28B | H | 0.4718 | 0.7331 | 0.3954 | 0.077 | Uiso | 1 | 1 | calc |
| C1L | C | 0.7508 (6) | 0.8367 (4) | 0.9477 (3) | 0.0521 (14) | Uani | 1 | i | d |
| O1L | O | 0.6267 (5) | 0.8403 (3) | 0.9593 (3) | 0.0793 (14) | Uani | 1 | i | d |
| O2L | O | 0.8130 (4) | 0.8862 (3) | 0.8976 (2) | 0.0595 (11) | Uani | 1 | i | d |
| C2L | C | 0.8308 (7) | 0.7682 (4) | 0.9940 (4) | 0.0692 (17) | Uani | 1 | i | d |
| H2L | H | 0.7934 | 0.7082 | 0.9802 | 0.083 | Uiso | 1 | 1 | calc. |
| O3L | O | 0.9655 (5) | 0.7716 (3) | 0.9651 (4) | 0.0935 (17) | Uani | 1 | i | d |
| H3L | H | 1.0127 | 0.7353 | 0.9918 | 0.140 | Uiso | 1 | 1 | calc |
| C3L | C | 0.8189 (9) | 0.7814 (7) | 1.0854 (5) | 0.108 (3) | Uani | 1 | i | d |
| H3L1 | H | 0.7804 | 0.7279 | 1.1106 | 0.162 | Uiso | 1 | 1 | calc |
| H3L2 | H | 0.7603 | 0.8324 | 1.0966 | 0.162 | Uiso | 1 | 1 | calc |
| H3L3 | H | 0.9082 | 0.7925 | 1.1088 | 0.162 | Uiso | 1 | 1 | calc |

Example 72

1-Cyclopropyl-3-[3-(5-Morpholin-4-ylmethyl-1H-Benzoimidazol-2-vD-1H-Pyrazol-4-yll-Urea salt stability at 40° C. 75% H Approximately 15 mg of samples for the stability study were gently ground by marble mortar and transferred to a Petri dish in a thin layer. Samples were then placed in sealed containers containing saturated NaCl solution with an excess of undissolved NaCl. This in ton was placed into an incubator held at 40° C. to provide an environment of 40° C. and <<75% relative humidity (RH). Samples were analysed by X-ray powder diffraction (XRPD) in regular intervals.

Samples for XRPD data collection were loaded into crystallographic capillary (from Hampton Research, made of Quartz, diameter=0.4 mm) Diffraction patterns were collected at room temperature using CuKa radiation ($\lambda$=1.5418 A) from a Rigaku rotating anode RU3HR, Osmic blue confocal optics, [1]A $\chi$ goniometer and a Rigaku HTC image plate detector. 2D Images were collected while spinning $\phi$ axis with a detector to crystal distance of 250 mm. Data collection was controlled by CrystalClear software and 2D images were converted to ID plot (2$\Theta$ vs. Intensity) by Datasqueeze (intensity averaged over the azimuthal angle 0<X<360° for 2$\Theta$ range 3-30° in 0.01° steps). In house program AstexXRPD was used for manipulation and visualisation of ID XRPD patterns.

XRPD patterns of the lactate salt, free base (FBI) and dihydrate free base (FB2) do not change over the period of 1-2 month while exposed to 40° C. and 75% RH. The XRPD patterns of the starting and stability tested samples of lactate salt, free base (FBI) and dihydrate free base (FB2) are provided in FIG. 6-8.

Figure 6:
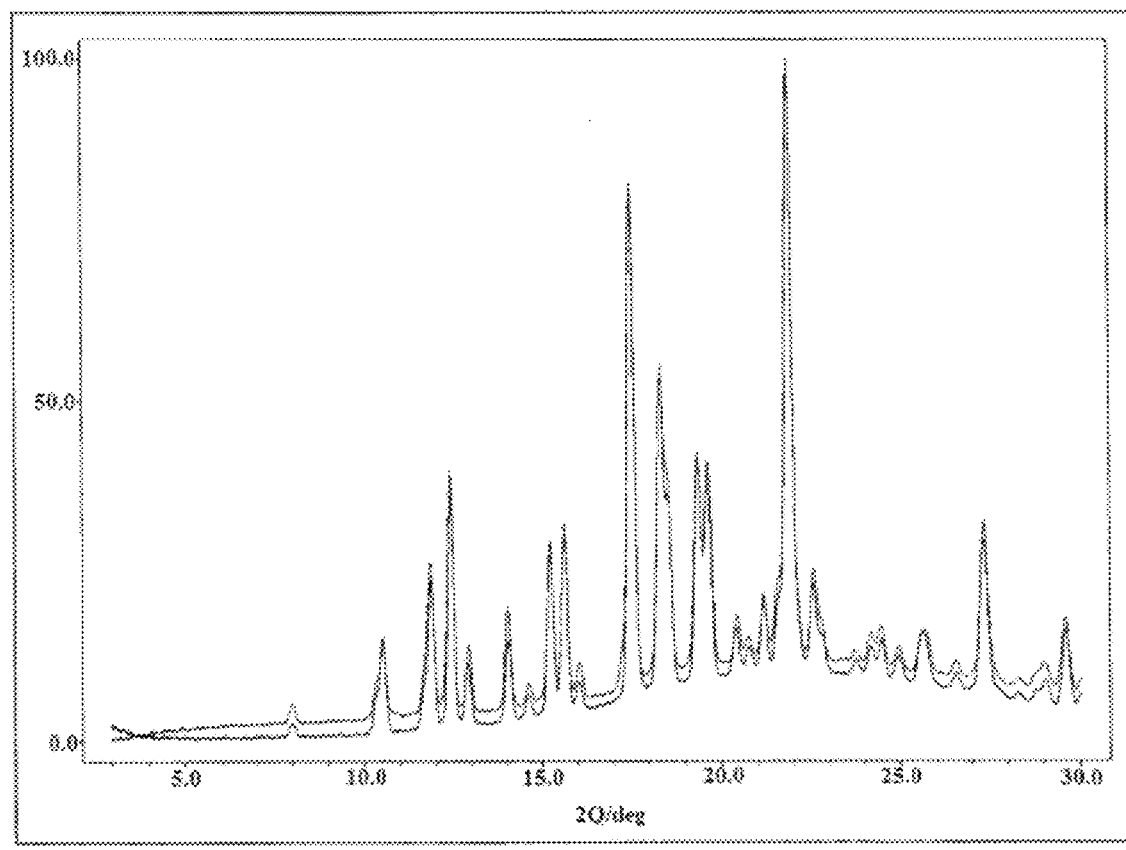
FIG. 6 shows the XRPD patterns of starting and stability tested samples of the L-lactate salt of 1-cyclopropyl-3-[3-(5-morpholin-4-ylmethyl-1H-benzoimidazol-2-yl)-1H-pyrazol-4-yl]-urea as described in Example 72 below.
Figure 7:
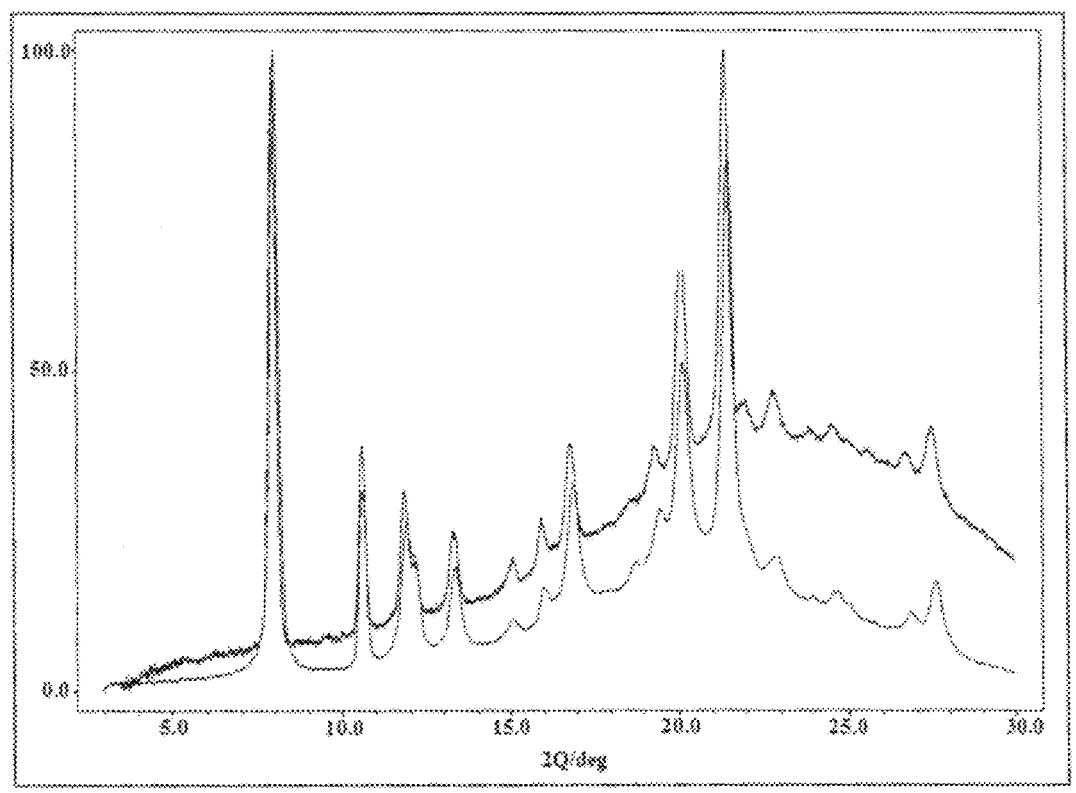
FIG. 7 shows the XRPD patterns of starting and stability tested samples of the free base (FBI) of 1-cyclopropyl-3-[3-(5-morpholin-4-ylmethyl-1H-benzoimidazol-2-yl)-1H-pyrazol-4-yl]-urea as described in Example 72 below.

The XRPD pattern for the L-lactate salt of 1-cyclopropyl-3-[3-(5-morpholin-4-ylmethyl-1H-benzoimidazol-2-yl)-1H-pyrazol-4-yl]-urea free base is provided in FIG. 6 and the details of the main peaks are listed in Table 5.

TABLE 5

| 2Θ/° | d/Å | I |
|---|---|---|
| 8.00 | 11.05 | 3 |
| 10.30 | 8.58 | 7 |
| 10.50 | 8.42 | 15 |
| 11.55 | 7.66 | 8 |
| 11.85 | 7.46 | 23 |
| 12.40 | 7.13 | 35 |
| 12.90 | 6.86 | 11 |
| 14.00 | 6.32 | 15 |
| 14.60 | 6.06 | 6 |
| 15.20 | 5.83 | 27 |
| 15.60 | 5.68 | 30 |
| 16.00 | 5.54 | 9 |
| 17.50 | 5.06 | 81 |
| 18.30 | 4.85 | 54 |
| 18.50 | 4.79 | 36 |
| 19.30 | 4.60 | 41 |
| 19.60 | 4.53 | 40 |
| 20.40 | 4.35 | 16 |
| 20.75 | 4.28 | 14 |
| 21.15 | 4.20 | 20 |
| 21.60 | 4.11 | 22 |
| 21.85 | 4.07 | 100 |
| 22.50 | 3.95 | 23 |
| 22.75 | 3.91 | 15 |
| 23.70 | 3.75 | 12 |
| 24.15 | 3.68 | 14 |
| 24.40 | 3.65 | 15 |
| 24.90 | 3.57 | 13 |
| 25.60 | 3.48 | 16 |
| 26.50 | 3.36 | 10 |
| 27.30 | 3.26 | 29 |

TABLE 5-continued

| 2Θ/° | d/Å | I |
|---|---|---|
| 28.30 | 3.15 | 6 |
| 29.00 | 3.08 | 9 |
| 29.50 | 3.03 | 15 |

Figure 8:
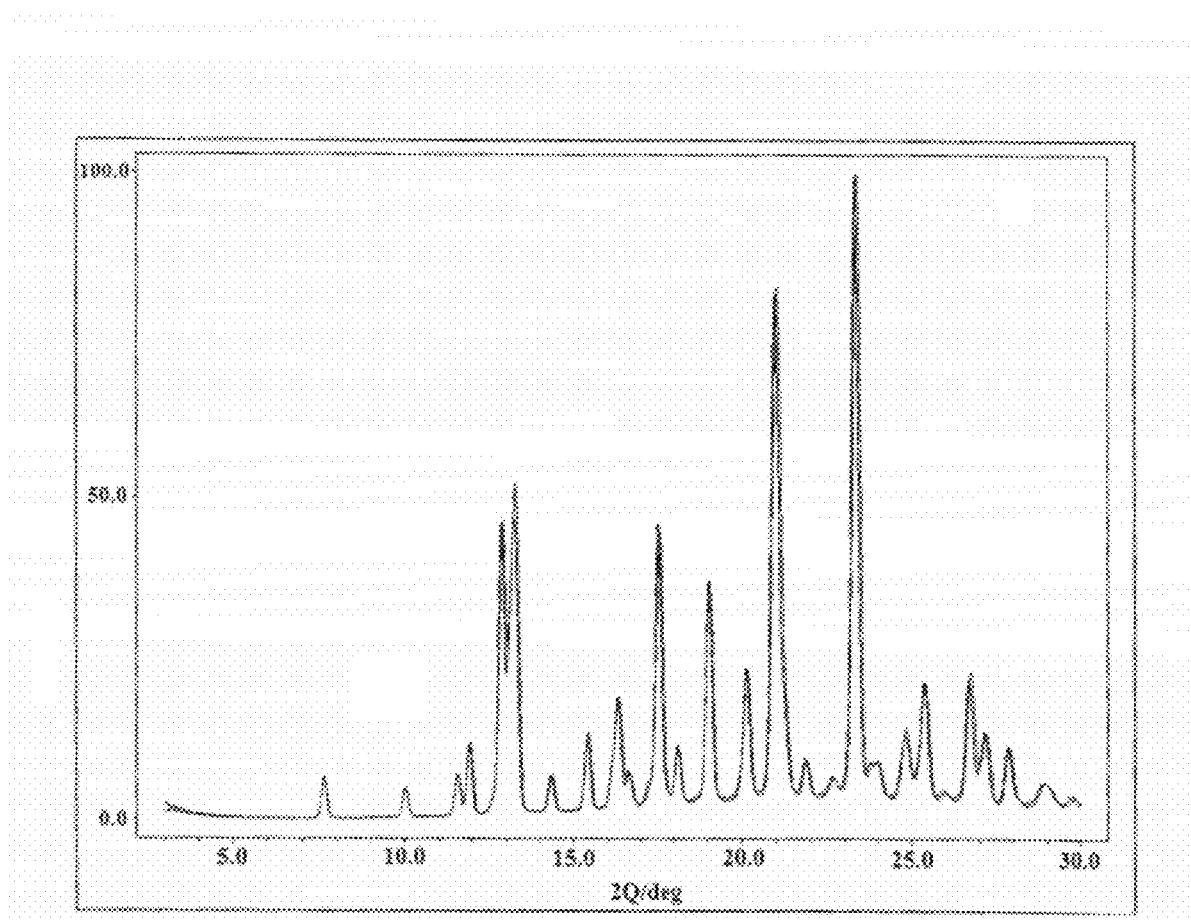
FIG. 8 shows the XRPD patterns of starting and stability tested samples of the free base dihydrate (FB2) of 1-cyclopropyl-3-[3-(5-morpholin-4-ylmethyl-1H-benzoimidazol-2-yl)-1H-pyrazol-4-yl]-urea as described in Example 72 below.

The XRPD pattern for the dihydrate free base FB2 form of 1-cyclo propyl-3-[3-(5-morpholin-4-ylmethyl-1H-benzoimidazol-2-yl)-1H-pyrazol-4-yl]-urea free base is provided in FIG. 8 and details on main peaks are listed in Table 6.

TABLE 6

| 2Θ/° | d/Å | I |
|---|---|---|
| 7.50 | 11.78 | 8 |
| 10.00 | 8.84 | 5 |
| 11.50 | 7.69 | 9 |
| 11.90 | 7.43 | 13 |
| 12.80 | 6.91 | 48 |
| 13.20 | 6.70 | 44 |
| 14.20 | 6.23 | 9 |
| 15.40 | 5.75 | 17 |
| 16.20 | 5.47 | 24 |
| 16.60 | 5.34 | 13 |
| 17.00 | 5.21 | 11 |
| 17.40 | 5.09 | 52 |
| 18.00 | 4.93 | 20 |
| 19.00 | 4.67 | 48 |
| 20.00 | 4.44 | 31 |
| 20.80 | 4.27 | 76 |
| 21.15 | 4.20 | 30 |
| 21.75 | 4.08 | 22 |
| 22.60 | 3.93 | 20 |
| 23.10 | 3.85 | 100 |
| 23.55 | 3.78 | 22 |
| 23.95 | 3.71 | 22 |
| 24.90 | 3.57 | 26 |
| 25.30 | 3.52 | 35 |
| 26.65 | 3.34 | 34 |
| 27.00 | 3.30 | 24 |
| 27.80 | 3.21 | 22 |
| 28.85 | 3.09 | 18 |
| 29.35 | 3.04 | 14 |

Biological Activity

Example 73

Measurement of Activated CDK2/CyclinA Kinase Inhibitory Activity Assay ($IC_{gn}$)

Compounds of the invention were tested for kinase inhibitory activity using the following protocol.

Activated CDK2/CyclinA (Brown et al, Nat. Cell Biol, 1, pp 438-443, 1999; Lowe, E. D., et al Biochemistry, 41, pp 15625-15634, 2002) is diluted to 125 pM in 2.5× strength assay buffer (5O mM MOPS pH 7.2, 62.5 mM β-glycerophosphate, 12.5 mM EDTA, 37.5 mM $MgCl_2$, 112.5 mM ATP, 2.5 mM DTT, 2.5 mM sodium orthovanadate, 0.25 mg/ml bovine seruni albumin), and 10 μl mixed with 10 μl of histone substrate mix (60 μl bovine histone H1 (Upstate Biotechnology, 5 mg/ml), 940 μl $H_2O$, 35 μCi $γ^{33}P$-ATP) and added to 96 well plates along with 5 μl of various dilutions of the test compound in DMSO (up to 2.5%). The reaction is allowed to proceed for 2 to 4 hours before being stopped with an excess of orthophosphoric acid (5 μl at 2%). $γ^{33}P$-ATP which remains unincorporated into the histone H1 is separated from phosphorylated histone H1 on a Millipore MAPH filter plate. The wells of the MAPH plate are wetted with 0.5% orthophosphoric acid, and then the results of the reaction are filtered with a Millipore vacuum filtration unit through the wells. Following filtration, the residue is washed twice with 200 μl of 0.5% orthophosphoric acid. Once the filters have dried, 20 μl of Microscint 20 scintillant is added, and then counted on a Packard Topcount for 30 seconds.

The % inhibition of the CDK2 activity is calculated and plotted in order to determine the concentration of test compound required to inhibit 50% of the CDK2 activity ($IC_{50}$).

The compounds of Examples 1, 10, 11, 18, 20, 22, 30, 31, 32, 46, 47 and 54 have $IC_{50}$ values of less than 1 μM in the CDK2 assay whereas the compounds of Examples 44, 45, 48, 51 and 53 have $IC_{50}$ values of less than 10 μM.

Example 74

Measurement of Activated CDK1/CyclinB Kinase Inhibitory Activity Assay ($TC_{5n}$)

CDK1/CyclinB assay is identical to the CDK2/CyclinA above except that CDK1/CyclinB (Upstate Discovery) is used and the enzyme is diluted to 6.25 nM.

The compounds of Examples 1, 4, 6, 10, 11, 13, 22, 42, 47 and 54 have $IC_{50}$ values of less than 1 μM in the CDK1 assay whereas the compounds of Examples 3, 8, 9, 16, 17, 20, 24, 28, 29, 31, 32, 34, 39, 41, 45, 46, 48, 49, 50, 51, 52, 53 and 56 have $IC_{50}$ values of less than 10 μM, and the compounds of Examples 2, 23, 26, 27, 33, 37 and 43 have $IC_{50}$ values of less than 50 μM Example 75

Aurora A Kinase Assays

Aurora A kinase activity can be determined using a Dissociative Enhanced Lanthanide Fluoro Immuno Assay (DELFIA) with a GSK3-derived biotinylated peptide. The amount of phosphorylated peptide produced is quantified by means of a phospho-specific primary antibody and europium-labelled anti-rabbit IgG antibody using time-resolved fluorescence at $λ_{ex}$=337 nm, $λ_{em}$=620 nm.

Kinase Reaction:

Assay reactions are set up in 96 well plates in a total reaction volume of 25 μl with 0.5 nM Aurora A (Upstate Discovery), 3 μM Biotin-CGPKGPGRRGRRRTSSFAEG, 15 μM ATP and various dilutions of compound in 1O mM MOPS, pH 7.0, 0.1 mg/ml BSA, 0.001% Brij-35, 0.5% glycerol, 0.2 mM EDTA, 1O mM $MgCl_2$, 0.01% β-mercaptoethanol and 2.5% DMSO. The reaction is allowed to proceed for 60 minutes at room temperature before stopping with 100 μl STOP buffer containing 100 mM EDTA, 0.05% Surfact-Amps20 (Pierce) and Ix Blocker™ BSA in TBS (Pierce).

Detection Step:

The reaction mixture is then transferred to a 96-well Neutravidin-coated plate (Pierce) and incubated for 30 minutes to capture the biotinylated peptide. After washing 5 times with 200 μl TBST buffer per well, a mixture of anti-phospho-(Ser/Thr)-AKT substrate antibody (Cell Signalling Technology) and Eu—$N_1$ anti-rabbit IgG (Perkin Elmer) is added to all wells and left for 1 hour. After a further washing step, DELFIA enhancement solution (Perkin Elmer) is added to all wells. After an incubation of 5 minutes, the wells are counted on a Fusion plate reader.

The compounds of Examples 1 to 56 all have $IC_5O$ values of less than 1 μM in the above assay. The hydrochloride salt of Example 6OH has an $IC_5Q$ of 0.0025 μM.

Example 76

Aurora B Kinase Assays

Kinase Reaction:

Assay reactions are set up in 96 well plates in a total reaction volume of 25 µl with 5 nM AuroraB (ProQinase), 3 µM Biotin-CGPKGPGRRGRRRTS SFAEG$_3$ 15 µM ATP and various dilutions of compound in 25 mM TRIS pH 8.5, 0.1 mg/ml BSA, 0.025% Surfact-Amps 20, 5 mM MgCl$_2$, 1 mM DTT, & 2.5% DMSO. The reaction is allowed to proceed for 90 minutes at room temperature before stopping with 1oo µl STOP buffer containing 1OO mM EDTA, 0.05% Surfact-am ρs20 (Pierce) and Ix Blocker™ BSA in TBS (Pierce).

The detection step is carried out as described for AuroraA.

In the Aurora B assay, the hydrochloride salt of Example 6OH exhibits 57% inhibition at a concentration of 0.003 µM.

Example 77

GSK3-B Kinase Inhibitory Activity Assay

GSK3-β (Upstate Discovery) is diluted to 7.5 nM in 25 mM MOPS, pH 7.00, 25 mg/ml BSA, 0.0025% Brij-35, 1.25% glycerol, 0.5 mM EDTA, 25 mM MgCl$_2$, 0.025% β-mercaptoethanol, 37.5 mM ATP and 10 µl mixed with 10 µl of substrate mix. The substrate mix for GSK3-β is 12.5 µM phospho-glycogen synthase peptide-2 (Upstate Discovery) in 1ml of water with 35 µCi γ$^{33}$P-ATP. Enzyme and substrate are added to 96 well plates along with 5 µl of various dilutions of the test compound in DMSO (up to 2.5%). The reaction is allowed to proceed for 3 hours (GSK3-β) before being stopped with an excess of orthophosphoric acid (5 µl at 2%). The filtration procedure is as for Activated CDK2/CyclinA assay above.

Example 78

CDK Selectivity Assays

78A. Protocol A

Compounds of the invention can be tested for kinase inhibitory activity against a number of different kinases using the general protocol described above in Example 3 but modified as set out below.

Kinases are diluted to a 1Ox working stock in 2O mM MOPS pH 7.0, 1 mM EDTA, 0.1% γ-mercaptoethanol, 0.01% Brij-35, 5% glycerol, 1 mg/ml BSA. One unit equals the incorporation of 1 nmol of phosphate per minute into 0.1 mg/ml histone H1, or CDK7 substrate peptide at 30° C. with a final ATP concentration of 1OO uM.

The substrate for all the CDK assays (except CDK7) is histone H1, diluted to 1Ox working stock in 2O mM MOPS pH 7.4 prior to use. The substrate for CDK7 is a specific peptide diluted to 1Ox working stock in deionised water.

Assay Procedure for CDK1/cyclinB, CDK2/cyclinA, CDK2/cyclinE. CDK3/cyclinE. CDK5/ü35. CDK6/cyclinD3:

In a final reaction volume of 25 µl, the enzyme (5-1O mU) is incubated with 8 mM MOPS pH 7.0, 0.2 mM EDTA, 0.1 mg/ml histone H1, 1O mM MgAcetate and [γ-$^{33}$P-ATP] (specific activity approx 500 cpm/µmol, concentration as required). The reaction is initiated by the addition Of Mg$^{2+}$ [γ-$^{33}$P-ATP]. After incubation for 40 minutes at room temperature the reaction is stopped by the addition of 5 µl of a 3% phosphoric acid solution. 10 ml of the reaction is spotted onto a P30 filter mat and washed 3 times for 5 minutes in 75 mM phosphoric acid and once in methanol prior to drying and counting.

Assay Procedure for CDK7/cyclinH/MAT1

In a final reaction volume of 25 µl, the enzyme (5-1O mU) is incubated with 8 mM MOPS pH 7.0, 0.2 mM EDTA, 500 µM peptide, 1O mM MgAcetate and [γ-$^{33}$P-ATP] (specific activity approx 500 cpm/pmol, concentration as required). The reaction is initiated by the addition of Mg$^{2+}$+[γ-$^{33}$P-ATP]. After incubation for 40 minutes at room temperature the reaction is stopped by the addition of 5 µl of a 3% phosphoric acid solution. 10 ml of the reaction is spotted onto a P30 filtermat and washed 3 times for 5 minutes in 75 mM phosphoric acid and once in methanol prior to drying and counting.

78A. Protocol B

The inhibitory activity against these enzymes was assayed at Upstate Discovery Ltd. Enzymes were prepared at 1Ox final concentration in enzyme buffer (as described in the table below). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 µl of a 3% phosphoric acid solution. Ten µl of the reaction mix was transferred to either a filtermatA or P30 filtermat and washed three times in 75 nM phosphoric acid and once in methanol before being dried for scintillation counting.

The test compound was tested at the concentrations detailed below in duplicate against all kinases and the percent activity compared to control was calculated. Where inhibition was high, an IC$_{50}$ was determined.

| Enzyme | Enzyme Buffer | Assay Buffer | Substrate | ATP Concentration (µM) |
|---|---|---|---|---|
| Cdk3 | A | A | 0.1 mg/ml Histone H1 | 200 |
| Cdk6 | A | A | 0.1 mg/ml Histone H1 | 200 |
| Cdk7 | A | A | 500 µM peptide | 90 |
| Cdk9 | A | A | 100 µM KTFCGTPEYLAPEVR REPRILSEEEQEMFRD FDYIADWC | 45 |

The Enzyme Buffers Used were:
A: 20 nM MOPS pH 7.0, 1 mM EDTA, 0.1% β-mercaptoethanol, 0.01% Brij-35, 5% glycerol, 1 mg/ml BSA The Assay Buffers Used were:
A: 8 mM MOPS pH 7.0, 0.2 mM EDTA, 10 mM Mg acetate

Example 79

Antiproliferative Activity

The antiproliferative activities of compounds of the invention can be determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. In addition, any morphological changes are recorded. Cell lines can be obtained from the ECACC (European Collection of cell Cultures).

In an assay using the HCT-1 16 cell line, the hydrochloride salt of Example 6OH has an $IC_{50}$ of 0.070 μM.

In particular, compounds of the invention were tested against the HCT-1 16 cell line (ECACC Reference: 91091005) derived from human colon carcinoma.

Many compounds of the invention were found to have $IC_{50}$ values of less than 25 μM in this assay and preferred compounds have $IC_{50}$ values of less than 1 μM. Alternatively many compounds of the invention were found to have the minimum concentration at which polyploidy or multinucleation is observed of less than 10 μM and preferred compounds have $IC_{50}$ values of less than 100 nM.

The compound 1-cyclopropyl-3-[3-(5-morpholin-4-ylmethyl-1H-benzoimidazol-2-yl)-1H-pyrazol-4-yl]-urea was found to have $IC_{50}$ values of less than 1 μM in this assay. In addition it was found to have the minimum concentration at which polyploidy or multinucleation is observed of less than 100 nM.

Example 80

A. General Colony Forming Assay Protocol

The effect of various treatment treatments of compounds on adherent tumour cell lines was assessed in a clonogenic assay.

Cells were seeded at a concentration of 75 to 100 cells/ml relevant culture media onto 6 or 24 well tissue culture plates and allowed to recover for 16 h.

Compound or vehicle control (DMSO) was added to duplicate wells to give a final DMSO concentration of 0.1%. Following compound addition, colonies were allowed to grow out for between 10 and 14 days for optimum discrete colony counting. Colonies were fixed in 2 ml Carnoys fixative (25% Acetic Acid, 75% Methanol) and stained in 2 ml 0.4% w/v crystal violet. The number of colonies in each well were counted. IC50 values were calculated by sigmoidal dose-response (variable slope) IC50 curves using Prism Graphpad Software.

B. Colony Forming Assay Protocol for 1-Cyclopropyl-3-[3-[(5-morpholin-4-ylmethyl-1H-benzoimidazol-2-yl)-1H-pyrazol-4-yl]-urea The effect of various treatment treatments of 1-cyclopropyl-3-[3-(5-morpholin-4-ylmethyl-1H-benzoimidazol-2-yl)-1H-pyrazol-4-yl]-urea on A2780, A549, HCT 116, HCT 116 N7, HT-29, MCF7, MIA-Pa-Ca-2, SW620 cell lines was assessed in a clonogenic assay.

Cells were seeded at a concentration of 75 to 100 cells/ml relevant culture media onto 6 or 24 well tissue culture plates and allowed to recover for 16 hours.

| Cell Line | Media | Comments |
|---|---|---|
| HCT 116 | DMEM + 10% FBS + GLUTAMAX I | |
| HCT 116 N7 | DMEM + 10% FBS + GLUTAMAX I + 0.4 mg/ml G418 | |
| HT-29 | McCoy'5a + 10% FBS + 2 mM L-Glutamine | |
| SW620 | L-15 + 10% FBS + GLUTAMAX I | Atmospheric $CO_2$ |
| A2780 | RPMI 1640 + 2 mM Glutamine + 10% FBS | |
| A549 | DMEM + 10% FBS + GLUTAMAX I | |
| MCF7 | EMEM + 10% FBS + 2 mM L-Glutamine + 1% NEAA | |
| MIA-Pa-Ca-2 | DMEM + 10% FBS + GLUTAMAX I | |

1-Cyclopropyl-3-[3-(5-morpholin-4-ylmethyl-1H-benzoimidazol-2-yl)-1H-pyrazol-4-yl]-urea or vehicle control (DMSO) was added to duplicate wells to give a final DMSO concentration of 0.1%. Following compound addition, colonies were allowed to grow out for between 10 and 14 days for optimum discrete colony counting. Colonies were fixed in 2 ml Carnoys fixative (25% Acetic Acid, 75% Methanol) and stained in 2 ml 0.4% w/v crystal violet. The number of colonies in each well were counted. Only multi-cellular colonies of approximately 50 cells or more which show proliferation from a single cell to a colony of many cells (i.e. complete cell cycles including successful cytokinesis) were scored. Single multi-¬ nucleated (polyploid) cells were not scored. $IC_{50}$ values were calculated by sigmoidal dose-response (variable slope) IC50 curves using Prism Graphpad Software.

The results of the assays are set out in Table C in the section entitled "Advantages of the Compounds of the Invention."

Example 81

Determination of Potency against Cytochrome P450

The potency of the compound of Example 24 against CYP450s 1A2, 2C9, 2C19, 3A4 and 2D6 was determined using the Pan Vera Vivid Cyp450 screening kits available from Invitrogen (Paisley, UK). CYPs are supplied in the form of baculosomes containing the CYP450 and NADPH reductase. Substrates are the fluorescent Vivid substrates.

The final reaction mixtures were as follows:

1A2
100 nM potassium phosphate, pH 8, 1% methanol, 2 μM 1A2 Blue vivid substrate, 100 μM $NADP^+$, 4 nM CYP450 1A2, 2.66 mM glucose-6-phosphate, 0.32 U/ml glucose-6-phosphate dehydrogenase.

2C9
50 mM potassium phosphate, pH 8, 1% methanol, 2 μM Green vivid substrate, 100 μM $NADP^+$, 8 nM CYP450 2C9, 2.66 mM glucose-6-phosphate, 0.32 U/ml glucose-6-phosphate dehydrogenase.

2C19
50 mM potassium phosphate, pH 8, 1% methanol, 8 μM Blue vivid substrate, 100 μM $NADP^+$, 4 nM CYP450 2Cl 9, 2.66 mM glucose-6-phosphate, 0.32 U/ml glucose-6-phosphate dehydrogenase.

3A4
100 mM potassium phosphate, pH 8, 1% methanol, 10 μM 3A4 Blue vivid substrate, 100 μM $NADP^+$, 2.5 nM CYP450 3A4, 2.66 mM glucose-6-phosphate, 0.32 U/ml glucose-6-phosphate dehydrogenase.

2D6
100 nM potassium phosphate, pH 8, 1% methanol, 5 μM 2D6 Blue vivid substrate, 100 μM $NADP^+$, 5 nM CYP450 2D6, 2.66 mM glucose-6-phosphate, 0.32 U/ml glucose-6-phosphate dehydrogenase.

Fluorescence was monitored for 20 min at 30 s intervals on a Molecular Devices Spectramax Gemini reader. Excitation and emission wavelengths were 390 nm and 460 nm for 1A2, 2C19 and 3A4, 390 nm and 485 nm for 2D6 and 485 nm and 530 nm for 2C9. Initial rates were determined from progress curves.

The test compound was made up in methanol and tested against the CYP450s at a concentration of 10 μM.

Pharmaceutical Formulations

Example 82

(т) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(Ii) Capsule Formulation

A capsule formulation is prepared by mixing 1OO mg of a compound of the formula (I) with 1OO mg lactose and filling the resulting mixture into standard opaque hard gelatin capsules.

(Iip Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

(v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

(Vp Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vip Lyophilised Formulation I

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(viii) Lyophilised Formulation II

Aliquots of formulated compound of formula (I) or s salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 milliter.

fix) Lyophilised Formulation for Use in Lv. Administration III

An aqueous buffered solution is prepared by dissolving 1-cyclopropyl-3-[3-(5-morpholin-4-ylmethyl-1H-benzoimidazol-2-yl)-1H-pyrazol-4-yl]-urea Z-lactic acid salt at a concentration of 12.86 mg/ml in a 0.02M citric acid buffer corrected to a pH of 4.5 with sodium hydroxide or hydrochloric acid.

The buffered solution is filled, with filtration to remove particulate matter, into a container (such as a class 1 glass vial) which is then partially sealed (e.g. by means of a Florotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle: for example:
Freezing—freeze to −40° C. over 2 hours and hold at −40° C. for 3 hours.
Primary drying—ramp −40° C. to −30° C. over 8 hours and hold at −30° C. for 7 hours.
Secondary drying—ramp to +30° C. over 4 hours and hold at +30° C. for 8-10 hours On completion of the freeze drying cycle the vials are back filled with nitrogen to atmospheric pressure, stoppered and secured (e.g. with an aluminium crimp). For intravenous administration, the freeze dried solid can be reconstituted into a pharmaceutically acceptable excipient, such as 0.9% saline or 5% dextrose. The solution can be dosed as is, or can be injected into an infusion bag (containing a pharmaceutically acceptable excipient, such as 0.9% saline or 5% dextrose), before administration.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

Example 83

Determination of Antifungal Activity

The antifungal activity of the compounds of the formula (I) can be determined using the following protocol.

The compounds are tested against a panel of fungi including *Candida parpsilosis, Candida tropicalis, Candida albicans*-ATCC 36082 and *Cryptococcus neoformans*. The test organisms are maintained on Sabouraud Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 M morpholine propanesulphonic acid (MOPS). The suspension is then centrifuged and washed twice with 0.85% NaCl before sonicating the washed cell suspension for 4 seconds (Branson Sonifier, model 350, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 µg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to 11 (concentration ranges are 64 to 0.125 µg/ml). Well 1 serves as a sterility control and blank for the spectrophotometric assays. Well 12 serves as a growth control. The microtitre plates are inoculated with 10 µl in each of well 2 to 11 (final inoculum size is $10^4$ organisms/ml). Inoculated plates are incubated for 48 hours at 35° C. The IC50 values are determined spectrophotometrically by measuring the absorbance at 420 run (Automatic Microplate Reader, DuPont Instruments, Wilmington, Del.) after agitation of the plates for 2 minutes with a vortex-mixer (Vorte-Genie 2 Mixer, Scientific Industries, Inc., Bolemia, N.Y.). The IC50 endpoint is defined as the lowest drug concentration exhibiting approximately 50% (or more) reduction of the growth compared with the control well. With the turbidity assay this is defined as the lowest drug concentration at which turbidity in the well is <50% of the control (IC50). Minimal Cytolytic Concentrations (MCC) are determined by sub-culturing all wells from the 96-well plate onto a Sabourand Dextrose Agar (SDA) plate, incubating for 1 to 2 days at 35° C. and then checking viability.

Example 84

Protocol for the Biological Evaluation of Control of In Vivo Whole Plant Fungal Infection Compounds of the formula (I) are dissolved in acetone, with subsequent serial dilutions in acetone to obtain a range of desired concentrations. Final treatment volumes are obtained by adding 9 volumes of 0.05% aqueous Tween-20™ or 0.01% Triton X-100™, depending upon the pathogen.

The compositions are then used to test the activity of the compounds of the invention against tomato blight (*Phytophthora infestans*) using the following protocol. Tomatoes (cultivar Rutgers) are grown from seed in a soil-less peat-based potting mixture until the seedlings are 10-20 cm tall. The plants are then sprayed to run-off with the test compound at a rate of 100 ppm. After 24 hours the test plants are inoculated by spraying with an aqueous sporangia suspension of *Phytophthora infestans*, and kept in a dew chamber overnight. The plants are then transferred to the greenhouse until disease develops on the untreated control plants.

Similar protocols are also used to test the activity of the compounds of the invention in combatting Brown Rust of Wheat (*Puccinia*), Powdery Mildew of Wheat (*Ervsiphe vraminis*), Wheat (*cultivar Monon*), Leaf Blotch of Wheat (*Septoria tritici*), and Glume Blotch of Wheat (*Leptosphaeria nodorum*).

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for treating a disease or condition comprising or arising from abnormal cell growth in a mammal, which method comprises administering to the mammal the compound 1-cyclopropyl-3-[3-(5-morpholin-4-ylmethyl-1H-benzoimidazol-2-yl)-1H-pyrazol-4-yl]-urea or a salt, solvate, tautomer, or N-oxide thereof, in an amount effective in inhibiting abnormal cell growth, wherein the disease or condition is selected from a solid tumour, non-Hodgkin's lymphoma, a leukemia, squamous cell carcinoma, colon cancer, ovarian cancer, lung cancer, breast cancer, pancreatic cancer, and esophageal carcinoma.

2. A method according to claim 1 wherein the disease or condition is a leukemia.

3. A method according to claim 2 wherein the disease or condition is a leukemia selected from relapsed or refractory acute myelogenous leukemia, myelodysplastic syndrome, acute lymphocytic leukemia and chronic myelogenous leukemia.

4. A method for the treatment of a disease or condition in a patient suffering from the disease or condition; which method comprises (i) subjecting a patient to a diagnostic test to determine whether the patient possesses the Ile31 variant of the Aurora A gene; and (ii) where the patient does possess the said variant, thereafter administering to the patient the compound 1-cyclopropyl-3-[3-(5-morpholin-4-ylmethyl-1H-benzoimidazol-2-yl)-1H-pyrazol-4-yl]-urea, or a salt, solvate, tautomer, or N-oxide thereof, wherein the disease or condition is selected from a solid tumour, non-Hodgkin's lymphoma, a leukemia, squamous cell carcinoma, colon cancer, ovarian cancer, lung cancer, breast cancer, pancreatic cancer, and esophageal carcinoma.

5. A method according to claim 3 wherein the disease or condition is chronic myelogenous leukemia.

6. A method according to claim 1 wherein the disease or condition is a solid tumour.

7. A method according to claim 1 wherein the disease or condition is non-Hodgkin's lymphoma.

8. A method according to claim 7 wherein the disease or condition is B-cell non-Hodgkin's lymphoma.

9. A method according to claim 8 wherein the disease or condition is selected from mantle cell lymphoma and diffuse large B-cell lymphoma.

10. A method according to claim 1 wherein the disease or condition is squamous cell carcinoma.

11. A method according to claim 1 wherein the disease or condition is selected from colon cancer, ovarian cancer, lung cancer, breast cancer, and pancreatic cancer.

12. A method according to claim 11 wherein the disease or condition is non-small cell lung carcinoma.

13. A method according to claim 1 wherein the disease or condition is esophageal carcinoma.

14. A method according to claim 1 which method comprises administering to the mammal the compound 1-cyclopropyl-3-[3-(5-morpholin-4-ylmethyl-1H-benzoimidazol-2-yl)-1H-pyrazol-4-yl]-urea or a salt, solvate, or tautomer thereof.

15. A method according to claim 1 which method comprises administering to the mammal the compound 1-cyclopropyl-3-[3-(5-morpholin-4-ylmethyl-1H-benzoimidazol-2-yl)-1H-pyrazol-4-yl]-urea or a salt thereof.

16. A method according to claim 15 wherein the disease or condition is a leukemia.

17. A method according to claim 15 wherein the disease or condition is non-Hodgkin's lymphoma.

18. A method according to claim 15 which method comprises administering to the mammal the compound 1-cyclopropyl-3-[3-(5-morpholin-4-ylmethyl-1H-benzoimidazol-2-yl)-1H-pyrazol-4-yl]-urea in the form of a lactate salt.

19. A method according to claim 15 which method comprises administering to the mammal an L-lactic acid salt of the 1-cyclopropyl-3-[3-(5-morpholin-4-ylmethyl-1H-benzoimidazol-2-yl)-1H-pyrazol-4-yl]-urea.

20. A method according to claim 4 which method comprises administering to the patient an L-lactic acid salt of the 1-cyclopropyl-3-[3-(5-morpholin-4-ylmethyl-1H-benzoimidazol-2-yl)-1H-pyrazol-4-yl]-urea.

\* \* \* \* \*